(12) United States Patent
Griffin et al.

(10) Patent No.: US 7,037,912 B2
(45) Date of Patent: May 2, 2006

(54) PROTEIN KINASE INHIBITORS

(75) Inventors: John H. Griffin, Atherton, CA (US); Yu-Hua Ji, Redwood City, CA (US); Edmund J. Moran, San Francisco, CA (US); Jonathan W. Wray, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 170 days.

(21) Appl. No.: 10/824,005

(22) Filed: Apr. 14, 2004

(65) Prior Publication Data

US 2004/0235870 A1 Nov. 25, 2004

Related U.S. Application Data

(62) Division of application No. 10/093,068, filed on Mar. 6, 2002, now Pat. No. 6,750,241, which is a continuation of application No. 09/732,438, filed on Dec. 7, 2000, now abandoned.

(60) Provisional application No. 60/169,996, filed on Dec. 8, 1999, and provisional application No. 60/266,316, filed on Dec. 8, 1999.

(51) Int. Cl.
 C07D 239/46 (2006.01)
 C07D 239/26 (2006.01)
 C07D 403/12 (2006.01)
 C07D 31/506 (2006.01)
 A61P 3/10 (2006.01)

(52) U.S. Cl. .................. 514/252.14; 544/295; 544/316; 544/331; 544/333; 544/335; 514/269; 514/275

(58) Field of Classification Search ................ 544/295, 544/316, 331, 333, 335; 514/252.14, 275, 514/269
See application file for complete search history.

(56) References Cited

U.S. PATENT DOCUMENTS

| 5,397,787 A | 3/1995 | Buzzetti et al. |
| 5,461,146 A | 10/1995 | Lewis et al. |
| 5,521,184 A | 5/1996 | Zimmermann |
| 5,593,991 A | 1/1997 | Adams et al. |
| 5,593,992 A | 1/1997 | Adams et al. |
| 5,670,527 A | 9/1997 | Adams et al. |
| 5,945,418 A | 8/1999 | Bemis et al. |
| 5,977,103 A | 11/1999 | Adams et al. |

FOREIGN PATENT DOCUMENTS

| WO | WO 94/26260 | 11/1994 |
| WO | WO 96/21452 | 7/1996 |
| WO | WO 96/33980 | 10/1996 |
| WO | WO 96/34867 | 11/1996 |
| WO | WO 97/19065 | 5/1997 |
| WO | WO 97/40019 | 10/1997 |
| WO | WO 98/18782 | 5/1998 |
| WO | WO 98/37881 | 9/1998 |
| WO | WO 99/24442 | 5/1999 |
| WO | WO 00/61578 | 10/2000 |

OTHER PUBLICATIONS

Adams et al., "Recent progress towards the identification of selective inhibitors of serine/threonine protein kinases", Current Opinion in Drug Discovery & Development, vol. 2(2), pp 96–109 (1999).

Ayyangar et al., "Anthraqulnone and Anthrone Series–XXIII/The Non–Identity of 1:3:8–Trihydroxy–2–Hydroxymethyl–Anthraquinone with Versicolorin and a Synthesis of Damnacanthol and Damnacanthal", Tetrahedron, vol. 6, pp 331–337 (1959).

Bajaj et al., Improved Preparative Synthesis of Plceatannol (3,4,3',5'–Tetrahydroxy–Trans–Stilbene), Rev. Latinoamer Quim., vol. 18(2), pp 79–80 (1987).

Bit et al., "Inhibitors of Protein Kinase C. 3. Potent and Highly Selective Bisindolylmaleimides by Conformational Restriction", J. Med. Chem., vol. 36, pp 21–29 (1993).

Bullington et al., "The Development of Novel and Selective $p58^{Ick}$ Tyrosine Kinse Inhibitors", Bioorganic & Medicinal Chemistry Letters 8, pp 2489–2494 (1998).

Bunin et al., "[26] Synthesis and Evaluation of 1,4–Benzodiaepine Libraries", Methods in Enzymology, vol. 267, pp 448–465 (1996).

Connolly et al., "Discovery and Structure–Activity Studies of a Novel Series of Pyrido[2,3–d]Pyrimidine Tyrosine Kinase Inhibitors", Bioorganic & Medicinal Chemistry Letters, vol. 7, No. 18, pp 2415–2420 (1997).

Duncia et al., "MEK Inhibitors:The Chemistry and Biological Activity of U0126, Its Analogs, and Cyclization Products", Bioorganic & Medicinal Chemistry Letters, vol. 8, pp 2839–2844 (1998).

Faltynek et al., "Damnacanthal is a Highly Potent, Selective Inhibitor of $p56^{Ick}$ Tyrosine Kinase Activity", Biochemistry, vol. 34, pp 12404–12410 (1995).

Fry et al., "Specific, irreversible inactivation of the epidermal growth factor receptor and erbB2, by a new class of tyrosine kinase inhibitor", Proc. Natl. Acad. Sci, USA, vol. 95, pp 12022–12027 (1998).

Furet et al., "Structure–Based Design, Synthesis, and X–ray Crystallography of a High–Affinity Antagonist of the Grb2–SH2 Domain Containing an Asparagine Mimetic", J. Med. Chem., vol. 42, pp 2358–2383 (1999).

Hamby et al., "Structure–Activity Relationships for a Novel Series of Pyrido[2,3–d]pyrimidine Tyrosine Kinase Inhibitors", J. Med. Chem. vol. 40, pp 2296–2303 (1997).

(Continued)

Primary Examiner—Mark L. Berch
Assistant Examiner—Kahsay Habte
(74) Attorney, Agent, or Firm—Jeffrey A. Hagenah; Joyce G. Cohen; Roberta P. Saxon

(57) ABSTRACT

Disclosed are compounds which inhibit or modulate the activity of protein kinases and pharmaceutical compositions containing such compounds. The disclosed compound contain two or more ligand moieties covalently linked together by one or more linking groups. Such compounds are useful for treating diseases or medical disorders mediated by protein kinases.

17 Claims, 35 Drawing Sheets

OTHER PUBLICATIONS

Hanefeld et al., "One–pot synthesis of tetrasubstituted pyrazoles–proof of regiochemistry", J. Chem. Soc., Perkin Trans. 1, pp 1545–1552 (1996).

Hanke et al., "Discovery of a Novel, Potent, and Src Family–selective Tyrosine Kinase Inhibitor", The Journal of Biological Chemistry, vol. 271, No. 2, Issue of Jan. 12, pp 695–701 (1996).

Henry et al., "Potent Inhibitors of the Map Kinase p38", Bioorganic & Medicinal Chemistry Letters 8, pp 3335–3340 (1998).

Henry et al., "6–Amino–2–(4–fluorophenyl)–4–methoxy–3–(4–pyridyl)–1H–pyrrolo[2,3–b]pyridine (RWJ 88354)cA Potent and Selective p38 Kinase Inhibitor", J. Med. Chem., vol. 41, pp 4196–4198 (1998).

Klutchko et al., "2–Substituted Aminopyrido[2,3–$d$] pyrimidin–7($BH$)–ones. Structure–Activity Relationships Against Selected Tyrosine Kinases and in Vitro and in Vivo Anticancer Activity", J. Med. Chem, vol. 41, pp 3276–3292 (1998).

Lawrence et al., "Protein Kinase Inhibitors: The Tyrosine–Specific Protein Kinases", Pharmacol. Ther., vol. 77, No. 2, pp 81–114 (1998).

Levitzki et al., "Tyrosine Kinase Inhibition:An Approach to Drug Development", Science, vol. 267, pp 1782–1788 (1995).

Maly et al., "Combinatorial target–guided ligand assembly: identification of potent subtype–selective c–Src Inhibitors", PNAS, vol. 97, No. 6, pp 2419–2424 (2000).

Myers et al., "The Preparation and SAR of 4–(Anilino), 4–(Phenoxy), and 4–(Thiophenoxy)–Quinazolines: Inhibitors of $p56_{1ck}$ and EGF–R Tyrosine Kinase Activity.", Bioorganic & Medicinal Chemistry Letters, vol. 7, No. 4, pp 417–420 (1997).

Profit et al., "Bivalent Inhibitors of Protein Tyrosine Kinases", J. Am. Chem. Soc., vol. 121, pp 280–283 (1999).

Ramdas et al., "Benzodiazepine Compounds as Inhibitors of the Src Protein Tyrosine Kinase: Screening of a Conbinatorial Library of 1,4–Benzodiazepines", Archives of Biochemistry and Biophysics, vol. 368, No. 2, pp 394–400 (1999).

Schoepfer et al., "Highly Potent Inhibitors of the Grb2–SH2 Domain", Bioorganic & Medicinal Chemistry Letters, vol. 9, pp 221–226 (1999).

Shibuya et al., "Syntheses of Two Pairs of Enantiomeric C18–Sphingosines and a Palmitoyl Analogue of Gaucher Spleen Glucocerebroside", Chem. Pharm. Bull., vol. 40(5), pp 1154–1165 (1992).

Smyth et al., "Non–Amine Based Analogues of Lavendustin A as Protein–Tyrosine Kinase Inhibitors", J. Med. Chem., vol. 36, pp 3010–3014 (1993).

Stover et al, "Recent advances in protein kinase inhibition: Current molecular scaffolds used for inhibitor synthesis", Current Opinion in Drug Discovery & Development, vol. 2(4), pp 274–285 (1999).

Sun et al., "Synthesis and Biological Evaluation of 3–Substituted Indolin–2–ones: A Novel Class of Tyrosine Kinase Inhibitors That Exhibit Selectivity toward Particular Receptor Tyrosine Kinases", J. Med. Chem., vol. 41, pp 2588–2603 (1998).

Tamaoki et al., "Staurosporine, A Potent Inhibitor of Phospholipid/Ca++ Dependent Protein Kinase", Biochemical and Biophysical Research Communications, vol. 135, No. 2, pp 397–402 (1986).

Trumpp–Kalimeyer et al., "Development of a Binding Model to Protein Tyrosine Kinases for Substituted Pyrido [2,3–d]pyrimidine Inhibitors", J. Med. Chem., vol. 41, pp 1752–1763 (1998).

Vu et al., "Discovery of Potent and Selective SH2 Inhibitors of the Tyrosine Kinase ZAP–70", J. Med. Chem., vol. 42, pp 4088–4098 (1999).

Williams et al., "Ro 09–2210 Exhibits Potent Anti–proliferative Effects on Activated T Cells by Selectively Blocking MKK Activity", Biochemistry, vol. 37, pp 9579–9585 (1998).

Yao et al., "Potent Inhibition of Grb2 SH2 Domain Binding by Non–Phosphate–Containing Ligands", J. Med. Chem., vol. 42, pp 25–35 (1999).

Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, pp 371–376 (1996).

Example 5 [E]
R = -(1,3)-CH$_2$-C$_6$H$_4$-CH$_2$-;
R$_8$ = R$_9$ = H; V = NH

Example 6 [F]
R = -(CH$_2$)$_3$-; R$_{10}$ = H; R$_{11}$ = -NH$_2$;
R$_{12}$ = R$_{13}$ = Br; Z = O Example 7 [G]
R = -(CH$_2$)$_2$(OCH$_2$CH$_2$)$_4$-; R$_{14}$ =
-CH$_2$C$_6$H$_4$-(p)-C$_6$H$_5$; R$_{15}$ = Cl;
R$_{16}$ = -OCH$_2$C$_6$H$_5$ Preparation 1

Preparation 2

Preparation 5

Example 23 [V]
R = -(1,4)-CH$_2$C$_6$H$_4$CH$_2$-; R$_{30}$ = H; R$_{31}$ = F; R$_{32}$ = -NH$_2$

Example 24 [W]
R = -(CH$_2$)-; R$_{33}$ = -(2,6)-Cl$_2$C$_6$H$_3$

Preparation 6

Example 27 [N]
R = (1,4)-(-CH$_2$CH$_2$O)$_2$-C$_6$H$_4$

Example 28 [N+O]
R = -(CH$_2$)$_5$-; R$_{26}$ = -C$_6$H$_4$-(4)-CH$_2$N(CH$_2$CH$_2$)$_2$NCH$_3$;
Het$_1$ = -(3)-C$_5$H$_4$N

Example 40

R = -(CH$_2$)$_{12}$-; R$_{41}$ = 4-Me;
R$_{42}$ = H; u = 2

Example 41

R = -(C$_6$H$_4$)$_2$CH$_2$;
R$_{41}$ = 4-Me; R$_{42}$ = H; u = 2

Example 42

R = -CH$_2$OCH$_2$CH$_2$OCH$_2$-;
R$_{44}$ = t-Bu; R$_{45}$ = R$_{46}$ = H; v = 4

Example 50
R = -C₆H₄-; Ar₄ = 3-Cl-4-F-C₆H₃

Example 52
R = -(CH$_2$)$_5$-; R$_{41}$ = 4-Me; R$_{42}$ = H;
R$_{47}$ = 5-Me; W = N; Y = CH; u = 2

Example 54
R = -(CH$_2$)$_3$C(O)[NH(CH$_2$)$_3$C(O)]$_6$NH(CH$_2$)$_3$-;
R$_{41}$ = 4-Me; R$_{42}$ = H; R$_{47}$ = 5-Me; W = N;
Y = CH; u = 2

Example 57
R = -4,4'-C$_6$H$_4$-C$_6$H$_4$-; R$_{47}$ =5-Me;
W = N; Y = CH; indole double bond at C$_2$-C$_3$

PROTEIN KINASE INHIBITORS

CROSS-REFERENCE TO RELATED APPLICATIONS

This application is a divisional application of U.S. application Ser. No. 10/093,068, filed Mar. 6, 2002, now U.S. Pat. No. 6,750,241 which is a continuation of U.S. application Ser. No. 09/732,438, filed Dec. 7, 2000, now abandoned which claims the benefit under 35 U.S.C. § 119(e) of U.S. Provisional Application No. 60/169,996, filed Dec. 8, 1999; and U.S. Provisional Application No. 60/266,316, filed Dec. 8, 1999 which was converted pursuant to 37 C.F.R. § 1.53(c)(2) from U.S. patent application Ser. No. 09/456,594, filed Dec. 8, 1999; the disclosures of which are incorporated herein by reference in their entirety.

BACKGROUND OF THE INVENTION

1. Field of the Invention

This invention relates to novel compounds which inhibit or modulate the activity of protein kinases and to pharmaceutical compositions comprising such compounds. This invention also relates to methods of treating diseases or medical conditions mediated by protein kinases using such compounds.

2. State of the Art

Protein kinases are enzymes which catalyze the phosphorylation of hydroxy groups on tyrosine, serine and threonine residues of proteins. See, for example, Hardie, G. and Hanks, S. (1995) *The Protein Kinase Facts Book I and II*, Academic Press, San Diego, Calif.; Stover, D. R. et al., *Current Opin. in Drug Discovery*, (1999) 2(4), 274–285; Adams, J. L., *Current Opin. in Drug Discovery*, (1999) 2(2), 96–109; and Lawrence D. S. et al., *Pharmacol. Ther.* (1998) 77(2), 81–114. By doing so, protein kinases mediate virtually all aspects of cell life including cell growth, cell differentiation and cell proliferation. In this regard, abnormal activity of protein kinases has been associated with a host of diseases or medical disorders, ranging from relatively non-life threatening diseases such as psoriasis to extremely virulent diseases such as glioblastoma (brain cancer). See, for example, Levitzki, A. et al., *Science*, (1995) 267, 1782–1788.

Accordingly, a need exists for compounds and compositions which inhibit or modulate the activity of protein kinases.

SUMMARY OF THE INVENTION

This invention provides novel compounds which inhibit or modulate the activity of protein kinases and pharmaceutical compositions comprising such compounds. Accordingly, the compounds and compositions of this invention are useful for treating diseases or medical disorders mediated by protein kinases.

The compounds of this invention are multimeric, i.e., they comprise two or more ligand moieties covalently linked together by one or more linking groups. While not wishing to be limited by theory, it is believed that each ligand moiety of these compounds binds to a ligand binding domain of a protein kinase or a related binding site, thereby inhibiting or modulating the activity of the protein kinase. By binding to multiple binding sites, compounds of this invention exhibit improved properties including, by way of example, increased efficacy, selectivity or duration of action, relative to the monomeric ligands.

Accordingly, in one of its composition aspects, this invention provides a compound of formula I:

$$(L)_p(X)_q \quad\quad\quad I$$

and pharmaceutically acceptable salts thereof; wherein:

p is an integer of from 2 to 10;

q is an integer of from 1 to 20;

each L is a ligand independently selected from the group consisting of:

(i) a moiety of formula III:

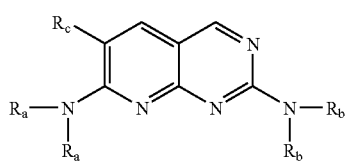

wherein each $R_a$ is independently selected from the group consisting of hydrogen, alkyl, substituted alkyl, alkenyl, substituted alkenyl, alkynyl, substituted alkynyl, acyl, acylamino, aryl, heteroaryl and a covalent bond linking the moiety to the linker;

each $R_b$ is independently selected from the group consisting of hydrogen, alkyl, substituted alkyl, alkenyl, substituted alkenyl, alkynyl, substituted alkynyl, acyl, acylamino, aryl, heteroaryl and a covalent bond linking the moiety to the linker;

$R_c$ is selected from the group consisting of aryl, alkaryl, heteroaryl and heterocycle;

provided one and only one of $R_a$ and $R_b$ comprises a covalent bond linking the moiety to the linker;

(ii) a moiety of formula IV:

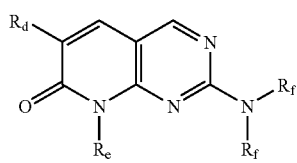

wherein $R_d$ is selected from the group consisting of aryl, alkaryl, heteroaryl and heterocycle;

$R_e$ is selected from the group consisting of hydrogen, alkyl, substituted alkyl, alkenyl, substituted alkenyl, alkynyl, substituted alkynyl, acyl and a covalent bond linking the moiety to the linker;

each $R_f$ is independently selected from the group consisting of hydrogen, alkyl, substituted alkyl, alkenyl, substituted alkenyl, alkynyl, substituted alkynyl, acyl, acylamino, aryl, heteroaryl and a covalent bond linking the moiety to the linker;

provided one and only one of $R_e$ or $R_f$ comprises a covalent bond linking the moiety to the linker;

(iii) a moiety of formula V:

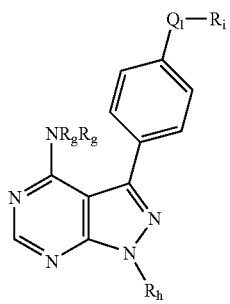

wherein
each $R_g$ is independently selected from the group consisting of hydrogen, alkyl, substituted alkyl, alkenyl, substituted alkenyl, alkynyl, substituted alkynyl and acyl;
$R_h$ is selected from the group consisting of hydrogen, alkyl, substituted alkyl, alkenyl, substituted alkenyl, alkynyl, substituted alkynyl and acyl;
$R_i$ is a covalent bond linking the moiety to the linker;
$Q_1$ is $NR_{i'}$, O, S, alkylene or a covalent bond, where $R_{i'}$ is hydrogen, alkyl, substituted alkyl, alkenyl, substituted alkenyl, alkynyl, substituted alkynyl, aryl or acyl;

(iv) a moiety of formula VI:

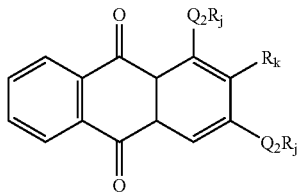

wherein
each $R_j$ is independently selected from the group consisting of hydrogen, alkyl, substituted alkyl, alkenyl, substituted alkenyl, alkynyl, substituted alkynyl, acyl and a covalent bond linking the moiety to the linker;
$R_k$ is selected from the group consisting of hydrogen, alkyl, substituted alkyl, alkenyl, substituted alkenyl, alkynyl, substituted alkynyl, alkoxy, hydroxy, halogen and —CHO;
each $Q_2$ is independently $NR_{j'}$, O and S, where $R_{j'}$ is hydrogen, alkyl, substituted alkyl, alkenyl, substituted alkenyl, alkynyl, substituted alkynyl or acyl;
provided one and only one of $R_j$ comprises a covalent bond linking the moiety to the linker;

(v) a moiety of formula VII:

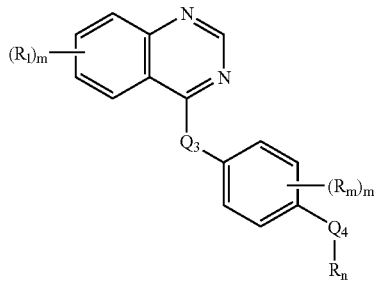

wherein
each $R_l$ and $R_m$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
$R_n$ is a covalent bond linking the moiety to the linker;
$Q_3$ is $NR_{n'}$, O, S or alkylene;
$Q_4$ is $NR_{n'}$, O, S, alkylene or a covalent bond, where each $R_{n'}$ in $Q_3$ and $Q_4$ is independently hydrogen, alkyl, substituted alkyl, alkenyl, substituted alkenyl, alkynyl, substituted alkynyl or acyl;
each m is independently an integer from 1 to 3;

(vi) a moiety of formula VIII:

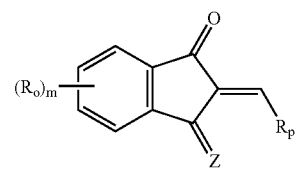

wherein
each $R_o$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
$R_p$ is aryl or heteroaryl, wherein the aryl or heteroaryl group is substituted with a covalent bond linking the moiety to the linker or with —OZ' where Z' is a covalent bond linking the moiety to the linker;
Z is 2H or O;
m is an integer from 1 to 3;

(vii) a moiety of formula IX:

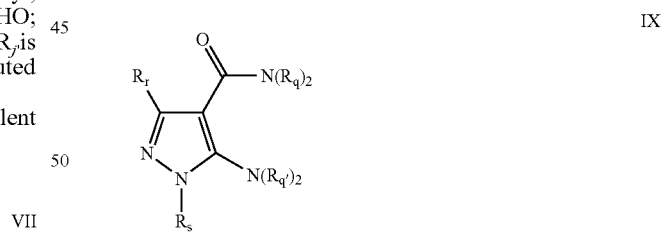

wherein
each $R_q$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl, heterocyclic and a covalent bond linking the moiety to the linker;
each $R_{q'}$ is independently selected from the group consisting of hydrogen, alkyl, substituted alkyl, alkenyl, substituted alkenyl, alkynyl, substituted alkynyl and acyl;
$R_s$ is selected from the group consisting of hydrogen, alkyl, substituted alkyl, alkenyl, substituted alkenyl, alkynyl, substituted alkynyl and acyl;

$R_f$ is aryl or heteroaryl, wherein the aryl or heteroaryl group is substituted with a covalent bond linking the moiety to the linker;

provided one and only one of $R_q$ or $R_r$ comprises a covalent bond linking the moiety to the linker;

(viii) a moiety of formula X:

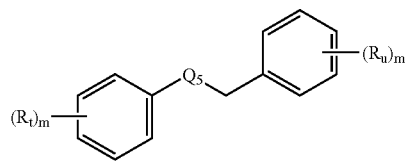

wherein each $R_t$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

each $R_u$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy and a covalent bond linking the moiety to the linker;

$Q_5$ is $NR_{t'}$, O, S or alkylene, where $R_{t'}$ is hydrogen, alkyl, substituted alkyl, alkenyl, substituted alkenyl, alkynyl, substituted alkynyl or acyl;

each m is independently an integer from 1 to 3;

provided one and only one of $R_u$ comprises a covalent bond linking the moiety to the linker;

(ix) a moiety of formula XI:

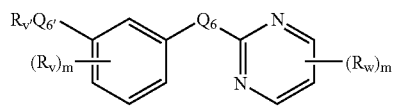

wherein each $R_v$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$R_{v'}$ is a covalent bond linking the moiety to the linker;

each $R_w$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$Q_6$ is $NR_{w'}$, O, S or alkylene, where $R_{w'}$ is hydrogen, alkyl, substituted alkyl, alkenyl, substituted alkenyl, alkynyl, substituted alkynyl or acyl;

$Q_{6'}$ is $NR_{v''}$, O, S or alkylene, where $R_{v''}$ is hydrogen, alkyl, substituted alkyl, alkenyl, substituted alkenyl, alkynyl, substituted alkynyl or acyl;

each m is independently an integer from 1 to 3;

(x) a moiety of formula XII:

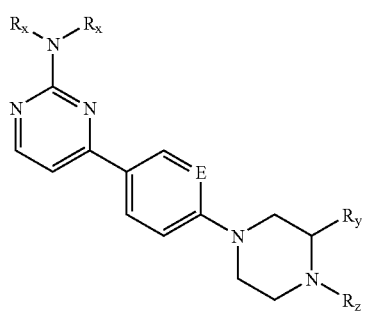

wherein each $R_x$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;

$R_y$ is independently selected from the group consisting of hydrogen, alkyl, substituted alkyl, alkenyl, substituted alkenyl, alkynyl and substituted alkynyl;

$R_z$ is a covalent bond linking the moiety to the linker;

E is CH or N;

(xi) a moiety of formula XIII:

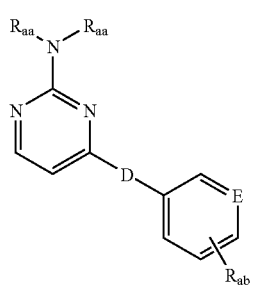

wherein each $R_{aa}$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;

$R_{ab}$ is alkyl, substituted alkyl, alkoxy, substituted alkoxy, amino, substitued amino, thioalkoxy, substituted thioalkoxy, wherein the alkyl, substituted alkyl, alkoxy, substituted alkoxy, amino, substitued amino, thioalkoxy or substituted thioalkoxy group is substituted with a covalent bond linking the moiety to the linker;

D is a covalent bond, $NR_{ab'}$, O or S, where $R_{ab'}$ is hydrogen, alkyl, substituted alkyl, alkenyl, substituted alkenyl, alkynyl, substituted alkynyl or acyl;

E is CH or N;
(xii) a moiety of formula XIV:

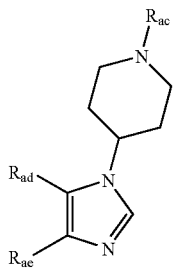

XIV wherein
$R_{ac}$ is a covalent bond linking the moiety to the linker;
$R_{ad}$ is selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;
$R_{ae}$ is aryl or heteroaryl;
(xiii) a moiety of formula XV:

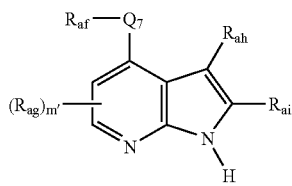

XV wherein
$R_{af}$ is selected from the group consisting of hydrogen, alkyl, substituted alkyl, alkenyl, substituted alkenyl, alkynyl, substituted alkynyl and acyl;
each $R_{ag}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
$R_{ah}$ is aryl or heteroaryl;
$R_{ai}$ is aryl or heteroaryl, wherein the aryl or heteroaryl group is substituted with a covalent bond linking the moiety to the linker;
$Q_7$ is $NR_{af'}$, O, S or alkylene, where $R_{af'}$ is hydrogen, alkyl, substituted alkyl, alkenyl, substituted alkenyl, alkynyl, substituted alkynyl or acyl;
m' is 1 or 2;
(xiv) a moiety of formula XVI:

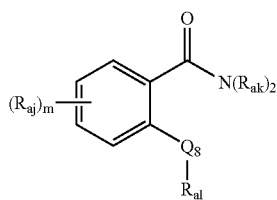

XVI wherein
each $R_{aj}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
$R_{al}$ is aryl or heteroaryl;
each $R_{ak}$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl, heterocyclic, and a covalent bond linking the moiety to the linker;
$Q_8$ is $NR_{al'}$, O, S or alkylene, where $R_{al'}$ is hydrogen, alkyl, substituted alkyl, alkenyl, substituted alkenyl, alkynyl, substituted alkynyl or acyl;
m is an integer from 1 to 3;
provided one and only one of $R_{ak}$ comprises a covalent bond linking the moiety to the linker;
(xv) a moiety of formula XVII:

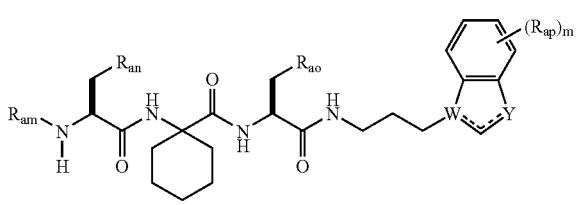

XVII wherein
$R_{am}$ is selected from the group consisting of hydrogen, alkyl, substituted alkyl, alkenyl, substituted alkenyl, alkynyl, substituted alkynyl, acyl and a covalent bond linking the moiety to the linker;
$R_{an}$ is selected from the group consisting of 4-phosphonomethylphenyl, 4-phosphonodifluoromethylphenyl, 3-carboxy-4-carboxymethoxyphenyl and 3,4-dihydroxyphenyl;
$R_{ao}$ is selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
each $R_{ap}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
W is N or CH;
Y is O, S, NH, N-Z', $CH_2$ or CH-Z', where Z' is a covalent bond linking the moiety to the linker;
m is an integer from 1 to 3;
----- is an optional double bond;
provided one and only one of $R_{am}$ and Y comprises a covalent bond linking the moiety to the linker;

(xvi) a moiety of formula XVIII:

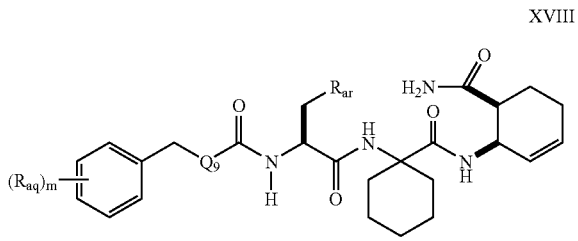

XVIII wherein each $R_{aq}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy, a covalent bond linking the moiety to the linker and —NH-Z', where Z' is a covalent bond linking the moiety to the linker;

$R_{ar}$ is selected from the group consisting of 4-phosphonomethylphenyl, 4-phosphonodifluoromethylphenyl, 3-carboxy-4-carboxymethoxyphenyl and 3,4-dihydroxyphenyl;

$Q_9$ is $N_{aq'}$, O, S or alkylene, where $R_{aq'}$ is hydrogen, alkyl, substituted alkyl, alkenyl, substituted alkenyl, alkynyl, substituted alkynyl or acyl;

m is an integer from 1 to 3;

provided one and only one of $R_{aq}$ comprises a covalent bond linking the moiety to the linker;

(xvii) a moiety of formula XIX:

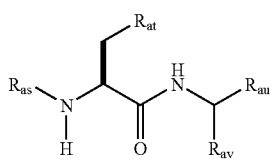

XIX wherein $R_{as}$ is selected from the group consisting of hydrogen, alkyl, substituted alkyl, alkenyl, substituted alkenyl, alkynyl, substituted alkynyl, acyl and a covalent bond linking the moiety to the linker;

$R_{at}$ is selected from the group consisting of 4-phosphonomethylphenyl, 4-phosphonodifluoromethylphenyl, 3-carboxy-4-carboxymethoxyphenyl and 3,4-dihydroxyphenyl;

$R_{au}$ is aryl or heteroaryl, wherein the aryl or heteroaryl group is substituted with a covalent bond linking the moiety to the linker or with —OZ', where Z' is a covalent bond linking the moiety to the linker;

$R_{av}$ is selected from the group consisting of hydrogen, alkyl, substituted alkyl, alkenyl, substituted alkenyl, alkynyl, substituted alkynyl, acyl and alkaryl;

provided one and only one of $R_{as}$ and $R_{au}$ comprises a covalent bond linking the moiety to the linker;

(xviii) a moiety of formula XX:

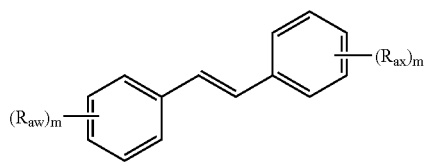

XX wherein each $R_{aw}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

each $R_{ax}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy, a covalent bond linking the moiety to the linker and —OZ', where Z' is a covalent bond linking the moiety to the linker;

each m is independently an integer from 1 to 3;

provided one and only one of $R_{ax}$ comprises a covalent bond linking the moiety to the linker;

(xix) a moiety of formula XXI:

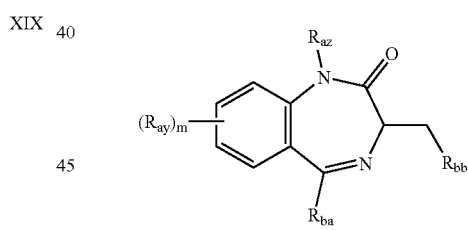

XXI wherein each $R_{ay}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$R_{az}$ is selected from the group consisting of hydrogen, alkyl, substituted alkyl, alkenyl, substituted alkenyl, alkynyl, substituted alkynyl, alkaryl, acyl and a covalent bond linking the moiety to the linker;

$R_{ba}$ is aryl or heteroaryl;

$R_{bb}$ is aryl or heteroaryl, wherein the aryl or heteroaryl group is substituted with a covalent bond linking the moiety to the linker or with —OZ', where Z' is a covalent bond linking the moiety to the linker;

m is an integer from 1 to 3;

provided one and only one of $R_{az}$ or $R_{bb}$ comprises a covalent bond linking the moiety to the linker;

(xx) a moiety of formula XXII:

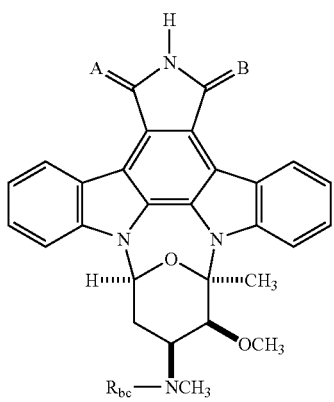

XXII wherein $R_{bc}$ is a covalent bond linking the moiety to the linker;

A and B are independently selected from the group consisting of 2H, O and S;

(xxi) a moiety of formula XXIII:

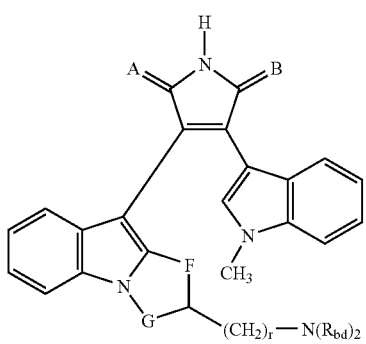

XXIII wherein each $R_{bd}$ is independently selected from the group consisting of hydrogen, alkyl, substituted alkyl, alkenyl, substituted alkenyl, alkynyl, substituted alkynyl, acyl and a covalent bond linking the moiety to the linker;

A and B are independently selected from the group consisting of 2H, O and S;

F and G are independently —CH$_2$— or —CH$_2$CH$_2$—;

r is an integer from 0 to 2;

provided one and only one of $R_{bd}$ comprises a covalent bond linking the moiety to the linker;

(xxii) a moiety of formula XXIV:

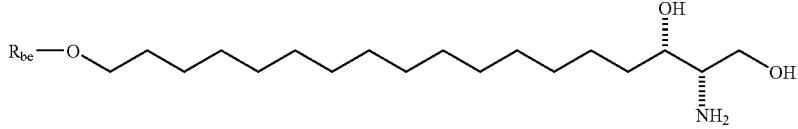

XXIV wherein $R_{be}$ is a covalent bond linking the moiety to the linker;

(xxiii) a moiety of formula XXV:

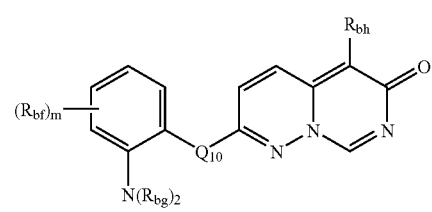

XXV wherein each $R_{bf}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

each $R_{bg}$ is independently selected from the group consisting of hydrogen, alkyl, substituted alkyl, alkenyl, substituted alkenyl, alkynyl, substituted alkynyl, acyl and a covalent bond linking the moiety to the linker;

$R_{bh}$ is aryl, heteroaryl or heterocyclic;

$Q_{10}$ is $NR_{bf}$, O, S or alkylene, where $R_{bf}$ is hydrogen, alkyl, substituted alkyl, alkenyl, substituted alkenyl, alkynyl, substituted alkynyl or acyl;

m is an integer from 1 to 3;

provided one and only one of $R_{bg}$ comprises a covalent bond linking the moiety to the linker;

(xxiv) a moiety of formula XXVI:

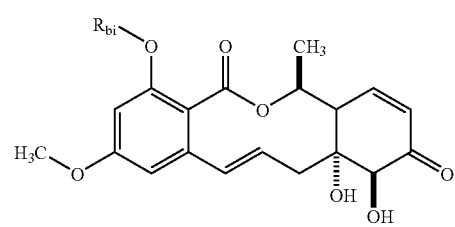

XXVI wherein
R$_{bi}$ is a covalent bond linking the moiety to the linker;
(xxv) a moiety of formula XXVII:

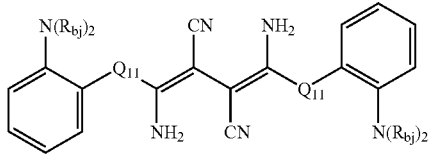

XXVII wherein
each R$_{bj}$ is independently selected from the group consisting of hydrogen, alkyl, substituted alkyl, alkenyl, substituted alkenyl, alkynyl, substituted alkynyl, acyl and a covalent bond linking the moiety to the linker;
Q$_{11}$ is NR$_{bj''}$, O, S or alkylene, where R$_{bj'}$ is hydrogen, alkyl, substituted alkyl, alkenyl, substituted alkenyl, alkynyl, substituted alkynyl or acyl;
provided one and only one of R$_{bj}$ comprises a covalent bond linking the moiety to the linker;
(xxvi) a moiety of formula XXVIII:

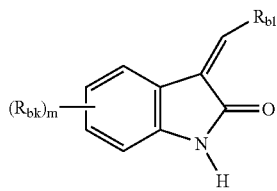

XXVIII wherein
each R$_{bk}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy, —SO—R$_{bk'}$ and —SO$_2$—R$_{bk'}$, where R$_{bk'}$ is alkyl, substituted alkyl, alkenyl, substituted alkenyl, alkynyl, substituted alkynyl, cycloalkyl, substituted cycloalkyl, aryl, heteroaryl or heterocyclic;
R$_{bl}$ is aryl or heteroaryl, wherein the aryl or heteroaryl group is substituted with a covalent bond linking the moiety to the linker or with —(CH$_2$)$_u$-Z', where Z' is a covalent bond linking the moiety to the linker and u is an integer from 1 to 3;
m is an integer from 1 to 3;
(xxvii) a moiety of formula XXIX:

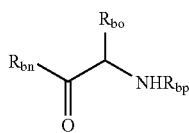

XXIX wherein
R$_{bn}$ is selected from the group consisting of alkoxy, substituted alkoxy, hydroxy and —OZ', where Z' is a covalent bond linking the moiety to the linker;
R$_{bo}$ is aryl or heteroaryl;
R$_{bp}$ is acyl, alkoxycarbonyl and a covalent bond linking the moiety to the linker;

provided one and only one of R$_{bn}$ and R$_{bp}$ comprises a covalent bond linking the moiety to the linker;
and further wherein each X is a linker independently selected from a group of the formula:

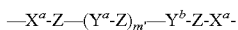

wherein
m' is an integer of from 0 to 20;
X$^a$ at each separate occurrence is selected from the group consisting of —O—, —S—, —NR—, —C(O)—, —C(O)O—, —C(O)NR—, —C(S), —C(S)O—, —C(S)NR— or a covalent bond;
Z is at each separate occurrence is selected from the group consisting of alkylene, substituted alkylene, cycloalkylene, substituted cycloalkylene, alkenylene, substituted alkenylene, alkynylene, substituted alkynylene, cycloalkenylene, substituted cycloalkenylene, arylene, heteroarylene, heterocyclene, or a covalent bond;
Y$^a$ and Y$^b$ at each separate occurrence are selected from the group consisting of: —C(O)NR'—, —NR'C(O)—, —NR'C(O)NR'—, —C(=NR')—NR'—, —NR'—C(=NR')—, —NR'—C(O)—O—, —N=C(R)—NR'—, —P(O)(OR')—O—, —S(O)$_n$CR'R''—, —S(O)$_n$—NR'—, —S—S— and a covalent bond; where n is 0, 1 or 2; and
R, R' and R'' at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.
Preferably, in formula I, q is less than p: More preferably, p is 2 and q is 1.
In a preferred embodiment, each ligand in the compound of formula I is independently selected from the group consisting of:
(i) a moiety of formula A:

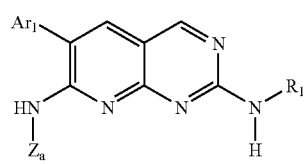

A (ii) a moiety of formula B:

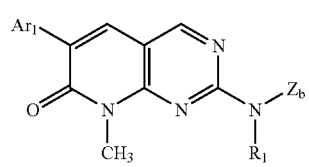

B wherein, in formula A and B,
R$_1$ is selected from the group consisting of hydrogen, alkyl of 1 to 6 carbon atoms and —(CH$_2$)$_v$—NR$_{28}$R$_{29}$, where v is an integer from 2 to 4;
Ar$_1$ is selected from the group consisting of an aryl, alkaryl and heterocycle;
R$_{28}$ is selected from group consisting of hydrogen and alkyl of 1 to 6 carbon atoms;
R$_{29}$ is selected from the group consisting of 4-pyrimidinyl, 2-methylaminopyrimidin-4-yl, 2-phenoxypyrimidin-4-yl, 2-(4-methoxyphenoxy) pyrimidin-4-yl, 2-(4-fluorophenoxy)pyrimidin-4-yl, 2-(4-aminocarbonylphenoxy)pyrimidin-4-yl, 2-(4-ethylphenoxy)

pyrimidin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, 2-(4-methoxyphenroxy)pyrimidin-4-yl, 4-pyridinyl, 2-phenoxypyridin-4-yl, 2-(4-methoxyphenoxy)pyridin-4-yl, 2-(4-fluorophenoxy)pyridin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, and 2-(4-methoxyphenoxy)pyrimidin-4-yl;

(iii) a moiety of formula C:

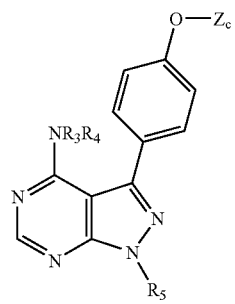

C wherein
$R_3$ is selected from the group consisting of hydrogen, alkyl of 1 to 6 carbon atoms and —CH$_2$CH$_2$OCH$_3$;
$R_4$ is selected from the group consisting of hydrogen, alkyl of 1 to 6 carbon atoms and alkylalkoxy;
$R_5$ is selected from the group consisting of hydrogen and alkyl of 1 to 6 carbon atoms;

(iv) a moiety of formula I):

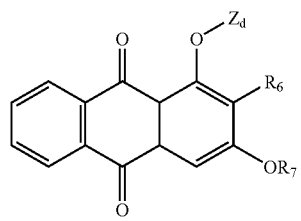

D wherein
$R_6$ is selected from the group consisting of substituted alkyl and —CHO;
$R_7$ is selected from the group consisting of hydrogen, alkyl and acyl;

(v) a moiety of formula E:

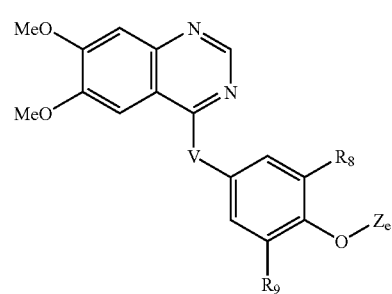

E wherein
$R_8$ is selected from the group consisting of hydrogen, alkoxy and halogen;
V is selected from the group consisting of amino, alkyl of 1 to 6 carbon atoms, S and O;
$R_9$ is selected from the group consisting of hydrogen, alkoxy and halogen;

(vi) a moiety of formula F:

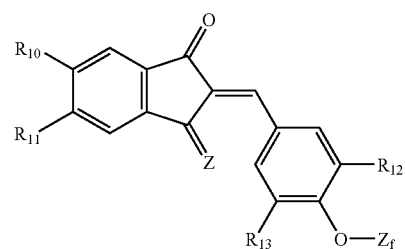

F wherein
$R_{10}$ is selected from the group consisting of hydrogen, alkoxy, amino and substituted amino;
$R_{11}$ is selected from the group consisting of hydrogen, alkoxy, halogens, amino, substituted amino and nitro;
$R_{12}$ is selected from the group consisting of hydrogen, hydroxy, alkoxy and halogen;
$R_{13}$ is selected from the group consisting of hydrogen, hydroxy, alkoxy and halogen;
Z is selected from the group consisting of 2H and O;

(vii) a moiety of formula H:

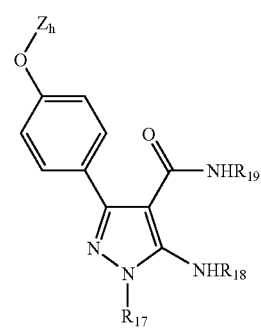

H wherein
$R_{17}$ and $R_{18}$ are independently selected from the group consisting of hydrogen and alkyl of 1 to 6 carbon atoms;
$R_{19}$ is selected from the group consisting of alkyl of 1 to 6 carbon atoms, —CH$_2$C(O)OEt, —(CH$_2$)$_3$OH, alkaryl, aryl and heteroaryl;

(viii) a moiety of formula N:

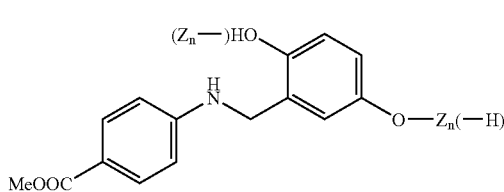

(IX) a moiety of formula O:

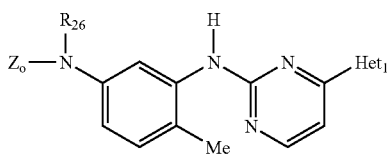

wherein
$R_{26}$ is selected from the group consisting of hydrogen and acyl;
$Het_1$ is heterocyclic or heteroaryl;

(x) a moiety of formula P:

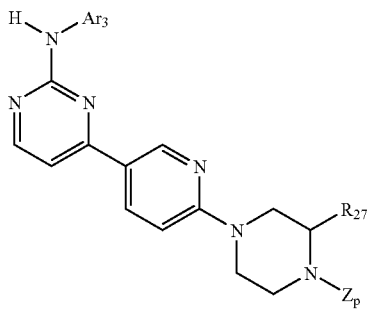

wherein
$R_{27}$ is selected from the group consisting of hydrogen, alkyl of 1 to 6 carbon atoms and substituted alkyl;
$Ar_3$ is aryl;

(xi) a moiety of formula S:

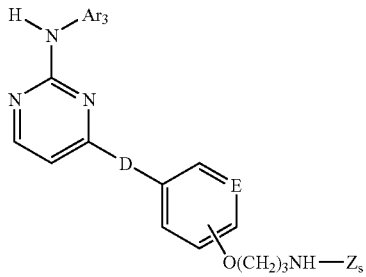

wherein
D is selected from the group consisting of a covalent bond, —NH—, —S— and —O—;
E is selected from the group consisting of CH and N;
$Ar_3$ is aryl;

(xii) a moiety of formula U:

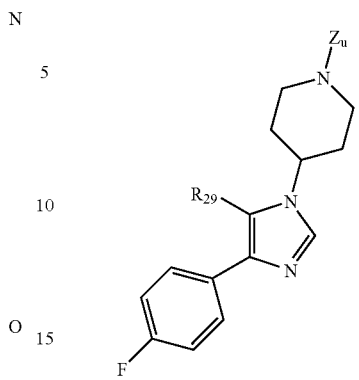

wherein
$R_{29}$ is selected from the group consisting of 4-pyrimidinyl, 2-methylaminopyrimidin-4-yl, 2-phenoxypyrimidin-4-yl, 2-(4-methoxyphenoxy)pyrimidin-4-yl, 2-(4-fluorophenoxy)pyrimidin-4-yl, 2-(4-aminocarbonylphenoxy)pyrimidin-4-yl, 2-(4-ethylphenoxy)pyrimidin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, 2-(4-methoxyphenoxy)pyrimidin-4-yl, 4-pyridinyl, 2-phenoxypyridin-4-yl, 2-(4-methoxyphenoxy)pyridin-4-yl, 2-(4-fluorophenoxy)pyridin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, and 2-(4-methoxyphenoxy)pyrimidin-4-yl;

(xiii) a moiety of formula V:

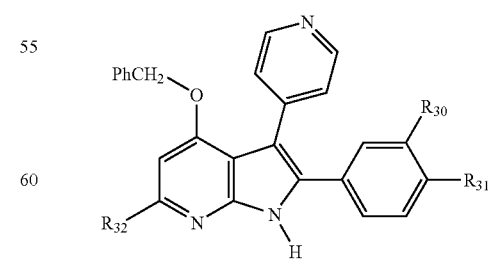

wherein
$R_{30}$ is selected from the group consisting of hydrogen, alkyl of 1 to 6 carbon atoms, halogen and alkoxy;

$R_{31}$ is selected from the group consisting of hydrogen, alkyl of 1 to 6 carbon atoms, halogen, alkoxy and $Z_v$;

$R_{32}$ is selected from the group consisting of hydrogen, amino, substituted amino, alkoxy, —NHCOCH$_3$, and $Z_v$, provided one and only one of $R_{31}$ and $R_{32}$ is $Z_v$; and (xiv) a moiety of formula Z:

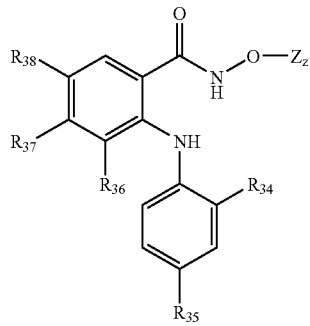

Z wherein $R_{34}$ is selected from the group consisting of hydrogen, hydroxy, alkyl, alkoxy, halogen and substituted alkyl;

$R_{35}$ is selected from the group consisting of hydrogen and halogen;

$R_{36}$, $R_{37}$, and $R_{38}$ are selected from the group consisting of hydrogen, —NO$_2$, alkyl, substituted alkyl, amino, substituted amino, alkoxy, hydroxy and halogen;

and further wherein $Z_a$, $Z_b$, $Z_c$, $Z_d$, $Z_e$, $Z_f$, $Z_h$, $Z_n$, $Z_o$, $Z_p$, $Z_s$, $Z_u$, $Z_v$, and $Z_z$, are covalent bonds linking the moiety to the linker;

and stereoisomers and analogs thereof.

In another preferred embodiment, the ligands employed are ligands for the SH2 or SH3 sites of protein kinases. In this embodiment, each ligand in the compound of formula I is independently selected from the group consisting of:

(i) a moiety of formula I:

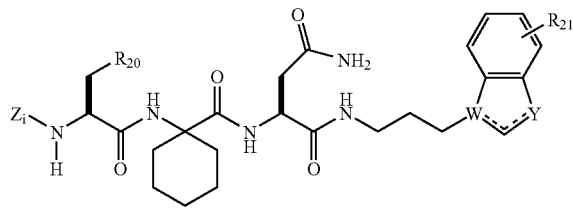

I (ii) a moiety of formula J:

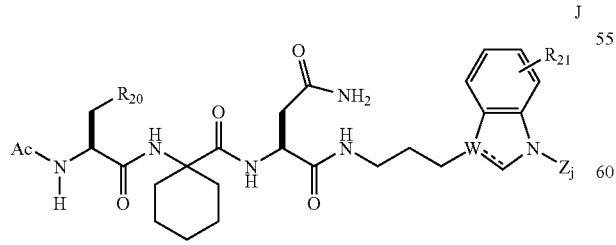

J wherein, in formula I and J,

W is selected from the group consisting of N and CH;

Y is selected from the group consisting of O, S and NH;

$R_{20}$ is selected from the group consisting of:

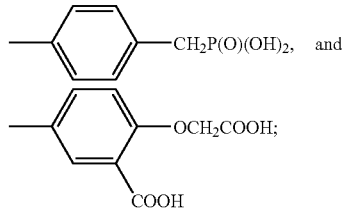

$R_{21}$, is selected from the group consisting of hydrogen, alkyl of 1 to 6 carbon atoms, alkoxy, amino and substituted amino;

----- is an optional double bond;

(iii) a moiety of formula K:

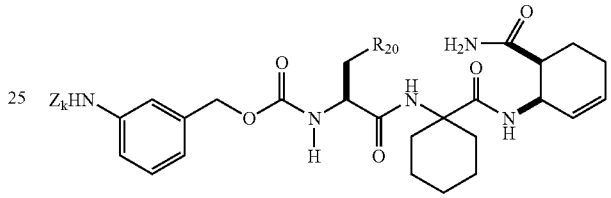

K wherein $R_{20}$ is selected from the group consisting of:

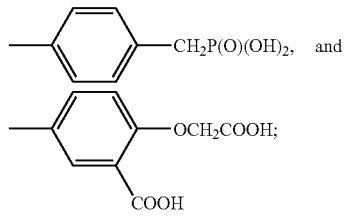

(iv) a moiety of formula L:

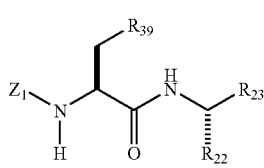

L (v) a moiety of formula M:

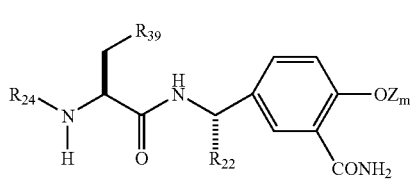

M wherein, in formula L and M, $R_{22}$ is selected from the group consisting of hydrogen, alkyl of 1 to 6 carbon atoms and substituted alkyl;

$R_{23}$ is

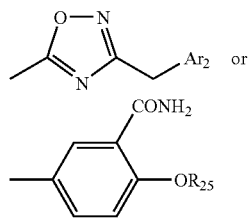

$R_{24}$ is selected from the group consisting of hydrogen and acyl;

$R_{25}$ is selected from the group consisting of alkyl and cycloalkyl;

$R_{39}$ is selected from the group consisting of

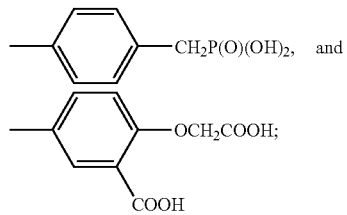

$Ar_2$ is selected from the group consisting of alkyl of 1 to 6 carbon atoms, substituted alkyl and aryl;

and further wherein $Z_i$, $Z_j$, $Z_k$, $Z_l$, and $Z_m$, are covalent bonds linking the moiety to the linker;

and stereoisomers and analogs thereof.

In still another preferred embodiment, the ligands employed are ligands for Src and Zap families of protein kinases. In this embodiment, each ligand in the compound of formula I is a moiety of formula Q:

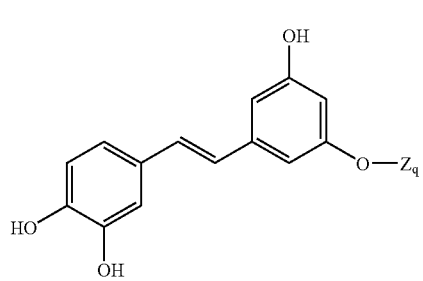

wherein $Z_q$ is a covalent bond linking the moiety to the linker;

and stereoisomers and analogs thereof.

In yet another preferred embodiment, the ligands employed are other ligands for the Src family of protein kinases. In this embodiment, each ligand in the compound of formula I is a moiety of formula G:

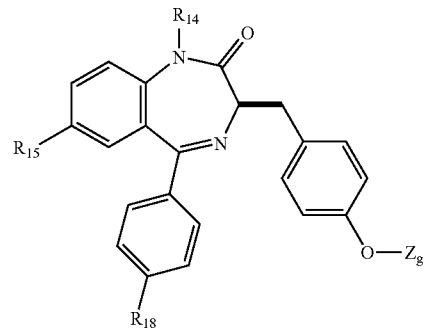

wherein $R_{14}$ is selected from the group consisting of hydrogen, alkyl of 1 to 6 carbon atoms and alkaryl;

$R_{15}$ is selected from the group consisting of hydrogen, alkoxy and halogen;

$R_{16}$ is selected from the group consisting of hydrogen, alkoxy, hydroxy and halogen;

and further wherein $Z_g$ is a covalent bond linking the moiety to the linker;

and stereoisomers and analogs thereof.

In another preferred embodiment, the ligands employed are ligands for the PKC family of protein kinases. In this embodiment, each ligand in the compound of formula I is independently selected from the group consisting of:

(i) a moiety of formula R:

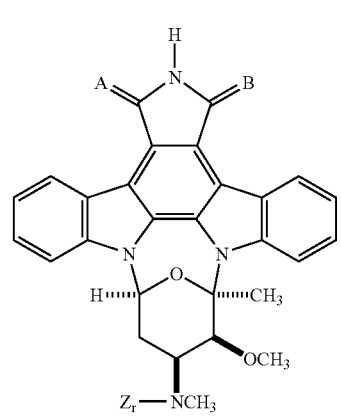

wherein

A and B are independently selected from the group consisting of 2H, S and O;

(ii) a moiety of formula T:

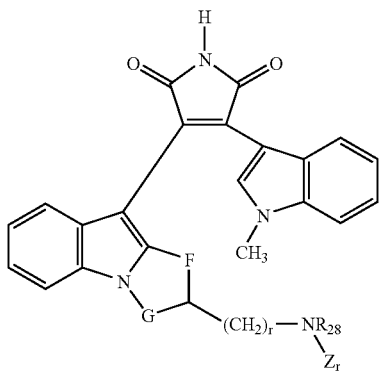

T wherein
F is selected from the group consisting of —CH$_2$— and —CH$_2$CH$_2$—;
G is selected from the group consisting of —CH$_2$— and —CH$_2$CH$_2$—;
R$_{28}$ is selected from the group consisting of hydrogen and alkyl of 1 to 6 carbon atoms;
r is 0, 1, or 2; and (iii) a moiety of formula AA:

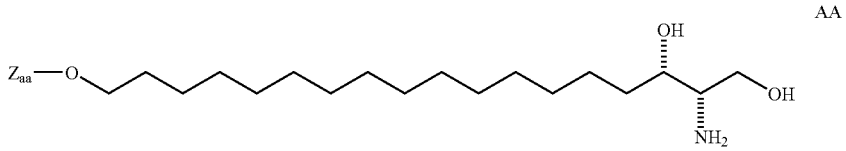

AA and further wherein Z$_r$, Z$_t$, and Z$_{aa}$, are covalent bonds linking the moiety to the linker;

and stereoisomers and analogs thereof.

In still another preferred embodiment, the ligands employed are ligands for the MAP family of protein kinases. In this embodiment, each ligand in the compound of formula I is independently selected from the group consisting of:

(i) a moiety of formula W:

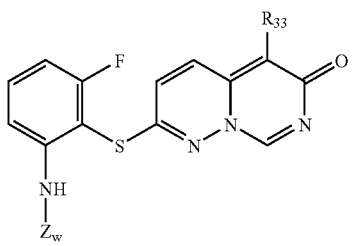

W wherein

R$_{33}$ is selected from the group consisting of aryl and heterocyclic;

(ii) a moiety of formula X:

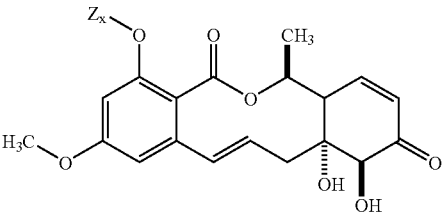

X (iii) a moiety of formula Y:

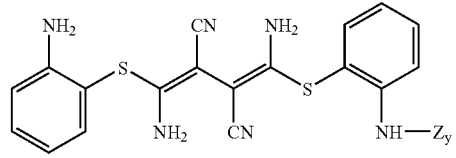

Y and further wherein Z$_w$, Z$_x$ and Z$_y$ are covalent bonds linking the moiety to the linker; and stereoisomers and analogs thereof.

In yet another preferred embodiment, the ligands employed are ligands for receptor tyrosine kinases. In this embodiment, each ligand of the compounds of formula I is independently selected from the group consisting of:

(i) a moiety of formula AB:

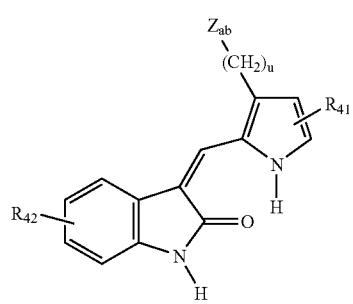

AB (ii) a moiety of formula AC:

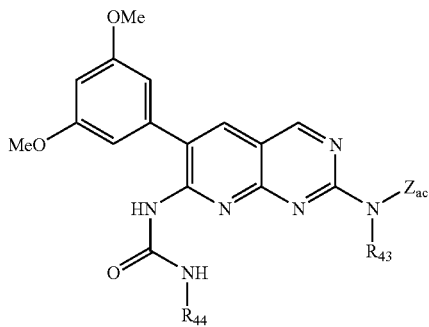

(iii) a moiety of formula AD:

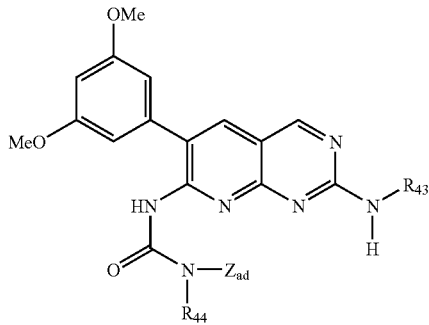

(iv) a moiety or formula AE:

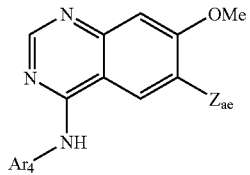

(v) a moiety of formula AF:

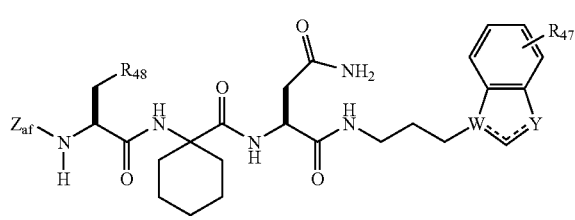

(vi) a moiety of formula AG:

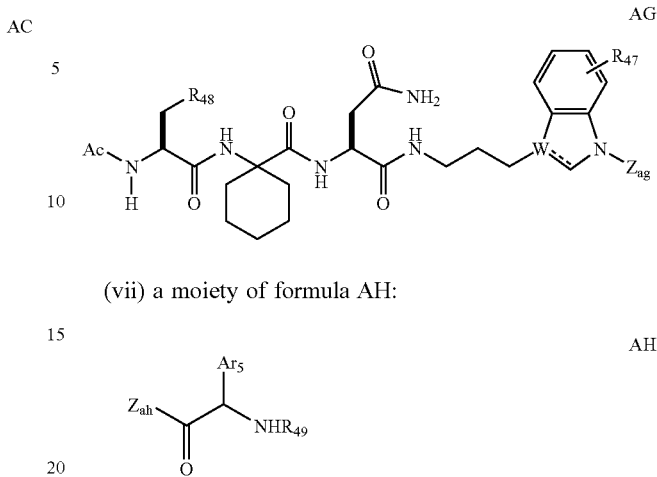

(vii) a moiety of formula AH:

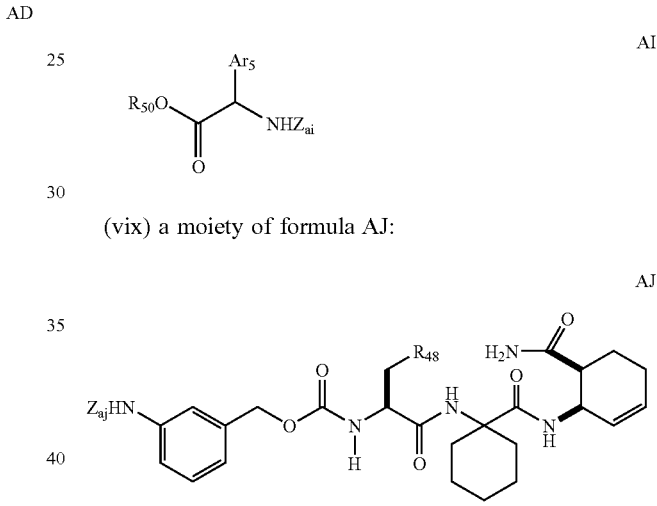

(viii) a moiety of formula AI:

AI $R_{50}O$ ... $Ar_5$ ... $NHZ_{ai}$ (vix) a moiety of formula AJ:

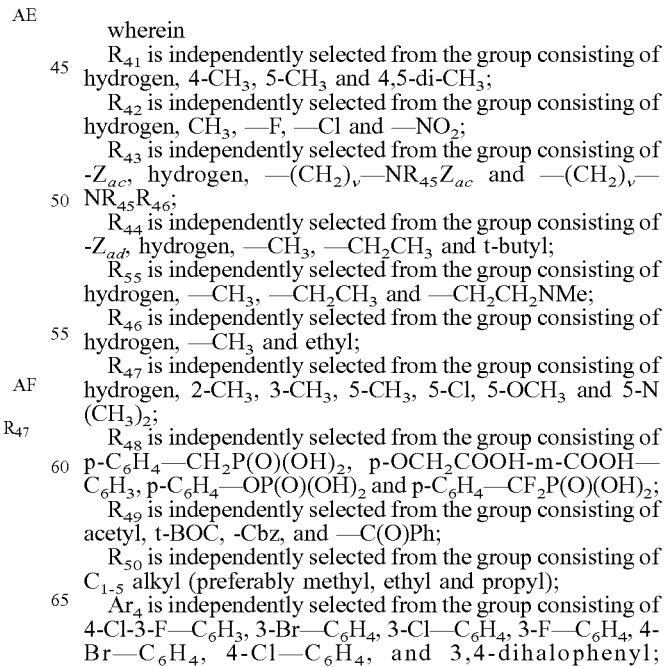

wherein
$R_{41}$ is independently selected from the group consisting of hydrogen, 4-$CH_3$, 5-$CH_3$ and 4,5-di-$CH_3$;
$R_{42}$ is independently selected from the group consisting of hydrogen, $CH_3$, —F, —Cl and —$NO_2$;
$R_{43}$ is independently selected from the group consisting of -$Z_{ac}$, hydrogen, —$(CH_2)_v$—$NR_{45}Z_{ac}$ and —$(CH_2)_v$—$NR_{45}R_{46}$;
$R_{44}$ is independently selected from the group consisting of -$Z_{ad}$, hydrogen, —$CH_3$, —$CH_2CH_3$ and t-butyl;
$R_{55}$ is independently selected from the group consisting of hydrogen, —$CH_3$, —$CH_2CH_3$ and —$CH_2CH_2NMe$;
$R_{46}$ is independently selected from the group consisting of hydrogen, —$CH_3$ and ethyl;
$R_{47}$ is independently selected from the group consisting of hydrogen, 2-$CH_3$, 3-$CH_3$, 5-$CH_3$, 5-Cl, 5-$OCH_3$ and 5-N$(CH_3)_2$;
$R_{48}$ is independently selected from the group consisting of p-$C_6H_4$—$CH_2P(O)(OH)_2$, p-$OCH_2COOH$-m-COOH—$C_6H_3$, p-$C_6H_4$—$OP(O)(OH)_2$ and p-$C_6H_4$—$CF_2P(O)(OH)_2$;
$R_{49}$ is independently selected from the group consisting of acetyl, t-BOC, -Cbz, and —C(O)Ph;
$R_{50}$ is independently selected from the group consisting of $C_{1-5}$ alkyl (preferably methyl, ethyl and propyl);
$Ar_4$ is independently selected from the group consisting of 4-Cl-3-F—$C_6H_3$, 3-Br—$C_6H_4$, 3-Cl—$C_6H_4$, 3-F—$C_6H_4$, 4-Br—$C_6H_4$, 4-Cl—$C_6H_4$, and 3,4-dihalophenyl;

Ar$_5$ is independently selected from the group consisting of C$_6$H$_5$, p-C$_6$H$_4$OH, and other substituted phenyl groups;
u is an integer from 1 to 3,
v is an integer from 2 to 4,
W is N or CH,
Y is CH or N;
and further wherein Z$_{ab}$, Z$_{ac}$, Z$_{ad}$, Z$_{ae}$, Z$_{af}$, Z$_{ag}$, Z$_{ah}$, Z$_{ai}$ and Z$_{aj}$ are covalent bonds linking the moiety to the linker;
and stereoisomers and analogs thereof.

In another preferred embodiment, the above ligands further comprise a moiety of formula AB':

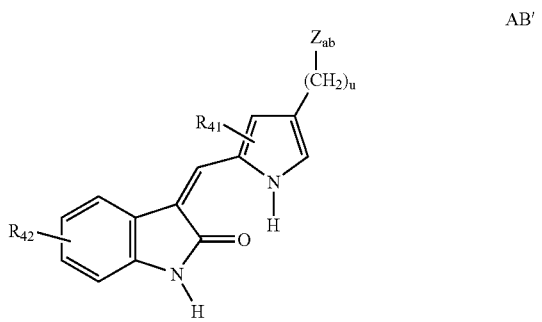

wherein R$_{41}$, R$_{42}$, u and Z$_{ab}$ are as defined herein.

In another preferred embodiment, each ligand in the compound of formula I is independently selected from the group consisting of a moiety of formula A, B, C, D, E, F, G, H, I, J, K, L, M, N, O, P, Q, R, S, T, U, V, W, X, Y, Z, AA, AB, AB', AC, AD, AE, AF, AG, AH, AI and AJ as defined herein.

Suitable analogs include alkylated, acylated, animated, thiolated, hydroxylated, amidated, carboxylated, phosphorylated, sulfonated and halogenated analogs thereof.

In another of its composition aspects, this invention provides a compound of formula II:

L-X-L    II wherein L and X are as defined herein; and pharmaceutically-acceptable salts thereof.

In yet another of its composition aspects, this invention provides a pharmaceutical composition comprising a pharmaceutically acceptable carrier and a thereapeutically effective amount of a compound of formula I or II, or a pharmaceutically acceptable salt thereof.

The compounds of this invention are effective inhibitors or mediators of protein kinase activity and as such, they are useful for treating diseases or medical disorders mediated by protein kinases. Accordingly, in one of its method aspects, this invention provides a method of treating a disease or medical disorder mediated by a protein kinase, the method comprising administering to a mammal a pharmaceutical composition comprising a pharmaceutically acceptable carrier and a thereaputically effective amount of a compound of formula I or II, or a pharmaceutically acceptable salt thereof. Representative diseases or medical disorders mediated by protein kinases include, by way of illustration, hyperproliferative disorders such as cancer, psoriasis, hepatic cirrhosis, diabetes, atherosclerosis, angiogenesis, restenosis, ocular diseases, rheumatoid arthritis and other inflammatory disorders, autoimmune disease and a variety of renal disorders.

This invention also provides a compound of formula I or II for use in medical therapy or for use in the manufacture of a formulation or medicament for treating a disease or medical condition mediated by a protein kinase.

DETAILED DESCRIPTION OF THE INVENTION

Figure 1:
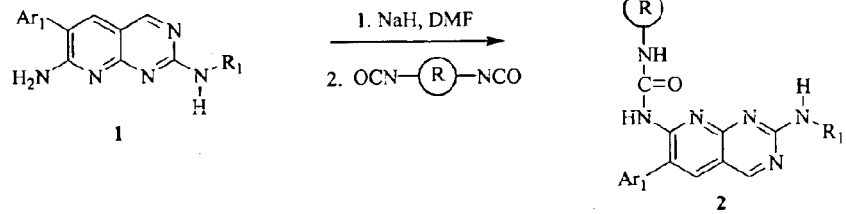
FIG. 1 is a schematic representation of the methods of Examples 1, 2, 3 and 4.
Figure 1:
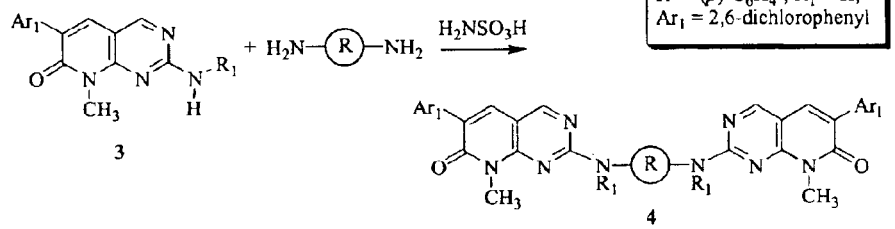
Figure 1:
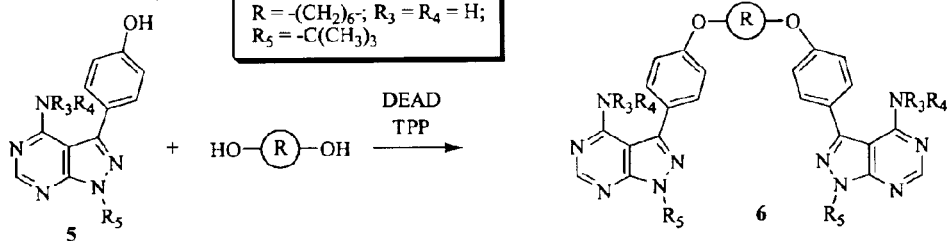
Figure 1:
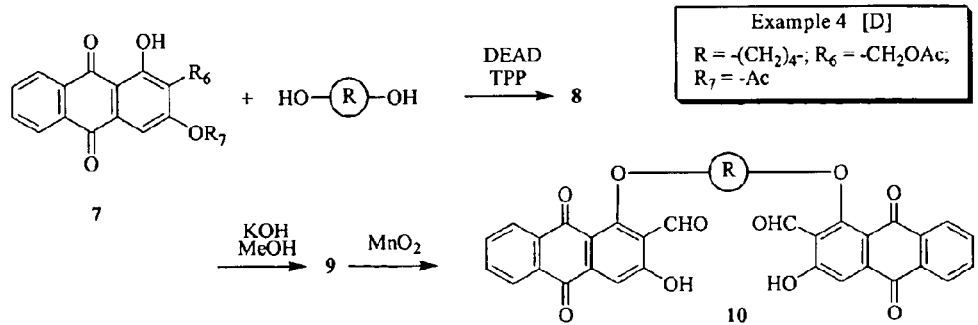

This invention is directed to compounds which inhibit or modulate the activity of protein kinases and to pharmaceutical compositions containing such compounds. This invention is also directed to methods for treating diseases or medical disorders mediated by protein kinases. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups-alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups-alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)2), methylene-t-butoxy (—CH$_2$—O—C(CH$_3$)$_3$) and the like.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g. phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "-C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "pseudohalide" refers to functional groups which react in displacement reactions in a manner similar to a halogen. Such functional groups include, by way of example, mesyl, tosyl, azido and cyano groups.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds, whether the isomers are those arising in the ligands, the likers, or the multivalent constructs including the ligands and linkers.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines; alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amines, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically acceptable cation" refers to the cation of a pharmaceutically acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyldiphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" as used herein generally denotes a compound or moiety (when attached to the linker) that inhibits or modulates the activity of a protein kinases. This term may include a compound which is not a specific inhibitor as long as it binds to the protein kinases, since such a compound may provide advantages in a multibinding compound formation of the present invention. The specific region or regions of the ligand that is (are) recognized by the enzyme is designated as the "ligand domain". A ligand may be either capable of binding to its target by itself, or may require the presence of one or more non-ligand components for binding (e.g., $Ca^{+2}$, $Mg^{+2}$ or a water molecule is required for the binding of a ligand to various ligand binding sites).

Examples of ligands useful in this invention are described herein. Those skilled in the art will appreciate that portions of the ligand structure that are not essential for specific molecular recognition and binding activity may be varied substantially, replaced or substituted with unrelated structures (for example, with ancillary groups as defined below)

and, in some cases, omitted entirely without affecting the binding interaction. The primary requirement for a ligand is that it has a ligand domain as defined above. It is understood that the term ligand is not intended to be limited to compounds known to be useful in binding to protein kinases. (e.g., known drugs). Those skilled in the art will understand that the term ligand can equally apply to a molecule that is not normally associated with enzyme binding properties. In addition, it should be noted that ligands that exhibit marginal activity or lack useful activity as monomers can be highly active as multivalent compounds because of the benefits conferred by multivalency.

The term "multibinding compound or agent" refers to a compound that is capable of multivalency, as defined below, and which has 2–10 ligands covalently bound to one or more linkers which may be the same or different. Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (protein kinases). The phrase "increased biological or therapeutic effect" includes, for example: increased affinity, increased selectivity for target, increased specificity for target, increased potency, increased efficacy, decreased toxicity, improved duration of activity or action, decreased side effects, increased therapeutic index, improved bioavailability, improved pharmacokinetics, improved activity spectrum, and the like. Preferably, the compounds of this invention are multibinding compounds which exhibit at least one and preferably more than one of the above-mentioned effects.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model). The finding that the multibinding agent produces an equivalent biological or therapeutic effect at a lower concentration than the aggregate unlinked ligand is indicative of enhanced potency.

The term "univalency" as used herein refers to a single binding interaction between one ligand as defined herein with one ligand binding site as defined herein. It should be noted that a compound having multiple copies of a ligand (or ligands) exhibits univalency when only one ligand is interacting with a ligand binding site.

The term "multivalency" as used herein refers to the concurrent binding of from 2 to 10 linked ligands (which may be the same or different) and two or more corresponding enzymes (ligand binding sites) on one or more enzymes which may be the same or different.

For example, two ligands connected through a linker that bind concurrently to two ligand binding sites would be considered as bivalency; three ligands thus connected would be an example of trivalency.

It should be understood that all compounds that contain multiple copies of a ligand attached to a linker or to linkers do not necessarily exhibit the phenomena of multivalency, i.e., that the biological and/or therapeutic effect of the multibinding agent is greater than the sum of the aggregate of unlinked ligands made available for binding to the ligand binding site (enzyme). For multivalency to occur, the ligands that are connected by a linker or linkers have to be presented to their ligand binding sites by the linker(s) in a specific manner in order to bring about the desired ligand-orienting result, and thus produce a multibinding event.

The term "selectivity" or "specificity" is a measure of the binding preferences of a ligand for different ligand binding sites (enzymes). The selectivity of a ligand with respect to its target ligand binding site relative to another ligand binding site is given by the ratio of the respective values of $K_d$ (i.e., the dissociation constants for each ligand-enzyme complex) and $K_i$ (i.e., the Michaelis-Menten inhibition constants for each enzyme-inhibitor interaction) or, in cases where a biological effect is observed below the $K_d$, the ratio of the respective $EC_{50}$'s (i.e., the concentrations that produce 50% of the maximum response for the ligand interacting with the two distinct ligand binding sites (enzymes)).

The term "ligand binding site" denotes the site on the protein kinase that recognizes a ligand domain and provides a binding partner for the ligand. The ligand binding site may be defined by monomeric or multimeric structures. This interaction may be capable of producing a unique biological effect, for example, agonism, antagonism, inhibition, modulatory effects, may maintain an ongoing biological event, and the like. However, in one embodiment, the ligand(s) merely bind to a ligand binding site and do not have agonistic or antagonistic activity.

Any substance that reduces the rate of an enzymatic conversion of substrate to product is defined as an "enzyme inhibitor". There are several fundamental mechanisms by which enzymatic processes may be inhibited, for example reversible competitive inhibition, noncompetitive and uncompetitive inhibition, irreversible inhibition, substrate adulteration, and substrate sequestration. In reversible competitive inhibition, the inhibitor combined reversibly with free enzyme in a manner that excludes or reduces binding by normal substrate for the enzyme. When a competitive inhibitor only reduces but does not totally exclude substrate binding, the inhibition is called partial competitive inhibition. In reversible noncompetitive inhibition, the inhibitor and substrate bind reversibly, randomly, and independently at different sites. The enzyme: substrate: inhibitor complex is totally inactive or the rate of conversion of substrate to product is reduced in partial noncompetitive inhibition. In reversible uncompetitive inhibition, the inhibitor can only bind to the enzyme-substrate complex. Enzymes may also be inhibited irreversibly; e.g., they may undergo inactivating covalent modification by inhibitors. Irreversible inhibitors fall into two broad categories, depending upon whether they require pre-activation by the enzyme. Irreversible inhibitors such as reactive affinity labels, often used to probe enzyme active site structure, are intrinsically reactive with their target active site and require no pre-activation. In contrast, mechanism-based inactivators ("suicide substrates") are not intrinsically reactive with chemical functional groups on the enzyme, but these molecules are converted to reactive species in a process catalyzed at the enzyme active sites. Finally, enzymes may be inhibited through mechanisms that do not involve direct interaction of the inhibitor with the enzyme. For example, inhibitors may bind to and sequester the substrate(s) for a given enzymatic process. In another possibility, inhibitors are activated by one enzyme and the activated species might inactivate or reversibly inhibit another enzyme, e.g. isoniazid. Additionally, viral reverse transcriptase incorporates nucleotide analogs into growing DNA strands, which terminates the possibility for chain extension, thus inhibiting the subsequent enzymatic process ("substrate adulteration")

The terms "agonism" and "antagonism" are well known in the art. Ligands which are full agonists are ligands which when bound trigger the maximum activity seen by the natural ligands. Ligands which are partial agonists are ligands which when bound trigger sub-maximum activity. Ligands which are antagonists are ligands that when bound, inhibit or prevent the activity arising from a natural ligand binding to the enzyme. Antagonists may be of the surmountable class (results in the parallel displacement of the dose-response curve of the agonist to the right in a dose dependent fashion without reducing the maximal response for the agonist) or insurmountable class (results in depression of the maximal response for a given agonist with or without the parallel shift). Ligands which are inverse agonists are ligands that, when bound, decrease the basal activity of the unbound enzyme or which provide an activity opposite of the natural agonist.

Ligands have measurable properties that relate to the interaction of the ligand and the enzyme. These include the affinity of the ligand for the enzyme, which relates to the energetics of the binding, the efficacy of the ligand for the enzyme, which relates to the functional downstream activity of the ligand, the kinetics of the ligand for the enzyme, which defines the onset of action and the duration of action, and the desensitization of the enzyme for the ligand. Selectivity defines the ratio of the affinity and/or efficacy of a ligand across two enzymes. The term "modulatory effect" refers to the ability of the ligand to change the activity of an agonist or antagonist through binding to a ligand binding site. It is a combination of these properties which provides the foundation for defining the nature of the functional response.

It should be recognized that the ligand binding sites of the enzyme that participate in biological multivalent binding interactions are constrained to varying degrees by their intra- and inter-molecular associations (e.g., such macromolecular structures may be covalently joined to a single structure, noncovalently associated in a multimeric structure, embedded in a membrane or polymeric matrix, and so on) and therefore have less translational and rotational freedom than if the same structures were present as monomers in solution.

The term "inert organic solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The phrase "disease or medical disorder mediated by a protein kinase" includes all disease states (i.e., pathologic conditions) which are caused by or associated in any manner with protein kinase activity. Such disease states include, by way of example only, hyperproliferative disorders such as cancer, psoriasis, hepatic cirrhosis, diabetes, atherosclerosis, angiogenesis, restenosis, ocular diseases, autoimmune disorders such as arthritis, in particular, rheumatoid arthritis and other inflammatory disorders and a variety of renal disorders.

The term "therapeutically effective amount" refers to that amount of compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified where appropriate by the symbol X or X', refers to a group or groups that covalently links from 2 to 10 ligands (as identified above) in a manner that provides for a compound capable of multivalency. Among other features, the linker is a ligand-orienting-entity that permits attachment of multiple copies of a ligand (which may be the same or different) thereto: In some cases, the linker may itself be biologically active. The term "linker" does not, however, extend to cover solid inert supports such as beads, glass particles, fibers, and the like. But it is understood that the compounds of this invention can be attached to a solid support if desired. For example, such attachment to solid supports can be made for use in separation and purification processes and similar applications.

The term "multimeric compound" refers to compounds comprising from 2 to 10 ligands covalently connected through at least one linker which compounds may or may not possess multibinding properties (as defined herein).

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of protein kinases, wherever such sites are located on the enzyme structure.

The ligands are covalently attached to the linker or linkers using conventional chemical techniques providing for covalent linkage of the ligand to the linker or linkers. Reaction chemistries resulting in such linkages are well known in the art and involve the use of complementary functional groups on the linker and ligand. Preferably, the complementary functional groups on the linker are selected relative to the functional groups available on the ligand for bonding or which can be introduced onto the ligand for bonding. Again, such complementary functional groups are well known in the art. For example, reaction between a carboxylic acid of either the linker or the ligand and a primary or secondary amine of the ligand or the linker in the presence of suitable, well-known activating agents results in formation of an amide bond covalently linking the ligand to the linker;

reaction between an amine of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table I below illustrates numerous complementary reactive groups and the resulting bonds formed by reaction there between.

TABLE I

Representative Complementary Binding Chemistries

| First Reactive Group | Second Reactive Group | Linkage |
|---|---|---|
| hydroxyl | isocyanate | urethane |
| amine | epoxide | β-hydroxyamine |
| sulfonyl halide | amine | sulfonamide |
| carboxyl | amine | amide |
| hydroxyl | alkyl/aryl halide | ether |
| aldehyde | amine/NaCNBH$_4$ | amine |
| ketone | amine/NaCNBH$_4$ | amine |
| amine | isocyanate | urea |

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-enzyme complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

A ligand is typically attached to the linker via a covalent bond. One skilled in the art will be able to readily identify functional groups suitable for linking a ligand to the linker. For example, methods of coupling various functional groups to form a stable covalent bond are described in March, "Advanced Organic Chemistry", 4th Edition, Wiley-Interscience, New York, N.Y. (1992).

Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof. Further examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains. Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (egg., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotectation of a carboxyl, hydroxyl, thiol or amino group by a change in pH, oxidation, reduction or other mechanisms known to those skilled in the art which result in removal of the protecting group, is within the scope of this invention.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that links the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

The simplest and most preferred compound is a bivalent compound which can be represented as L-X-L, where each L is independently a ligand which maybe the same or different and each X is independently the linker. A trivalent compound could also be represented in a linear fashion, i.e., as a sequence of repeated units L-X-L-X-L, in which L is a ligand and is the same or different at each occurrence, as can X. However, a trimer can also be a radial compound comprising three ligands attached to a central core, and thus represented as $(L)_3X$, where the linker X could include, for example, an aryl or cycloalkyl group. Tetravalent compounds can be represented in a linear array, e.g.,

L-X-L-X-L-X-L in a branched array, e.g.,

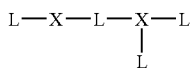

(a branched construct analogous to the isomers of butane—n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker. The same considerations apply to higher compounds of this invention containing 5–10 ligands. However, for agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

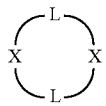

and variants thereof.

All of the above variations are intended to be within the scope of the invention defined by the formula $(L)_p(X)_q$.

With the foregoing in mind, a preferred linker may be represented by the following formula:

$$-X^a-Z-(Y^a-Z)_m-Y^b-Z-X^a-$$

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

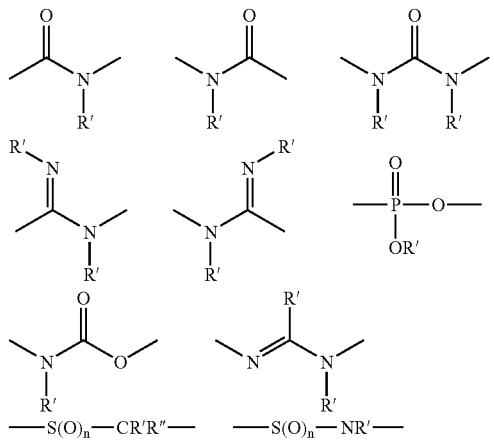

—S—S— or a covalent bond;

in which:

n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In one embodiment of this invention, the linker (i.e., X or X') is selected those shown in Table II:

TABLE II

Representative Linkers
Linker

—HN—(CH$_2$)$_2$—NH—C(O)—(CH$_2$)—C(O)—NH—(CH$_2$)$_2$—NH—
—HN—(CH$_2$)$_2$—NH—C(O)—(CH$_2$)$_2$—C(O)—NH—(CH$_2$)$_2$—NH—
—HN—(CH$_2$)$_2$—NH—C(O)—(CH$_2$)$_3$—C(O)—NH—(CH$_2$)$_2$—NH—
—HN—(CH$_2$)$_2$—NH—C(O)—(CH$_2$)$_4$—C(O)—NH—(CH$_2$)$_2$—NH—
—HN—(CH$_2$)$_2$—NH—C(O)—(CH$_2$)$_5$—C(O)—NH—(CH$_2$)$_2$—NH—
—HN—(CH$_2$)$_2$—NH—C(O)—(CH$_2$)$_6$—C(O)—NH—(CH$_2$)$_2$—NH—
—HN—(CH$_2$)$_2$—NH—C(O)—(CH$_2$)$_7$—C(O)—NH—(CH$_2$)$_2$—NH—
—HN—(CH$_2$)$_2$—NH—C(O)—(CH$_2$)$_8$—C(O)—NH—(CH$_2$)$_2$—NH—
—HN—(CH$_2$)$_2$—NH—C(O)—(CH$_2$)$_9$—C(O)—NH—(CH$_2$)$_2$—NH—
—HN—(CH$_2$)$_2$—NH—C(O)—(CH$_2$)$_{10}$—C(O)—NH—(CH$_2$)$_2$—NH—
—HN—(CH$_2$)$_2$—NH—C(O)—(CH$_2$)$_{11}$—C(O)—NH—(CH$_2$)$_2$—NH—
—HN—(CH$_2$)$_2$—NH—C(O)—(CH$_2$)$_{12}$—C(O)—NH—(CH$_2$)$_2$—NH—
—HN—(CH$_2$)$_2$—NH—C(O)—Z—C(O)—NH—(CH$_2$)$_2$—NH— where Z is 1,2-phenyl
—HN—(CH$_2$)$_2$—NH—C(O)—Z—C(O)—NH—(CH$_2$)$_2$—NH— where Z is 1,3-phenyl
—HN—(CH$_2$)$_2$—NH—C(O)—Z—C(O)—NH—(CH$_2$)$_2$—NH— where Z is 1,4-phenyl
—HN—(CH$_2$)$_2$—NH—C(O)—Z—O—Z—C(O)—NH—(CH$_2$)$_2$—NH— where Z is 1,4-phenyl
—HN—(CH$_2$)$_2$—NH—C(O)—(CH$_2$)$_2$—CH(NH—C(O)—(CH$_2$)$_8$—CH$_3$)—C(O)—NH—(CH$_2$)$_2$—

TABLE II-continued

Representative Linkers

Linker

NH—
—HN—(CH$_2$)$_2$—NH—C(O)—(CH$_2$)—O—(CH$_2$)—C(O)—NH—(CH$_2$)$_2$—NH—
—HN—(CH$_2$)$_2$—NH—C(O)—Z—C(O)—NH—(CH$_2$)$_2$—NH—
where Z is 5-(n-octadecyloxy)-1,3-phenyl
—HN—(CH$_2$)$_2$—NH—C(O)—(CH$_2$)$_2$—CH(NH—C(O)—Z)—C(O)—NH—(CH$_2$)$_2$—NH—
where Z is 4-biphenyl
—HN—(CH$_2$)$_2$—NH—C(O)—Z—C(O)—NH—(CH$_2$)$_2$—NH—
where Z is 5-(n-butyloxy)-1,3-phenyl
—HN—(CH$_2$)$_2$—NH—C(O)—(CH$_2$)$_8$-trans-(CH=CH)—C(O)—NH—(CH$_2$)$_2$—NH—
—HN—(CH$_2$)$_2$—NH—C(O)—(CH$_2$)$_2$—CH(NH—C(O)—(CH$_2$)$_{12}$—CH$_3$)—C(O)—NH—(CH$_2$)$_2$—NH—
—HN—(CH$_2$)$_2$—NH—C(O)—(CH$_2$)$_2$—CH(NH—C(O)—Z)—C(O)—NH—(CH$_2$)$_2$—NH—
where Z is 4-(n-octyl)-phenyl
—HN—(CH$_2$)—Z—O—(CH$_2$)$_6$—O—Z—(CH$_2$)—NH— where Z is 1,4-phenyl
—HN—(CH$_2$)$_2$—NH—C(O)—(CH$_2$)$_2$—NH—C(O)—(CH$_2$)$_3$—C(O)—NH—(CH$_2$)$_2$—C(O)—NH—(CH$_2$)$_2$—NH—
—HN—(CH$_2$)$_2$—NH—C(O)—(CH$_2$)$_2$—CH(NH—C(O)—Ph)—C(O)—NH—(CH$_2$)$_2$—NH—
—HN—(CH$_2$)$_2$—NH—C(O)—(CH$_2$)—N+((CH$_2$)$_9$—CH$_3$)(CH$_2$—C(O)—NH—(CH$_2$)$_2$—NH$_2$)—(CH$_2$)—C(O)—NH—(CH$_2$)$_2$—NH—
—HN—(CH$_2$)$_2$—NH—C(O)—(CH$_2$)—N((CH$_2$)$_9$—CH$_3$)—(CH$_2$)—C(O)—NH—(CH$_2$)$_2$—NH—
—HN—(CH$_2$)$_2$—NH—C(O)—(CH$_2$)$_2$—NH—C(O)—(CH$_2$)$_2$—NH—C(O)—CH$_2$)$_3$—C(O)—NH—(CH$_2$)$_2$—C(O)—NH—(CH$_2$)$_2$—C(O)—NH—(CH$_2$)$_2$—NH—
—HN—(CH$_2$)$_2$—NH—C(O)—Z—C(O)—NH—(CH$_2$)$_2$—NH—
where Z is 5-hydroxy-1,3-phenyl In another embodiment, the linker has the formula:

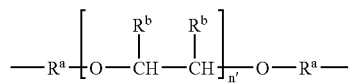

wherein each $R^a$ is independently selected from the group consisting of a covalent bond, alkylene, substituted alkylene and arylene;

each $R^b$ is independently selected from the group consisting of hydrogen, alkyl and substituted alkyl; and n' is an integer ranging from 1 to about 20.

In yet another embodiment, the linker has the formula: —(CH$_2$)$_{n''}$—, where n'' is an integer of from about 2 to about 40; preferably, from about 4 to about 20; and still more preferably, from about 6 to about 18.

In view of the above description of the linker, it is understood that the term "linker" when used in combination with the term "multibinding compound" includes both a covalently contiguous single linker (e.g., L-X-L) and multiple covalently non-contiguous linkers (L-X-L-X-L) within the multibinding compound.

Lipands

Preferred ligands for use in this invention are those moieties having formula A–AJ as defined herein. Within these preferred ligands, more preferred substituents include the following:

In Formula A and B:

$R_1$ is preferably selected from the group consisting of hydrogen, methyl and —NR$_{28}$R$_{29}$.

Ar$_1$ is preferably selected from the group consisting of phenyl, 2,6-Cl—C$_6$H$_3$, 4-biphenyl, thiophen-3-yl, and 2,6-dimethylphenyl.

$R_{28}$ is preferably selected from group consisting of hydrogen and methyl.

In Formula C:

$R_3$ is preferably selected from the group consisting of hydrogen, —CH$_3$, —CH$_2$CH$_2$CH$_3$ and —CH$_2$CH$_2$OCH$_3$.

$R_4$ is preferably selected from the group consisting of hydrogen, —CH$_3$, —CH$_2$CH$_2$CH$_3$, and —CH$_2$QCH$_3$.

$R_5$ is preferably selected from the group consisting of hydrogen, —CH$_3$, —CH$_2$CH$_3$, n-propyl, isopropyl and tert-butyl.

In Formula D:

$R_6$ is preferably selected from the group consisting of —CH$_2$OH and —CHO.

$R_7$ is preferably selected from the group consisting of hydrogen and acetyl.

In Formula E:

$R_8$ is preferably selected from the group consisting of hydrogen, —OMe and —Cl.

V is preferably selected from the group consisting of NH, CH$_2$ and O.

$R_9$ is preferably selected from the group consisting of hydrogen and —OMe.

In Formula F:

$R_{10}$ is preferably selected from the group consisting of hydrogen, —OMe and —NH$_2$.

$R_{11}$ is preferably selected from the group consisting of hydrogen, —OMe, —Cl, —NO$_2$, —NH$_2$ and —Br.

$R_{12}$ is preferably selected from the group consisting of hydrogen, —Br, —Cl and —OMe.

$R_{13}$ is preferably selected from the group consisting of hydrogen, —OH, —OMe, —Br and —Cl.

In Formula G:

$R_{14}$ is preferably selected from the group consisting of hydrogen, —CH$_3$, —CH$_2$Ph, —CH$_2$-(4-CH$_3$)Ph, and —CH$_2$(4-Ph)Ph.

$R_{15}$ is preferably selected from the group consisting of hydrogen, —F, —Cl, —Br, and —OMe.

$R_{16}$ is preferably selected from the group consisting of hydrogen, —F, —Cl, —Br, —OH and —OMe.

In Formula H:

$R_{17}$ and $R_{18}$ are preferably selected from the group consisting of hydrogen and —CH$_3$.

$R_{19}$ is preferably selected from the group consisting of tert-butyl, phenyl, 4-Br—C$_6$H$_4$—, —CH$_2$C(O)OEt, 2-pyridyl, 2-naphthyl, 2-CH$_3$—C$_6$H$_4$—, 4-OMe—C$_6$H$_4$—, 4-NO$_2$—C$_6$H$_4$—, 3-NO$_2$—C$_6$H$_4$—, 3-NH$_2$—C$_6$H$_4$—, —(CH$_2$)$_3$OH, 3-HOOC—C$_6$H$_4$—, 4-HOOC—C$_6$H$_4$—, 3-(—C(O)NH(CH$_2$)$_2$NHBOC)—C$_6$H$_4$—, 3-(—C(O)NH $(CH_2)_2NH_2)-C_6H_4-$, 3-($-C(O)NH(CH_2)_3NHBOC)-$$C_6H_4-$, 3-($-C(O)NH(CH_2)_3NH_2)-C_6H_4-$, 4-($-C(O)NH(CH_2)_3NHBOC)-C_6H_4-$ and 4-($-C(O)NH(CH_2)_3NH_2)-C_6H_4-$.

In Formula I and J:

W is preferably selected from the group consisting of N and CH.

Y is preferably selected from the group consisting of O and NH.

$R_{21}$ is preferably selected from the group consisting of hydrogen, 2-methyl, 3-methyl, 5-methyl 5-Cl, 5-OH, 5-OMe and 5-NMe$_2$.

In Formula L and M:

$R_{22}$ is preferably selected from the group consisting of hydrogen, $-CH_3$, $-CH_2CONH_2$, $-CH_2CH_2CONH_2$, $-CH_2$-3-indolyl, $-CH_2CH_3$ and $-CH_2OH$.

$R_{24}$ is preferably selected from the group consisting of hydrogen, $-C(O)CH_3$, $-C(O)C_6H_5$.

$Ar_2$ is preferably selected from the group consisting of $-CH_2C_6H_4$-4-$OR_{25}$, $-CH_2C_6H_5$, $-CH_2C_6H_4$-4-$CF_3$, $-CH_2C_6H_4$-4-$CH_3$, $-CH_2C_6H_4$-4-Cl, $-CH_2C_6H_4$-3-Cl, $-CH_2C_6H_4$-4-F, $-CH_2C_6H_4$-4-Br, $-CH_2C_6H_4$-4-I, $-CH_2C_6H_3$-3-Cl-4-l, $-CH_2C_6H_3$-3,4-di-Cl, $-CH_2C_6H_3$-3,4-di-Br, $-CH_2C_6H_3$-3-Br-4-I, $-CH_2C_6H_3$-3-Br-4-Cl and $-CH_2$-(2-naphthyl).

In Formula P:

$R_{27}$ is preferably selected from the group consisting of hydrogen, $-CH_3$, $-CH_2CH_3$, $-CH_2OH$, $-CH(CH_3)_2$, $-CH_2N(CH_3)_2$, $-CH_2CH_2OH$, $-N(CH_3)_2$, 2-hydroxyazetidin-1-yl $Ar_3$ is preferably selected from the group consisting of 3,4,5-tri-OMe-$C_6H_2-$, 3,5-di-OMe-$C_6H_3-$, 3,4-di-OMe-$C_6H_3-$, 3,5-di-Me-$C_6H_3-$ and 3,4-di-Me-$C_6H_3-$.

In Formula O:

$R_{26}$ is preferably selected from the group consisting of hydrogen, $-COCH_3$, $-COC_6H_5$, $-COC_6H_4$-4-$CH_2N(CH_2CH_2)_2NCH_3$, $-CO$-4-pyridyl, $-CO$-3-pyridyl, $-CO$-2-pyridyl, $-CO$-4-Cl$-C_6H_5$, $-CO$-4-Cl$-C_6H_5$, $-CO$-2-COOH$-C_6H_5$, $-CO$-n-$C_6H_{13}$, $-CO$-2-MeO$-C_6H_5$, $-CO$-4-F$-C_6H_5$, $-CO$-4-CN$-C_6H_5$, $-CO$-cyclohexyl, $-CO$-4-Me-$C_6H_5$ and $-CO$-2-$C_{10}H_7$.

In Formula S:

D is preferably selected from the group consisting of a covalent bond, $-NH-$ and $-O-$.

$Ar_3$ is preferably selected from group consisting of 3,4,5-tri-OMe-$C_6H_2-$, 3,5-di-OMe-$C_6H_3-$, 3,4-di-OMe-$C_6H_3-$, 3,5-di-Me-$C_6H_3-$ and 3,4-di-Me-$C_6H_3-$.

In Formula T:

$R_{28}$ is preferably selected from the group consisting of hydrogen and $-CH_3$.

In Formula V:

$R_{30}$ is preferably selected from the group consisting of hydrogen, $-F$, $-Cl$ and $-I$.

$R_{31}$ is preferably selected from the group consisting of hydrogen, $-F$, $-OEt$.

$R_{32}$ is preferably selected from the group consisting of hydrogen, $-NH_2$, $-OMe$, $-NHAc$, $-NHBn$ and $-NMe_2$.

In Formula W:

$R_{33}$ is preferably selected from the group consisting of $-C_6H_5$, 2,6-Cl$-C_6H_3-$, 2,4-$C_{12}-C_6H_3-$, 4-F$-C_6H_4-$, 2-Cl$-C_6H_4-$, 2-Me-$C_6H_4-$, 3,4-$C_{12}-C_6H_3-$, 4-MeO$-C_6H_4-$ and 2-MeO$C_6H_4-$.

In Formula Z:

$R_{34}$ is preferably selected from the group consisting of hydrogen, $-OH$, alkyl, alkoxy, $-F$, $-Cl$, $-Br$, $-I$, $-CF_3$ and $-CN$.

$R_{35}$ is preferably selected from the group consisting of $-I$ and $-Br$.

$R_{36}$, $R_{37}$, and $R_{38}$ are preferably selected from the group consisting of hydrogen, $-F$, $-Cl$, $-Br$, $-I$, $-OH$, $-CF_3$, alkoxy, $-NO_2$ and alkylamino.

In one embodiment, this invention is directed to homodimers of the formula L-X-L, where each L is selected from a ligand moiety of formula III–XXIX or formula A–AJ, and X is as defined herein. In another embodiment, this invention is directed to heterodimers of the formula L-X-L, where each L is selected from a ligand moiety of formula III–XXIX or formula A–AJ provided both ligands are not the same moiety, and X is as defined herein.

Ligands of formula III–XXIX and A–AJ (and precursors and analogs thereof) are known in the art and can be readily prepared using art-recognized starting materials, reagents and reaction conditions. By way of illustration, patents and publications disclose compounds, intermediates and procedures useful in the preparation of ligands of formulas III–XXIX and A–AJ or related compounds suitable for use in this invention are disclosed in the examples herebelow. Additionally, the following documents (and references cited therein) describe the synthesis of ligands useful in this invention: Connolly et al, Bio. and Med. Chem. Let., 1997, 7(18) 2415–2420 (formula III); Trumpp-Kallmeyer et al, J. Med. Chem., 1998, 41, 1752–1763 (formula IV); Hunke et al., J. B. C. 1996, 271(2), 695–701 (formula V); Faltznek et al., Biochemistry, 1995, 34, 12404–12410 (formula VI); Fry et al., P.N.A.S., 1998, 95(20) 12022–12027 (formula VII); Bullinton et al., Bio. Med. Chem. Lett., 1998, 8, 2489–2494 (formula VIII); Davis et al., WO 97/40019 (formula IX); Zimmerman U.S. Pat. No. 5,521,184 (formula X); Zimmermun et al., Arch. Pharm. (Weinheim), 1996, 329(7), 371–376 (formula XI); Davis et al., WO 98/18782 (formula XII); Davis et al., WO 97/19065 (formula XIII); Adams et al., WO 96/21452 and U.S. Pat. Nos. 5,593,992 and 5,670,527 (formula XIV); Henry et al., J. Med. Chem., 1998, 41(22) 4196–4198 (formula XV); Bridges, WO 98/37881 (formula XVI); Schoepfer et al., Bio. Med. Chem. Lett., 1999, 9, 221–226 (formula XVII and XVIII); Furet et al., J. Med. Chem., 1999, 42, 2358–2363 (formula XVIII); Smyth et al., J. Med. Chem., 1993, 36, 3010–3020 (formula XX); Ramdus et al., Archives of Biochem. and Biophys., 1999, 368(2), 394–400 (formula XXI); Tamaoki et al., Biochem. Biophy. Res. Comm., 1986, 135(2), 397–402 (formula XXII); Stover et al., Current Opinion in Drug Discovery, 1999, 2(4), 274–285 (formula XXIII); Shibuya et al., Chem. Pharm. Bull., 1992, 40, 1154–1165 (formula XXIV); Meyers et al., B. Med. Chem. Lett., 1997, 7, 417–420 (formula XXV); Williams et al., Biochemistry, 1998, 37, 9579–9585 (formula XXVI); Duncia et al., B. Med., Chem. Lett., 1998, 8, 2839–2844 (formula XXVII); and Farmitalai et al., U.S. Pat. No. 5,397,787.

The ligands of the present invention may be selective for a particular protein kinase or be selective for more than one protein kinase. Additionally, the ligands may be competitive or noncompetitive for a particular protein kinase. The ligand selectivity needed can be determined by one of skill in the art for the particular desired result.

Preparation of Compounds

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Third Edition, Wiley, N.Y., 1999, and references cited therein.

Any compound which is an inhibitor of protein kinases can be used as a ligand in this invention. As discussed above, numerous such inhibitors are known in the art and any of these known compounds or derivatives thereof may be employed as ligands in this invention. Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures. The patents and publications set forth above provide numerous examples of suitably functionalized inhibitors of protein kinases, and intermediates thereof, which may be used as ligands in this invention.

The ligands can be covalently attached to the linker through any available position on the ligands, provided that when the ligands are attached to the linker, at least one of the ligands retains its ability to bind to the protein kinases. Certain sites of attachment of the linker to the ligand are preferred based on known structure-activity relationships. Preferably, the linker is attached to a site on the ligand where structure-activity studies show that a wide variety of substituents are tolerated without loss of activity.

It will be understood by those skilled in the art that the following methods may be used to prepare other compounds of this invention. Ligand precursors, for example, ligands containing a leaving group or a nucleophilic group, can be covalently linked to a linker precursor containing a nucleophilic group or a leaving group, using conventional reagents and conditions.

Other methods are well known to those of skill in the art for coupling molecules such as the ligands described herein with the linker molecules described herein. For example, two equivalents of ligand precursor with a halide, tosylate, or other leaving group, can be readily coupled to a linker precursor containing two nucleophilic groups, for example, amine groups, to form a dimer. The leaving group employed in this reaction may be any conventional leaving group including, by way of example, a halogen such as chloro, bromo or iodo, or a sulfonate group such as tosyl, mesyl and the like. When the nucleophilic group is a phenol, any base which effectively deprotonates the phenolic hydroxyl group may be used, including, by way of illustration, sodium carbonate, potassium carbonate, cesium carbonate, sodium hydride, sodium hydroxide, potassium hydroxide, sodium ethoxide, triethylamine, diisopropylethylamine and the like. Nucleophilic substition reactions are typically conducted in an inert diluent, such as tetrahydrofuran, N,N-dimethylformamide, N,N-dimethylacetamide, acetone, 2-butanone, 1-methyl-2-pyrrolidinone and the like. After the reaction is complete, the dimer is typically isolated using conventional procedures, such as extraction, filtration, chromatography and the like.

By way of further illustration, dimers with a hydrophilic linker can be formed using a ligand precursor containing nucleophilic groups and a a polyoxyethylene containing leaving groups, for example, poly(oxyethylene) dibromide (where the number of oxyethylene units is typically an integer from 1 to about 20). In this reaction, two molar equivalents of the ligand precursor are reacted with one molar equivalent of the poly(oxyethylene) dibromide in the presence of excess potassium carbonate to afford a dimer. This reaction is typically conducted in N,N-dimethylformamide at a temperature ranging from about 25° C. to about 100° C. for about 6 to about 48 hours.

Alternatively, the linker connecting the ligands may be prepared in several steps. Specifically, a ligand precursor can first be coupled to an "adapter", i.e., a bifunctional group having a leaving group at one end and another functional group at the other end which allows the adapter to be coupled to a intermediate linker group. In some cases, the functional group used to couple to the intermediate linker is temporarily masked with a protecting group ("PG"). Representative examples of adapters include, by way of illustration, tert-butyl bromoacetate, 1-Fmoc-2-bromoethylamine, 1-trityl-2-bromoethanethiol, 4-iodobenzyl bromide, propargyl bromide and the like. After the ligand precursor is coupled to the adapter and the protecting group is removed from the adapter's functional group (if a protecting group is present) to form an intermediate, two molar equivalents of the intermediate are then coupled with an intermediate linker to form a dimer.

Ligand precursors can be coupled with adapters which include both leaving groups and protecting groups to form protected intermediates. The leaving group employed in this reaction may be any conventional leaving group including, by way of example, a halogen such as chloro, bromo or iodo, or a sulfonate group such as tosyl, mesyl and the like. Similarly, any conventional protecting group may be employed including, by way of example, esters such as the methyl, tert-butyl, benzyl ("Bn") and 9-fluorenylmethyl ("Fm") esters.

Protected intermediates can then be deprotected using conventional procedures and reagents to afford deprotected intermediates. For example, tert-butyl esters are readily hydrolyzed with 95% trifluoroacetic acid in dichloromethane; methyl ester can be hydrolyzed with lithium hydroxide in tetrahydrofuran/water; benzyl esters can be removed by hydrogenolysis in the presence of a catalyst, such as palladium on carbon; and 9-fluorenylmethyl esters are readily cleaved using 20% piperidine in DMF. If desired, other well-known protecting groups and deprotecting procedures may be employed in these reactions to form deprotected intermediates.

Similarly, ligand precursors having an adapter with an amine functional group can be prepared. Ligand precursors can be coupled with adapters which include leaving groups and protected amine groups to afford protected intermediates. The leaving group employed in this reaction may be any conventional leaving group. Similarly, any conventional amine protecting group may be employed including, by way of example, trityl, tert-butoxycarbonyl ("Boc"), benzyloxy-carbonyl ("CBZ") and 9-fluorenylmethoxy-carbonyl ("Fmoc"). After coupling the adapter to the ligand precursor, the resulting protected intermediate is deprotected to afford a ligand precursor including an amine group using conventional procedures and reagents. For example, a trityl group is readily removed using hydrogen chloride in acetone; a Boc group is removed using 95% trifluoroacetic acid in dichloromethane; a CBZ group can be removed by hydrogenolysis in the presence of a catalyst, such as palladium on carbon; and a 9-fluorenylmethoxycarbonyl group is readily cleaved using 20% piperidine in DMF to afford the deblocked amine. Other well-known amine protecting groups and deprotecting procedures may be employed in these reactions to form amine-containing intermediates and related compounds.

Ligand precursors having an adapter, for example, one including a free carboxylic acid group or a free amine group, can be readily coupled to intermediate linkers having complementary functional groups to form compounds as described herein. For example, when one component includes a carboxylic acid group, and the other includes an amine group, the coupling reaction typically employs a conventional peptide coupling reagent and is conducted under conventional coupling reaction conditions, typically in the presence of a trialkylamine, such as ethyldiisopropylamine. Suitable coupling reagents for use in this reaction include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, may be employed in this reaction. Typically, this coupling reaction is conducted at a temperature ranging from about 0° C. to about 60° C. for about 1 to about 72 hours in an inert diluent, such as THF, to afford the dimer.

The compounds described herein can also be prepared using a wide variety of other synthetic reactions and reagents. For example, ligand precursors having aryliodide, carboxylic acid, amine and boronic acid functional groups can be prepared. Hydroxymethyl pyrrole can be readily coupled under Mitsunobu reaction conditions to various phenols to provide, after deprotection, functionalized intermediates. The Mitsunobu reaction is typically conducted by reacting hydroxymethyl pyrrole and the appropriate phenol using diethyl azodicarboxylate (DEAD) and triphenylphosphine at ambient temperature for about 48 hours. Deprotection, if necessary, using conventional procedures and reagents then affords the functionalized intermediates.

The functionalized intermediates can be employed in the synthesis of compounds. For example, aryliodide intermediates can be coupled with bis-boronic acid linkers to provide dimers. Typically, this reaction is conducted by contacting two molar equivalents of the aryliodide and one molar equivalent of the bis-boronic acid in the presence of tetrakis(triphenylphosphine)palladium(0), sodium carbonate and water in refluxing toluene.

Aryliodide intermediates can also be coupled with acrylate intermediates or alkyne intermediate to afford dimers. These reactions are typically conducted by contacting two molar equivalents of aryliodide intermediates with one molar equivalent of either acrylates or alkynes in the presence of dichlorobis(triphenylphosphine)palladium (II), copper (I) iodide and diisopropylethylamine in N,N-dimethylformamide to afford the respective dimers.

As will be readily apparent to those of ordinary skill in the art, the synthetic procedures described herein or those known in the art may be readily modified to afford a wide variety of compounds within the scope of this invention.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their target binding site(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a ligand bound to its target allows one to identify one or more sites where linker attachment will not preclude the ligand/target interaction. Alternatively, evaluation of ligand/target binding by nuclear magnetic resonance will permit the identification of sites non-essential for ligand/target binding. See, for example, Fesik, et al., U.S. Pat. No. 5,891,643, the disclosure of which is incorporated herein by reference in its entirety. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a ligand bound to its target, and then consider modifying this ligand by attaching to it a second copy of the same ligand with a linker which allows the second ligand to interact with the same target at sites proximal to the first binding site, which include elements of the target that are not part of the formal ligand binding site and/or elements of the matrix surrounding the formal binding site, such as the membrane. Here, the most favorable orientation for interaction of the second ligand molecule may be achieved by attaching it to the linker at a position which abrogates activity of the ligand at the first binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heteromeric constructs bearing two different ligands that bind to common or different targets.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linker Selection

In the linkers employed to generate multibinding compounds, the selection of linkers employed will typically take into consideration the following factors:

Valency: In most instances, the divalent linkers are used. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length: Linkers are chosen in a range of lengths to allow the spanning of a range of inter-ligand distances that encompass the distance preferable for a given divalent interaction. In some instances the preferred distance can be estimated rather precisely from high-resolution structural information of targets. In other instances where high-resolution structural information is not available, one can make use of simple models to estimate the maximum distance between binding sites either on adjacent enzymes or at different locations on the same enzyme. In situations where two binding sites are present on the same target (or target subunit for multisubunit targets), preferred linker distances are 2–20 Å, with more preferred linker distances of 3–12 Å. In situations where two binding sites reside on separate target sites, preferred linker distances are 20–100 Å, with more preferred distances of 30–70 Å.

Linker Geometry and Rigidity: The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties: The physical properties of linkers are nominally determined by the chemical constitution and bonding patterns of the linker, and linker physical properties impact the overall physical properties of the candidate multibinding compounds in which they are included. A range of linker compositions can be selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups: Linker chemical functional groups are selected to be compatible with the chemistry chosen to connect linkers to the ligands and to impart the range of physical properties sufficient to span initial examination of this parameter.

Suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

Representative Complementary Binding Chemistries

| First Reactive Group | Second Reactive Group | Linkage |
|---|---|---|
| hydroxyl | isocyanate | urethane |
| amine | epoxide | β-hydroxyamine |
| sulfonyl halide | amine | sulfonamide |
| carboxyl acid | amine | amide |
| hydroxyl | alkyl/aryl halide | ether |
| aldehyde | amine(+ reducing agent) | amine |
| ketone | amine(+ reducing agent) | amine |
| amine | isocyanate | urea |

Exemplary compounds suitable for use as linking groups include the following difunctional compounds identified as X-1 through X-418 below:

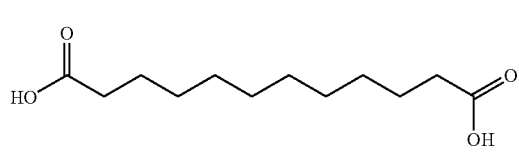

X-1

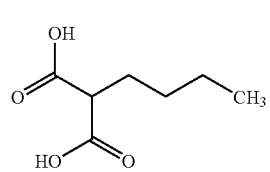

X-2

-continued
X-3
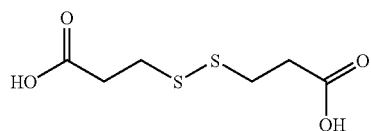
X-4
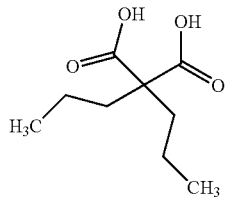
X-5
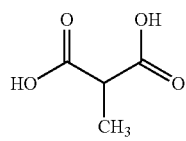
X-6
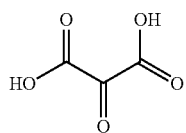
X-7
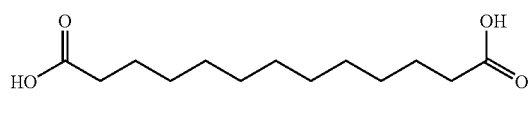
X-8
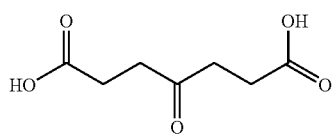
X-9
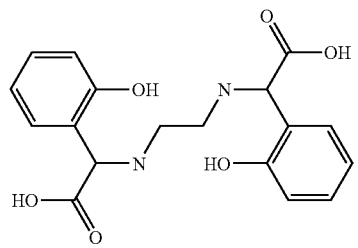
X-10
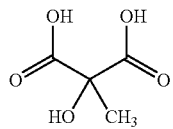
X-11
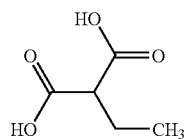
X-12
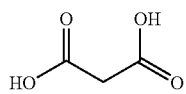
X-13
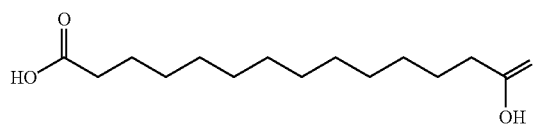
X-14
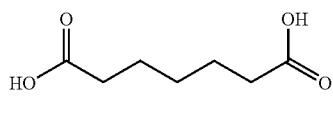
X-15
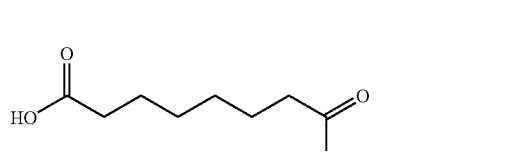
X-16
X-17
X-18
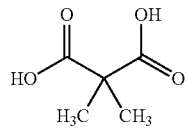

-continued
X-19 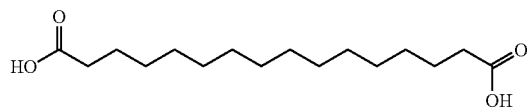
X-20 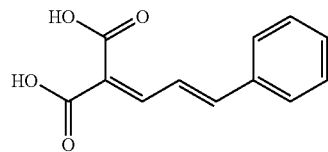
X-21 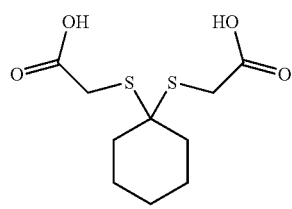
X-22 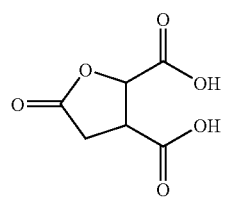
X-23 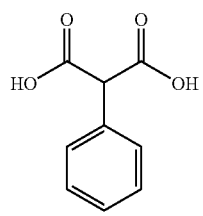
X-24 
X-25 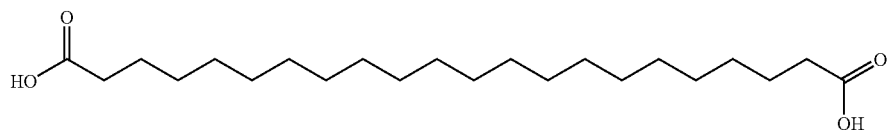
X-26 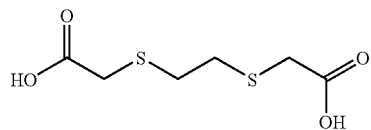
X-27 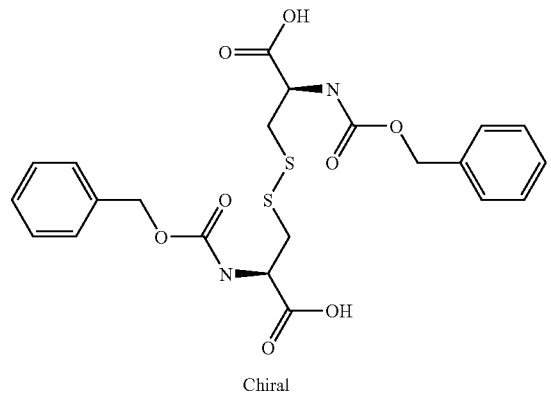
Chiral
X-28 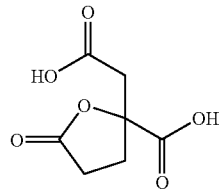
X-29 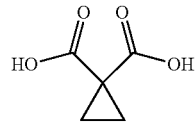
X-30 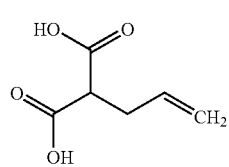
X-31 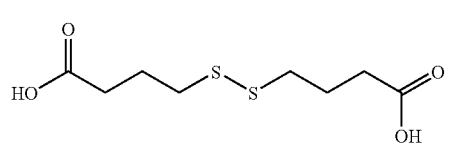

-continued
X-32
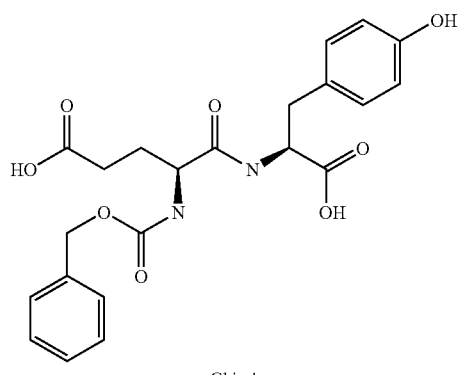
Chiral
X-33
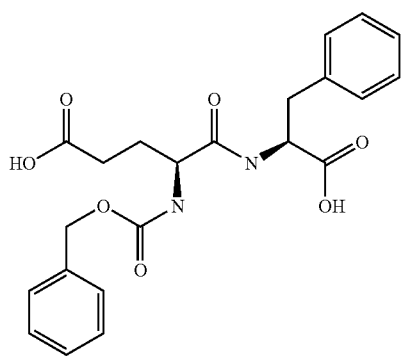
Chiral
X-34
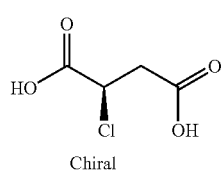
Chiral
X-35
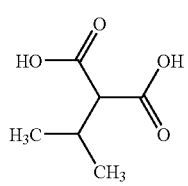
X-36
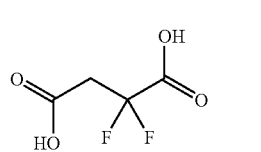
X-37
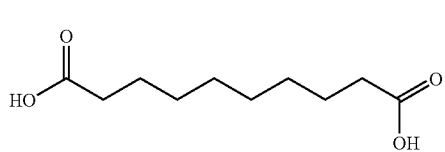
X-38
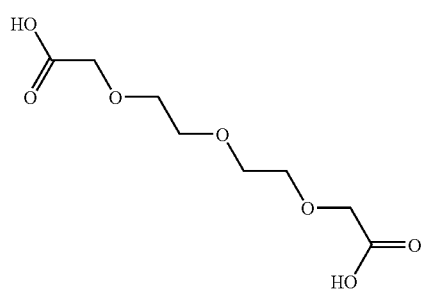
X-39
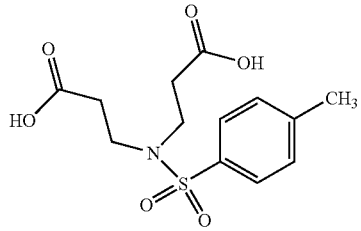
X-40
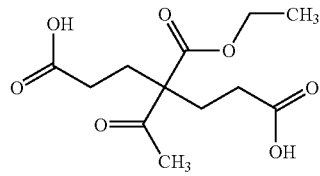
X-41
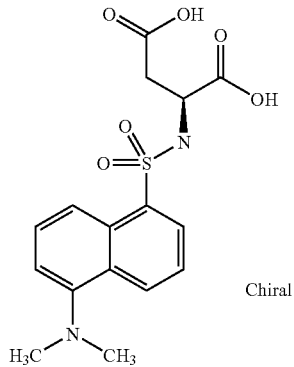
Chiral
X-42
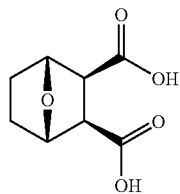
X-43
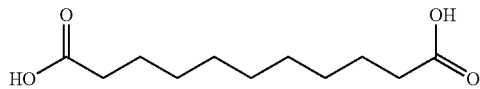

| | |
|---|---|
| 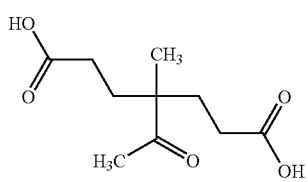 X-44 | 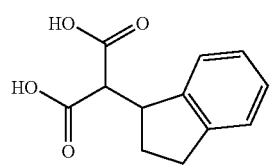 X-45 |
| 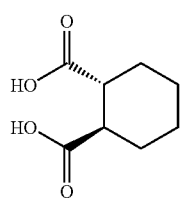 X-46 | 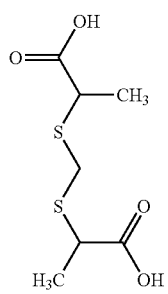 X-47 |
| 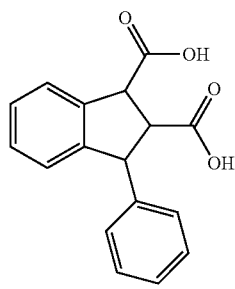 X-48 | |
| 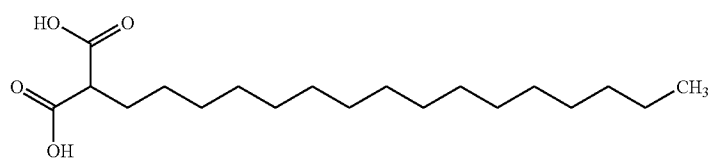 X-49 | |
| 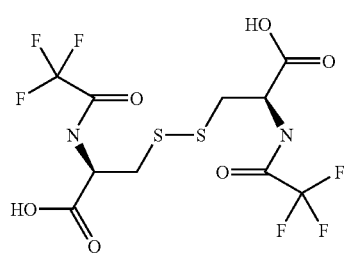 X-50<br>Chiral | 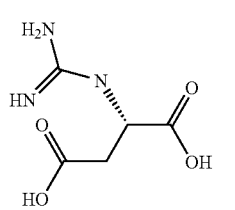 X-51 |
| 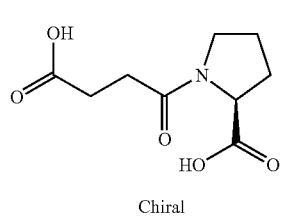 X-52<br>Chiral | X-53 |

-continued
X-54
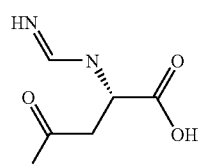
Chiral
X-55
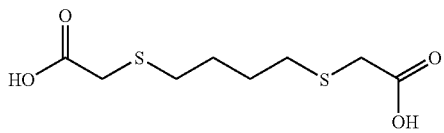
X-56
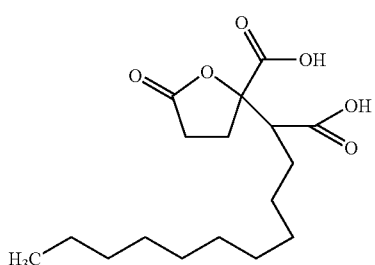
X-57
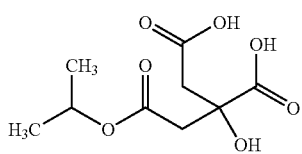
X-58
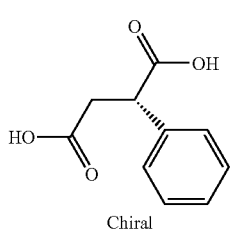
Chiral
X-59
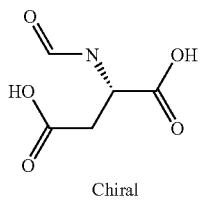
Chiral
X-60
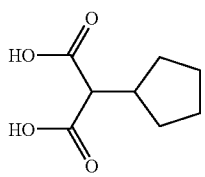
X-61
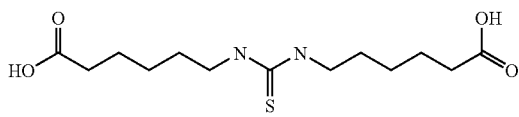
X-62
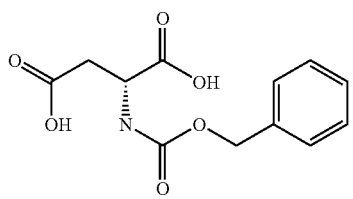
X-63
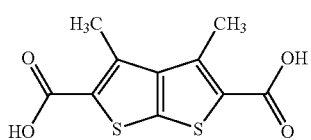
X-64
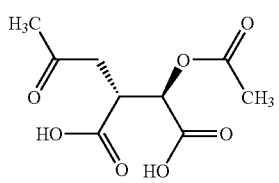
Chiral
X-65
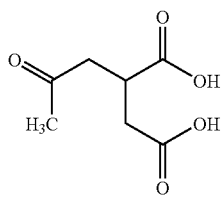
X-66
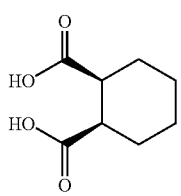
X-67
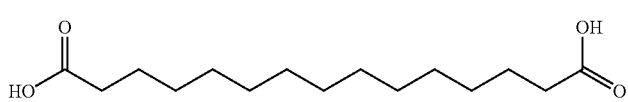

-continued
X-68
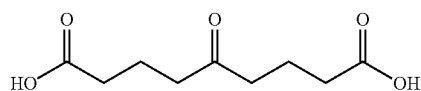
X-69
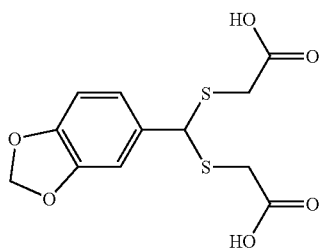
X-70
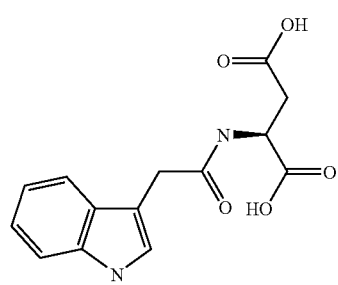
Chiral
X-71
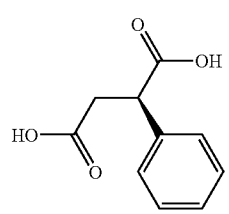
Chiral
X-72
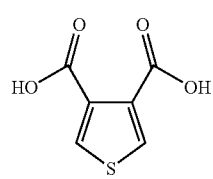
X-73
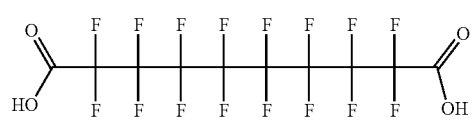
X-74
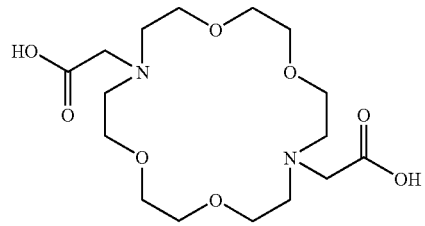
X-75
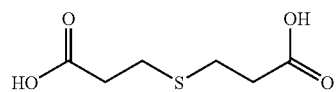
X-76
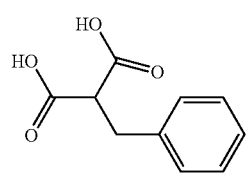
X-77
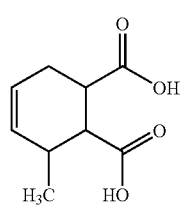
X-78
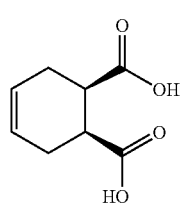
X-79
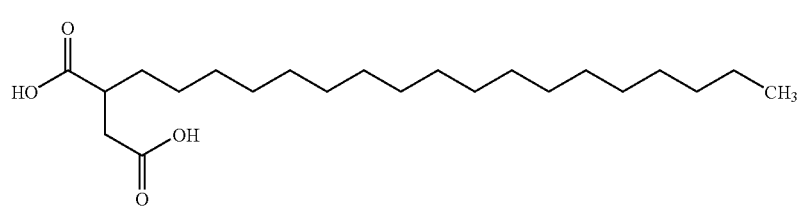

X-80
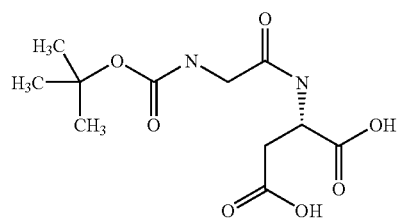
Chiral
X-81
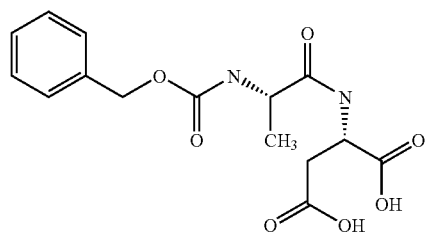
Chiral
X-82
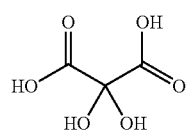
X-83
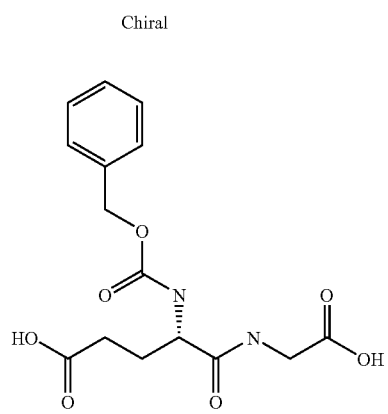
Chiral
X-84
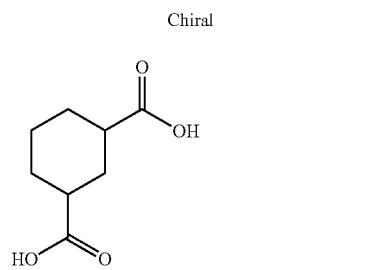
X-85
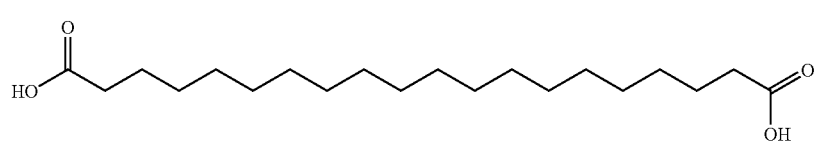
X-86
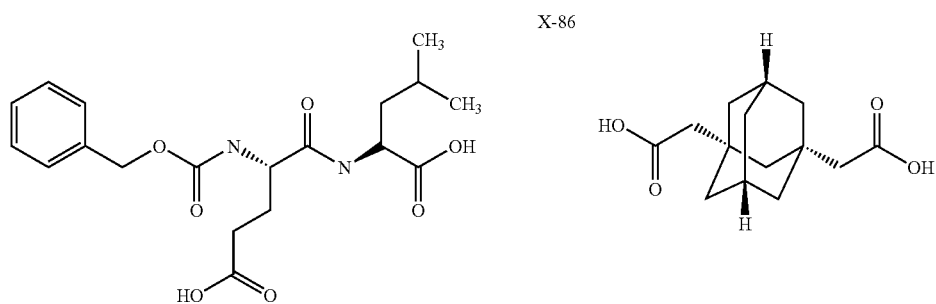
Chiral
X-87
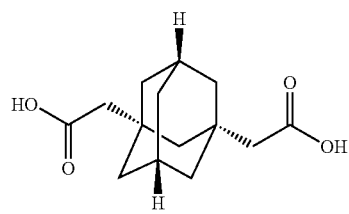
X-88
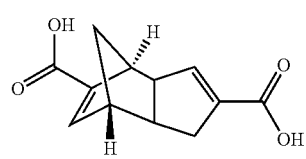
X-89
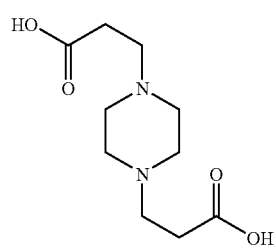

-continued
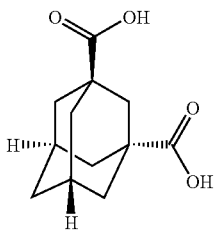
X-90
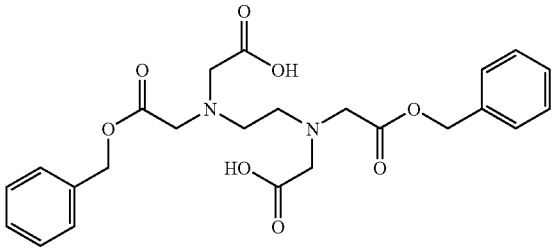
X-91
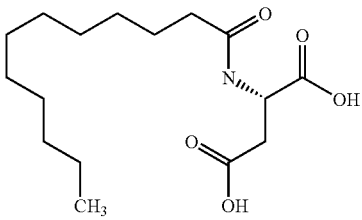
X-92
Chiral
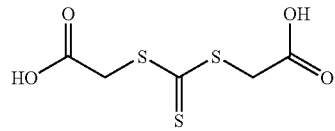
X-93
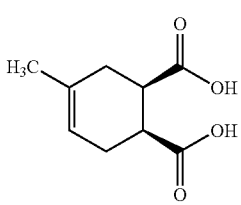
X-94
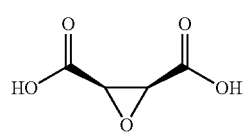
X-95
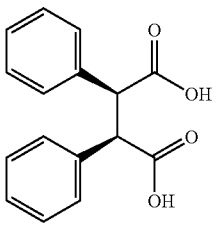
X-96
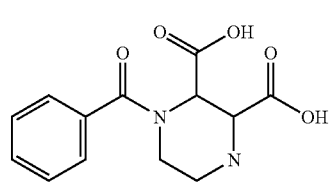
X-97
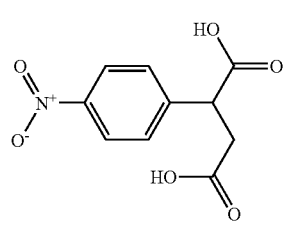
X-98
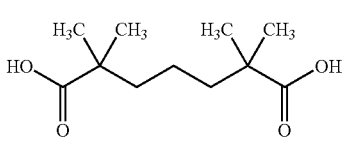
X-99
X-100

-continued
X-101 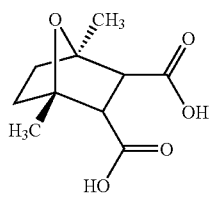
X-102 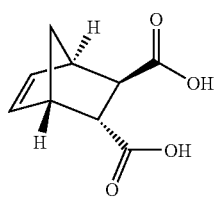
X-103 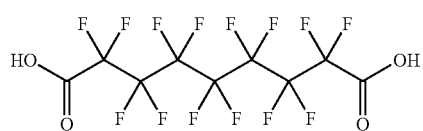
X-104 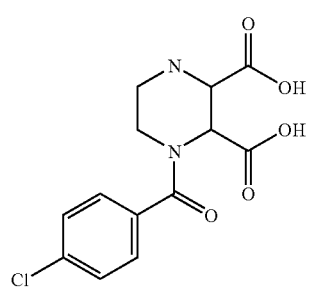
X-105 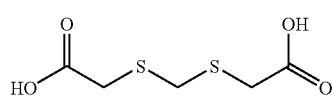
X-106 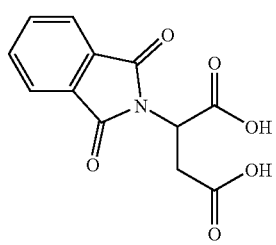
X-107 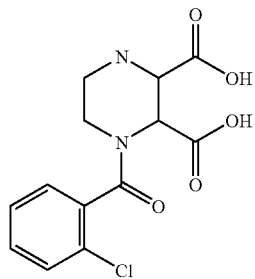
X-108 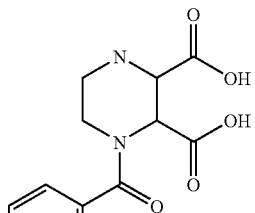
X-109 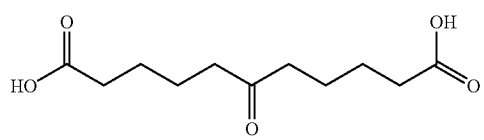
X-110 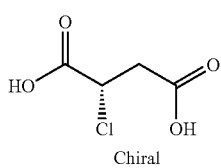
Chiral
X-111 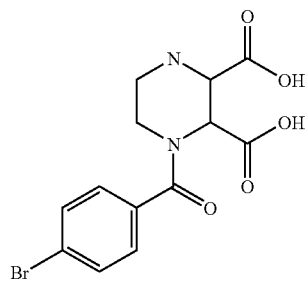
X-112 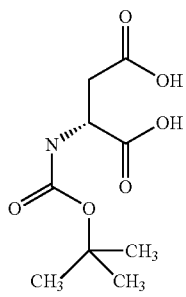
Chiral -continued
X-113 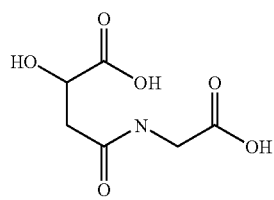
X-114 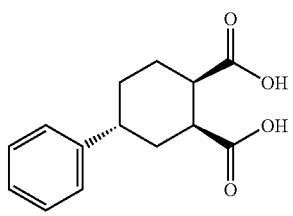
X-115 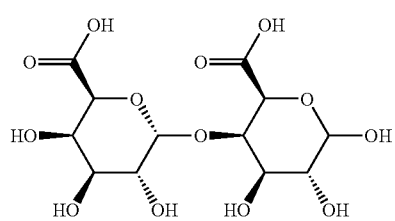
X-116 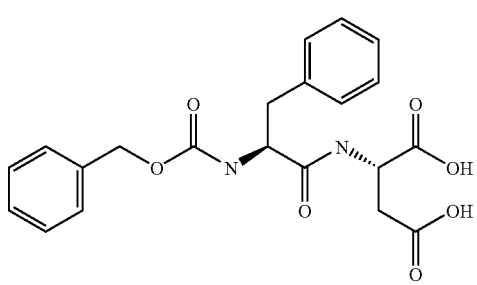
Chiral
Chiral
X-117 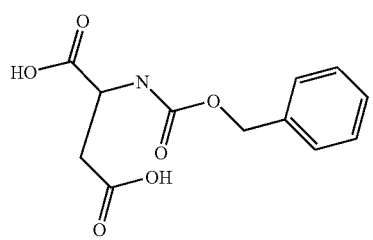
X-118 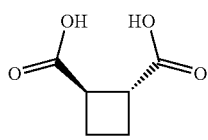
X-119 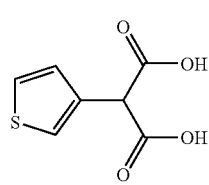
X-120 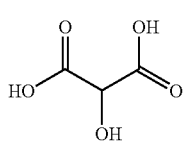
X-121 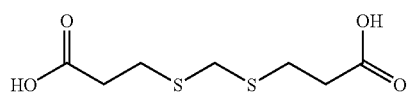
X-122 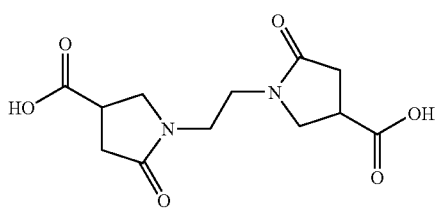
X-123 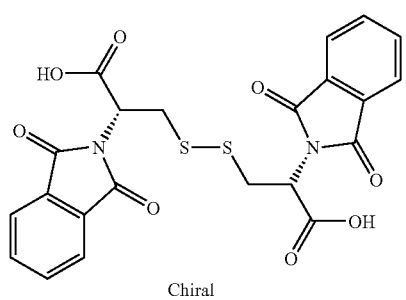
X-124 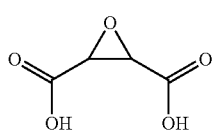
Chiral X-125
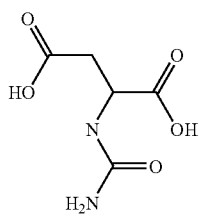
X-126
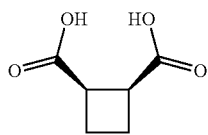
X-127
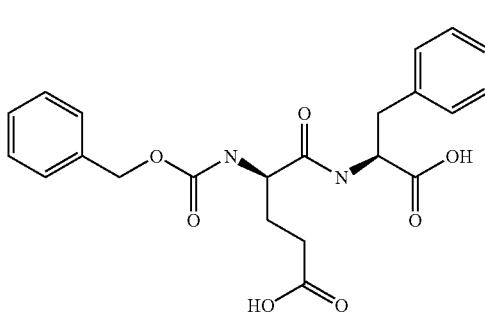
X-128
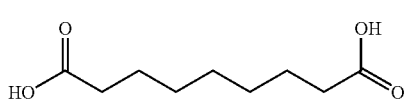
X-129
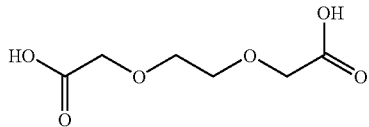
X-130
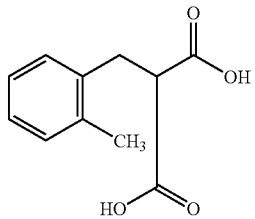
Disulfonyl Halides
X-131
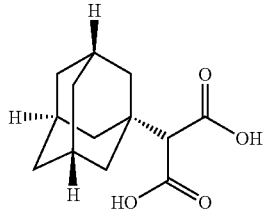
X-132
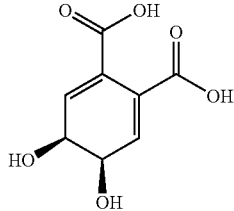
X-133
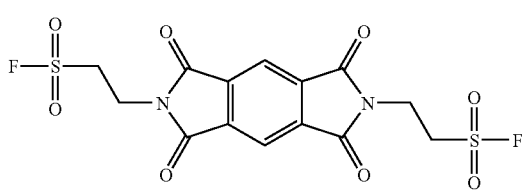
X-134
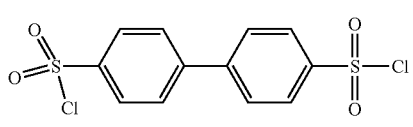
X-135
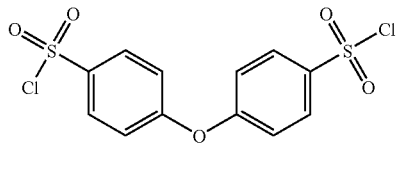
X-136
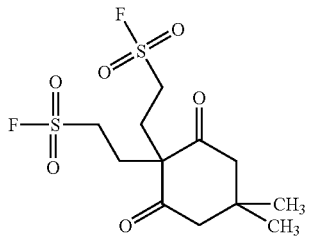
X-137
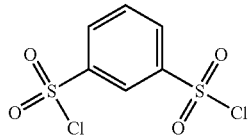
X-138
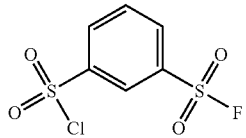

| X-139 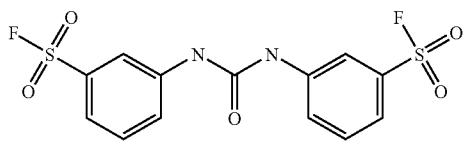 | X-140 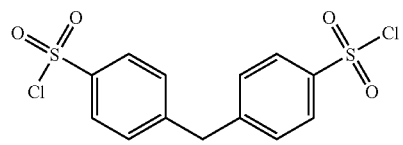 |
| --- | --- |
| X-141 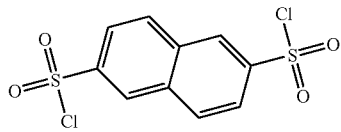 | X-142 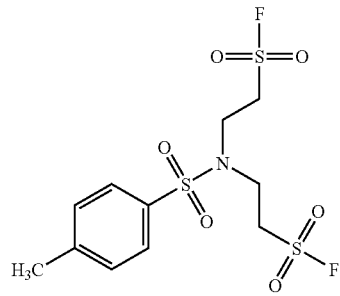 |
| X-143 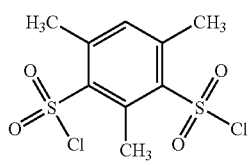 | X-144 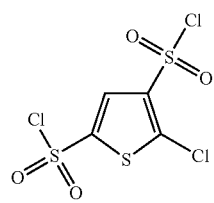 |
| X-145 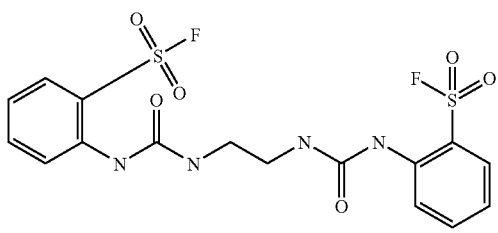 | X-146 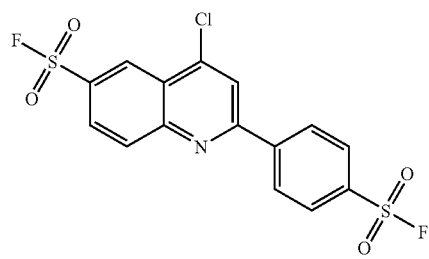 |
| X-147 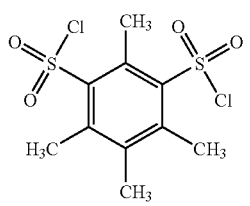 | X-148 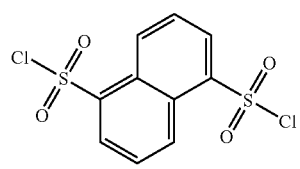 |
| X-149 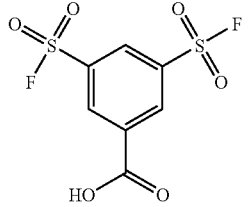 | X-150 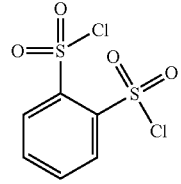 |
| X-151 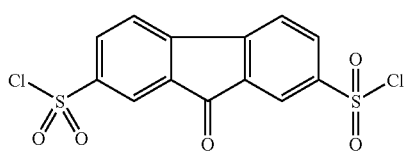 | X-152 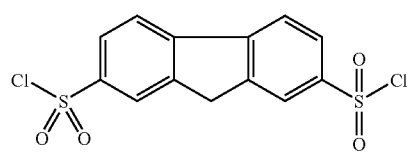 |
Dialdehydes -continued
X-153
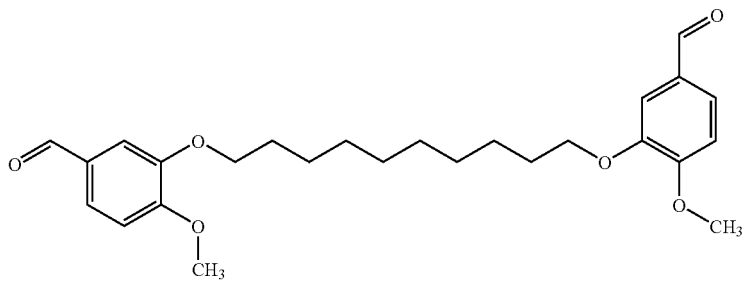
X-154
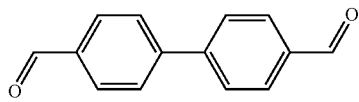
X-155
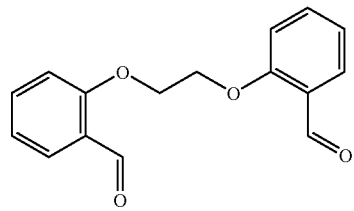
X-156
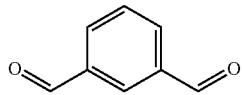
X-157
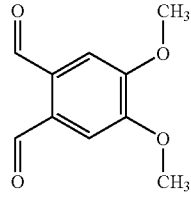
X-158
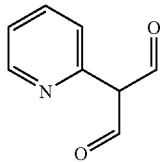
X-159
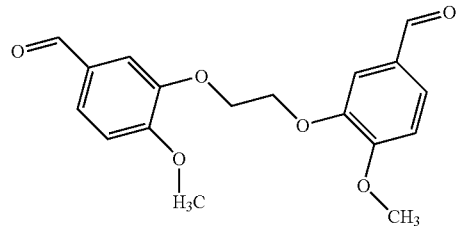
X-160
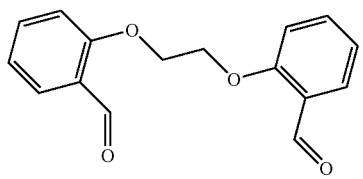
X-161
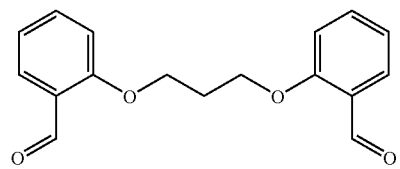
X-162
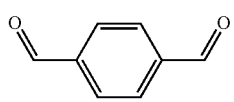
X-163
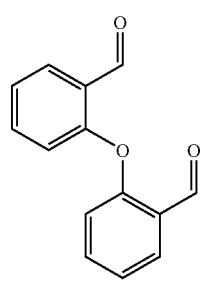
X-164
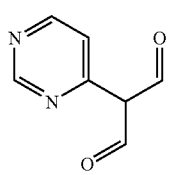
X-165
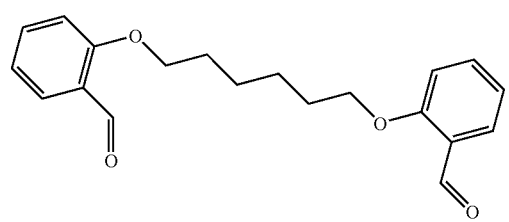

-continued
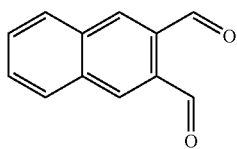
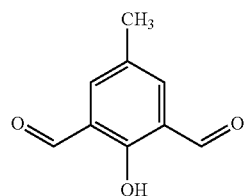
X-166
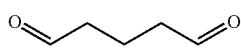
X-167
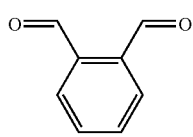
X-168
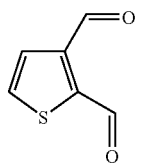
X-169
X-170
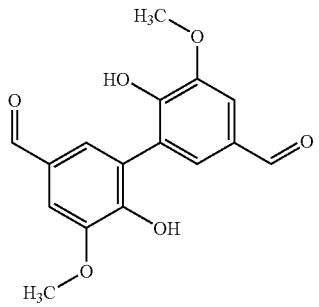
X-171
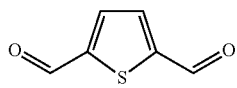
Dihalides
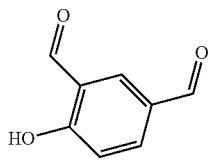
X-172
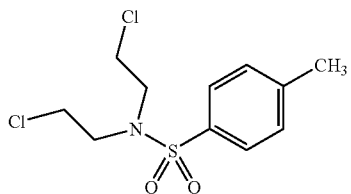
X-173
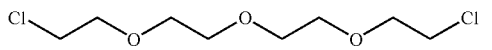
X-174
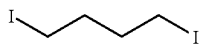
X-175
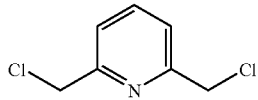
X-176
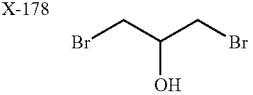
X-177
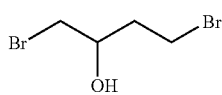
X-178
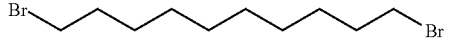
X-179
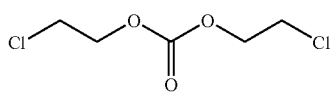
X-180
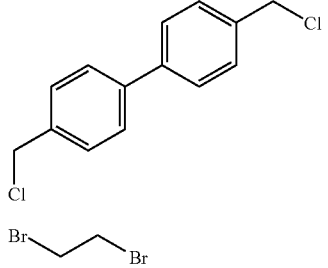
X-181
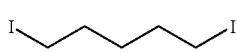
X-182
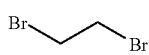
X-183
X-184
X-185

-continued

-continued
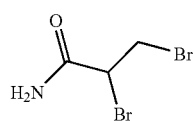 X-208
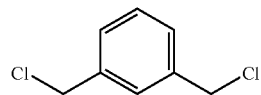 X-209
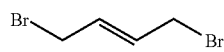 X-210
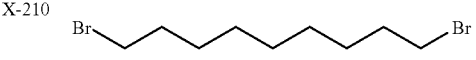 X-211
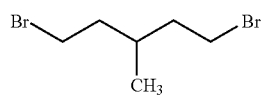 X-212
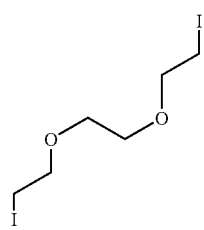 X-213
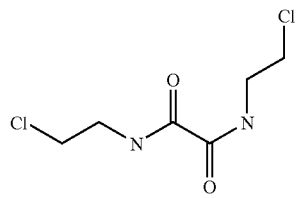 X-214
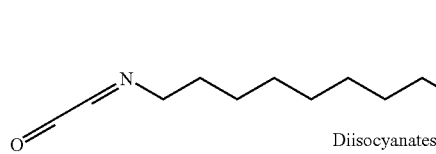 X-215
Diisocyanates
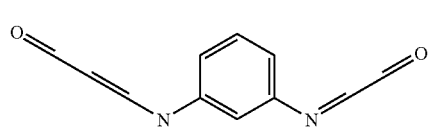 X-216
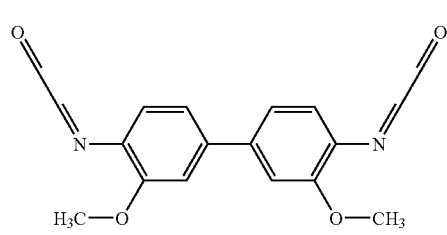 X-217
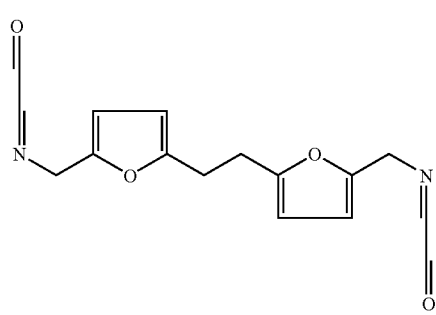 X-218
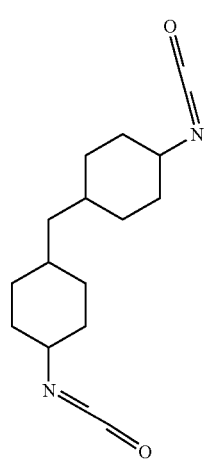 X-219

-continued
X-220
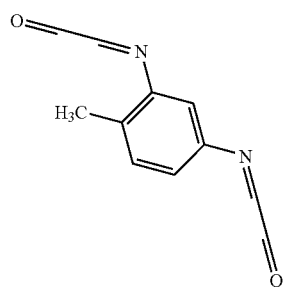
X-221
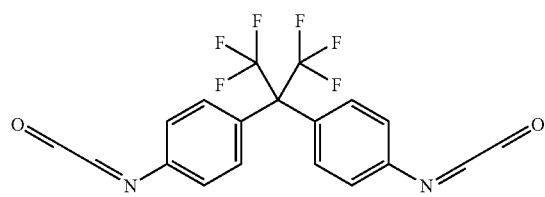
X-222
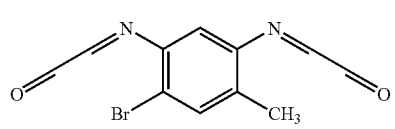
X-223
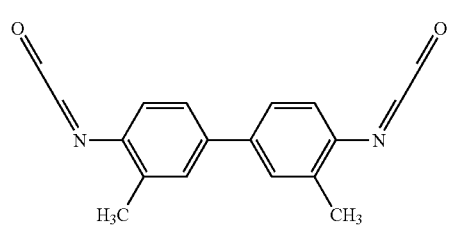
X-224
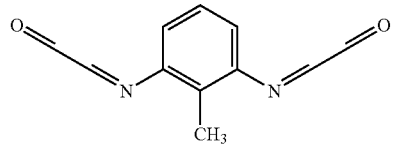
X-225
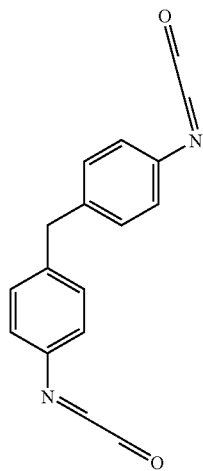
X-226
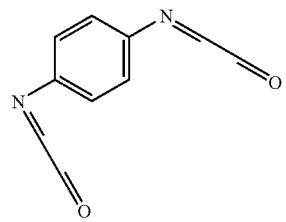
X-227
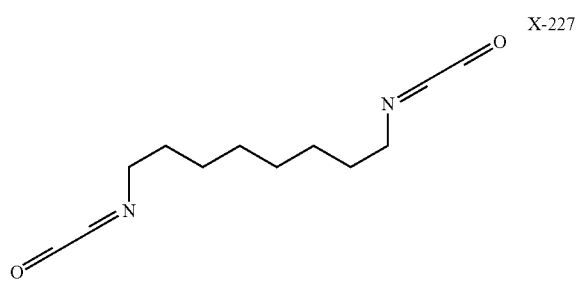
X-228
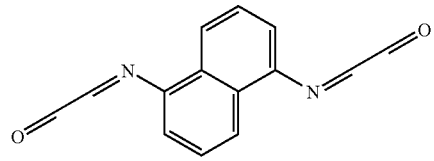
X-229
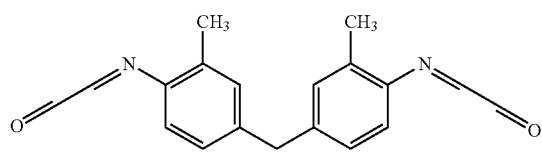
X-230
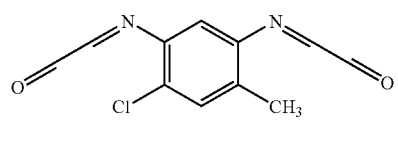

-continued
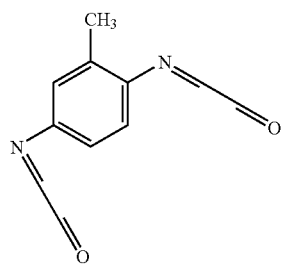
X-231
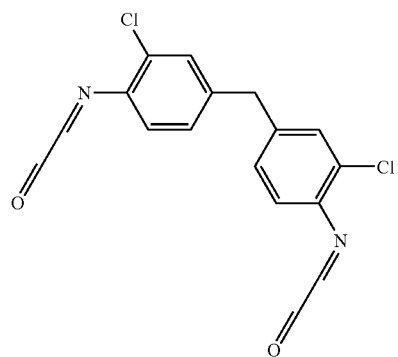
X-232
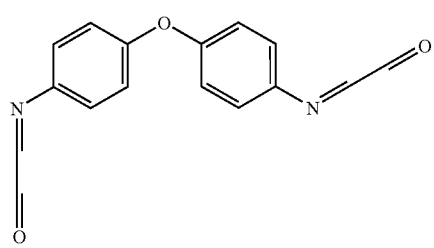
X-233
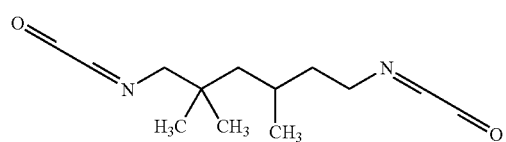
X-234
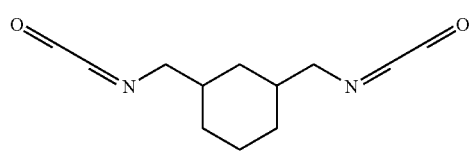
X-235
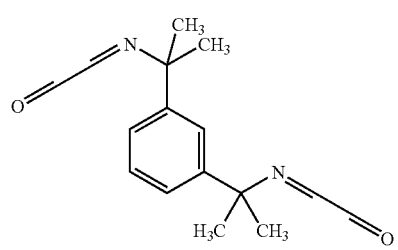
X-236
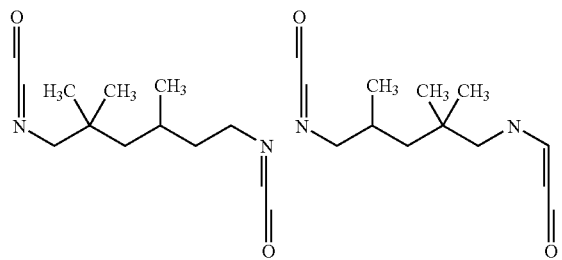
X-237
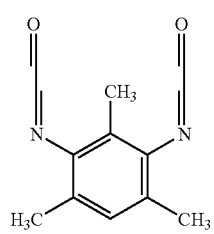
X-238

-continued
X-239
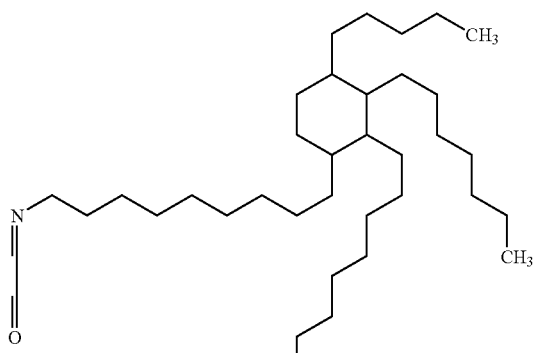
X-240
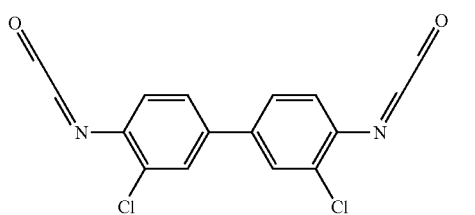
X-241
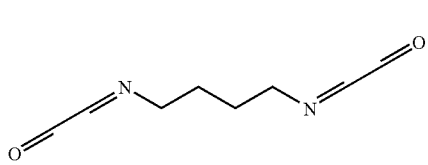
X-242
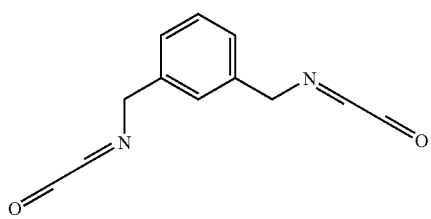
X-243
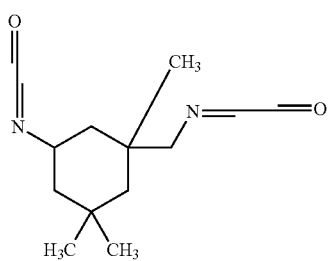
X-244
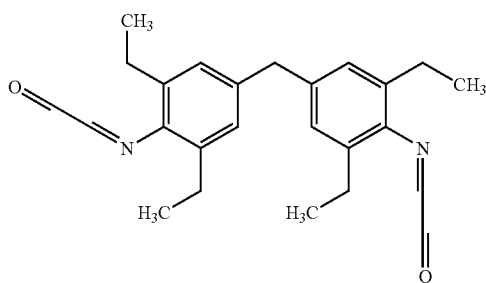
X-245
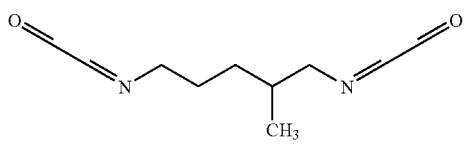
X-246
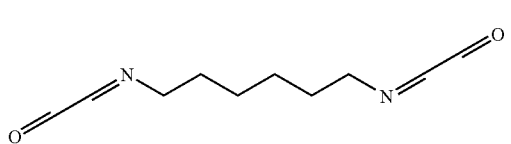
X-247
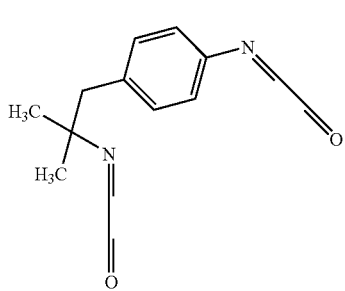
X-248
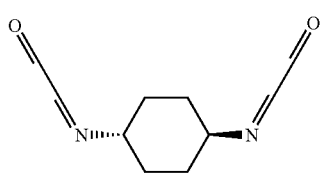

-continued
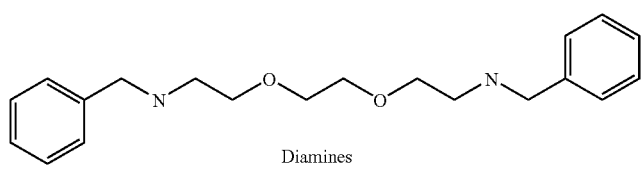
Diamines
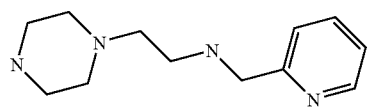 X-250
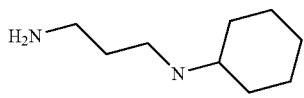 X-251
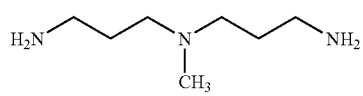 X-252
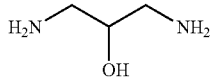 X-253
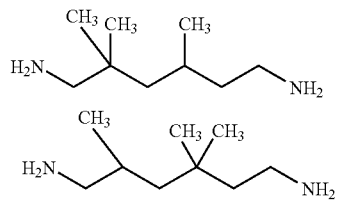 X-254
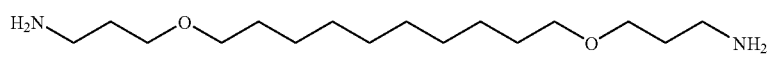 X-255
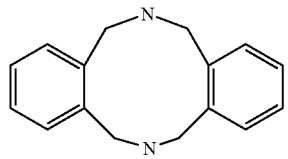 X-256
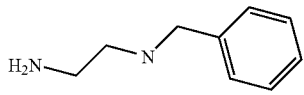 X-257
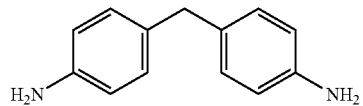 X-258
 X-259
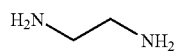 X-260
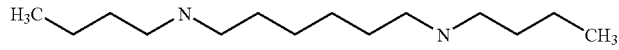 X-261
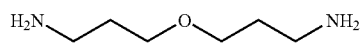 X-262
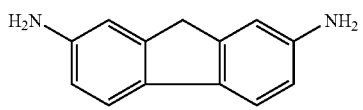 X-263
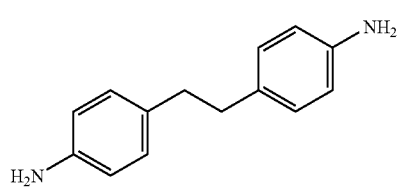 X-264
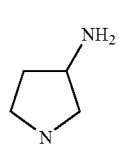 X-265
X-266

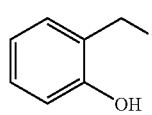 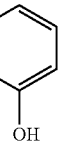 X-267
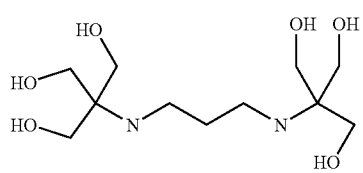 
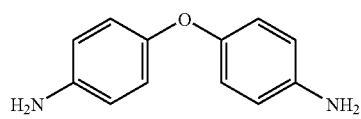
X-268 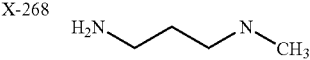 X-269
X-270 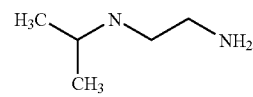 X-271
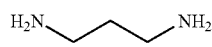
X-272 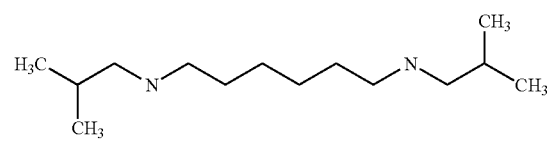 X-273
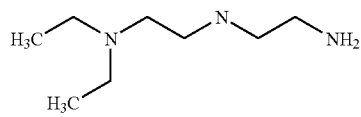 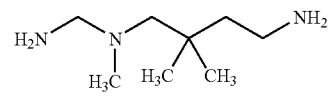 X-274 X-275
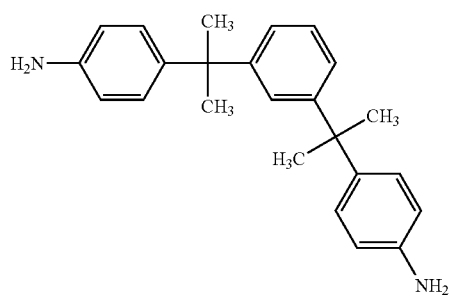 X-276 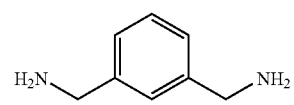 X-277
X-278 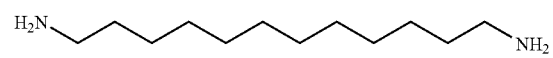 X-279
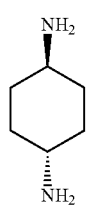
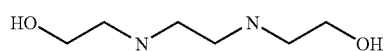 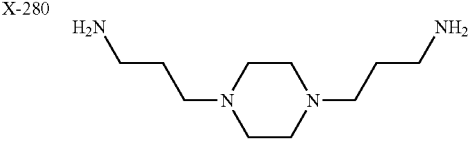 X-280 X-281

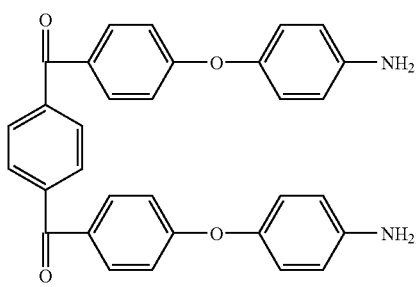
X-282
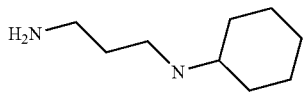
X-283
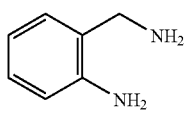
X-284
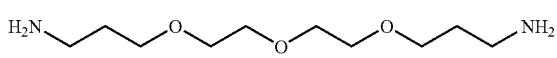
X-285
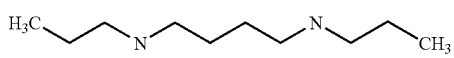
X-286
X-287
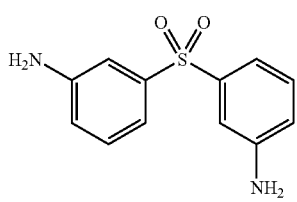
X-288
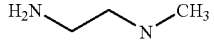
X-289
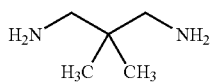
X-290
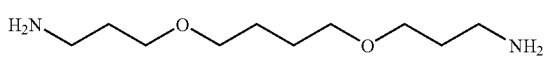
X-291
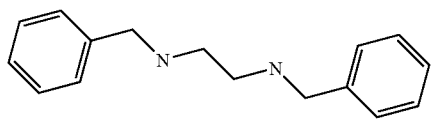
X-292
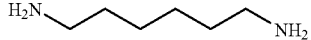
X-293
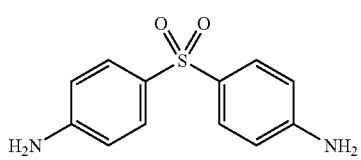
X-294
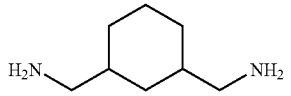
X-295
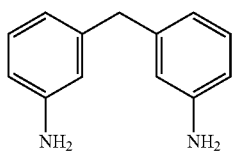
X-296
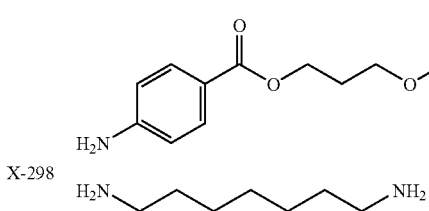
X-297
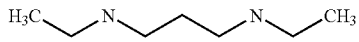
X-298
X-299
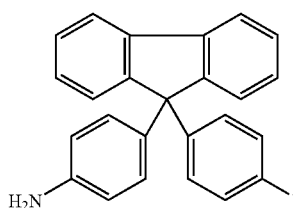
X-300
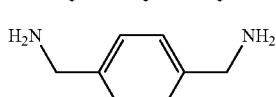
X-301
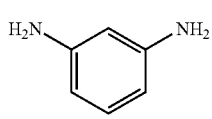
X-302

-continued
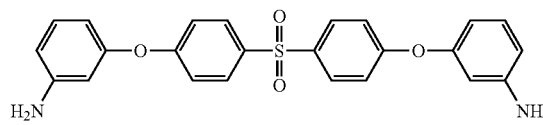
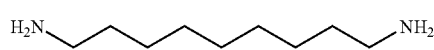
X-304
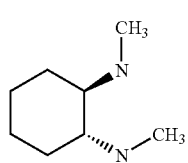
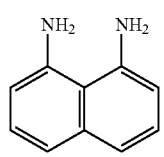
Chiral
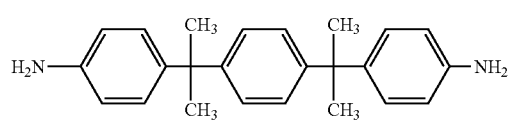
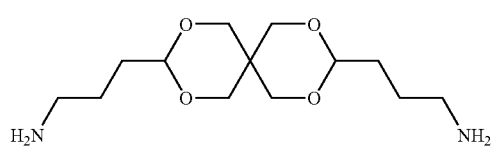
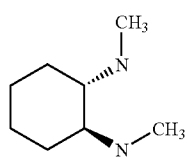
Chiral
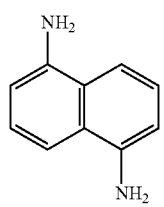
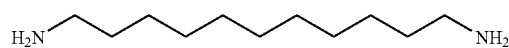
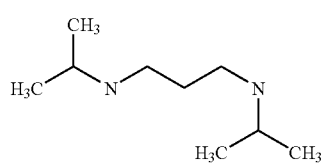
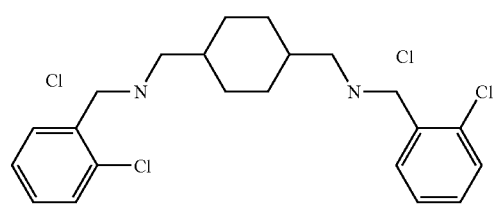
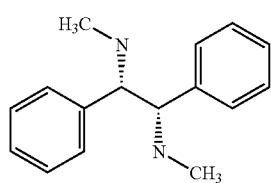
Chiral
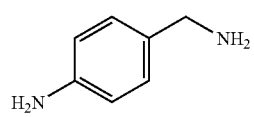
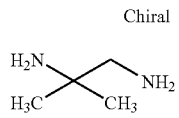
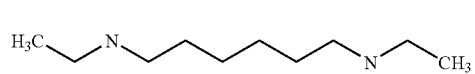

-continued
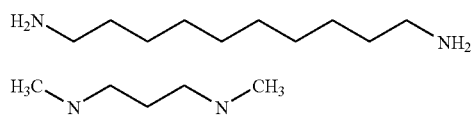
X-322
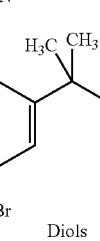
X-324
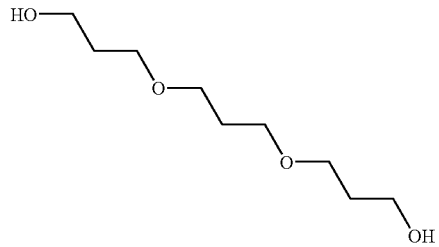
Diols
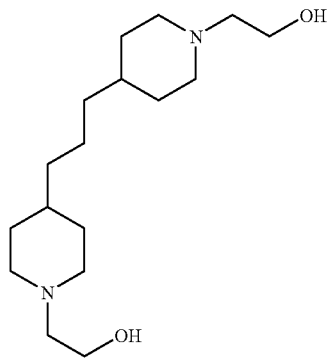
X-327
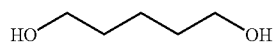
X-331
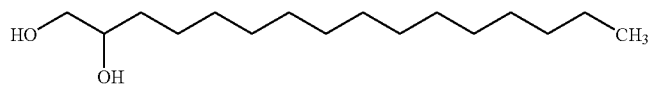
X-332
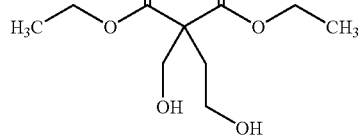
X-333
X-335
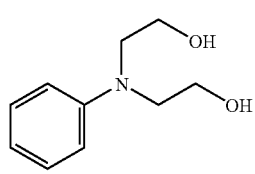

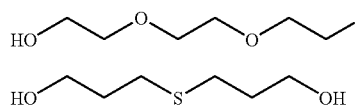
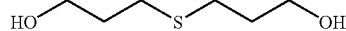
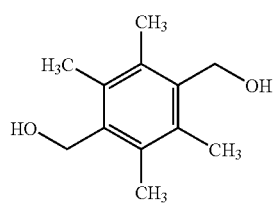
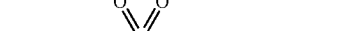
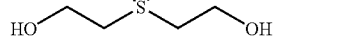
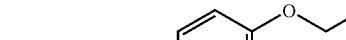
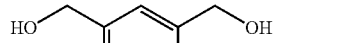
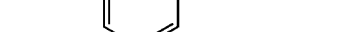
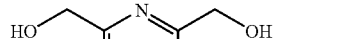
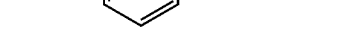

-continued
X-359 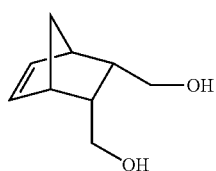 X-360 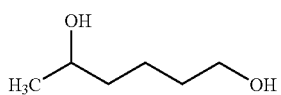
X-361 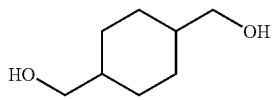 X-362 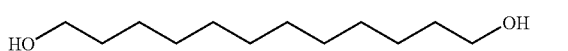
X-363 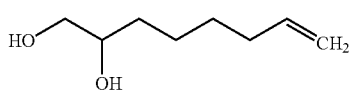 X-364 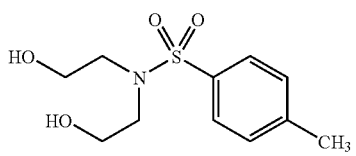
X-365 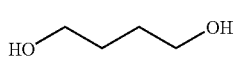 X-366 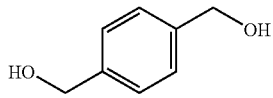
X-367 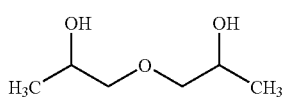 X-368 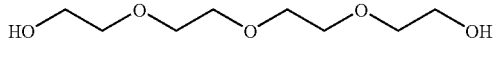
X-369 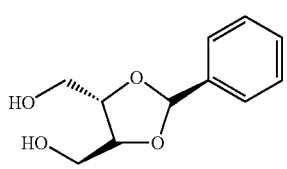 X-370 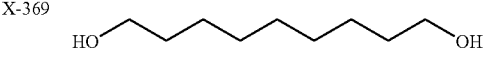
X-371 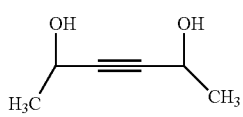 X-372 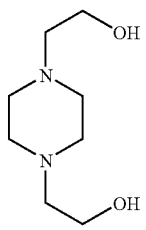
X-373 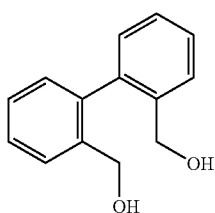
X-374 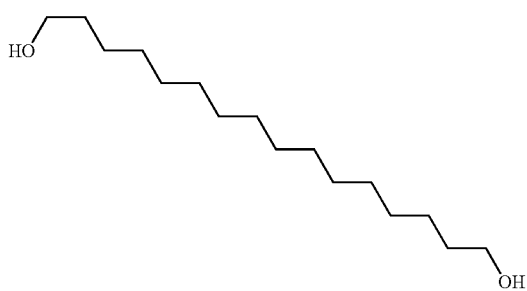

-continued
X-375 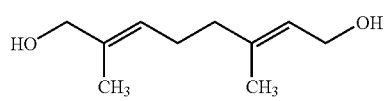 X-376
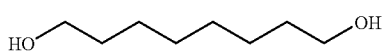
X-377 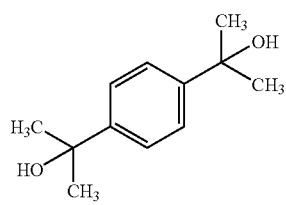 X-378
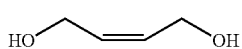
X-379 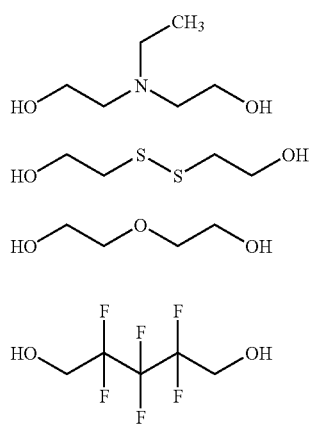 X-380
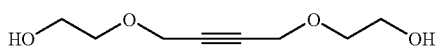
X-381 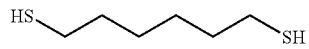 X-382
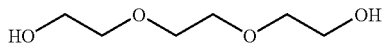
X-383  X-384
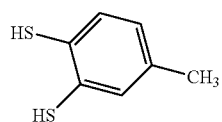 X-385 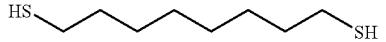 X-386
Dithiols
X-387 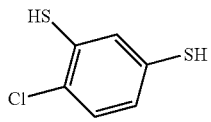 X-388
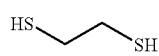 X-389 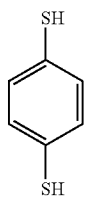 X-390
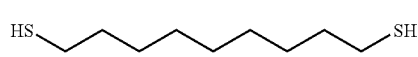 X-391 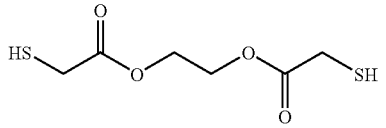 X-392
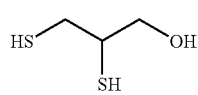 X-393 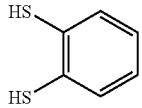 X-394
X-395 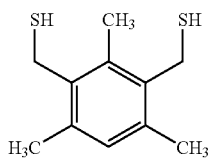 X-396

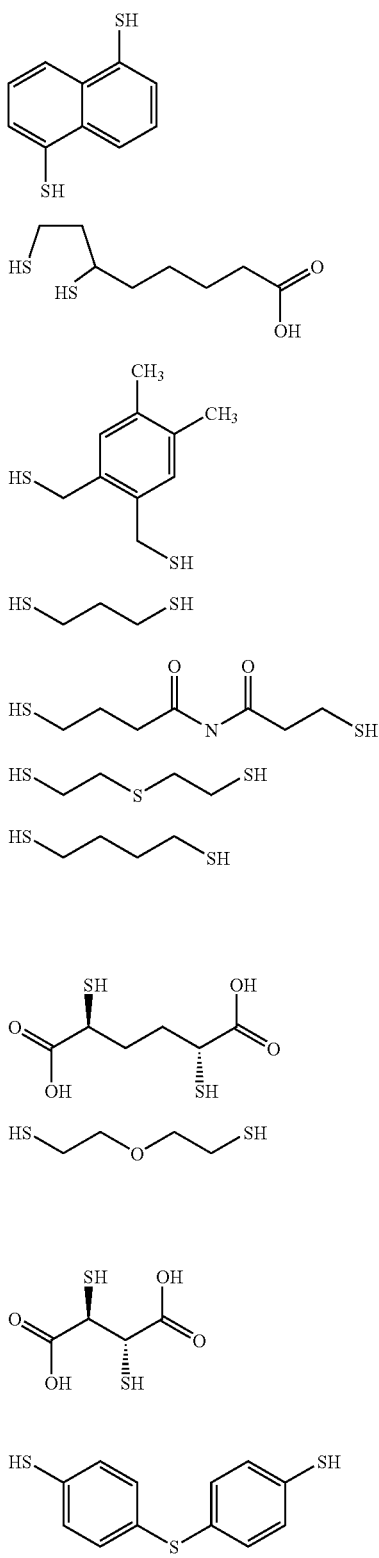

Ligand moieties suitable for coupling with the above compounds include those of formula III–XXIX as defined herein (and their preferred embodiments of formula A–AJ as defined herein). Accordingly, representative dimeric compounds of this invention include compounds having a first ligand, L-1, selected from a ligand moiety of formula III–XXX (or formula A–AJ); and a second ligand, L-2, and linker selected from the following (where L-2 is selected from a ligand moiety of formula III–XXX or of formula A–AJ):

| | | | | | |
|---|---|---|---|---|---|
| L-2/X-1- | L-2/X-2- | L-2/X-3- | L-2/X-4- | L-2/X-5- | L-2/X-6- |
| L-2/X-7- | L-2/X-8- | L-2/X-9- | L-2/X-10- | L-2/X-11- | L-2/X-12- |
| L-2/X-13- | L-2/X-14- | L-2/X-15- | L-2/X-16- | L-2/X-17- | L-2/X-18- |
| L-2/X-19- | L-2/X-20- | L-2/X-21- | L-2/X-22- | L-2/X-23- | L-2/X-24- |
| L-2/X-25- | L-2/X-26- | L-2/X-27- | L-2/X-28- | L-2/X-29- | L-2/X-30- |
| L-2/X-31- | L-2/X-32- | L-2/X-33- | L-2/X-34- | L-2/X-35- | L-2/X-36- |
| L-2/X-37- | L-2/X-38- | L-2/X-39- | L-2/X-40- | L-2/X-41- | L-2/X-42- |
| L-2/X-43- | L-2/X-44- | L-2/X-45- | L-2/X-46- | L-2/X-47- | L-2/X-48- |
| L-2/X-49- | L-2/X-50- | L-2/X-51- | L-2/X-52- | L-2/X-53- | L-2/X-54- |
| L-2/X-55- | L-2/X-56- | L-2/X-57- | L-2/X-58- | L-2/X-59- | L-2/X-60- |
| L-2/X-61- | L-2/X-62- | L-2/X-63- | L-2/X-64- | L-2/X-65- | L-2/X-66- |
| L-2/X-67- | L-2/X-68- | L-2/X-69- | L-2/X-70- | L-2/X-71- | L-2/X-72- |
| L-2/X-73- | L-2/X-74- | L-2/X-75- | L-2/X-76- | L-2/X-77- | L-2/X-78- |
| L-2/X-79- | L-2/X-80- | L-2/X-81- | L-2/X-82- | L-2/X-83- | L-2/X-84- |
| L-2/X-85- | L-2/X-86- | L-2/X-87- | L-2/X-88- | L-2/X-89- | L-2/X-90- |
| L-2/X-91- | L-2/X-92- | L-2/X-93- | L-2/X-94- | L-2/X-95- | L-2/X-96- |
| L-2/X-97- | L-2/X-98- | L-2/X-99- | L-2/X-100- | L-2/X-101- | L-2/X-102- |
| L-2/X-103- | L-2/X-104- | L-2/X-105- | L-2/X-106- | L-2/X-107- | L-2/X-108- |
| L-2/X-109- | L-2/X-110- | L-2/X-111- | L-2/X-112- | L-2/X-113- | L-2/X-114- |
| L-2/X-115- | L-2/X-116- | L-2/X-117- | L-2/X-118- | L-2/X-119- | L-2/X-120- |
| L-2/X-121- | L-2/X-122- | L-2/X-123- | L-2/X-124- | L-2/X-125- | L-2/X-126- |
| L-2/X-127- | L-2/X-128- | L-2/X-129- | L-2/X-130- | L-2/X-131- | L-2/X-132- |
| L-2/X-133- | L-2/X-134- | L-2/X-135- | L-2/X-136- | L-2/X-137- | L-2/X-138- |
| L-2/X-139- | L-2/X-140- | L-2/X-141- | L-2/X-142- | L-2/X-143- | L-2/X-144- |
| L-2/X-145- | L-2/X-146- | L-2/X-147- | L-2/X-148- | L-2/X-149- | L-2/X-150- |
| L-2/X-151- | L-2/X-152- | L-2/X-153- | L-2/X-154- | L-2/X-155- | L-2/X-156- |
| L-2/X-157- | L-2/X-158- | L-2/X-159- | L-2/X-160- | L-2/X-161- | L-2/X-162- |
| L-2/X-163- | L-2/X-164- | L-2/X-165- | L-2/X-166- | L-2/X-167- | L-2/X-168- |
| L-2/X-169- | L-2/X-170- | L-2/X-171- | L-2/X-172- | | |
| L-2/X-173- | L-2/X-174- | L-2/X-175- | L-2/X-176- | L-2/X-177- | L-2/X-178- |
| L-2/X-179- | L-2/X-180- | L-2/X-181- | L-2/X-182- | L-2/X-183- | L-2/X-184- |
| L-2/X-185- | L-2/X-186- | L-2/X-187- | L-2/X-188- | L-2/X-189- | L-2/X-190- |
| L-2/X-191- | L-2/X-192- | L-2/X-193- | L-2/X-194- | L-2/X-195- | L-2/X-196- |
| L-2/X-197- | L-2/X-198- | L-2/X-199- | L-2/X-200- | L-2/X-201- | L-2/X-202- |
| L-2/X-203- | L-2/X-204- | L-2/X-205- | L-2/X-206- | L-2/X-207- | L-2/X-208- |
| L-2/X-209- | L-2/X-210- | L-2/X-211- | L-2/X-212- | L-2/X-213- | L-2/X-214- |
| L-2/X-215- | L-2/X-216- | L-2/X-217- | L-2/X-218- | L-2/X-219- | L-2/X-220- |
| L-2/X-221- | L-2/X-222- | L-2/X-223- | L-2/X-224- | L-2/X-225- | L-2/X-226- |
| L-2/X-227- | L-2/X-228- | L-2/X-229- | L-2/X-230- | L-2/X-231- | L-2/X-232- |
| L-2/X-233- | L-2/X-234- | L-2/X-235- | L-2/X-236- | L-2/X-237- | L-2/X-238- |
| L-2/X-239- | L-2/X-240- | L-2/X-241- | L-2/X-242- | L-2/X-243- | L-2/X-244- |
| L-2/X-245- | L-2/X-246- | L-2/X-247- | L-2/X-248- | L-2/X-249- | L-2/X-250- |
| L-2/X-251- | L-2/X-252- | L-2/X-253- | L-2/X-254- | L-2/X-255- | L-2/X-256- |
| L-2/X-257- | L-2/X-258- | L-2/X-259- | L-2/X-260- | L-2/X-261- | L-2/X-262- |
| L-2/X-263- | L-2/X-264- | L-2/X-265- | L-2/X-266- | L-2/X-267- | L-2/X-268- |
| L-2/X-269- | L-2/X-270- | L-2/X-271- | L-2/X-272- | L-2/X-273- | L-2/X-274- |
| L-2/X-275- | L-2/X-276- | L-2/X-277- | L-2/X-278- | L-2/X-279- | L-2/X-280- |
| L-2/X-281- | L-2/X-282- | L-2/X-283- | L-2/X-284- | L-2/X-285- | L-2/X-286- |
| L-2/X-287- | L-2/X-288- | L-2/X-289- | L-2/X-290- | L-2/X-291- | L-2/X-292- |
| L-2/X-293- | L-2/X-294- | L-2/X-295- | L-2/X-296- | L-2/X-297- | L-2/X-298- |
| L-2/X-299- | L-2/X-300- | L-2/X-301- | L-2/X-302- | L-2/X-303- | L-2/X-304- |
| L-2/X-305- | L-2/X-306- | L-2/X-307- | L-2/X-308- | L-2/X-309- | L-2/X-310- |
| L-2/X-311- | L-2/X-312- | L-2/X-313- | L-2/X-314- | L-2/X-315- | L-2/X-316- |
| L-2/X-317- | L-2/X-318- | L-2/X-319- | L-2/X-320- | L-2/X-321- | L-2/X-322- |
| L-2/X-323- | L-2/X-324- | L-2/X-325- | L-2/X-326- | L-2/X-327- | L-2/X-328- |
| L-2/X-329- | L-2/X-330- | L-2/X-331- | L-2/X-332- | L-2/X-333- | L-2/X-334- |
| L-2/X-335- | L-2/X-336- | L-2/X-337- | L-2/X-338- | L-2/X-339- | L-2/X-340- |
| L-2/X-341- | L-2/X-342- | L-2/X-343- | L-2/X-344- | L-2/X-345- | L-2/X-346- |
| L-2/X-347- | L-2/X-348- | L-2/X-349- | L-2/X-350- | L-2/X-351- | L-2/X-352- |
| L-2/X-353- | L-2/X-354- | L-2/X-355- | L-2/X-356- | L-2/X-357- | L-2/X-358- |
| L-2/X-359- | L-2/X-360- | L-2/X-361- | L-2/X-362- | L-2/X-363- | L-2/X-364- |
| L-2/X-365- | L-2/X-366- | L-2/X-367- | L-2/X-368- | L-2/X-369- | L-2/X-370- |
| L-2/X-371- | L-2/X-372- | L-2/X-373- | L-2/X-374- | L-2/X-375- | L-2/X-376- |
| L-2/X-377- | L-2/X-378- | L-2/X-379- | L-2/X-380- | L-2/X-381- | L-2/X-382- |
| L-2/X-383- | L-2/X-384- | L-2/X-385- | L-2/X-386- | L-2/X-387- | L-2/X-388- |
| L-2/X-389- | L-2/X-390- | L-2/X-391- | L-2/X-392- | L-2/X-393- | L-2/X-394- |
| L-2/X-395- | L-2/X-396- | L-2/X-397- | L-2/X-398- | L-2/X-399- | L-2/X-400- |
| L-2/X-401- | L-2/X-402- | L-2/X-403- | L-2/X-404- | L-2/X-405- | L-2/X-406- |
| L-2/X-407- | L-2/X-408- | L-2/X-409- | L-2/X-410- | L-2/X-411- | L-2/X-412- |
| L-2/X-413- | L-2/X-414- | L-2/X-415- | L-2/X-416- | L-2/X-417- | L-2/X-418- |

Combinatorial Chemistry

The compounds of this invention can be prepared by efficient combinatorial and/or parallel synthesis methods. First, one identifies a ligand or mixture of ligands which each contain at least one reactive functionality and a library of linkers which each include at least two functional groups having complementary reactivity to at least one of the reactive functional groups of the ligand. Next one prepares a multimeric ligand compound library by combining at least two stoichiometric equivalents of the ligand or mixture of ligands with the library of linkers under conditions wherein the complementary functional groups react to form a covalent linkage between the linker and at least two of the ligands. The multimeric ligand compounds produced in the library can be assayed to identify multimeric ligand compounds which possess multibinding properties. The method can also be performed using a library of ligands and a linker or mixture of linkers.

The preparation of the multimeric ligand compound library can be achieved by either the sequential or concurrent combination of the two or more stoichiometric equivalents of the ligands with the linkers. The multimeric ligand compounds can be dimeric, for example, homomeric or heteromeric. A heteromeric ligand compound library can be prepared by sequentially adding a first and second ligand.

Each member of the multimeric ligand compound library can be isolated from the library, for example, by preparative liquid chromatography mass spectrometry (LCMS). The linker or linkers can be flexible linkers, rigid linkers, hydrophobic linkers, hydrophilic linkers, linkers of different geometry, acidic linkers, basic linkers, linkers of different polarization and/or polarizability or amphiphilic linkers. The linkers can include linkers of different chain lengths and/or which have different complementary reactive groups. In one embodiment, the linkers are selected to have different linker lengths ranging from about 2 to 100 Å. The ligand or mixture of ligands can have reactive functionality at different sites on the ligands. The reactive functionality can be, for example, carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof, as long as the reactive functionality on the ligand is complementary to at least one of the reactive groups on the linker so that a covalent linkage can be formed between the linker and the ligand.

A library of multimeric ligand compounds can thus be formed which possesses multivalent properties.

Multimeric ligand compounds possessing multibinding properties can be identified in an iterative method by preparing a first collection or iteration of multimeric compounds by contacting at least two stoichiometric equivalents of the ligand or mixture of ligands which target the protein kinases with a linker or mixture of linkers, where the ligand or mixture of ligands includes at least one reactive functionality and the linker or mixture of linkers includes at least two functional groups having complementary reactivity to at least one of the reactive functional groups of the ligand. The ligand(s) and linker(s) are reacted under conditions which form a covalent linkage between the linker and at least two of the ligands. The first collection or iteration of multimeric compounds can be assayed to assess which if any of the compounds possess multibinding properties. The process can be repeated until at least one multimeric compound is found to possess multibinding properties. By evaluating the particular molecular constraints which are imparted or are consistent with imparting multibinding properties to the multimeric compound or compounds in the first iteration, a second collection or iteration of multimeric compounds which elaborates upon the particular molecular constraints can be assayed, and the steps optionally repeated to further elaborate upon said molecular constraints. For example, the steps can be repeated from between 2 and 50 times, more preferably, between 5 and 50 times.

Utility

The compounds of this invention inhibit or modulate the activity of protein kinases which are known to mediate numerous diseases or medical disorders, especially hyperproliferative disorders. Accordingly, the compounds and pharmaceutical compositions of the invention are useful for treating disorders mediated by protein kinases.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like.

In therapeutic or prophylactic applications, compositions are administered to a patient already suffering from, or disposed toward, for example, any of the diseases or medical disorders mediated by protein kinases, in an amount sufficient to at least partially reduce the symptoms. Amounts effective for this use will depend on the judgment of the attending clinician depending upon factors such as the degree or severity of the disorder in the patient, the age, weight and general condition of the patient, and the like. The pharmaceutical compositions of this invention may contain more than one compound of the present invention.

As noted above, the compounds administered to a patient are in the form of pharmaceutical compositions described above which can be administered by a variety of routes including oral, rectal, transdermal, subcutaneous, intravenous, intramusclar, etc. These compounds are effective as both injectable and oral deliverable pharmaceutical compositions. Such compositions are prepared in a manner well known in the pharmaceutical art and comprise at least one active compound.

The compounds of this invention can also be administered in the form of pro-drugs, i.e., as derivatives which are converted into a biologically active compound in vivo. Such pro-drugs will typically include compounds in which, for example, a carboxylic acid group, a hydroxyl group or a thiol group is converted to a biologically liable group, such as an ester, lactone or thioester group which will hydrolyze in vivo to reinstate the respective group.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ML dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

A formulation may be prepared as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

EXAMPLES

The following preparative and biological examples are offered to illustrate this invention and are not to be construed in any way as limiting the scope of this invention. Unless otherwise stated, all temperatures are in degrees Celsius.

In the examples below, the following abbreviations have the following meanings. If an abbreviation is not defined, it has its generally accepted meaning.

| | |
|---|---|
| Å = | Angstroms |
| cm = | centimeter |
| DCC = | dicyclohexyl carbodiimide |
| DMF = | N,N-dimethylformamide |
| DMSO = | dimethylsulfoxide |
| EDTA = | ethylenediaminetetraacetic acid |
| g = | gram |
| HPLC = | high performance liquid chromatography |
| MEM = | minimal essential medium |
| mg = | milligram |
| MIC = | minimum inhibitory concentration |
| min = | minute |
| mL = | milliliter |
| mm = | millimeter |
| mmol = | millimol |
| N = | normal |
| THF = | tetrahydrofuran |
| μL = | microliters |
| μm = | microns |

Example 1 (See FIG. 1)

Preparation of a Formula I Compound wherein p is 2, q is 1, and the Ligand, L, is 2,7-diamino-6-(2,6-dichlorophenyl)pyrido[2,3-d]pyrimidine (1, $R_1$=H; $Ar_1$=2,6-dichlorophenyl) Linked to X via the 7-amine Through a Urea Group.

Sodium hydride (3.3 mmols) is added in portions to a stirred mixture of 2,7-diamino-6-(2,6-dichlorophenyl)pyrido[2,3-d]pyrimidine (1, $R_1$=H; $Ar_1$=—$C_6H_3$-(2,6)-$Cl_2$; 3 mmols) (J. M. Hamby, et. al., J. Med. Chem., 1997, 40, 2296–2303) and DMF (5 mL) wider an inert atmosphere. After stirring for one hour at room temperature, 1,4-diisocyanatobutane (1.5 mmols) is added and the mixture is stirred an additional 18 hours. The reaction mixture is filtered and the solids are washed with DMF. The combined filtrate is concentrated by evaporation under reduced pressure. Water is added to the residue and the solids are collected by filtration, washed with water and a small portion of ether, and air dried. The solids are purified by chromatography, giving the desired Formula I compound 2 wherein R=—$(CH_2)_4$—; $R_1$=H; and $Ar_1$=—$C_6H_3$-(2,6)-$Cl_2$.

Example 2 (See FIG. 1)

Preparation of a Formula I Compound wherein p is 2, q is 1, and the Ligand, L, is 2-amino-6-(2,6-dichlorophenyl)pyrido[2,3-d]pyrimidin-7-one (3, $R_1$=H; $Ar_1$=2,6-dichlorophenyl) Linked to X via the 2-amino Group.

A mixture of 2-amino-6-(2,6-dichlorophenyl)pyrido[2,3-d]pyrimidin-7-one (3, $R_1$=H; $Ar_1$=—$C_6H_3$-(2,6)-$Cl_2$; 2 mmols) (S. R. Klutchko, et. al., J. Med. Chem. 1998, 41, 3276–3292), sulfamic acid (4 mmols), and 1,4-diaminobenzene (1 mmol) and DMF (1 mL) is stirred and heated to 150° C. under an inert atmosphere. The reaction is monitored by tlc and, when complete, is cooled to room temperature and aqueous $Na_2CO_3$ (10 mL) is added. The mixture is extracted with $CH_2Cl_2$, the organic extract is washed with half-saturated saline, dried ($Na_2SO_4$), filtered and concentrated under reduced pressure to give the crude product. The desired Formula I compound (4, wherein R=—$C_6H_4$—; $R_1$=H; $Ar_1$=—$C_6H_3$-(2,6)-$Cl_2$) is obtained by purification of the crude product with the use of HPLC.

Example 3 (See FIG. 1)

Preparation of a Formula I Compound wherein p is 2, q is 1, and the Ligand, L, is 4-amino-1-(1,1-dimethyl)ethyl-3-(4-hydroxyphenyl)pyrazolo[3,4-d]pyrimidine (5, where $R_3$=$R_4$=H; $R_5$=—$C(CH_3)_3$) linked through a phenoxy ether bond to the linker X.

Diethyl azodicarboxylate (2 mmol) is added dropwise via a syringe to a stirred solution of triphenylphosphine (2 mmol) in THF (5 mL) under an inert atmosphere and at room temperature. To this is added a solution of 4-amino-1-(1,1-dimethyl)ethyl-3-(4-hydroxyphenyl)pyrazolo[3,4-d]pyrimidine (5, where $R_3$=$R_4$=H; $R_5$=—$C(CH_3)_3$; 2 mmols) (prepared by the method of U. Hanefeld, et. al., J. Chem. Soc., Perkin Trans. 1, 1996, 1545–1552) and hexane-1,6-diol (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired Formula I compound 6 wherein R=—($CH_2$)$_6$—; $R_3$=$R_4$=H; and $R_5$=—C($CH_3$)$_3$.

Example 4 (See FIG. 1)

Preparation of a Formula I Compound wherein p is 2, q is 1, and the ligand, L, is Damnacanthal (7, $R_6$=—CHO; $R_7$=H) Linked through a Phenoxy Ether Bond to the Linker X.

Step 1. Diethyl azodicarboxylate (2 mmol) is added dropwise via a syringe to a stirred solution of triphenylphosphine (2 mmol) in THF (5 mL) under an inert atmosphere and at room temperature. To this is added a solution of lucidin-2,3-diacetate (7, R=—$CH_2$OAc; $R_7$=—Ac; 2 mmols) (N. R. Ayyangar, et. al., Tetrahedron, 1959, 6, 331–337) and butane-1,4-diol (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired compound 8 wherein R=—($CH_2$)$_4$—; $R_6$=—$CH_2$OAc; $R_7$=—Ac.

Step 2. A solution of 8 [R=—($CH_2$)$_4$—; $R_6$=—$CH_2$OAc; $R_7$=—Ac; 2 mmol] in 5% KOH in $H_2$O (5 mL) is stirred under an inert atmosphere at room temperature. The reaction is followed by tlc and when complete, is cooled in an ice-water bath, carefully acidified by the addition of cold 1 M HCl, diluted with EtOAc and washed several times with water and brine. The organic layer is dried ($Na_2SO_4$), filtered and concentrated under reduced pressure to give the crude product. The desired product 9 [R=—($CH_2$)$_4$—; $R_6$=—$CH_2$OH; $R_7$=—H] is obtained by purification of the crude product by use of HPLC.

Step 3. A solution of 9 [R=—($CH_2$)$_4$—; $R_6$=—$CH_2$OH; $R_7$=—H; 1 mmol] in toluene (5 mL) is stirred with activated manganese dioxide (0.5 g) and the mixture is heated to reflux temperature. The reaction is monitored by tlc and when complete, the mixture is cooled to room temperature, filtered through Celite and the filtrate concentrated under reduced pressure. The crude reaction product is purified by HPLC, giving the desired Formula I compound 10 [R=—($CH_2$)$_4$—].

Figure 2:
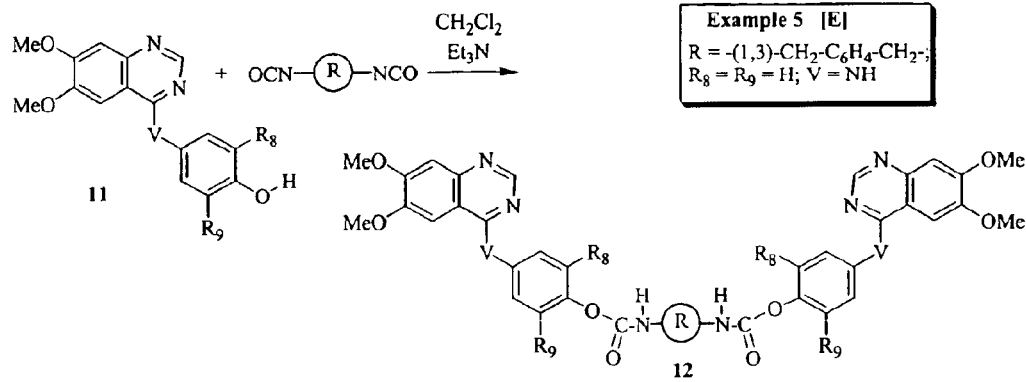
FIG. 2 is a schematic representation of the methods of Examples 5, 6, and 7.
Figure 2:
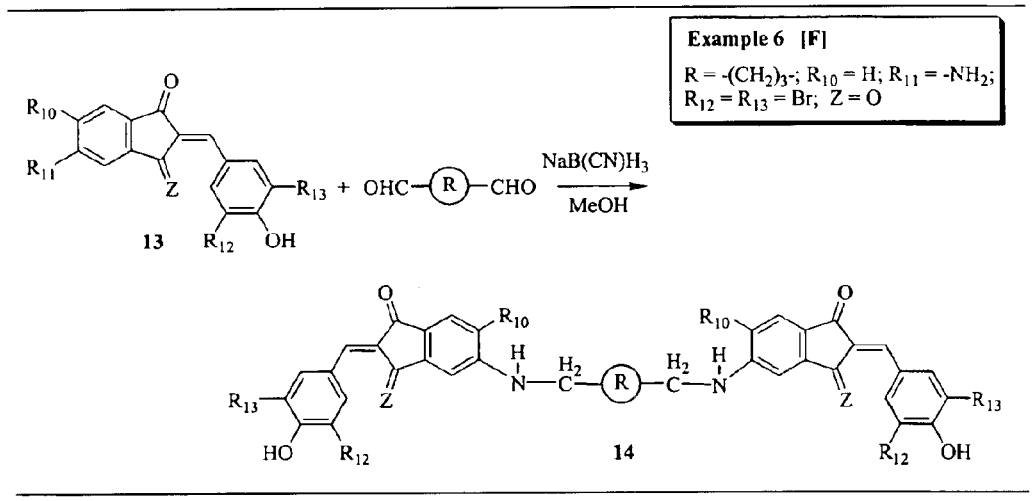
Figure 2:
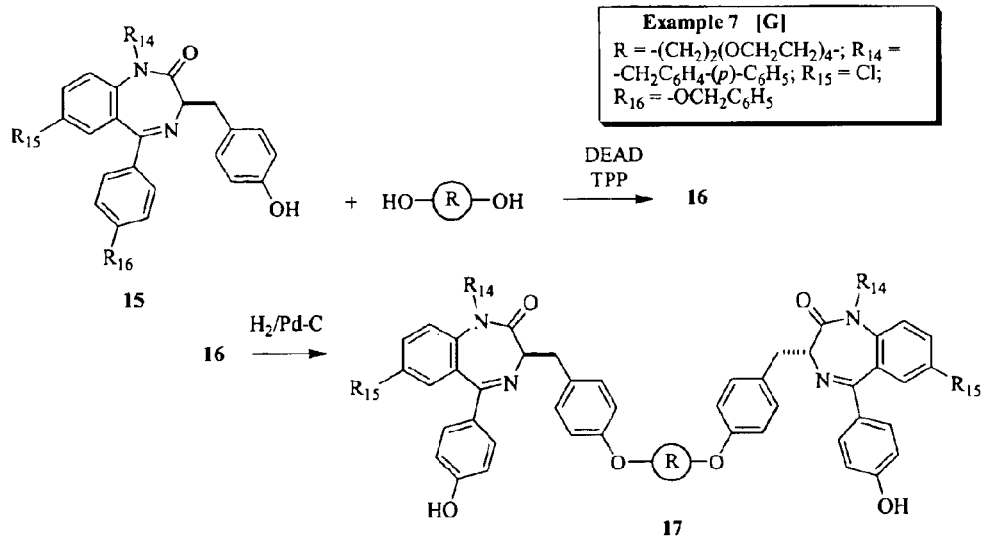

Example 5 (See FIG. 2)

Preparation of a Formula I Compound wherein p is 2, q is 1, and the Ligand, L, is 6,7-dimethoxy-N-(4-hydroxyphenyl)-4-quinazolinamine (11, $R_8$=$R_9$=H; V=NH) Linked Through a Urethane Bond to the Linker X.

A solution of 1,3-bis(isocyanatomethyl)benzene (1 mmol) in $CH_2Cl_2$ (5 mL) containing $Et_3$N (0.2 mL) is stirred and cooled in an ice-water bath under an inert atmosphere. To this is added dropwise a solution of 6,7-dimethoxy-N-(4-hydroxyphenyl)-4-quinazolinamine (11, $R_8$=$R_9$=H; V=NH; 2 mmols) (M. R. Myers, et. al., Bioorg. Med. Chem Lett. 1997, 7, 417–420) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired Formula I compound 12, wherein R=-(1,3)—$CH_2$—$C_6H_4$—$CH_2$—; $R_8$=$R_9$=H; V=NH is obtained by purification of the crude product with the use of HPLC.

Example 6 (See FIG. 2)

Preparation of a Formula I Compound wherein p is 2, q is 1, and the Ligand, L, is 5-amino-2-[(3,5-dibromo-4-hydroxyphenyl)methylene]-1H-indene-1,3(2H)-dione (13, $R_{10}$=H; $R_{11}$=—$NH_2$; $R_{12}$=$R_{13}$=Br; Z=O) linked through an amine bond to the linker X.

A solution of 5-amino-2-[(3,5-dibromo-4-hydroxyphenyl)methylene]-1H-indene-1,3(2H)-dione (13, $R_{10}$=H; $R_{11}$=—$NH_2$; $R_{12}$=$R_{13}$=Br; Z=O; 2 mmols) (J. L. Bullington, et. al., Bioorg. Med. Chem. Lett. 1998, 8, 2489–2494) in methanol (8 mL) is acidified with acetic acid to pH 6.5 (pH meter) under a nitrogen atmosphere. Glutaric dialdehyde (1 mmol) is added neat followed by sodium cyanoborohydride (3.1 mmols). The course of the reaction is followed by thin layer chromatography. After reaction occurs, the reaction solution is quenched in water and the aqueous mixture is acidified with aqueous HCl. The mixture is extracted with $CH_2Cl_2$, the organic extracts are washed with half-saturated saline, dried ($Na_2SO_4$), filtered and concentrated under reduced pressure to give the crude product. The desired Formula I compound (14, wherein R=—($CH_2$)$_3$—; $R_{10}$=H; $R_{12}$=$R_{13}$=Br; Z=O) is obtained by purification of the crude product with the use of HPLC.

Example 7 (See FIG. 2)

Preparation of a Formula I Compound wherein p is 2, q is 1, and the Ligand, L, is 7-chloro-1,3-dihydro-5-(4-hydroxyphenyl)-3-(4-hydroxyphenyl)methyl-1-(4-phenylphenyl)methyl-2H-1,4-benzodiazepin-2-one (15, where $R_{14}$=—$CH_2C_6H_4$-(p)-$C_6H_5$; $R_{15}$=Cl; $R_{16}$=—$CH_2C_6H_5$) Linked Through a Phenoxy Ether Bond to the Linker X.

Step 1. Diethyl azodicarboxylate (2 mmol) is added dropwise via a syringe to a stirred solution of triphenylphosphine (2 mmol) in THF (5 mL) under an inert atmosphere and at room temperature. To this is added a solution of 7-chloro-1,3-dihydro-5-(4-hydroxyphenyl)-3-(4-hydroxyphenyl)methyl-1-(4-phenylphenyl)methyl-2H-1,4-benzodiazepin-2-one (15; $R_{14}$=—$CH_2C_6H_4$-(p)-$C_6H_5$; $R_{15}$=Cl; $R_{16}$=—$CH_2C_6H_5$; 2 mmols) (prepared by the methods of B. A. Bunnin, et. al., Methods Enzymol. 1996, 267, 448–465) and penta(ethylene glycol) (1 mmol) in THF (1 mL). The resulting solution is stirred at RT and the progress of the reaction is followed by tlc. After reaction occurs, solvent is removed by evaporation under reduced pressure and the residue is purified by HPLC, giving compound 16 wherein $R_{14}$=—$CH_2C_6H_4$-(p)-$C_6H_5$; $R_{15}$=Cl; and $R_{16}$=—$CH_2C_6H_5$.

Step 2. Ammonium formate (160 mg, 2.5 mmol) and 10% Pd/C (50 mg) are added to a solution of the compound (16, $R_{14}$=—$CH_2C_6H_4$-(p)-$C_6H_5$; $R_{15}$=Cl; and $R_{16}$=—$CH_2C_6H_5$; 2 mmol) from the preceding reaction in methanol (4 mL) and THF (2 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. $NaHCO_3$ and with half-saturated brine, then dried ($Na_2SO_4$), filtered and concentrated underreduced pressure to give the crude product. The desired Formula I compound (17, R=—($CH_2$)$_2$($OCH_2$)$_4$—; $R_{14}$=—$CH_2C_6H_4$-(p)-$C_6H_5$; and $R_{15}$=Cl;) is obtained by purification of the crude product with HPLC.

Figure 3:
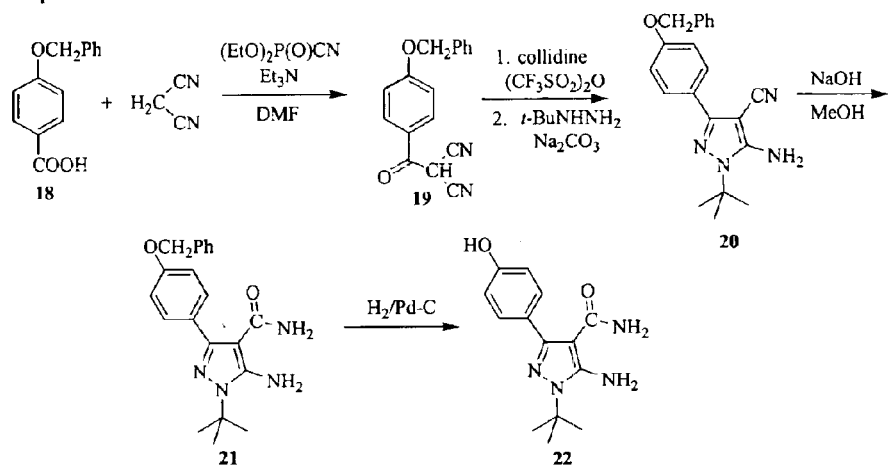
FIG. 3 is a schematic representation of the methods of Preparation 1 and Example 8.
Figure 3:
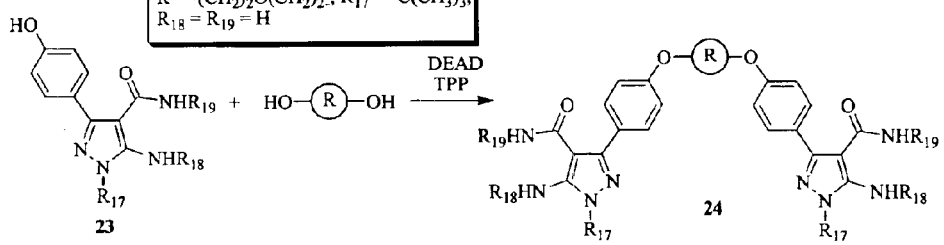

Preparation 1 (See FIG. 3)

Preparation of 5-amino-1-(1,1-dimethylethyl)-3-(4-hydroxyphenyl)pyrazole-4-carboxamide (22).

The procedures of P. D. Davis, et. al., WO 97/40019 (30 Oct. 1997) are followed.

Step 1. Diethylcyanophosphonate (5 mmol) and triethylamine (15 mmol) are added to a solution of 4-benzyloxybenzoic acid (18, 5 mmol) and malononitrile (4.8 mmol) in DMF (10 mL) stirred at 0° C. After the addition is complete, stirring is continued as the solution is allowed to warm to ambient temperature. Progress of the reaction is followed by tlc and when complete, the reaction solution is concentrated under reduced pressure. The residue is taken up in EtOAc and washed with cold 1N HCl and then with aq. $NaHCO_3$. The alkaline bicarbonate wash is acidified with 6N HCl and the mixture is extracted with EtOAc. The combined EtOAc extract solutions are dried ($Na_2SO_4$), filtered and concentrated under reduced pressure, giving the desired 4-benzyloxybenzoylmalononitrile 19. The product is used in the next step without further purification.

Step 2. Collidine (6 mmol) and trifluoromethanesulfonic anhydride (3.5 mmol) are added to a solution of 19 (3 mmol) in $CH_2Cl_2$ (20 mL) and the mixture is stirred at room temperature. The reaction is monitored by tlc and when complete solvent is removed under reduced pressure. The residue is dissolved in tetrahydrofuran (25 mL), a suspension of t-butyl hydrazine hydrochloride (3 mmol) and $Na_2CO_3$ (4 mmol) in THF is added and the mixture is stirred and heated to reflux temperature. The reaction is followed by tlc and when complete, the mixture is cooled and solvent removed under reduced pressure. The residue is partitioned between EtOAc and cold 1N HCl, the layers are separated and the organic layer is washed with water and with half-saturated brine, dried ($Na_2SO_4$), filtered and concentrated. The crude residue is purified by chromatography, giving the cyanopyrazole 20.

Step 3. A solution of 20 (2 mmol) in ethanol (15 mL) and aqueous 10M NaOH (3 mL) is stirred and heated to reflux temperature. The progress of the reaction is followed by tlc and when complete, the solution is cooled and the ethanol is removed by evaporation under reduced pressure. Water is added to remaining mixture and the precipitated solid is collected and purified by crystallization, giving 5-amino-1-(1,1-dimethylethyl)-3-(4-benzyloxyphenyl)pyrazole-4-carboxamide (21).

Step 4. Ammonium formate (160 mg, 2.5 mmol) and 10% Pd/C (50 mg) are added to a solution of 21 (2 mmol) from the preceding reaction in methanol (4 mL) and THF (2 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. $NaHCO_3$ and with half-saturated brine, then dried ($Na_2SO_4$), filtered and concentrated under reduced pressure to give the crude product. The desired 5-amino-1-(1,1-dimethylethyl)-3-(4-hydroxyphenyl)pyrazole-4-carboxamide 22 is obtained by purification of the crude product with HPLC.

Example 8 (See FIG. 3)

Preparation of a Formula I Compound wherein p is 2, q is 1, and the Ligand, L, is 5 amino-1-(1,1-dimethylethyl)-3-(4-hydroxyphenyl)pyrazole-4-carboxamide (23, where $R_{17}$=—C($CH_3$)$_3$; $R_{18}$=$R_{19}$=H) Linked through a Phenoxy Ether Bond to the Linker X.

Diethyl azodicarboxylate (2 mmol) is added dropwise via a syringe to a stirred solution of triphenylphosphine (2 mmol) in THF (5 mL) under an inert atmosphere and at room temperature. To this is added a solution of 5-amino-1-(1,1-dimethylethyl)-3-(4-hydroxyphenyl)pyrazole-4-carboxamide (23, where $R_{17}$=—C($CH_3$)$_3$; $R_{18}$=$R_{19}$=H; 2 mmols) and di(ethylene glycol) (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired Formula I compound 24 wherein R=—($CH_2$)$_2$O($CH_2$)$_2$—; $R_{17}$=—C($CH_3$)$_3$; $R_{18}$=$R_{19}$=H.

Figure 4:
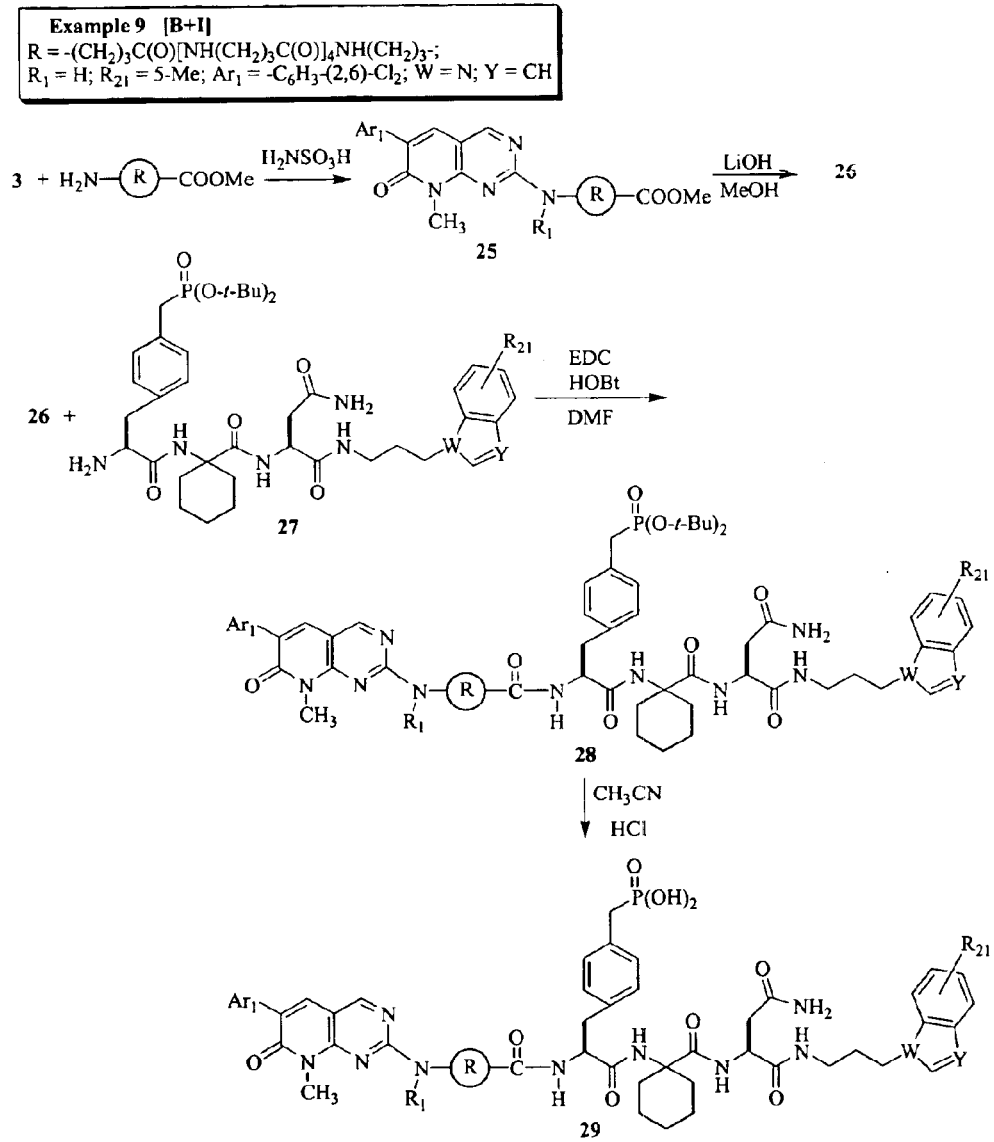
FIG. 4 is a schematic representation of the methods of Example 9.

Example 9 (See FIG. 4)

Preparation of a Formula I Compound wherein p is 2, q is 1, one Ligand, $L_1$, is 2-amino-6-(2,6-dichlorophenyl)pyrido[2,3-d]pyrimidin-7-one (3, $R_1$=H; $Ar_1$=2,6-dichlorophenyl) Linked to X via the 2-amino Group and a Second Ligand, $L_2$, is the Compound 27 (where $R_{21}$=5-$CH_3$; W=N; Y=CH) Linked via an Amide Bond to the Linker X.

Step 1. A mixture of 2-amino-6-(2,6-dichlorophenyl)pyrido[2,3-d]pyrimidin-7-one (3, $R_1$=H; $Ar_1$=—$C_6H_3$-(2,6)-$Cl_2$; 2 mmols) (S. R. Klutchko, et. al.), sulfamic acid (4 mmols), and (abu)$_6$, methyl ester, (where abu is γ-aminobutyric acid; 2 mmols) (A. A. Profit, et. al., J. Am. Chem. Soc. 1999, 121, 280–283) and DMF (2 mL) is stirred and heated to 150° C. under an inert atmosphere. The reaction is monitored by tlc and, when complete, is cooled to room temperature and aqueous $Na_2CO_3$ (10 mL) is added. The mixture is extracted with $CH_2Cl_2$, the organic extract is washed with half-saturated saline, dried ($Na_2SO_4$), filtered and concentrated under reduced pressure to give the crude product. Pure compound 25, wherein R=—($CH_2$)$_3$C(O)[NH($CH_2$)$_3$C(O)]$_4$NH($CH_2$)$_3$—; $R_1$=H; $Ar_1$=—$C_6H_3$-(2,6)-$Cl_2$, is obtained by purification of the crude product with the use of HPLC.

Step 2. A solution of the product (25, R=—($CH_2$)$_3$C(O)[HN($CH_2$)$_3$C(O)]$_4$NH—($CH_2$)$_3$—; $R_1$=H; $Ar_1$=—$C_6H_3$-(2,6)-$Cl_2$; 2 mmols) of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed by lyophilization and the dry, crude carboxylic acid 26 is used directly in the next reaction.

Step 3. The product 26 (2 mmols) from the preceding experiment is carefully dried and placed in a solution in dry DMF (5 mL) with the amine 140, ($R_{21}$=5-$CH_3$; W=N; and Y=CH; 2 mmols) (for preparation of 140, see Preparation 8) and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried and concentrated under reduced pressure. The product, 28 [R=—($CH_2$)$_3$C(O)—[HN($CH_2$)$_3$C(O)]$_4$NH($CH_2$)$_3$—; $R_1$=H; $Ar_1$=—$C_6H_3$-(2,6)-$Cl_2$; $R_{21}$=5-$CH_3$; W=N; and Y=CH] is obtained by purification of the crude product by use of HPLC.

Step 4. A solution of the product 28 [R=—($CH_2$)$_3$C(O)[HN($CH_2$)$_3$C(O)]$_4$NH—($CH_2$)$_3$—; $R_1$=H; $Ar_1$=—$C_6H_3$-(2,6)-$Cl_2$; $R_{21}$=5-$CH_3$; W=N; and Y=CH; 2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 29, wherein R=—($CH_2$)$_3$C(O)[HN($CH_2$)$_3$C(O)]$_4$NH($CH_2$)$_3$—; $R_1$=H; $Ar_1$=—$C_6H_3$-(2,6)-$Cl_2$; $R_{21}$=5-$CH_3$; W=N; and Y=CH, as the ammonium salt.

Figure 5:
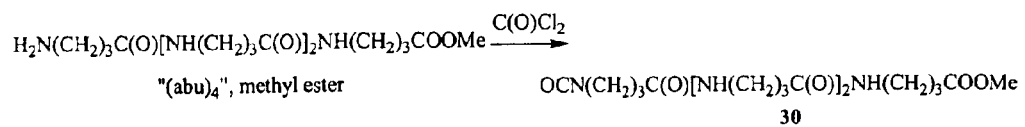
FIG. 5 is a schematic representation of the methods of Preparation 2 and Example 10.
Figure 5:
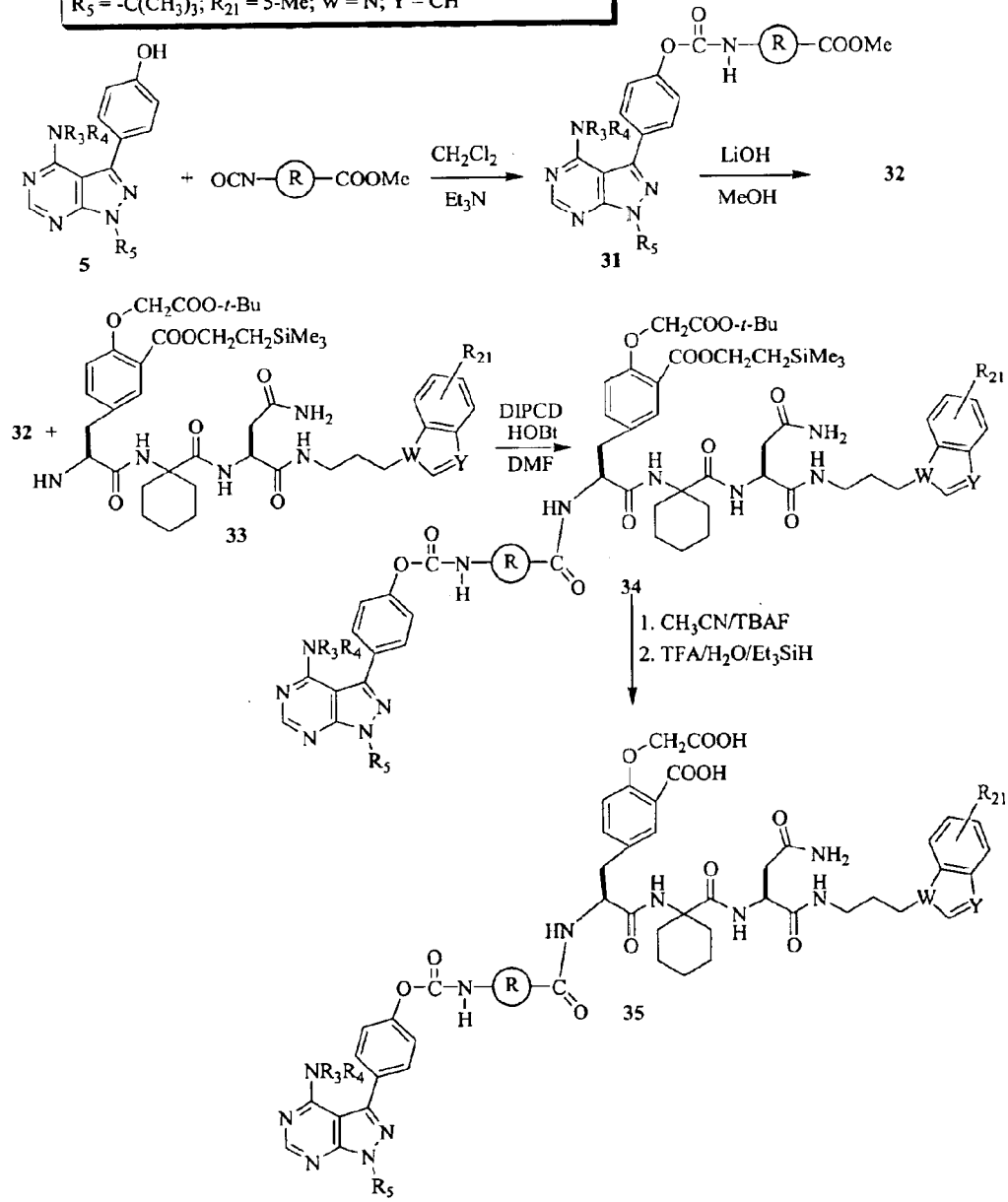

Preparation 2 (See FIG. 5)

Preparation of Isocyanate 30.

Phosgene (20 mmol) in $CH_2Cl_2$ (5 mL) is added dropwise to a stirred solution of the amine, $H_2N(CH_2)_3C(O)[HN(CH_2)_3C(O)]_2NH(CH_2)_3COOMe$ (5 mmol), in $CH_2Cl_2$ (20 mL) and $Et_3N$ (50 mmol). The solution is stirred at room temperature for 18 hours after which aqueous 10% $Na_2CO_3$ is added and the mixture is stirred vigorously for another 30 minutes. The layers are separated, NaCl (solid) is added to the aqueous layer and the liquid phase is extracted with $CH_2Cl_2$. The combined organic extracts are washed with brine, are dried ($Na_2SO_4$), filtered and concentrated. The crude isocyanate 30 is use without further purification.

Example 10 (See FIG. 5)

Preparation of a Formula I Compound wherein p is 2, q is 1, one ligand, $L_1$, is 4-amino-1-(1,1-dimethyl)ethyl-3-(4-hydroxyphenyl)pyrazolo[3,4-d]pyrimidine (5, where $R_3=R_4=H$; $R_5=-C(CH_3)_3$) linked through a phenoxy carbamate bond to the linker X and a second ligand, $L_2$, is the compound 33 (where $R_{21}=5-CH_3$; W=N; and Y=CH) linked via an amide bond to the linker X.

Step 1. A solution of $OCN(CH_2)_3C(O)[HN(CH_2)_3C(O)]_2NH(CH_2)_3COOMe$ (30, 2 mmols) in $CH_2Cl_2$ (5 mL) containing $Et_3N$ (0.2 mL) is stirred and cooled in an ice-water bath under an inert atmosphere. To this is added dropwise a solution of 5 ($R_3=R_4=H$; $R_5=-C(CH_3)_3$; 2 mmols) in $CH_2Cl_2$ (5 mL). After addition is complete, the cooling bath is removed and the reaction solution is warmed to reflux temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. Pure compound 31, wherein $R=-(CH_2)_3C(O)[HN(CH_2)_3C(O)]_2NH(CH_2)_3-$; $R_3=R_4=H$; $R_5=-C(CH_3)_3$ is obtained by purification of the crude product with the use of HPLC.

Step 2. A solution of the product 31 [$R=-(CH_2)_3C(O)[HN(CH_2)_3C(O)]_2NH(CH_2)_3-$; $R_3=R_4=H$; $R_5=-C(CH_3)_3$; 2 mmols] of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed by lyophilization and the dry, crude carboxylic acid 32 is used directly in the next reaction.

Step 3. The dry product 32 [$R=-(CH_2)_3C(O)[HN(CH_2)_3C(O)]_2NH(CH_2)_3-$; $R_3=R_4=H$; $R_5=-C(CH_3)_3$; 2 mmols] from the preceding experiment is placed in a solution in dry DMF (5 mL) with 146 ($R_{21}=5$-Me; W=N; Y=CH; 2 mmols) (for preparation of 146, see Preparation 9) (1 mmol), and 1-hydroxybenzotriazole (2.5 mmols) under an inert atmosphere. The solution is stirred, cooled in an ice-water bath and protected from the atmosphere with a drying tube. To the stirred solution is added diispropylcarbodiimide (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried and concentrated under reduced pressure. The desired product, 34 wherein $R=-(CH_2)_3C(O)[HN(CH_2)_3C(O)]_2NH(CH_2)_3-$; $R_3=R_4=H$; $R_5=-C(CH_3)_3$; $R_{21}=5-CH_3$; W=N; and Y=CH is obtained by purification of the crude product by use of HPLC.

Step 4. The compound 34 [$R=-(CH_2)_3C(O)[HN(CH_2)_3C(O)]_2NH(CH_2)_3-$; $R_3=R_4=H$; $R_5=-C(CH_3)_3$; $R_{21}=5-CH_3$; W=N; and Y=CH; 2 mmols] obtained by the preceding reaction is stirred in acetonitrile (4 mL) containing tetrabutylammonium fluoride for 48 hours. Solvent is removed, and the residue is dissolved in a mixture of trifluoroacetic acid-water-triethylsilane (95:5:3) and is stirred at room temperature for 2 hours. Solvent is removed under reduced pressure and the residue is purified by chromatography, giving the Formula I compound 35, $R=-(CH_2)_3C(O)[HN(CH_2)_3C(O)]_2NH(CH_2)_3-$; $R_3=R_4=H$; $R_5=-C(CH_3)_3$; $R_{21}=5-CH_3$; W=N; and Y=CH.

Figure 6:
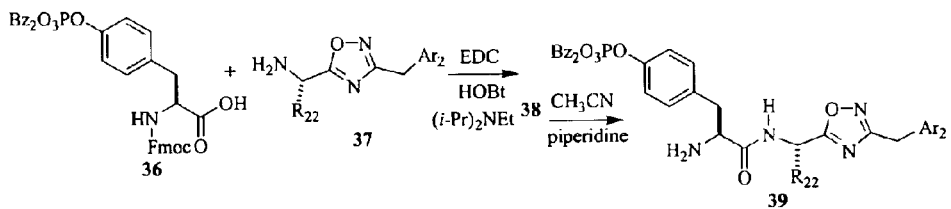
FIG. 6 is a schematic representation of the methods of Preparation 3 and Example 11.
Figure 6:
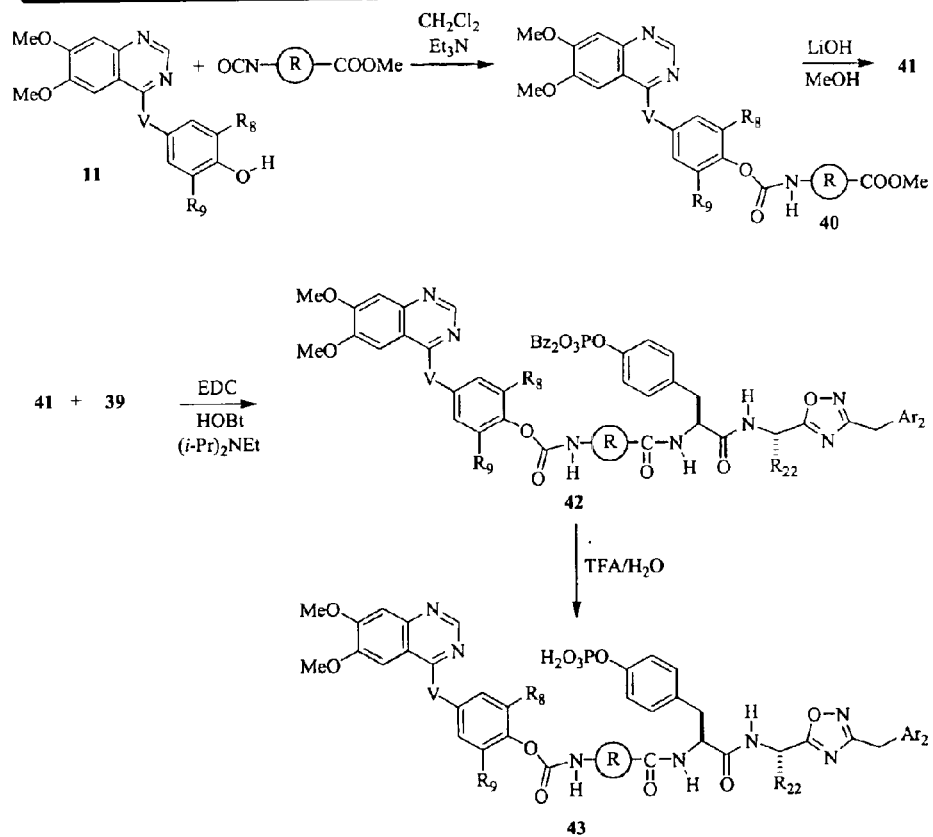

Preparation 3 (See FIG. 6)

Preparation of Compound 39.

Step 1. A solution of Fmoc-Tyr($PO_3Bz_2$)—OH (36, 1 mmol) (C. B. Vu, et. al., J. Med. Chem. 1999, 42, 4088–4098) and (S)-2-(4-trifluoromethylphenyl)$_4$-(1-aminoethyl)-1,2,4-oxadiazole (37, $R_{22}=-CH_3$; $Ar_2=-C_6H_4$-(p)-$CF_3$; 1.5 mmol) (C. B. Vu, et. al.) in $CH_2Cl_2$ (5 mL) and dry DMF (2 mL) is stirred under an inert atmosphere at room temperature. 1-Hydroxybenzotriazole (1.5 mmols) and 1-ethoxy-3-[3-(dimethylamino)propyl] carbodiimide hydrochloride (1.5 mmols) are added to the solution followed by diisopropylethylamine (2 mmols). The reaction mixture is stirred at room temperature and the progress of the reaction is followed by tlc. When the reaction is complete, the solvent is removed under reduced pressure and the residue is taken up in EtOAc. The organic solution is washed with 5% aqueous $NaHCO_3$, water, 10% aqueous citric acid, with half saturated brine and is dried ($Na_2SO_4$), filtered and concentrated. The crude product is purified by chromatography, giving 38.

Step 2. A solution of 38 (1 mmol) in dry acetonitrile (4 mL) and piperidine (0.2 mL) is stirred at room temperature under an inert atmosphere for 3 hours. The solvent is removed under reduced pressure and the amine product 39 ($R_{22}=-CH_3$; $Ar_2=-C_6H_4$-(p)-$CF_3$) is purified by chromatography.

Example 11 (See FIG. 6)

Preparation of a Formula I Compound wherein p is 2, q is 1, one Ligand, $L_1$, is 6,7-dimethoxy-N-(4-hydroxyphenyl)-4-quinazolinamine (11, $R_8=R_9=H$; V=NH) Linked through a Urethane Bond to the Linker X and a Second Ligand, $L_2$, is the Compound 39 ($R_{22}=-CH_3$; $Ar_2=-C_6H_4$-(p)-$CF_3$; and where Bz is Replaced by H) Linked via an Amide Bond to the Linker.

Step 1. A solution of $OCN(CH_2)_3C(O)[HN(CH_2)_3C(O)]_2NH(CH_2)_3COOMe$ (30, 2 mmols) in $CH_2Cl_2$ (5 mL) containing $Et_3N$ (0.2 mL) is stirred and cooled in an ice-water bath under an inert atmosphere. To this is added dropwise a solution of 6,7-dimethoxy-N-(4-hydroxyphenyl)-4-quinazolinamine (11, $R_8=R_9=H$; Y=NH; 2 mmols) (M. R. Myers, et. al., Bioorg. Med. Chem Lett. 1997, 7, 417–420) in $CH_2Cl_2$(5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. Pure compound 40, $R=-(CH_2)_3C(O)[HN(CH_2)_3C(O)]_2NH(CH_2)_3-$; $R_8=R_9=H$ V=NH, is obtained by purification of the crude product with the use of HPLC.

Step 2. A solution of the product 40 [$R=-(CH_2)_3C(O)[HN(CH_2)_3C(O)]_2NH(CH_2)_3-$; $R_8=R_9=H$; V=NH; 2 mmols] of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed by lyophilization and the dry, crude carboxylic acid 41 is used directly in the next reaction.

Step 3. A solution of 41 (1 mmol) and 39, $R_{22}$=—$CH_3$; $Ar_2$=—$C_6H_4$-(p)-$CF_3$, (1 mmol) in $CH_2Cl_2$ (5 mL) and dry DMF (2 mL) is stirred under an inert atmosphere at room temperature. 1-Hydroxybenzotriazole (1.5 mmols) and 1-ethoxy-3-[3-(dimethylamino)propyl]carbodiimide hydrochloride (1.5 mmols) are added to the solution followed by diisopropylethylamine (2 mmols). The reaction mixture is stirred at room temperature and the progress of the reaction is followed by tlc. When the reaction is complete, the solvent is removed under reduced pressure and the residue is taken up in EtOAc. The organic solution is washed with 5% aqueous $NAHCO_3$, water, 10% aqueous citric acid, with half saturated brine and is dried ($Na_2SO_4$), filtered and concentrated. The crude product is purified by chromatography, giving 42, R=—$(CH_2)_3C(O)[HN(CH_2)_3C(O)]_2NH(CH_2)_3$—; $R_8$=$R_9$=H; $R_{22}$=—$CH_3$; $Ar_2$=—$C_6H_4$—(p)-$CF_3$; V=NH.

Step 4. A solution of 42, R=—$(CH_2)_3C(O)[HN(CH_2)_3C(O)]_2NH(CH_2)_3$—; $R_4$=$R_9$=H; $R_{22}$=—$CH_3$; $Ar_2$=—$C_6H_4$-(p)-$CF_3$; V=NH, (1 mmol) in 95:5 trifluoroacetic acid-water is stirred at room temperature for 3 hours. The solution is concentrated by evaporating the solvent with a stream of nitrogen. The residue is treated with ether giving the product as a precipitate. The desired formula I compound 43 [R=—$(CH_2)_3C(O)[HN(CH_2)_3C(O)]_2NH(CH_2)_3$—; $R_8$=$R_9$=H; $R_{22}$=—$CH_3$; $Ar_2$=—$C_6H_4$—(p)-$CF_3$; V=NH] is purified by reversed phase HPLC.

Figure 7:
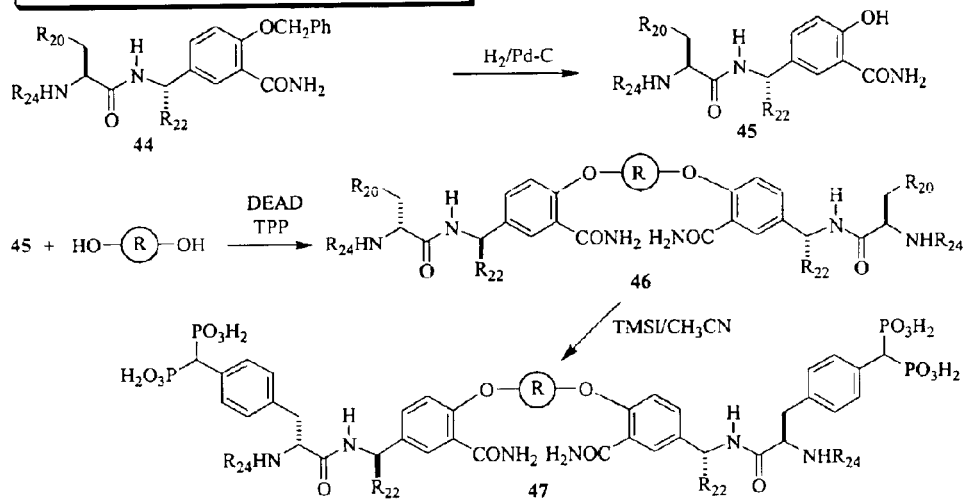
FIG. 7 is a schematic representation of the methods of Preparation 4 and Examples 12 and 13.
Figure 7:
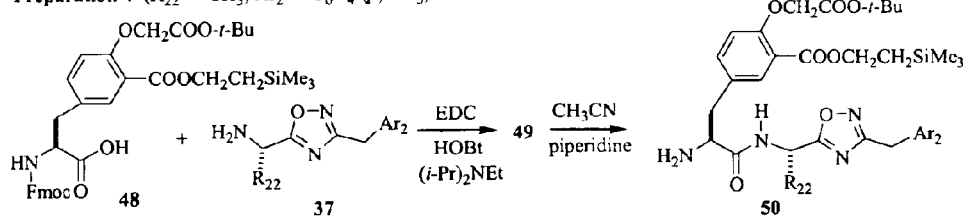
Figure 7:
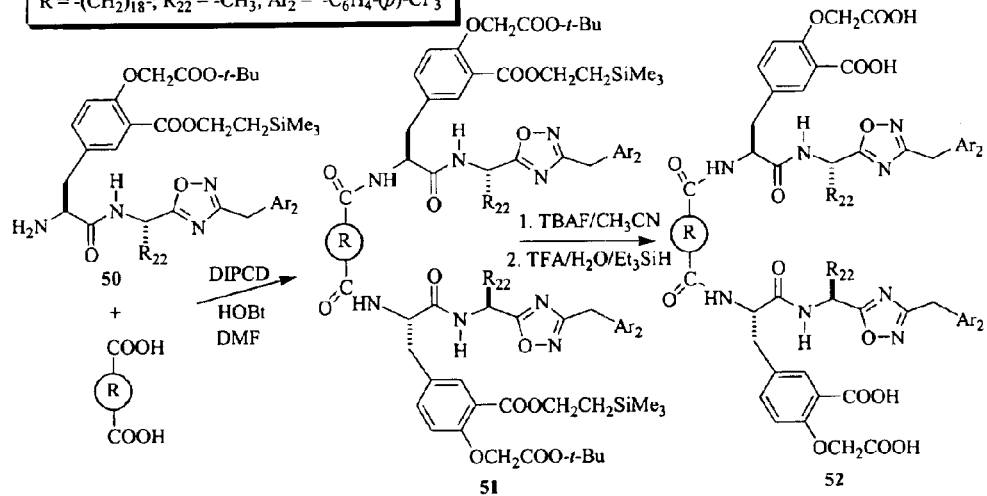

Example 12 (See FIG. 7)

Preparation of a Formula I Compound wherein p is 2, q is 1, and the Ligand, L, is the Compound 44 [$R_{20}$=—$C_6H_4$-p-$CH(PO_3H_2)_2$; $R_{22}$=—$CH_3$; $R_{24}$=—$COCH_3$] Linked through a Phenoxy Ether Bond to the Linker X.

Step 1. Ammonium formate (160 mg, 2.5 mmol) and 10% Pd/C (50 mg) are added to a solution of 44 ($R_{20}$=—$C_6H_4$-(p)-$CH(PO_3Et_2)_2$; $R_{22}$=—$CH_3$; $R_{24}$=—$COCH_3$; 2 mmol) (prepared by the methods of M. Weigele, et. al., WO 99/24442) in methanol (4 mL) and THF (2 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. $NaHCO_3$ and with half-saturated brine, then dried ($Na_2SO_4$), filtered and concentrated under reduced pressure to give the crude product. The desired 45 is obtained by purification of the crude product with HPLC.

Step 2. Diethyl azodicarboxylate (2 mmol) is added dropwise via a syringe to a stirred solution of triphenylphosphine (2 mmol) in THF (5 mL) under an inert atmosphere and at room temperature. To this is added a solution of 45 [$R_{20}$=—$C_6H_4$-(p)-$CH(PO_3Et_2)_2$; $R_{22}$=—$CH_3$; $R_{24}$=—$COCH_3$; 2 mmols) and trans-cyclohexane-1,4-dimethanol (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired compound 46 wherein R=(trans)-1,4-$CH_2$-(cyclo)-$C_6H_{10}CH_2$—; $R_{20}$=—$C_6H_4$-(p)-$CH(PO_3Et_2)_2$; $R_{22}$=—$CH_3$; $R_{24}$=—$COCH_3$.

Step 3. A solution of 46 [R=(trans)-1,4-$CH_2$-(cyclo)-$C_6H_{10}CH_2$—; $R_{20}$=—$C_6H_4$-(p)-$CH(PO_3Et_2)_2$; $R_{22}$=—$CH_3$; $R_{24}$=—$COCH_3$; 1 mmol] and iodotrimethylsilane (20 mmols) in $CH_3CN$ (10 mL) is prepared at −10° C. and is stirred at this temperature until the reaction is complete as detected by tlc. Saturated aqueous $NaHCO_3$ is added followed by 10% aqueous sodium hydrogen sulfite. The $CH_3CN$ is evaporated under reduced pressure and the aqueous solution is lyophilized. The residue purified by reversed phase HPLC, giving the desired Formula I compound 47 [R=(trans)-1,4-$CH_2$-(cyclo)-$C_6H_{10}CH_2$—; $R_{22}$=—$CH_3$; $R_{24}$=—$COCH_3$].

Preparation 4 (See FIG. 7)

Preparation of Compound 50 ($R_{22}$=—$CH_3$; $Ar_2$=—$C_6H_4$-p)-$CF_3$).

Step 1. A solution of carboxylic acid 48, 2 mmol) (Z.-J. Yao, et. al., J. Med. Chem. 1999, 42, 25–35) and (S)-2-(4-trifluoromethylphenyl)-4-(1-aminoethyl)-1,2,4-oxadiazole (37, $R_{22}$=—$CH_3$; $Ar_2$=—$C_6H_4$-(p)-$CF_3$; 2 mmol) (C. B. Vu, et. al.) in $CH_2Cl_2$ (5 mL) and dry DMF (2 mL) is stirred under an inert atmosphere at room temperature. 1-Hydroxybenzotriazole (2.5 mmols) and 1-ethoxy-3-[3-(dimethylamino)propyl] carbodiimide hydrochloride (2.5 mmols) are added to the solution followed by diisopropylethylamine (3 mmols). The reaction mixture is stirred at room temperature and the progress of the reaction is followed by tlc. When the reaction is complete, the solvent is removed under reduced pressure and the residue is taken up in EtOAc. The organic solution is washed with 5% aqueous $NaHCO_3$, water, 10% aqueous citric acid, with half saturated brine and is dried ($Na_2SO_4$), filtered and concentrated. The crude product is purified by chromatography, giving 49.

Step 2. A solution of 38 (2 mmol) in dry acetonitrile (4 mL) and piperidine (0.25 mL) is stirred at room temperature under an inert atmosphere for 3 hours. The solvent is removed under reduced pressure and the amine product 50 ($R_{22}$=—$CH_3$; $Ar_2$=—$C_6H_4$-(p)-$CF_3$) is purified by chromatography.

Example 13 (See FIG. 7)

Preparation of a Formula I Compound wherein p is 2, q is 1, and the Ligand, L, is the Molecule L, where $R_{20}$=—$C_6H_3$-4-$OCH_2COOH$-3-COOH; $R_{22}$=—$CH_3$; and $R_2$=-(3-$C_6H_4$-(p)-$CF_3$)-1,2,4-oxadiazo-5-yl, Linked through an Amide Bond to the Linker X.

Step 1. The product (50, $R_{22}$=—$CH_3$; $Ar_2$=—$C_6H_4$-(p)-$CF_3$; 2 mmols) from the preceding experiment is placed in a solution in dry DMF (5 mL) with eicosa-1,20-dioic acid (1 mmol), and 1-hydroxybenzotriazole (2.5 mmols) under an inert atmosphere. The solution is stirred, cooled in an ice-water bath and protected from the atmosphere with a drying tube. To the stirred solution is added diisopropylcarbodiimide (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried and concentrated under reduced pressure. The desired product, 51, wherein R=—$(CH_2)_{18}$—; $R_2$=—$CH_3$; $Ar_2$=—$C_6H_4$-(p)-$CF_3$, is obtained by purification of the crude product by use of HPLC.

Step 2. The compound 51 (R=—$(CH_2)_{18}$—; $R_2$=—$CH_3$; $Ar_2$=—$C_6H_4$-(p)-$CF_3$; 2 mmols) obtained by the preceding reaction is stirred in acetonitrile (4 mL) containing tetrabutylammonium fluoride for 48 hours. Solvent is removed, and the residue is dissolved in a mixture of trifluoroacetic acid-water-triethylsilane (95:5:3) and is stirred at room temperature for 2 hours. Solvent is removed under reduced pressure and the residue is purified by chromatography, giving the Formula I compound 52, R=—$(CH_2)_{18}$—; $R_{22}$=—$CH_3$; $Ar_2$=—$C_6H_4$-(p)-$CF_3$.

Figure 8:
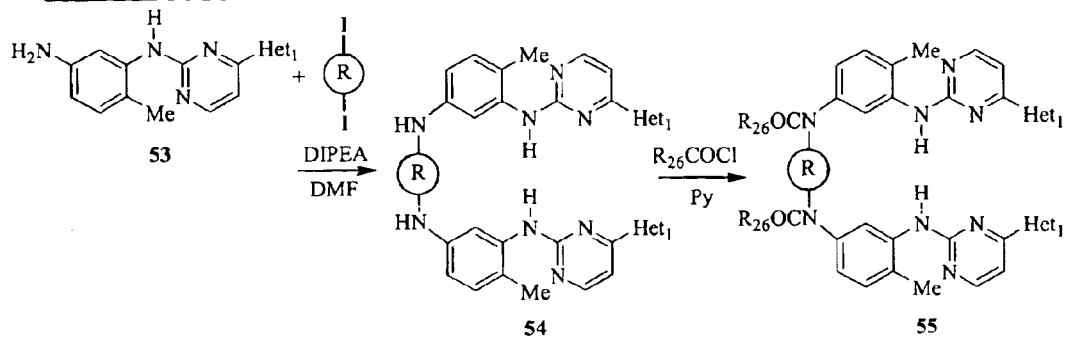
FIG. 8 is a schematic representation of the methods of Examples 14, 15 and 16.
Figure 8:
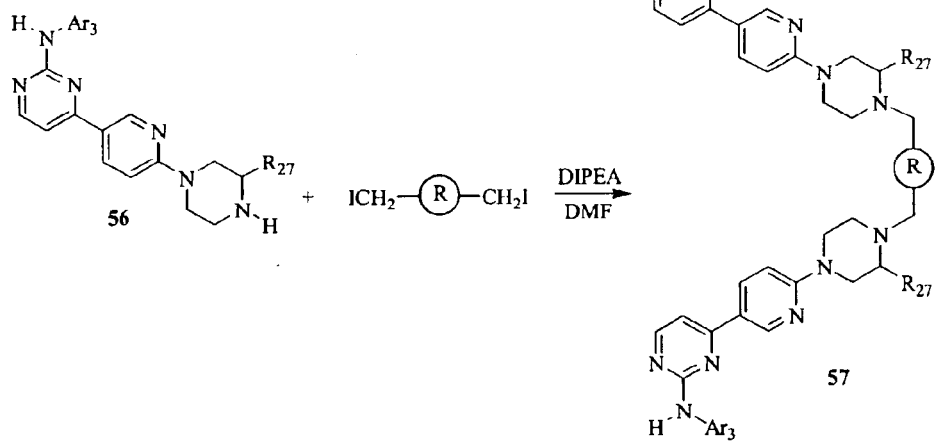
Figure 8:
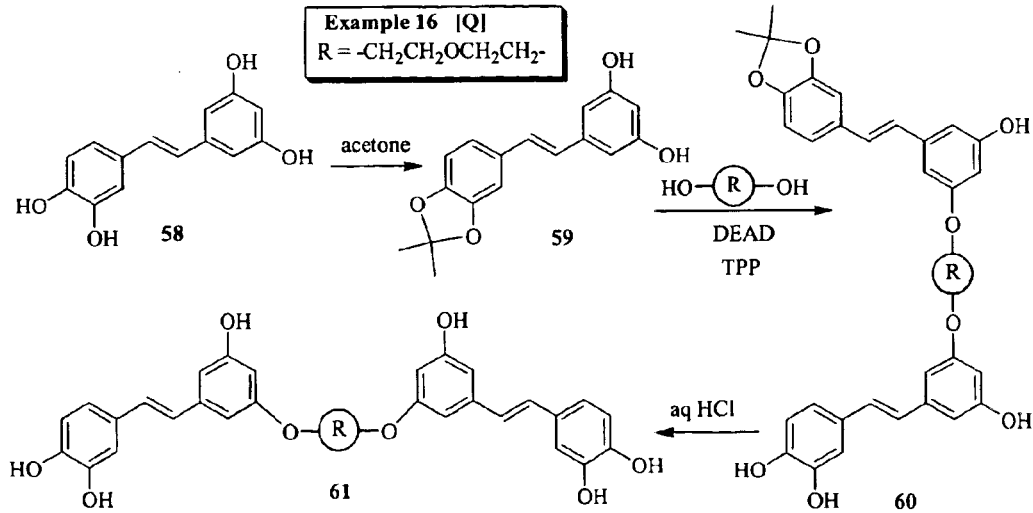

Example 14 (See FIG. 8)

Preparation of a Formula I Compound wherein p is 2, q is 1, and the Ligand, L, is 4-[(4-methyl-1-piperazinyl)methyl]-N-[4-methyl-3-[[4-(3-pyridinyl)-2-pyrimidinyl]amino]phenyl]benzamide Linked through an Amine Bond to the Linker X.

Step 1. A solution of N-(5-amino-2-methylphenyl)-4-(3-pyridinyl)-2-pyrimidineamine (53, $Het_1$=-(3)-$C_5H_4N$; 2 mmols) (J. Zimmermann, U.S. Pat. No. 5,521,184, 28 May 1996), 1,8-diiodooctane (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired compound [54, R=—$(CH_2)_8$—; $Het_1$=-(3)-$C_5H_4N$] is obtained by purification of the crude product by use of HPLC.

Step 2. A solution of 54 (R=—$(CH_2)_8$—; $Het_1$=-(3)-$C_5H_4N$; 1 mmol) and 4-(4-methylpiperazinomethyl)benzoyl chloride (2 mmols) (J. Zimmermann) in pyridine (5 mL) is stirred at room temperature. The reaction is followed by tlc and when complete, water (10 mL) is added, the mixture is cooled on an ice bath and the precipitate is collected by filtration. The precipitate is washed with water, dried and purified by HPLC, giving the desired Formula I compound 55 wherein R=—$(CH_2)_8$—; $R_{26}$=—$C_6H_4$-(4)-$CH_2N(CH_2CH_2)_2NCH_3$; $Het_1$=-(3)-$C_5H_4N$.

Example 15 (See FIG. 8)

Preparation of a Formula I Compound wherein p is 2, q is 1, and the Ligand, L, is 4-[6-(1-piperazinyl)-3-pyridinyl]-N-(3,4,5-trimethoxyphenyl)2-pyrimidinamine Linked through the Piperazine Amine Bond to the Linker X.

A solution of 4-[6-(1-piperazinyl)-3-pyridinyl]-N-(3,4,5-trimethoxyphenyl)-2-pyrimidineamine (56, $R_{27}$=H; $Ar_3$=(3,4,5-OMe)-$C_6H_2$—; 2 mmols) (P. D. Davis, et. al., WO 98/18782, 7 May 1998), 1,2-bis-(2-iodoethoxy)ethane (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired Formula I compound [57, R=—$CH_2OCH_2CH_2OCH_2$—; $R_2$=H; $Ar_3$=(3,4,5-OMe)-$C_6H_2$—] is obtained by purification of the crude product by use of HPLC.

Example 16 (See FIG. 8)

Preparation of 2 Formula I Compound wherein p is 2, q is 1, and the Ligand, L, is Piceatannol (58) Linked via an Ether Bond to the Linker X.

Step 1. A solution of piceatannol (58; 10 mmols) (R. Bajaj, et. al., Rev. Latinoamer. Quim. 1987, 18, 79–80) in acetone is heated at the reflux temperature until the reaction is complete as detected by tlc. Solvent is removed under reduced pressure and the product 59 is used without further purification in subsequent reactions.

Step 2. Diethyl azodicarboxylate (3 mmol) is added dropwise via a syringe to a stirred solution of triphenylphosphine (3 mmol) in THF (5 mL) under an inert atmosphere and at room temperature. To this is added a solution of piceatannol acetonide (59; 3 mmols) and di(ethylene glycol) (1 mmol) in THF (1 mL). The resulting solution is stirred at RT and the progress of the reaction is followed by tlc. After reaction occurs, solvent is removed by evaporation under reduced pressure and the residue is purified by HPLC, giving the compound 60 (R=—$CH_2CH_2OCH_2CH_2$—).

Step 3. A mixture of 60 (R=—$CH_2CH_2OCH_2CH_2$—; 2 mmols) with 6 N aqueous HCl is heated at reflux temperature until the reaction is complete as determined by tlc. The solution is cooled to room temperature and is extracted thoroughly with $CH_2Cl_2$. The combined organic extracts are washed with water and with half-saturated brine, dried ($Na_2SO_4$), filtered and concentrated. The product is purified using reversed phase HPLC, giving the desired formula I compound 61 (R=—$CH_2CH_2OCH_2CH_2$—).

Figure 9:
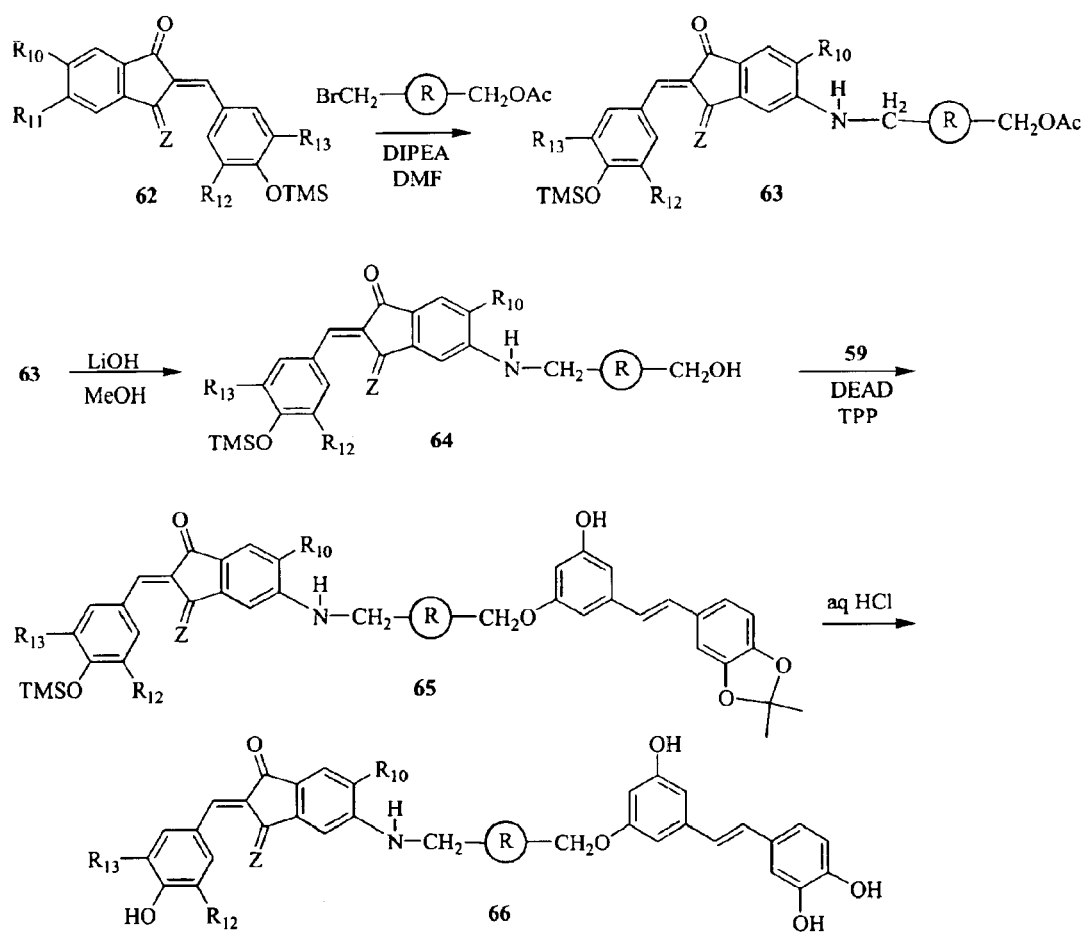
FIG. 9 is a schematic representation of the methods of Example 17.

Example 17 (See FIG. 9)

Preparation of a Formula I Compound wherein p is 2, q is 1, one Ligand, L, is 5-amino-2-[(3,5-dibromo-4-hydroxyphenyl)methylene]-1H-indene-1,3(2H)-dione (13, $R_{10}$=H; $R_{11}$=—$NH_2$; $R_{12}$=$R_{13}$=Br; Z=O) Linked through an Amine Bond to the Linker X and a Second Ligand is Piceatannol (58) Linked via an Ether Bond to X.

Step 1. A solution of 5-amino-2-[(3,5-dibromo-4-hydroxyphenyl)methylene]-1H-indene-1,3(2H)-dione-O-TMS (62, $R_{10}$=H; $R_{11}$=—$NH_2$; $R_{12}$=$R_{13}$=Br; Z=O; 2 mmol) and 6-bromo-1-hexanol, acetate (2 mmol), and diisopropylethylamine (0.2 mL) in DMF (3 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$). filtered and concentrated under reduced pressure to give the crude product. The compound 63, R=—$(CH_2)_4$—; $R_{10}$=H; $R_{12}$=$R_{13}$=Br; Z=O, is obtained by purification of the crude product by use of HPLC.

Step 2. A solution of the product 63 [R=—$(CH_2)_4$—; $R_{10}$=H; $R_{12}$=$R_{13}$=Br; Z=O; 2 mmols] of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 8 by the addition of dilute aq. hydrochloric acid. The solvent is removed under reduced pressure and the crude product 64 [R=—$(CH_2)_4$—; $R_{10}$=H; $R_{12}$=$R_{13}$=Br; Z=O] is purified by chromatography.

Step 3. Diethyl azodicarboxylate (2 mmol) is added dropwise via a syringe to a stirred solution of triphenylphosphine (2 mmol) in THF (5 mL) under an inert atmosphere and at room temperature. To this is added a solution of piceatannol acetonide (59; 2 mmols) and compound 64 [R=—$(CH_2)_4$—; $R_{10}$=H; $R_{12}$=$R_{13}$=Br; Z=O; 1 mmol] in THF (1 mL). The resulting solution is stirred at RT and the progress of the reaction is followed by tlc. After reaction occurs, solvent is removed by evaporation under reduced pressure and the residue is purified by HPLC, giving the compound 65 [R=—$(CH_2)_4$—; $R_{10}$=H; $R_{12}$=$R_{13}$=Br; Z=O].

Step 4. A mixture of 65 2 mmols) with 6 N aqueous HCl is heated at reflux temperature until the reaction is complete as determined by tlc. The solution is cooled to room temperature and is extracted thoroughly with $CH_2Cl_2$. The combined organic extracts are washed with water and with half-saturated brine, dried ($Na_2SO_4$), filtered and concentrated. The product is purified using reversed phase HPLC, giving the desired formula I compound 66 [R=—$(CH_2)_4$—; $R_{10}$=H; $R_{12}$=$R_{13}$=Br; Z=O].

Figure 10:
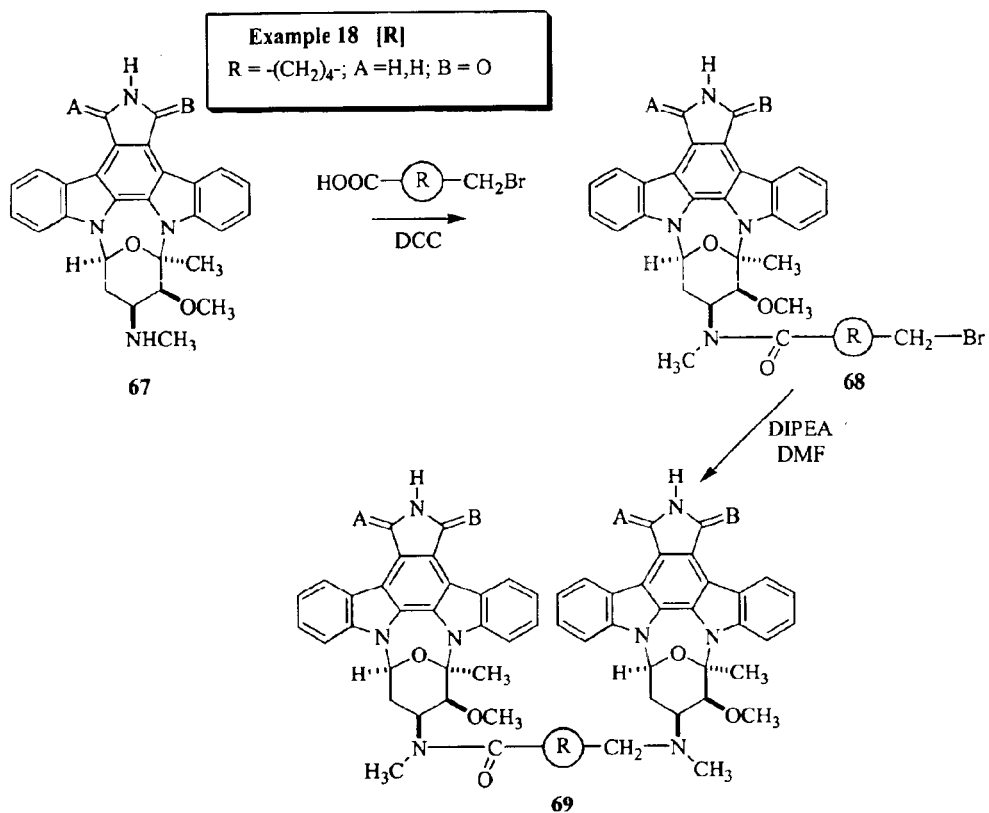
FIG. 10 is a schematic representation of the methods of Examples 18 and 19.
Figure 10:
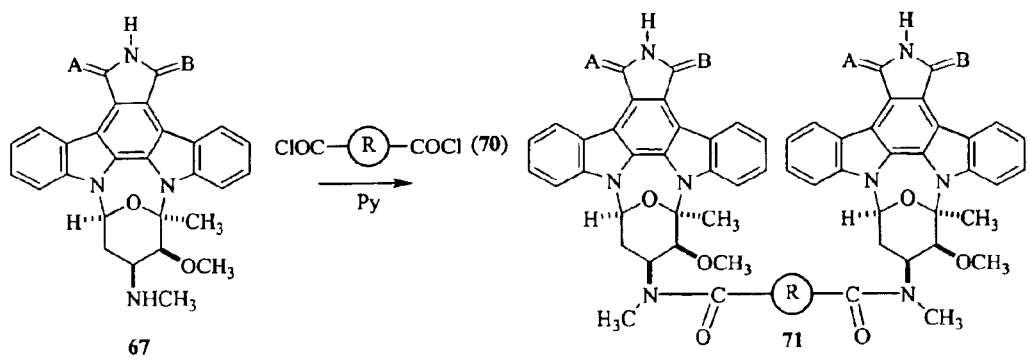

Example 18 (See FIG. 10)

Preparation of a Formula I Compound wherein p is 2, q is 1, and one Ligand, $L_1$, is Staurosporine Linked through the Amine Bond to the Linker X and a Second Ligand is Staurosporine Linked through an Amide Bond to the Linker.

Step 1. A solution of staurosporine (67, A=H, H; B=0; 2 mmols) (G. Caravatti, et. al., Bioorg. Med. Chem. Lett. 1994, 4, 399404), 6-bromohexanoic acid (2 mmol), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. Pure compound 68 (R=—$(CH_2)_4$—; A=H, H; B=O) is obtained by chromatography of the crude reaction product.

Step 2. A solution of 68, R=—$(Cl_2)_4$—; A=H, H; B=0 (1 mmol), staurosporine (67, 1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired Formula I compound 69, R=—$(CH_2)_4$—; A=H, H; B=O, is obtained by purification of the crude product by use of HPLC.

Example 19 (See FIG. 10)

Preparation of a Formula I Compound wherein p is 2, q is 1, and the Ligand, L, Staurosporine (67, A=H, H; B=O) Linked through the Amine Bond by an Acyl Group to the Linker X.

A solution of 67 [A=H, H; B=0; 2 mmols] and terephthaloyl chloride (70, 1 mmol) in $CH_2Cl_2$ (5 mL) containing pyridine is stirred at room temperature. The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound 71, wherein R=-(1,4)-$C_6H_4$—; A=H, H; B=O is obtained by purification of the crude product with the use of HPLC.

Figure 11:
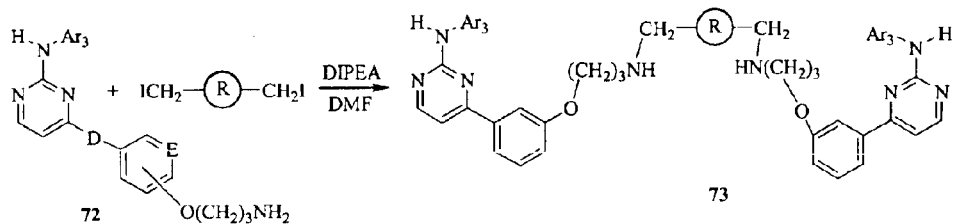
FIG. 11 is a schematic representation of the methods of Examples 20, 21 and 22.
Figure 11:
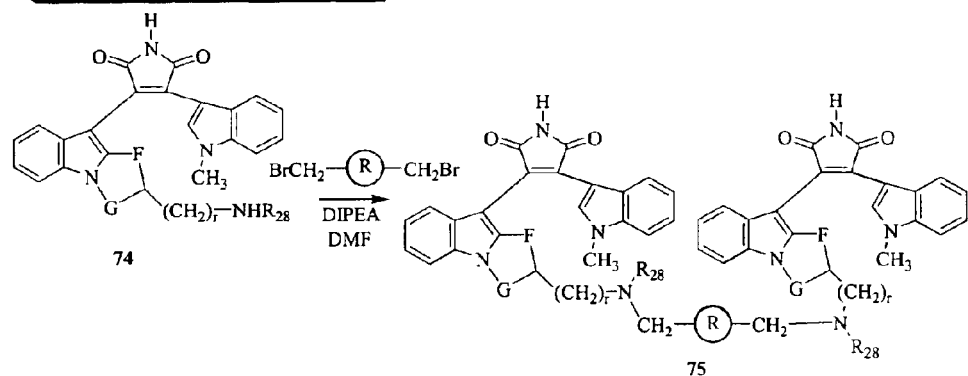
Figure 11:
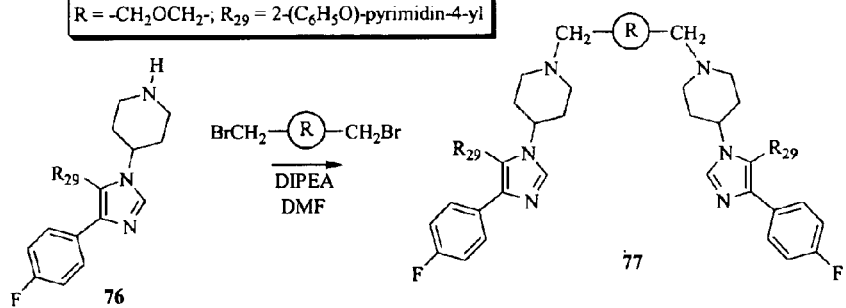

Example 20 (See FIG. 11)

Preparation of a Formula I Compound wherein p is 2, q is 1, and the Ligand, L, is 4-[3-(3-aminopropyloxy)phenyl]-N-(3,4,5-trimethoxyphenyl)-2-pyrimidineamine (72, where D=Single Bond; E=CH; —$O(CH_2)_3NH_2$ is Attached at C-3; and $Ar_3$=(3,4,5)-$(MeO)_3$—$C_6H_2$) Linked through the Amine Bond to the Linker X.

A solution of 4-[3-(3-aminopropyloxy)phenyl]-N-(3,4,5-trimethoxyphenyl)-2-pyrimidineamine (72, where D=single bond; E=CH; —$O(CH_2)_3NH_2$ is attached at C-3; and $Ar_3$= (3,4,5)$(Meo)_3$—$C_6H_2$); 2 mmols) (P. D. Davis, et. al., WO 97/19065, 29 May 1997),1,3-diiodopropane (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired Formula I compound [73, R=—$CH_2$—; D=single bond; E=CH; —$O(CH_2)_3NH$— is attached at C-3; and $Ar_3$=(3,4,5)-$(MeO)_3$—$C_6H_2$)] is obtained by purification of the crude product by use of HPLC.

Example 21 (See FIG. 11)

Preparation of a Formula I Compound wherein p is 2, q is 1, and the Ligand, L, is 3-(6,7,8,9-tetrahydro-8-aminomethyl)pyrido[1,2-a]indol-10-yl)-4-(1-methyl-1H-indol-3-yl)-1H-pyrrole-2,5-dione (74, $R_{28}$=H; F=—$CH_2$—; G=—$CH_2CH_2$—; r=1) Linked through the Amine Bond to the Linker X.

A solution of 3-(6,7,8,9-tetrahydro-8-aminomethyl) pyrido[1,2-a]indol-10-yl)-4-(1-methyl-1H-indol-3-yl)-1H-pyrrole-2,5-dione (74, $R_{28}$=H; F=—$CH_2$—; G=—$CH_2CH_2$—; r=1; 2 mmols) (R. A. Bit, et. al., J. Med. Chem. 1993, 36, 21–29), 2-bromoethyl ether (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired Formula I compound 75, where R=—$CH_2OCH_2$—; $R_{28}$=H; F=—$CH_2$—; G=—$CH_2CH_2$—; and r=1, is obtained by purification of the crude product by use of HPLC.

Example 22 (See FIG. 11)

Preparation of a Formula I Compound wherein p is 2, q is 1, and the Ligand, L, is 4-(4-fluorophenyl)=-(4-piperidinyl)-5-(2-phenoypyrimid-4-yl)imidazole [76, $R_{29}$=2-$(C_6H_5O)$-pyrimidin-4-yl] Linked through the Piperidine Amine Bond to the Linker X.

A solution of 4-(4-fluorophenyl)-1-(4-piperidinyl)-5-(2-phenoxypyrimidin-4-yl)imidazole [76, $R_{29=2}$-$(C_6H_5O)$-pyrimidin-4-yl; 2 mmols] (J. L. Adams, et. al., U.S. Pat. No. 5,977,103, 2 Nov. 1999), 2-bromoethyl ether (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired Formula I compound [77, R=—$CH_2OCH_2$—; $R_{29}$= 2-$(C_6H_5O)$-pyrimidin-4-yl] is obtained by purification of the crude product by use of HPLC.

Figure 12:
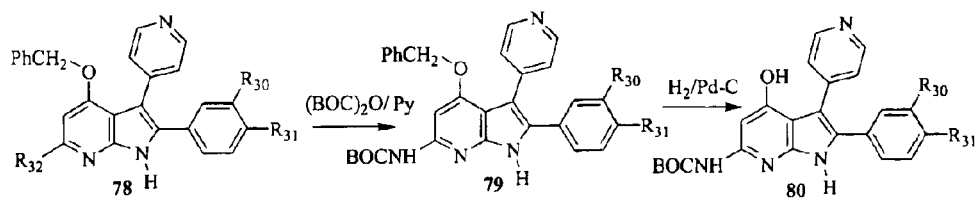
FIG. 12 is a schematic representation of the methods of Preparation 5 and Examples 23 and 24.
Figure 12:
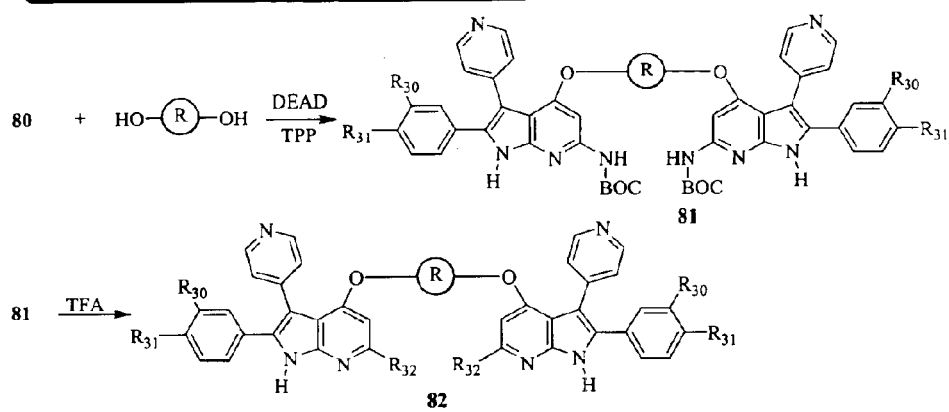
Figure 12:
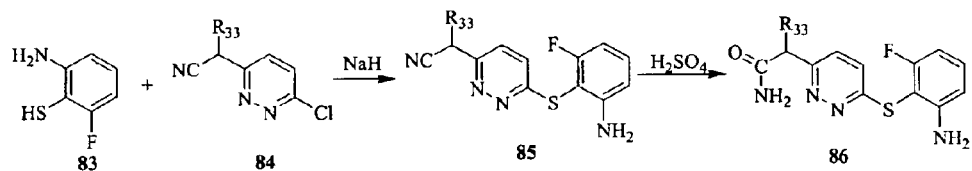
Figure 12:
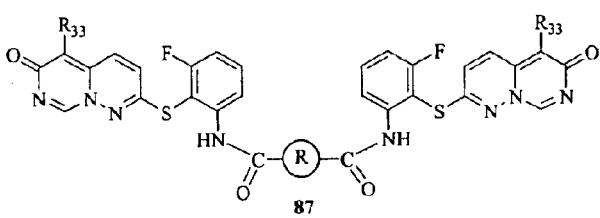

Preparation 5 (See FIG. 12)

Preparation of 6-N-(1,1-dimethylethyl)oxycarbonyl-2-(4-fluorophenyl)-4-hydroxy-3-(4-pyridinyl)-1H-pyrrolo[2,3-b]pyridin-6-amine (80).

Step 1. A solution of 78 ($R_{30}$=H; $R_{31}$=F; $R_{32}$=—$NH_2$; 5 mmol) (J. R. Henry, et. al., Bioorg. Med. Chem. Lett. 1998, 8, 3335–3340), di-t-butylcarbonate (6 mmol) and triethylamine (7 mmol) in THF (25 mL) is stirred at room temperature for 18 hours. The volume of solvent is reduced to about 5 mL by evaporation under reduced pressure, EtOAc (50 mL) is added and the mixture is washed with saturated aqueous $NaHCO_3$ and with half-saturated brine, dried ($Na_2SO_4$), filtered and concentrated. The desired product 79 ($R_{30}$=H; $R_{31}$=F) is purified by chromatography.

Step 2. Ammonium formate (160 mg, 2.5 mmol) and 10% Pd/C (50 mg) are added to a solution of 79 ($R_{30}$=H; $R_{31}$=F; 2 mmol) in methanol (4 mL) and THF (2 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. NaHCO$_3$ and with half-saturated brine, then dried (Na$_2$SO$_4$), filtered and concentrated under reduced pressure to give the crude product. The desired 80 ($R_{30}$=H; $R_{31}$=F) is obtained by purification of the crude product with HPLC.

Example 23 (See FIG. 12)

Preparation of a Formula I Compound wherein 6 is 2, q is 1, and the ligand, L, is 2-(4-fluorophenyl)-4-hydroxy-3-(4-pyridinyl)(1H-pyrrolo[2,3-b]pyridin-6-amine (78, $R_{30}$=H; $R_{31}$=F; $R_{32}$=—NH$_2$) Linked through a Phenoxy Ether Bond to the Linker X.

Step 1. Diethyl azodicarboxylate (2 mmol) is added dropwise via a syringe to a stirred solution of triphenylphosphine (2 mmol) in THF (5 mL) under an inert atmosphere and at room temperature. To this is added a solution of 80 ($R_{30}$=H; $R_{31}$=F; 2 mmols) and 1,4-benzenedimethanol (1 mmol) in THF (1 mL). The resulting solution is stirred at RT and the progress of the reaction is followed by tlc. After reaction occurs, solvent is removed by evaporation under reduced pressure and the residue is purified by HPLC, giving compound 81 wherein R=(1,4)—CH$_2$C$_6$H$_4$CH$_2$—; $R_{30}$=H; $R_{31}$=F.

Step 2. A solution of 81 [R=(1,4)-CH$_2$C$_6$H$_4$CH$_2$—; $R_{30}$=H; $R_{31}$=F; 2 mmol] in CH$_2$Cl$_2$ (5 mL) and trifluoroacetic acid (3 mL) is stirred at room temperature and the reaction is monitored by tlc. After reaction is complete, additional CH$_2$Cl$_2$ is added to the solution which then is poured into ice cold aqueous Na$_2$CO$_3$, mixed well and the layers separated. The organic layer is washed with water and with half-saturated brine, is dried (Na$_2$SO$_4$), filtered and concentrated. The residual crude product is purified by chromatography, giving the desired Formula I compound 82 wherein R=(1,4)-CH$_2$C$_6$H$_4$CH$_2$—; $R_{30}$=H; $R_{31}$=F; $R_{32}$=—NH$_2$.

Example 24 (See FIG. 12)

Preparation of a Formula I Compound wherein p is 2, q is 1, and the Ligand, L, is 5-(2,6-dichlorophenyl)-2-[(2-fluorophenyl)thio]-6H-pyrimido[1,6-b]pyridazin-6-one Linked through a Carboxamide Bond to the Linker X.

Step 1. 2-Amino-6-fluorothiophenol (83, 5 mmol) is added under an inert atmosphere to a mixture of sodium hydride (5 mmol, from an oil suspension that is pre-washed with hexane) and dry tetrahydrofuran (10 mL). The mixture is stirred for 30 minutes and then a solution of 3-chloro-6-(2,6-dichlorophenyl)cyanomethylpyridazine (84, $R_{33}$=2,6-Cl$_2$—C$_6$H$_3$; 5 mmol) (G. W. Bemis, et. al., U.S. Pat. No. 5,945,418, 31 Aug. 1999) in THF (15 mL) is added. The mixture is stirred and heated to reflux temperature. Reaction progress is followed by tlc and when complete, the mixture is concentrated under reduced pressure. Aqueous 1M NaOH is added to the residue and the mixture is extracted with CH$_2$Cl$_2$, the extracts are washed with water and with half-saturated brine, dried (Na$_2$SO$_4$), filtered and concentrated. The crude product is purified by chromatography, giving compound 85 ($R_{33}$=2,6-Cl$_2$—C$_6$H$_3$).

Step 2. A mixture of 85 ($R_{33=2,6}$-C$_{12}$—C$_6$H$_3$; 3 mmol) and concentrated sulfuric acid (8 mL) is heated at a temperature of 100° C. for one hour. The reaction solution is cooled in an ice bath and the pH is adjusted to 8 by the careful addition of cold 5M NaOH. The mixture is extracted with CH$_2$Cl$_2$, the extracts are washed with water and with half-saturated brine, dried (Na$_2$SO$_4$), filtered and concentrated. The crude product is purified by chromatography, giving compound 86 ($R_{33}$=2,6-Cl$_2$—C$_6$H$_3$).

Step 3. A solution of 86 ($R_{33}$=2,6-Cl$_2$—C$_6$H$_3$; 2 mmol), malonic acid (1 mmol), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. Dry toluene (10 mL) and N,N-dimethylformamide dimethyl acetal (2 mmol) are added to the crude product and the mixture is heated to 100° C. The reaction is followed by tlc and when complete, the reaction is cooled. The precipitate is collected by filtration, dissolved in ethyl acetate and re-precipitated with the addition of diethyl ether, giving the desired Formula I compound 87, R=—(CH$_2$)—; $R_{33}$=2,6-Cl$_2$—C$_6$H$_3$.

Figure 13:
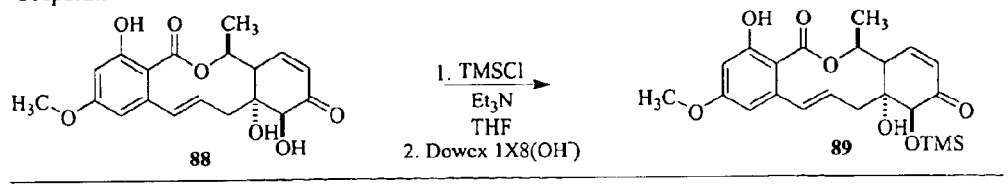
FIG. 13 is a schematic representation of the methods of Preparation 6 and Examples 25 and 26.
Figure 13:
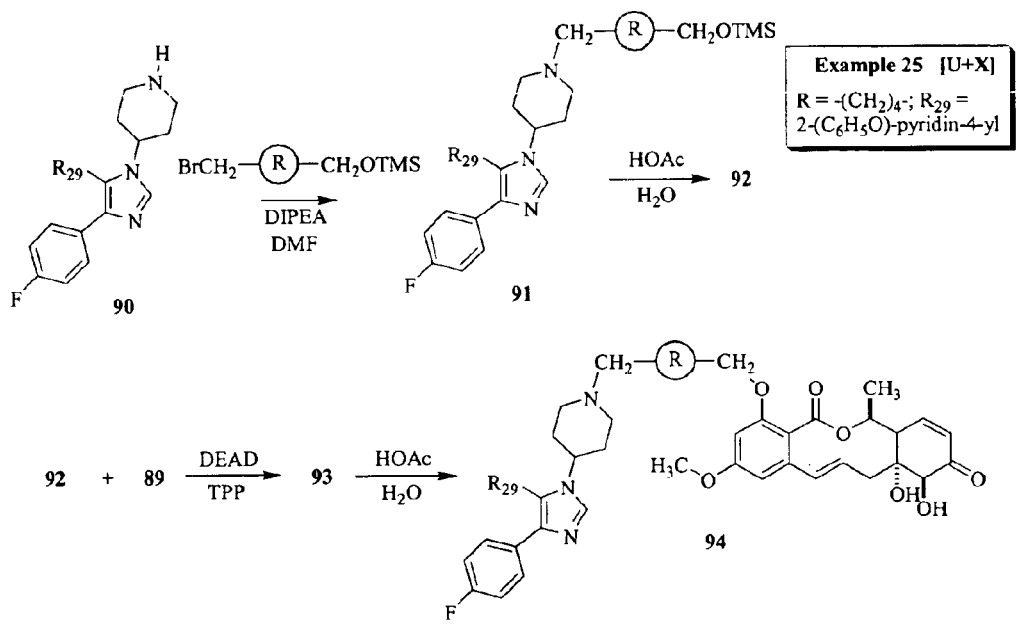
Figure 13:
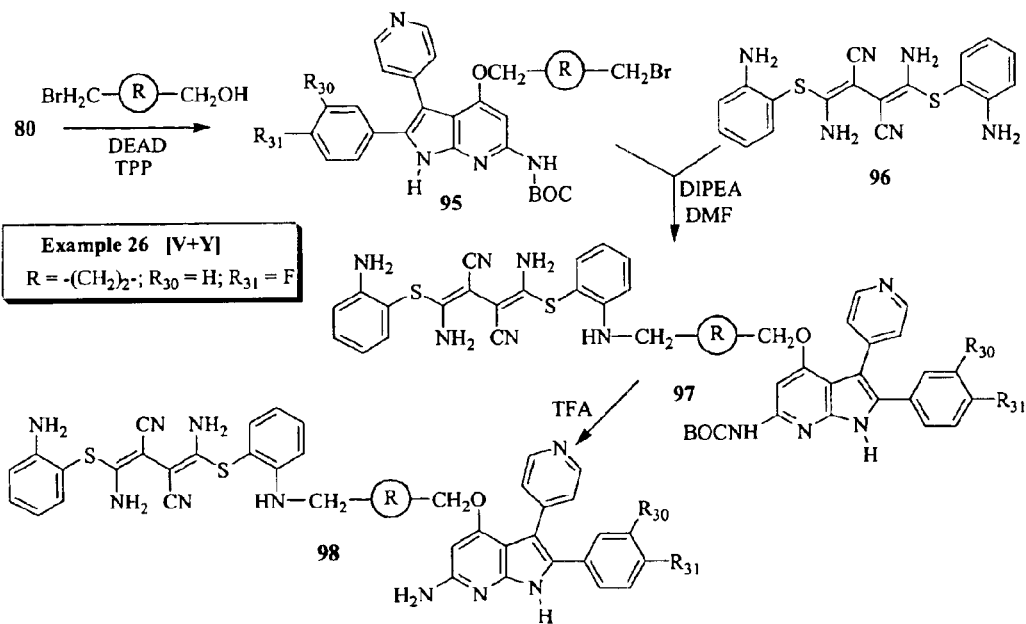

Preparation 6 (See FIG. 13)

Preparation of 89.

A solution of 88 (5 mmol) (D. H. Williams, et. al., Biochemistry, 1998, 37, 9579–9585), chlorotrimethylsilane (6 mmol), and triethylamine (50 mmol) in dry THF (5 mL) is stirred at room temperature for 8 hours. Solvent is removed under reduced pressure and the residue is taken up in ethanol (5 mL). Dowex 1×8 (OH$^-$) (3 mmol) is added and the mixture is stirred 5 hours at RT. After filtration, solvent is removed under reduced pressure. The residue is washed thoroughly with CH$_2$Cl$_2$ which in turn is washed with water and with half-saturated brine, dried (Na$_2$SO$_4$), filtered and concentrated. The crude product is purified by chromatography, giving compound 89.

Example 25 (See FIG. 13)

Preparation of a Formula I Compound wherein p is 2, q is 1, and one Ligand, L$_1$, is 4-(4-fluorophenyl)-1-(4-piperidinyl)-5-(2-phenoxypyridin-4-yl)imidazole [90, $R_{29}$=2-(C$_6$H$_5$O)-pyridin-4-yl] Linked through the Piperidine amine Bond to the Linker X and a Second Ligand, L$_2$, is Compound 88 Linked to the Linker through a Phenoxy Bond.

Step 1. A solution of 4-(4-fluorophenyl)-1-(4-piperidinyl)-5-(2-phenoxypyridin-4-yl)imidazole [90, $R_{29}$=2-(C6H$_5$O)-pyridin-4-yl; 2 mmols] (J. L. Adams, et. al., U.S. Pat. No. 5,977,103, 2 Nov. 1999), 6-bromohexanol-O-TMS (2 mmol), and diisopropylethylamine (0.2 mL) in DMF (5 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The combined organic extracts are washed with water and with brine and then dried (Na$_2$SO$_4$), filtered and concentrated under reduced pressure to give the crude product. Compound 91, R=—(CH$_2$)$_4$—; $R_{29}$=2-(C$_6$H$_5$O)-pyridin-4-yl, is obtained by purification of the crude product by use of HPLC.

Step 2. A solution of 91 [R=—(CH$_2$)$_4$—; $R_{29}$=2-(C$_6$H$_5$O)-pyridin-4-yl; 2 mmol] in HOAc—H$_2$O (4:1) (5 mL) is stirred under an inert atmosphere at room temperature. The reaction is followed by tlc and when complete, is diluted with EtOAc and washed several times with water and dilute aq. Na$_2$CO$_3$. The organic layer is dried (Na$_2$SO$_4$), filtered and concentrated under reduced pressure to give the crude product. The desired alcohol 92 [R=—(CH$_2$)$_4$—; $R_{29}$=2-

($C_6H_5O$)-pyridin-4-yl] is obtained by purification of the crude product by use of HPLC.

Step 3. Diethyl azodicarboxylate (2 mmol) is added dropwise via a syringe to a stirred solution of triphenylphosphine (2 mmol) in THF (5 mL) under an inert atmosphere and at room temperature. To this is added a solution of 89 (1 mmol) and 92 [R=—($CH_2$)$_4$—; $R_{29}$=2-($C_6H_5O$)-pyridin-4-yl; 1 mmol] in THF (1 mL). The resulting solution is stirred at RT and the progress of the reaction is followed by tlc. After reaction occurs, solvent is removed by evaporation under reduced pressure and the residue is purified by HPLC, giving the desired compound 93 wherein R=—($CH_2$)$_4$—; $R_{29}$=2-($C_6H_5O$)-pyridin-4-yl.

Step 4. A solution of 93 [R=—($CH_2$)$_4$—; $R_{29}$=2-($C_6H_5O$)-pyridin-4-yl; 2 mmol] in HOAc—$H_2O$ (4:1) (5 mL) is stirred under an inert atmosphere at room temperature. The reaction is followed by tlc and when complete, is diluted with EtOAc and washed several times with water and dilute aq. $Na_2CO_3$. The organic layer is dried ($Na_2SO_4$), filtered and concentrated under reduced pressure to give the crude product. The desired Formula I compound 94 [R=—($CH_2$)$_4$—; $R_{29}$=2-$C_6H_5O$)-pyridin-4-yl] is obtained by purification of the crude product by use of HPLC.

Example 26 (See FIG. 13)

Preparation of a Formula I Compound wherein p is 2, q is 1, and one Ligand, $L_1$, is 2-(4-fluorophenyl)$_4$-hydroxy-3-(4-pyridinyl)-1H-pyrrolo[2,3-b]pyridin-6-amine (78, $R_{30}$=H; $R_{31}$=F; $R_{32}$=—$NH_2$) Linked through a Phenoxy Ether Bond to the Linker X and a Second Ligand, $L_2$, is Z,Z-bis{amino[(2-aminophenyl)thio]methylene}butanedinitrile (96) Linked via an Aryl Amino Group to the Linker.

Step 1. Diethyl azodicarboxylate (2 mmol) is added dropwise via a syringe to a stirred solution of triphenylphosphine (2 mmol) in THF (5 mL) under an inert atmosphere and at room temperature. To this is added a solution of 80 ($R_{30}$H; $R_{31}$=F; 2 mmol) and 4-bromobutanol-O-TMS (2 mmols) in THF (5 mL). The resulting solution is stirred at RT and the progress of the reaction is followed by tlc. After reaction occurs, solvent is removed by evaporation under reduced pressure and the residue is purified by HPLC, giving compound 95 (R=—($CH_2$)$_2$—; $R_{30}$=H; $R_{31}$=F).

Step 2. A solution of 95 (R=—($CH_2$)$_2$—; $R_{30}$=H; $R_{31}$=F; 2 mmol), compound 96 (2 mmol) (J. V. Duncia, et. al., Bioorg. Med. Chem. Lett. 1998, 8, 2839–2844), and diisopropylethylamine (0.5 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. Compound 97, R=—($CH_2$)$_2$—; $R_{30}$=H; $R_{31}$=F, is separated from the other products of the reaction by the use of HPLC.

Step 3. A solution of 97 [R=—($CH_2$)$_2$—; $R_{30}$=H; $R_{31}$=F; 1 mmol] in $CH_2Cl_2$ (5 mL) and trifluoroacetic acid (3 mL) is stirred at room temperature and the reaction is monitored by tlc. After reaction is complete, additional $CH_2Cl_2$ is added to the solution which then is poured into ice cold aqueous $Na_2CO_3$, mixed well and the layers separated. The organic layer is washed with water and with half-saturated brine, is dried ($Na_2SO_4$), filtered and concentrated. The residual crude product is purified by chromatography, giving the desired Formula I compound 98 wherein R=—($CH_2$)$_2$—; $R_{30}$=H; $R_{31}$=F.

Figure 14:
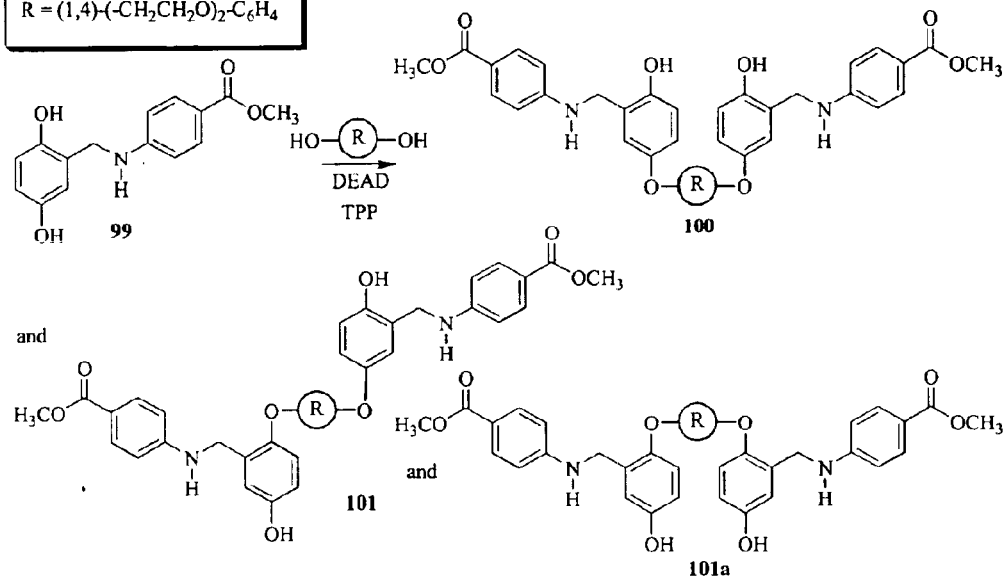
FIG. 14 is a schematic representation of the methods of Examples 27 and 28.
Figure 14:
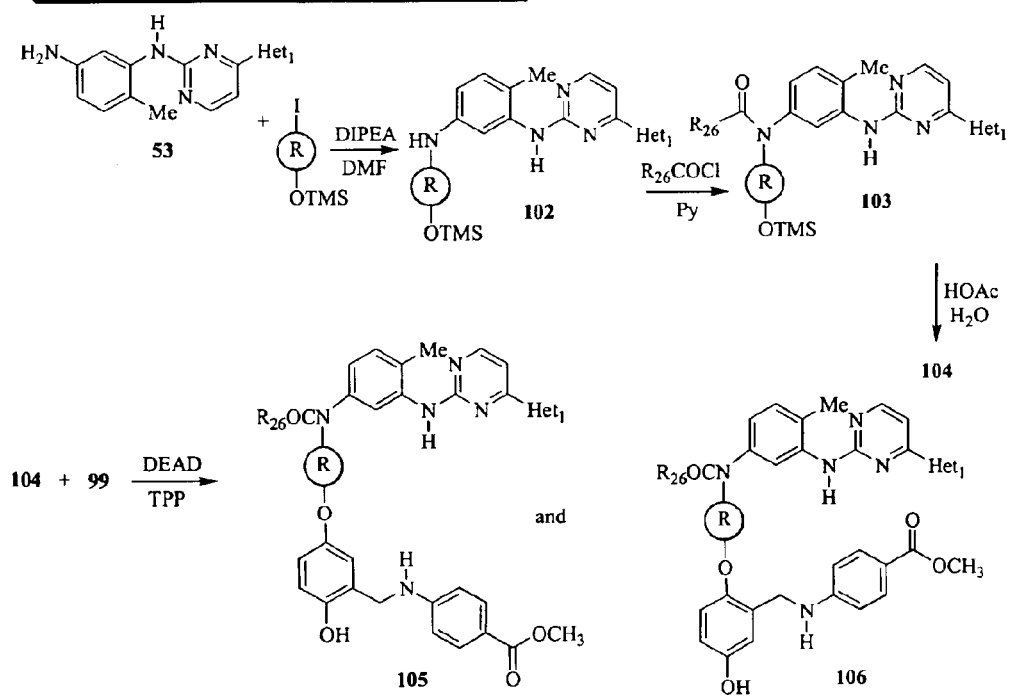

Example 27 (See FIG. 14)

Preparation of a Formula I Compound wherein p is 2, q is 1, and the Ligand, L, is 4-{[1(2,5-dihydroxyphenyl)methyl]amino}benzoic Acid, Methyl Ester, (99) Linked through a Phenoxy Ether Bond to the Linker X.

Diethyl azodicarboxylate (2 mmol) is added dropwise via a syringe to a stirred solution of triphenylphosphine (2 mmol) in THF (5 mL) under an inert atmosphere and at room temperature. To this is added a solution of 4-{[(2,5-dihydroxyphenyl)methyl]amino}benzoic acid, methyl ester (99; 2 mmol) (A. Levitski et al., WO 94/26260) and 2,2'-(1,4-phenylenedioxy)diethanol (1 mmol) in THF (3 mL). Tile resulting solution is stirred at RT and the progress of the reaction is followed by tlc. After reaction occurs, solvent is removed by evaporation under reduced pressure and the residue is purified by HPLC, giving the desired Formula I compounds 100, 101 and 101a where R=(1,4)-(—$CH_2CH_2O$)$_2$—$C_6H_4$.

Example 28 (See FIG. 14)

Preparation of a Formula I Compound wherein p is 2, q is 1, and one Ligand, $L_1$, is 4-[(4-methyl-1-piperazinyl)methyl]-N-[4-methyl-3-[[4-(3-pyridinyl)-2-pyrimidinyl]amino]phenyl]benzamide Linked through an Amine Bond to the Linker X and a Second Ligand, $L_2$, is 4-{[(2,5-dihydroxyphenyl)methyl]amino}benzoic acid, Methyl Ester, (99) Linked through a Phenoxy Ether Bond to the Linker.

Step 1. A solution of N-(5-amino-2-methylphenyl)-4-(3-pyridinyl)-2-pyrimidineamine (53, $Het_1$=-(3)—$C_5H_4N$; 2 mmol) (J. Zimmermann, U.S. Pat. No. 5,521,184, 28 May 1996), 5-iodopentanol-O-TMS (2 mmol), and diisopropylethylamine (0.4 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired compound [102, R=—($CH_2$)$_5$—; $Het_1$=-(3)—$C_5H_4N$] is obtained by purification of the crude product by use of HPLC.

Step 2. A solution of 102 (R=—($CH_2$)$_5$—; $Het_1$=-(3)—$C_5H_4N$; 1 mmol) and 4-(4-methylpiperazinomethyl)benzoyl chloride (2 mmol) in pyridine (5 mL) is stirred at room temperature. The reaction is followed by tlc and when complete, water (10 mL) is added, the mixture is cooled on an ice bath and the precipitate is collected by filtration. The precipitate is washed with water, dried and purified by HPLC, giving compound 103 wherein R=—($CH_2$)$_5$—; $R_{26}$=—$C_6H_4$-(4)-$CH_2N(CH_2CH_2)_2NCH_3$; $Het_1$=-(3)-$C_5H_4N$.

Step 3. A solution of 103 [R=—($CH_2$)$_5$—; $R_{26}$=—$C_6H_4$-(4)-$CH_2N(CH_2CH_2)_2NCH_3$; $Het_1$=-(3)-$C_5H_4N$; 2 mmol] in HOAc—$H_2O$ (4:1) (5 mL) is stirred under an inert atmosphere at room temperature. The reaction is followed by tlc and when complete, is diluted with EtOAc and washed several times with water and dilute aq. $Na_2CO_3$. The organic layer is dried ($Na_2SO_4$), filtered and concentrated under reduced pressure to give the crude product. Alcohol 104 [R=—($CH_2$)$_5$—; $R_{26}$=—$C_6H_4$-(4)-$CH_2N(CH_2CH_2)_2NCH_3$; $Het_1$=-(3)-$C_5H_4N$] is obtained by purification of the crude product by use of HPLC.

Step 4. Diethyl azodicarboxylate (2 mmol) is added dropwise via a syringe to a stirred solution of triphenylphosphine (2 mmol) in THF (5 mL) under an inert atmosphere and at room temperature. To this is added a solution of 4-{[(2,5-dihydroxyphenyl)methyl]amino}benzoic acid, methyl ester (99; 2 mmol) and 104 (R=—(CH$_2$)$_5$—; R$_{26}$=—C$_6$H$_4$-(4)-CH$_2$N(CH$_2$CH$_2$)$_2$NCH$_3$; Het$_1$=-(3)-C$_5$H$_4$N; 2 mmol) in THF (3 mL). The resulting solution is stirred at RT and the progress of the reaction is followed by tlc. After reaction occurs, solvent is removed by evaporation under reduced pressure and the residue is purified by HPLC, giving the desired Formula I compounds 105 and 106 where R=—(CH$_2$)$_5$—; R$_{26}$=—C$_6$H$_4$-(4)-CH$_2$N(CH$_2$CH$_2$)NCH$_3$; Het$_1$=-(3)-C$_5$H$_4$N.

Figure 15:
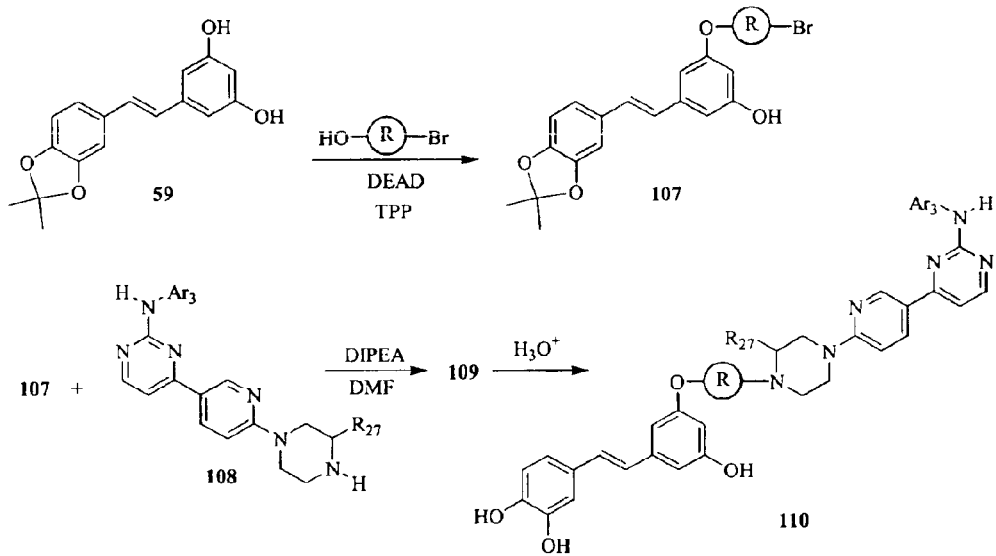
FIG. 15 is a schematic representation of the methods of Examples 29 and 30.
Figure 15:
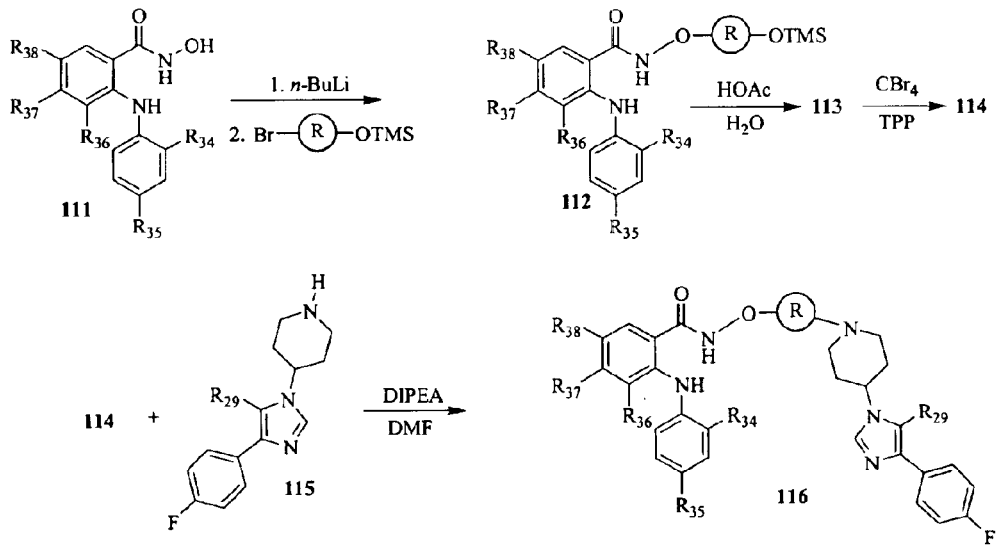

Example 29 (See FIG. 15)

Preparation of a Formula I Compound wherein p is 2, q is 1, and one Ligand, L$_1$, is Piceatannol (58) Linked via an Ether Bond to the Linker X and a Second Ligand, L$_2$, is 4-{6-[1-(3-methyl)piperazinyl]-3-pyridinyl}-N-(3,4,5-trimethoxphenyl)-2-pyrimidinamine [108, R$_{27}$=—CH$_3$; Ar$_3$=(3,4,5)-(OMe)$_3$—C$_6$H$_2$] Linked through the Piperazine Amine Bond to the Linker X.

Step 1. Diethyl azodicarboxylate (3 mmol) is added dropwise via a syringe to a stirred solution of triphenylphosphine (3 mmol) in THF (5 mL) under an inert atmosphere and at room temperature. To this is added a solution of piceatannol acetonide (59; 3 mmols) and 8-bromo-3,6-dioxaoctanol (2 mmol) in THF (1 mL). The resulting solution is stirred at RT and the progress of the reaction is followed by tlc. After reaction occurs, solvent is removed by evaporation under reduced pressure and the residue is purified by HPLC, separating compound 107 (R=—CH$_2$CH$_2$OCH$_2$CH$_2$OCH$_2$CH$_2$—) from excess, unreacted starting material.

Step 2. A solution of 4-{6-[1-(6-methyl)piperazinyl]-3-pyridinyl}-N-(3,4,5-trimethoxyphenyl)-2-pyrimidinamine (108, R$_{27}$=—CH$_3$; Ar$_3$=(3,4,5)-(OMe)$_3$—C$_6$H$_2$—; 1 mmol) (P. D. Davis, et. al., WO 98/18782, 7 May 1998), compound 107 (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The combined organic extracts are washed with water and with brine and then dried (Na$_2$SO$_4$), filtered and concentrated under reduced pressure to give the crude product. The desired compound [109, R=—CH$_2$CH$_2$OCH$_2$CH$_2$OCH$_2$CH$_2$—; R$_{27}$=—CH$_3$; Ar$_3$=(3,4,5-OMe)-C$_6$H$_2$—] is obtained by purification of the crude product by use of HPLC.

Step 3. A mixture of 109 (R=—CH$_2$CH$_2$OCH$_2$CH$_2$OCH$_2$CH$_2$—; R$_{27}$=—CH$_3$; Ar$_3$=(3,4,5-OMe)-C$_6$H$_2$; 1 mmol) with 6 N aqueous HCl is heated at reflux temperature until the reaction is complete as determined by tlc. The solution is cooled to room temperature, adjusted to pH 8 by careful addition of cold 2N NaOH, and extracted thoroughly with CH$_2$Cl$_2$. The combined organic extracts are washed with water and with half-saturated brine, dried (Na$_2$SO$_4$), filtered and concentrated. The product is purified using reversed phase HPLC, giving the desired Formula I compound 110 where R=—CH$_2$CH$_2$OCH$_2$CH$_2$OCH$_2$CH$_2$—; R$_{27}$=—CH$_3$; Ar$_3$=(3,4,5-OMe)-C$_6$H$_2$.

Example 30 (See FIG. 15)

Preparation of a Formula I Compound wherein p is 2, q is 1, and one Ligand, L$_1$, is 4-(4-fluorophenyl)-1-(4-piperidinyl)-5-(2-methylaminopyrimidin-4-yl)imidazole [115, R$_{29}$=2-(—NHCH$_3$)-pyrimidin-4-yl] Linked through the Piperidine Amine Bond to the Linker X and a Second Ligand, L$_2$, is N-hydroxy-2-(2-chloro-4-iodo)phenylamino-3,4-difluorobenzamide (111, R$_{34}$=Cl; R$_{35}$=I; R$_{36}$=R$_{37}$=F; R$_{38}$=H) Linked via the Hydroxamate Oxygen to the Linker.

Step 1. n-Butyl lithium (2 mmol) is added to a stirred solution of N-hydroxy-2-(2-chloro-4-iodo)phenylamino-3,4-difluorobenzamide (111, R$_{34}$=Cl; R$_{35}$=I; R$_{36}$=R$_{37}$=F; R$_{38}$=H; 2 mmol) (A. J. Bridges, WO 98/37881, 3 Sep. 1998) in dry THF (10 mL) under an inert atmosphere. The solution is stirred for 30 minutes and then 4-bromobutanol-O-TMS (2 mmol) is added and stirring continued while monitoring the reaction by tlc. When the reaction is complete, the mixture is quenched by the addition of cold aqueous 10% Na$_2$CO$_3$ (1 mL). Solvent is removed under reduced pressure leaving an aqueous mixture. Water is added and the mixture is extracted with CH$_2$Cl$_2$, the organic extracts are washed with water, with half-saturated brine, dried (Na$_2$SO$_4$), filtered and concentrated. The residue is chromatographed, giving 112 (R=—(CH$_2$)$_4$—; R$_{34}$=Cl; R$_{35}$=I; R$_{36}$=R$_{37}$=F; R$_{38}$=H).

Step 2. A solution of 112 [R=—(CH$_2$)$_4$—; R$_{34}$=Cl; R$_{35}$=I; R$_{36}$=R$_{37}$=F; R$_{38}$=H; 2 mmol] in HOAc—H$_2$O (4:1) (5 mL) is stirred under an inert atmosphere at room temperature. The reaction is followed by tlc and when complete, is diluted with EtOAc and washed several times with water and dilute aq. Na$_2$CO$_3$. The organic layer is dried (Na$_2$SO$_4$), filtered and concentrated under reduced pressure to give the crude product. Compound 113 [R=—(CH$_2$)$_4$—; R$_{34}$=Cl; R$_{35}$=I; R$_{36}$=R$_{37}$=F; R$_{38}$=H] is obtained by purification of the crude product by use of HPLC.

Step 3. A solution, cooled to the temperature of an ice-water bath, containing compound 113 (2 mmol), triphenylphosphine (3 mmol), and carbon tetrabromide (4 mmol) in CH$_2$Cl$_2$ (10 mL) is prepared and is stirred. The cooling bath is removed and the solution is stirred at room temperature. The progress of the reaction is followed by tlc and after reaction occurs, the solution is diluted with additional CH$_2$Cl$_2$, washed with aqueous 5% NaHCO$_3$, with water and with half-saturated brine. The organic layer is separated, dried (Na$_2$SO$_4$), filtered and concentrated under reduced pressure to give the crude product. The desired compound [114, wherein R=—(CH$_2$)$_4$—; R$_{34}$=Cl; R$_{35}$=I; R$_{36}$=R$_{37}$=F; R$_{38}$=H] is obtained by purification of the crude product by use of HPLC.

Step 4. A solution of 4-(4-fluorophenyl)-1-(4-piperidinyl)-5-(2-methylaminopyrimidin-4-yl)imidazole [115, R$_{29}$=2-(—NHCH$_3$)-pyrimidin-4-yl; 1 mmol] (J. L. Adams et al., WO96/21452; U.S. Pat. Nos. 5,593,992; 5,593,991 and 5,670,527), 114 (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The combined organic extracts are washed with water and with brine and then dried (Na$_2$SO$_4$), filtered and concentrated under reduced pressure to give the crude product. The desired Formula I compound [116, R=—(CH$_2$)$_4$—; R$_{29}$=2-(—NHCH$_3$)-pyrimidin-4-yl; R$_{34}$=Cl; R$_{35}$=I; R$_{36}$=R$_{37}$=F; R$_{38}$=H] is obtained by purification of the crude product by use of HPLC.

Figure 16:
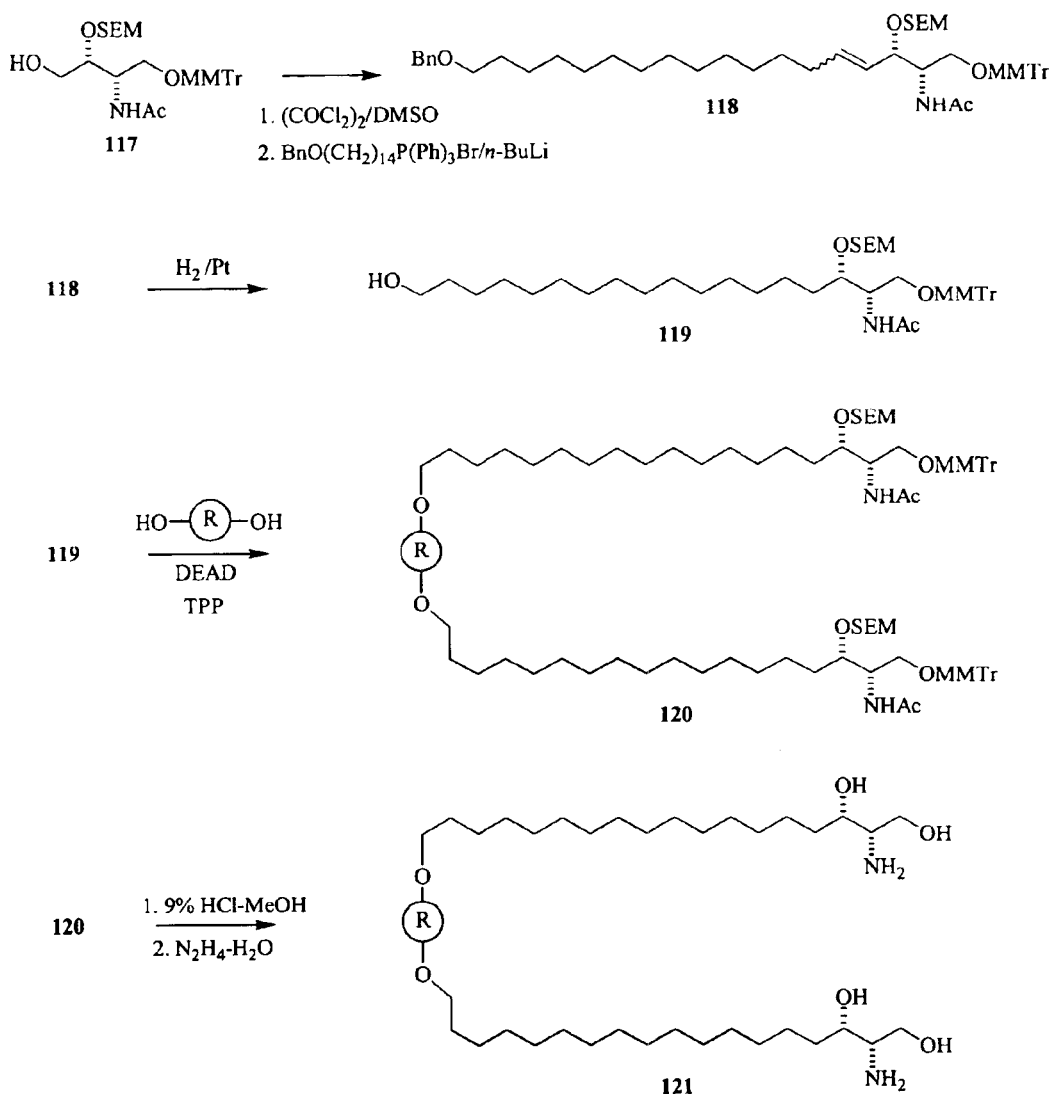
FIG. 16 is a schematic representation of the methods of Example 31.

Example 31 (See FIG. 16)

Preparation of a Formula I Compound wherein p is 2, q is 1, and the Ligand, L, is (2S,3S)-2-amino-1,3,18-octadecanetriol Linked via the C-18 Oxygen to the Linker X through an Ether Bond.

The procedures of H. Shibuya, et. al., Chem. Pharm. Bull. 1992, 40, 1154–1165 are followed. Abbreviations are: SEM=trimethylsilylethoxymethyl; MMTr=monomethoxytrityl.

Steps 1 and 2. A solution of DMSO (6 mmol) in $CH_2Cl_2$ (5 mL) is added to a solution of oxalyl chloride (3 mmol) in $CH_2Cl_2$ (2 mL) and the solution is stirred at −78° C. under an inert atmosphere for 15 minutes. A solution of the protected amine-diol 117 (3 mmol) (H. Shibuya and coworkers) in $CH_2Cl_2$ (3 mL) is added and the resulting solution is stirred at −78° C. for 30 minutes. Triethylamine (12 mmol) is added to the solution which then is allowed to warm to room temperature. Additional $CH_2Cl_2$ is added and the organic solution is washed with half-saturated brine, dried ($Na_2SO_4$), filtered and concentrated, leaving the crude aldehyde. At the same time, the Wittig reagent to be used in the next step is prepared. n-Butyl lithium (3 mmol) is added to (14-benzyloxy)tetradecyltriphenylphosphonium bromide (3 mmol) (prepared from 14-bromotetradecanol-O-benzyl ether by standard methods) in THF (3 mL). A solution of the crude oxidation product in THF (5 mL) is added and the resulting solution is stirred at 0° C. while being monitored by tlc. When reaction is complete, ice water is added and the mixture is extracted with $CH_2Cl_2$. The organic phase is washed with water, with half-saturated brine, dried ($Na_2SO_4$), filtered and concentrated. The residue is chromatographed using HPLC, giving both cis and trans double bond isomers of the desired compound 118.

Step 3. A solution of the double bond isomers of 118 (2 mmol) in methanol (3 mL) is stirred with $PtO_2$ in an atmosphere of $H_2$ at room temperature for four hours. The catalyst is removed by filtration and is washed with additional methanol. The solvent is removed by evaporation and the residue is purified by chromatography, giving the desired compound 119.

Step 4. Diethyl azodicarboxylate (3 mmol) is added dropwise via a syringe to a stirred solution of triphenylphosphine (3 mmol) in THF (5 mL) under an inert atmosphere and at room temperature. To this is added a solution of 119 (2 mmols) and resorcinol (1 mmol) in THF (1 mL). The resulting solution is stirred at RT and the progress of the reaction is followed by tlc. After reaction occurs, solvent is removed by evaporation under reduced pressure and the residue is purified by HPLC, giving pure compound 120 (R=1,3-$C_6H_4$).

Step 5. The O-protecting groups of 120 are removed by treating a sample (1 mmol) of the compound with 9% HCl in methanol (5 mL) for 15 minutes at room temperature. The reaction mixture is neutralized with silver carbonate powder, solids are removed by filtration and the solvent is evaporated to give the intermediate product. This product is placed together with 80% hydrazine hydrate (3 mL) in a sealed tube and warmed to 90° C. for 18 hours. The mixture is concentrated under reduced pressure and the crude reaction product is purified by chromatography, giving the desired Formula I compound 121, R=1,3-$C_6H_4$.

Preparation 7
3-Amino-Z-pTyr-$Ac_6$c-(1S,2R)-Achec-$NH_2$, di-t-butyl ester (125).

Compound 125 is prepared with the method used by P. Furet, et. al., J. Med Chem. 1999, 42, 2358–2363 for the synthesis of 3-Amino-Z-pTyr-$Ac_6$c-(1S,2R)-Achec-$NH_2$ except that $N^3$-Fmoc-Tyr[$PO_3$(t-Bu)$_2$]-OH is used in place of $N^3$-Fmoc-Tyr($PO_3H_2$)—OH.

Figure 17:
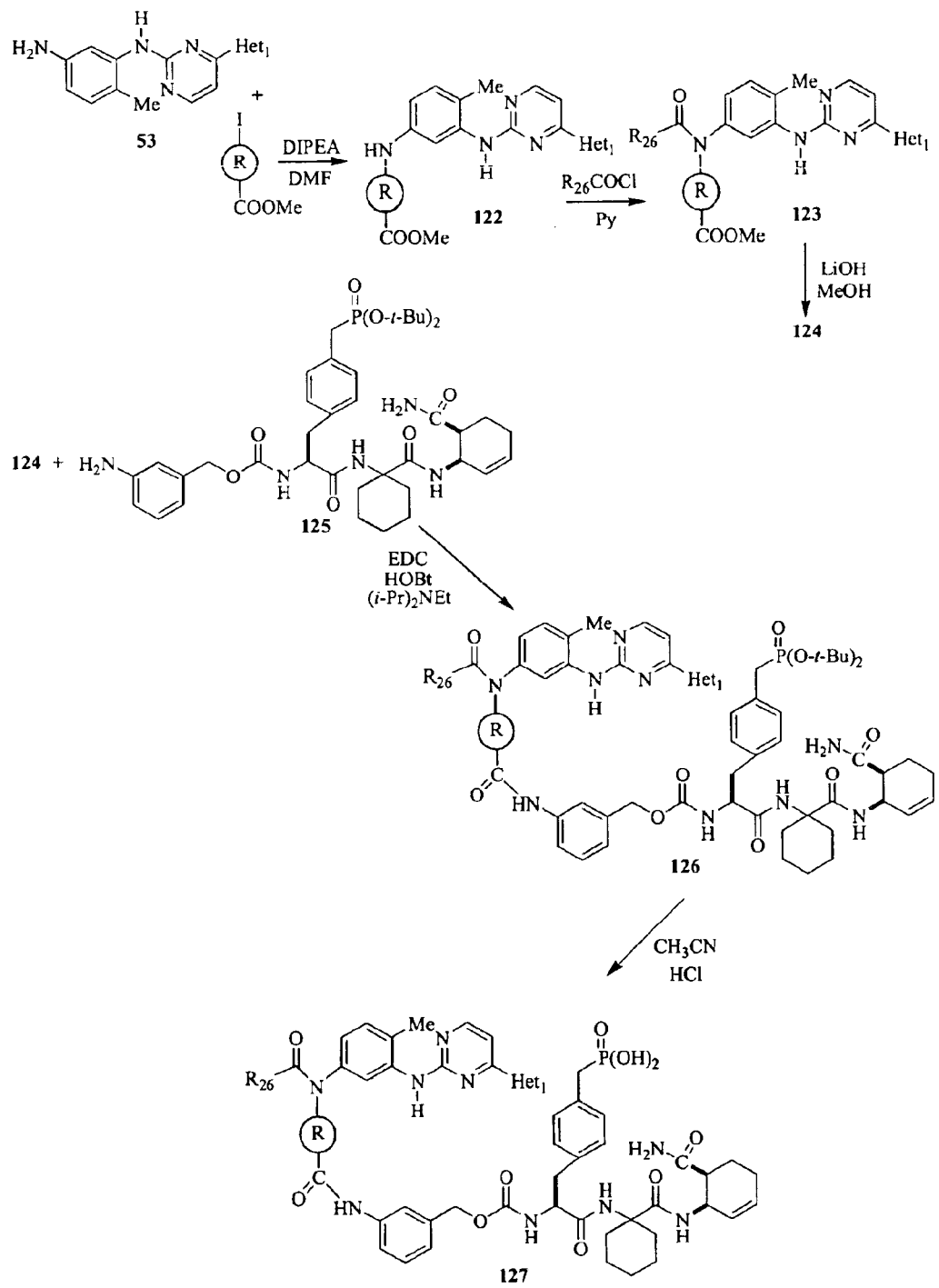
FIG. 17 is a schematic representation of the methods of Example 32.

Example 32 (See FIG. 17)
Preparation of a Formula I Compound wherein p is 2, q is 1, and one Ligand, $L_1$, is 4-[(4-methyl-1-piperazinyl)methyl]-N-[4-methyl-3-[[4-(3-pyridinyl)-$_2$-pyrimidinyl]aminolphenyl]benzamide linked through an Amine Bond to the linker X and a Second Ligand, $L_2$, is Compound 125 Linked through an Amide Bond to the linker.

Step 1. A solution of N-(5-amino-2-methylphenyl)-4-(3-pyridinyl)-2-pyrimidineamine (53, $Het_1$=-(3)-$C_5H_4N$; 2 mmol) (J. Zimmermann, U.S. Pat. No. 5,521,184, 28 May 1996), 6-iodohexanoic acid, methyl ester, (2 mmol), and diisopropylethylamine (0.4 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The combined organic extracts are washed with water and with brine and then dried ($Na_2SO_4$), filtered and concentrated under reduced pressure to give the crude product. The desired compound [122, R=—$(CH_2)_5$—; $Het_1$=-(3)-$C_5H_4N$] is obtained by purification of the crude product by use of HPLC.

Step 2. A solution of 122 (R=—$(CH_2)_5$—; $Het_1$=-(3)-$C_5H_4N$; 2 mmol) and 4-(4-methylpiperazinomethyl)benzoyl chloride (2 mmol) in pyridine (5 mL) is stirred at room temperature. The reaction is followed by tlc and when complete, water (10 mL) is added, the mixture is cooled on an ice bath and the precipitate is collected by filtration. The precipitate is washed with water, dried and purified by HPLC, giving compound 123 wherein R=—$(CH_2)_5$—; $R_{26}$=—$C_6H_4$-(4)-$CH_2N(CH_2CH_2)_2NCH_3$; $Het_1$=-(3)-$C_5H_4N$.

Step 3. A solution of the product 123 [R=—$(CH_2)_5$—; $R_{26}$=—$C_6H_4$-(4)-$CH_2N(CH_2CH_2)_2NCH_3$; $Het_1$=-(3)-$C_5H_4N$; 2 mmols] of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed under reduced pressure and the crude product 124 [R=—$(CH_2)_5$—; $R_{26}$=—$C_6H_4$-(4)-$CH_2N(CH_2CH_2)_2NCH_3$; $Het_1$=-(3)-$C_5H_4N$] is used without purification in the next step.

Step 4. A solution of 124 (1 mmol), 125 (1 mmol), and 1-hydroxybenzotriazole (2 mmols) in dry DMF (5 mL) is prepared under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried ($Na_2SO_4$), filtered and concentrated under reduced pressure. The product, 126, is obtained by purification of the crude product by use of HPLC.

Step 5. A solution of the product 126 (1 mmol) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 127, where R=—$(CH_2)_5$—; $R_{26}$=—$C_6H_4$-(4)—$CH_2N(CH_2CH_2)_2NCH_3$; $Het_1$=-(3)—$C_5H_4N$, as the ammonium salt.

Figure 18:
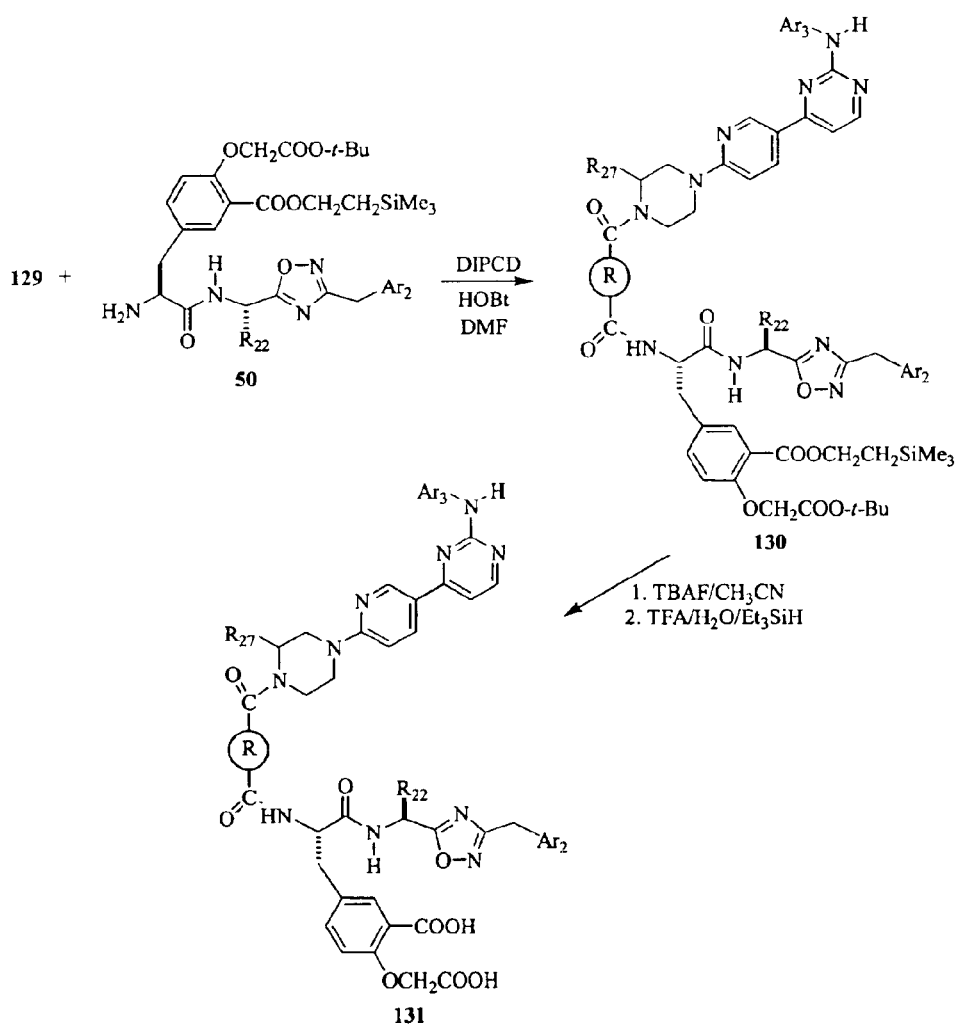
FIG. 18 is a schematic representation of the methods of Example 33.

Example 33 (See FIG. 18)
Preparation of a Formula I Compound wherein p is 2, q is 1, and one Ligand, $L_1$, is Compound 50 Linked via an Amide bond to the Linker X and a Second Ligand, $L_2$, is 4-[6(1-piperazinyl)-3-pyridinyl]-N-(3,4,5-trimethoxyphenyl)-2-pyrimidinamine (56) Linked through the Piperazine Amine Bond to the Linker X.

Step 1. A solution of 4-[6-(1-piperazinyl)-3-pyridinyl]-N-(3,4,5-trimethoxyphenyl)-2-pyrimidinamine (56, $R_{27}$=H; $Ar_3$=(3,4,5)-(OMe)$_3$—C$_6$H$_2$—; 2 mmol) (P. D. Davis, et. al., WO 98/18782, 7 May 1998), 1-iodohexanoic acid, methyl ester, (2 mmol), and diisopropylethylamine (0.3 mL) in DMF (5 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The combined organic extracts are washed with water and with brine and then dried (Na$_2$SO$_4$), filtered and concentrated under reduced pressure to give the crude product. The desired Formula I compound [128, R=—(CH$_2$)$_4$—; $R_{27}$=H; $Ar_3$=(3,4,5)-(OMe)$_3$—C$_6$H$_2$—] is obtained by purification of the crude product by use of HPLC.

Step 2. A solution of the product 128 [R=—(CH$_2$)$_4$—; $R_{27}$=H; $Ar_3$=(3,4,5)-(OMe)$_3$-C$_6$H$_2$—; 2 mmols] of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed under reduced pressure and the crude product 129 [R=—(CH$_2$)$_4$—; $R_{27}$=H; $Ar_3$=(3,4,5)-(OMe)$_3$—C$_6$H$_2$—] is used without further purification in the next step.

Step 3. Compound 50, $R_{22}$=—CH$_3$; $Ar_2$=—C$_6$H$_4$-(p)-CF$_3$; (1 mmol) in a solution in dry DMF (5 mL) with 129 [R=—(CH$_2$)$_4$—; $R_{27}$=H; $Ar_3$=(3,4,5)-(OMe)$_3$—C$_6$H$_2$—; 1 mmol], and 1-hydroxybenzotriazole (2.5 mmols) under an inert atmosphere. The solution is stirred, cooled in an ice-water bath and protected from the atmosphere with a drying tube. To the stirred solution is added diisopropylcarbodiimide (2.1 mmol). The course of the reaction is followed by tlc. The cooling bath is removed and after reaction occurs, the reaction mixture is partitioned between methylene chloride and saturated aqueous NaHCO$_3$. The organic layer is washed with water and brine, dried and concentrated under reduced pressure. The desired product, 130, wherein R=—(CH$_2$)$_4$—; $R_{22}$=—CH$_3$; $Ar_2$=—C$_6$H$_4$-(p)-CF$_3$; $R_{27}$=H; $Ar_3$=(3,4,5)-(OMe)$_3$—C$_6$H$_2$-, is obtained by purification of the crude product by use of HPLC.

Step 4. The compound 130 [R=—(CH$_2$)$_4$—; $R_{22}$=—CH$_3$; $Ar_2$=—C$_6$H$_4$-(p)-CF$_3$; $R_{27}$=H; $Ar_3$=(3,4,5)-(OMe)$_3$—C$_6$H$_2$—; 2 mmols] obtained by the preceding reaction is stirred in acetonitrile (4 mL) containing tetrabutylammonium fluoride for 48 hours. Solvent is removed, and the residue is dissolved in a mixture of trifluoroacetic acid-water-triethylsilane (95:5:3) and is stirred at room temperature for 2 hours. Solvent is removed under reduced pressure and the residue is purified by chromatography, giving the Formula I compound 131, R=—(CH$_2$)$_4$—; $R_{22}$=—CH$_3$; $Ar_2$=—C$_6$H$_4$-(p)-CF$_3$; $R_{27}$=H; $Ar_3$=(3,4,5)-(OMe)$_3$—C$_6$H$_2$—.

Figure 19:
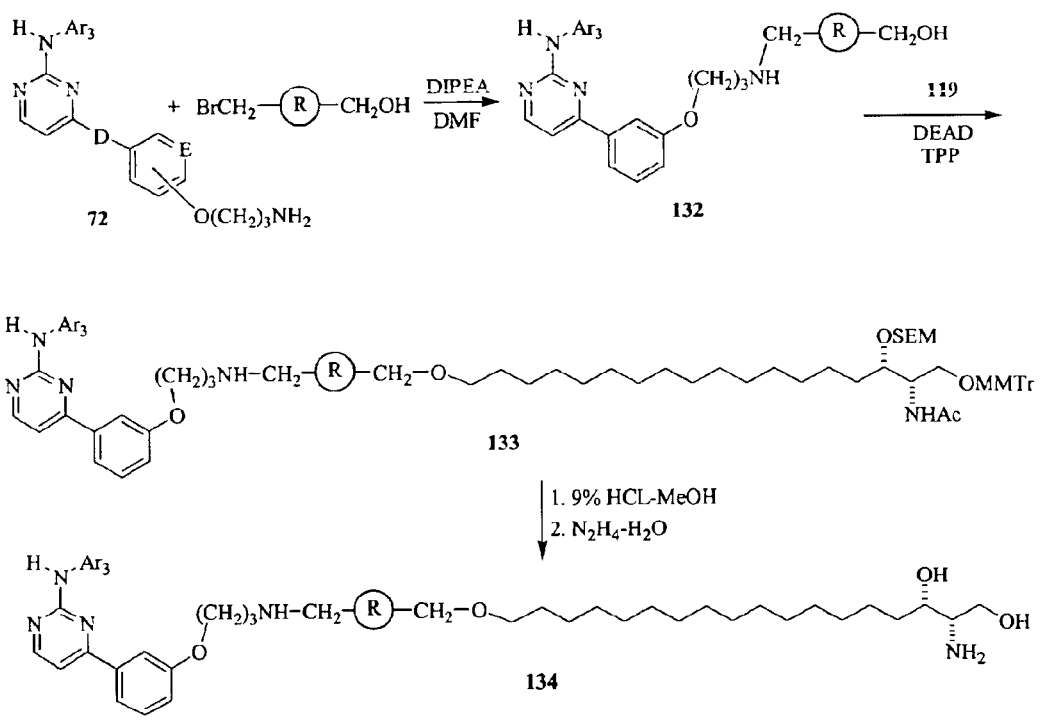
FIG. 19 is a schematic representation of the methods of Example 34.

Example 34 (See FIG. 19)

Preparation of a Formula I Compound wherein p is 2, q is 1, one Ligand, $L_1$, is 4-[3-(3-aminopropyloxy)phenyl]-N-(3,4,5-trimethoxyphenyl)-2-pyrimidineamine (72, where D=Single Bond; E=CH; —O(CH$_2$)$_3$NH$_2$ is Attached at C-3; and $Ar_3$=(3,4,5)-(MeO)$_3$—C$_6$H$_2$) Linked through the Amine Bond to the Linker X and a Second Ligand, $L_2$, is (2S,3S)-2-amino-1,3,18-octadecanetriol Linked via the C-18 Oxygen to the Linker X through an Ether Bond.

Step 1. A solution of 4-[3-(3-aminopropyloxy)phenyl]-N-(3,4,5-trimethoxyphenyl)-2-pyrimidineamine (72, where D=single bond; E=CH; —O(CH$_2$)$_3$NH$_2$ is attached at C-3; and $Ar_3$=(3,4,5)-(MeO)$_3$—C$_6$H$_2$); 2 mmol) (P. D. Davis, et. al., WO 97/19065, 29 May 1997), 1-iodopropanol (2 mmol), and diisopropylethylamine (0.35 mL) in DMF (5 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The combined organic extracts are washed with water and with brine and then dried (Na$_2$SO$_4$), filtered and concentrated under reduced pressure to give the crude product. Compound 132, R=—CH$_2$; D=single bond; E=CH; —O(CH$_2$)$_3$NH— is attached at C-3; and $Ar_3$=(3,4,5)-(MeO)$_3$—C$_6$H$_2$), is obtained by purification of the crude product by use of HPLC.

Step 2. Diethyl azodicarboxylate (3 mmol) is added dropwise via a syringe to a stirred solution of triphenylphosphine (3 mmol) in THF (5 mL) under an inert atmosphere and at room temperature. To this is added a solution of 132 (1 mmol) and 119 (1 mmol) in THF (3 mL). The resulting solution is stirred at RT and the progress of the reaction is followed by tlc. After reaction occurs, solvent is removed by evaporation under reduced pressure and the residue is purified by HPLC, giving pure compound 133 [R=—CH$_2$; D=single bond; E=CH; —O(CH$_2$)$_3$NH— is attached at C-3; and $Ar_3$=(3,4,5)-(MeO)$_3$—C$_6$H$_2$)].

Step 3. The O-protecting groups of 133 are removed by treating a sample (1 mmol) of the compound with 9% HCl in methanol (5 mL) for 15 minutes at room temperature. The reaction mixture is neutralized with silver carbonate powder, solids are removed by filtration and the solvent is evaporated to give the intermediate diol-amide. This product is placed together with 80% hydrazine hydrate (3 mL) in a sealed tube and warmed to 90° C. for 18 hours. The mixture is concentrated under reduced pressure and the crude reaction product is purified by chromatography, giving the desired Formula I compound 134, R=—CH$_2$; D=single bond; E=CH; —O(CH$_2$)$_3$NH— is attached at C-3; and $Ar_3$=(3,4,5)-(MeO)$_3$—C$_6$H$_2$).

Figure 20:
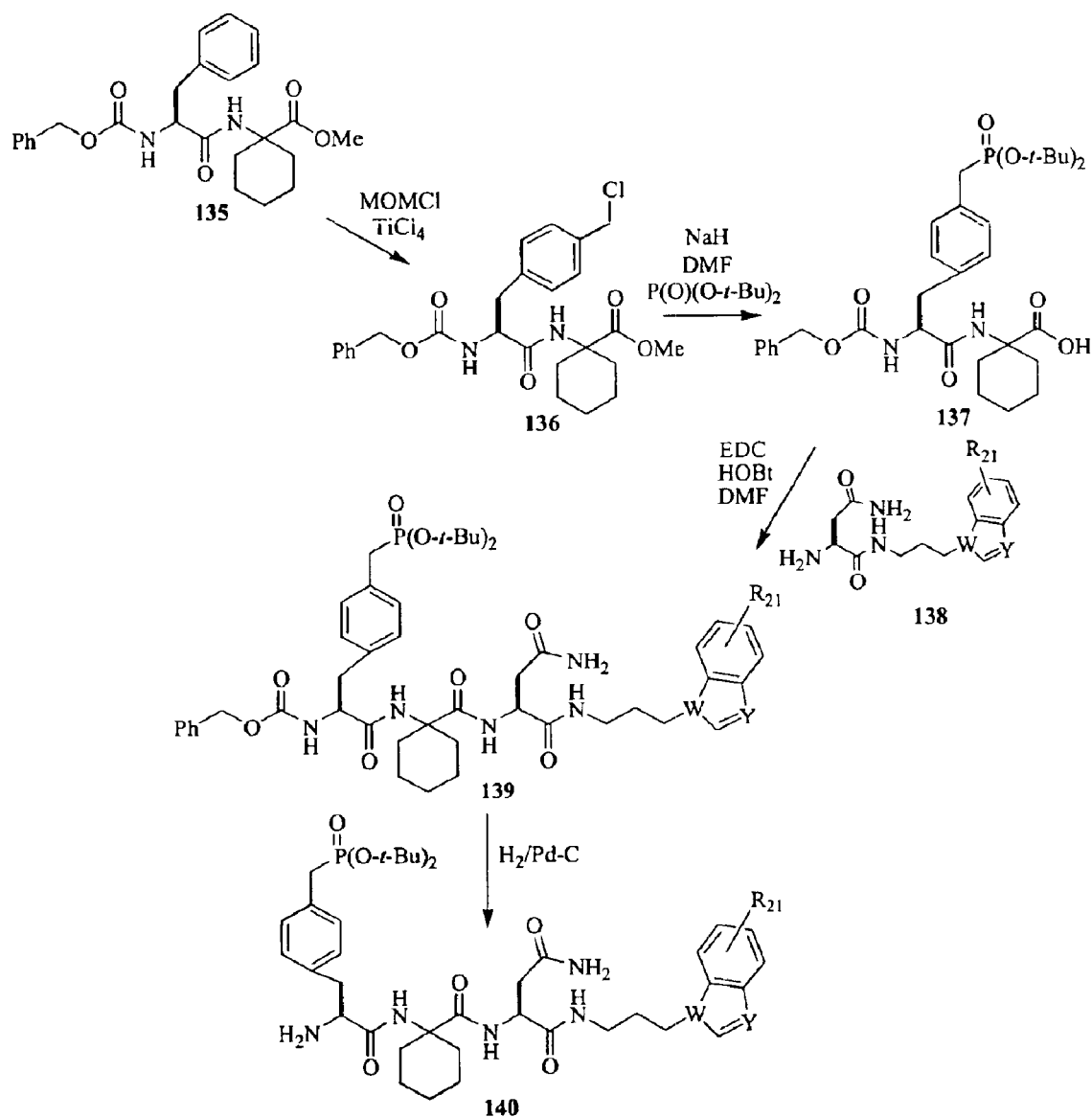
FIG. 20 is a schematic representation of the methods of Preparation 8.

Preparation 8 (See FIG. 20)

Preparation of Compound 140.

Step 1. A mixture of N-Cbz-phenylalanine-(1-methoxycarbonylcyclohexyl)amide (135; 5 mmols) (J. Schoepfer, et. al.; Bioorg. Med. Chem. Letters 1999, 9, 221–226), chloromethyl methyl ether (25 mmols), and titanium(IV) chloride (10 mmols) is stirred at 50° C. under an inert atmosphere. The progress of the reaction is followed by tlc. When the reaction is complete, it is quenched by the addition of ice and aqueous Na$_2$CO$_3$. The resulting mixture is extracted with CH$_2$Cl$_2$, the organic extract is washed with half-saturated saline, dried (Na$_2$SO$_4$), filtered and concentrated under reduced pressure to give the crude product. The desired compound (136) is obtained by chromatographic purification of the crude product.

Step 2. A solution of di-t-butyl phosphite (4.2 mmols) in dry DMF (1 mL) is added to a stirred mixture of 136 (4 mmols) and NaH (5 mmols) in dry DMF (5 mL). The resulting mixture is stirred at RT under an inert atmosphere and is monitored by tlc. When reaction is complete, the mixture is added slowly to ice and aqueous 1N NaOH. The aqueous mixture is extracted with ether, the layers separated and the aqueous layer is carefully acidified with cold aqueous 10% NaHSO$_4$. The acidic aqueous mixture is extracted with CH$_2$Cl$_2$, the organic extract is washed with half-saturated saline, dried (Na$_2$SO$_4$), filtered and concentrated under reduced pressure to give the crude product. The desired compound (137) is used without further purification in the next reaction.

Step 3. The product (137; 2 mmols) from the preceding experiment is dried and placed in a solution in dry DMF (5 mL) with the amine 138 ($R_{21}$=5-$CH_3$; W=N; and Y=CH; 2 mmols) (Schoepfer, et. al.) and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried ($Na_2SO_4$), and concentrated under reduced pressure. The product, 139, $R_{21}$=5-$CH_3$; W=N; and Y=CH, is obtained by purification of the crude product by use of HPLC.

Step 4. Ammonium formate (160 mg, 2.5 mmol) and 10% Pd/C (50 mg) are added to a solution of the compound (139, $R_{21}$=5-$CH_3$; W=N; and Y=CH) from the preceding reaction in methanol (2 mL) and THF (1 mL). The mixture is stirred at room temperature. The reaction is monitored by tlc and after reaction occurs, the mixture is filtered through Celite and rinsed with ethyl acetate. Ethyl acetate is added to the filtrate and the solution is washed successively with aq. $NaHCO_3$ and with half-saturated brine, then dried ($Na_2SO_4$), filtered and concentrated under reduced pressure to give the crude product. Compound 140, $R_{21}$=5-$CH_3$; W=N; and Y=CH, is obtained by purification of the crude product with HPLC.

Figure 21:
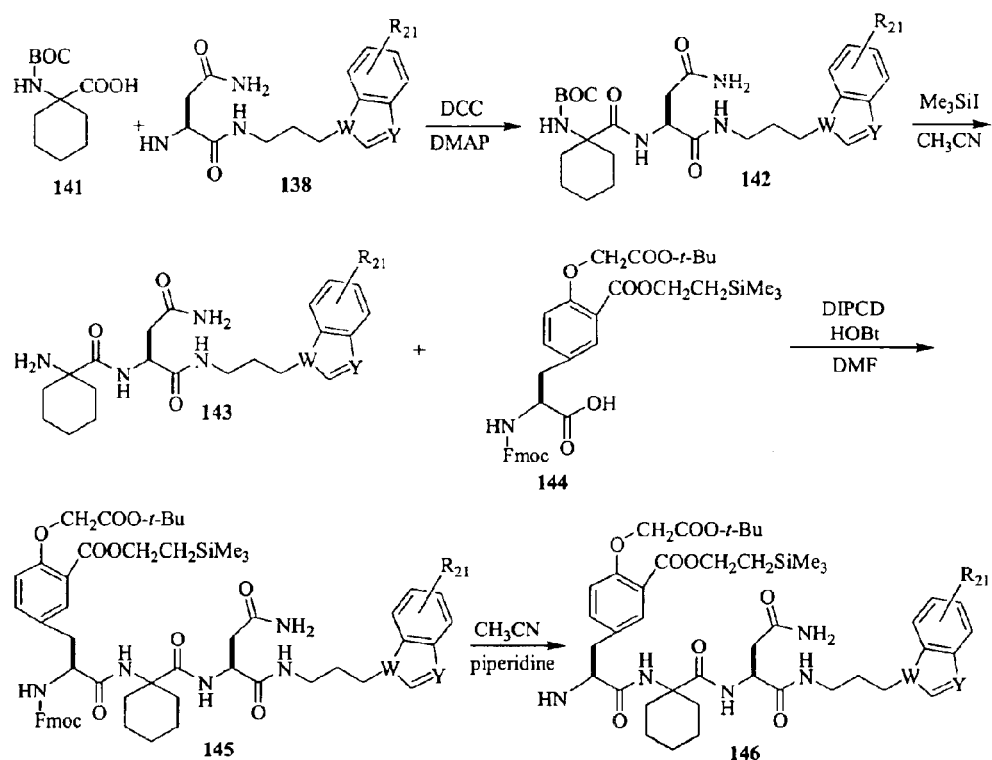
FIG. 21 is a schematic representation of the methods of Preparation 9.

Preparation 9 (See FIG. 21)
Preparation of Compound 146.

Step 1. A solution of N-BOC-1-aminocyclohexane carboxylic acid (141; 3 mmols), the asparagine amide 138, ($R_7$=5-$CH_3$; W=N; Y=CH; 3 mmols) (Schoepfer, et. al.), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 3.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. Compound 142, wherein $R_{21}$=5-$CH_3$; W=N; and Y=CH, is obtained by purification of the crude product with the use of HPLC.

Step 2. A solution of the product (142, $R_{21}$=5-$CH_3$; W=N; and Y=CH; 3 mmols) from the preceding reaction and $Me_3SiI$ in MeCN (5 mL) is stirred at room temperature. After reaction occurs as detected by tlc, the solution is diluted with EtOAc and then washed with 10% $Na_2CO_3$ and with water-brine. The organic layer is dried ($Na_2SO_4$), filtered and concentrated under reduced pressure to give the crude product. The desired compound (143, wherein $R_{21}$=5-$CH_3$; W=N; and Y=CH) is obtained by purification of the crude product with the use of HPLC.

Step 3. The product (143, $R_{21}$=5-$CH_3$; W=N; and Y=CH; 2 mmols) from the preceding experiment is carefully dried and placed in a solution in dry DMF (5 mL) with the carboxylic acid 144 (2 mmols) (Z.-J. Yao, et. al.; J. Med. Chem. 1999, 42, 25–35), and 1-hydroxybenzotriazole (2.5 mmols) under an inert atmosphere. The solution is stirred, cooled in an ice-water bath and protected from the atmosphere with a drying tube. To the stirred solution is added diisopropylcarbodiimide (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried and concentrated under reduced pressure. The desired product, 145, wherein $R_{21}$=5-$CH_3$; W=N; and Y=CH, is obtained by purification of the crude product by use of HPLC.

Step 4. A solution of 145 ($R_{21}$=5-$CH_3$; W=N; and Y=CH; 2 mmols) in dry acetonitrile (5 mL) and piperidine (0.25 mL) is stirred at RT under an inert atmosphere for 3 hours. The solvent is removed under reduced pressure and the crude residual product (146, $R_{21}$=5-$CH_3$; W=N; Y=CH) is used, as described in Example 10, without further purification.

Figure 22:
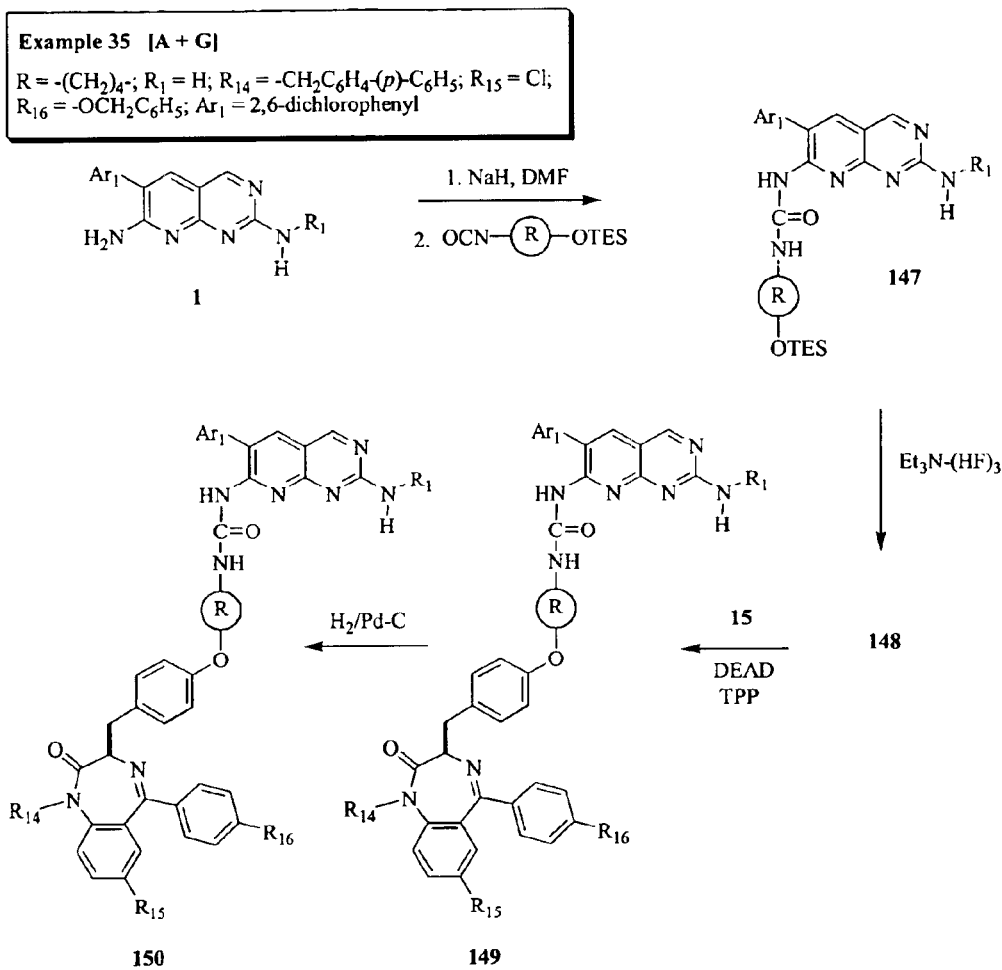
FIG. 22 is a schematic representation of the methods of Example 35.

Example 35 (See FIG. 22)

Preparation of a Formula I Compound wherein p is 2, q is 1, and one Ligand, $L_1$, is 2,7-diamino-6-(2,6-dichlorophenyl)pyrido[2,3-d]pyrimidine (1, $R_1$=H; $Ar_1$=2,6-dichlorophenyl) Linked to X via the 7-amine through a Urea Group and a Second Ligand, $L_2$, is 7-chloro-1,3-dihydro-5-(4-hydroxyphenyl)-3-(4-hydroxyphenyl)methyl-1-(4-phenylphenyl)methyl-2H-1,4-benzodiazepin-2-one (15, where $R_{14}$=—$CH_2C_6H_4$-(p)-$C_6H_5$; $R_{15}$=Cl; $R_{16}$=—$CH_2C_6H_5$) Linked through a Phenoxy Ether Bond to the Linker X.

Step 1. Sodium hydride (3.3 mmols) is added in portions to a stirred mixture of 2,7-diamino-6-(2,6-dichlorophenyl)pyrido[2,3-d]pyrimidine (1, $R_1$=H; $Ar_1$=—$C_6H_3$-(2,6)-$Cl_2$; 3 mmols) (J. M. Hamby, et. al.) and DMF (5 mL) under an inert atmosphere. After stirring for one hour at room temperature, 4-isocyanatobutan-1-ol-O-TES (3 mmols) is added and the mixture is stirred an additional 18 hours. The reaction mixture is filtered and the solids are washed with DMF. The combined filtrate is concentrated by evaporation under reduced pressure. Water is added to the residue and the solids are collected by filtration, washed with water and a small portion of ether, and air dried. The solids are purified by chromatography, giving compound 147 wherein R=—($CH_2$)$_4$—; $R_1$=H; and $Ar_1$=—$C_6H_3$-(2,6)-$Cl_2$.

Step 2. A solution of 147 [R=—($CH_2$)$_4$—; $R_1$=H; and $Ar_1$=—$C_6H_3$-(2,6)-$Cl_2$; 2.5 mmol] in acetonitrile (5 mL) and $Et_3N$—(HF)$_3$ (20 mmol) is stirred at room temperature. After reaction occurs as detected by tlc, the solution is diluted with EtOAc and washed with half-saturated brine. The organic layer is dried ($Na_2SO_4$), filtered and concentrated, giving the crude product. Alcohol 148 [R=—($CH_2$)$_4$—; $R_1$=H; and $Ar_1$=—$C_6H_3$-(2,6)-$Cl_2$] is purified by chromatography.

Step 3. Diethyl azodicarboxylate (3 mmol) is added dropwise via a syringe to a stirred solution of triphenylphosphine (3 mmol) in THF (5 mL) under an inert atmosphere and at room temperature. To this is added a solution of 148 (2 mmol) and 15 ($R_{14}$=—$CH_2C_6H_4$-(p)-$C_6H_5$; $R_{15}$=Cl; $R_{16}$=—$CH_2C_6H_5$; 2 mmol) in THF (5 mL). The resulting solution is stirred at RT and the progress of the reaction is followed by tlc. After reaction occurs, solvent is removed by evaporation under reduced pressure and the residue is purified by HPLC, giving pure compound 149 [R=—($CH_2$)$_4$—; $R_1$=H; $R_{14}$=—$CH_2C_6H_4$-(p)-$C_6H_5$; $R_{15}$=Cl; $R_{16}$=—$CH_2C_6H_5$; $Ar_1$=—$C_6H_3$-(2,6)-$Cl_2$].

Step 4. Ammonium formate (160 mg, 2.5 mmol) and 10% Pd/C (50 mg) are added to a solution of the compound 149 [R=—($CH_2$)$_4$—; $R_1$=H; $R_{14}$=—$CH_2C_6H_4$-(p)-$C_6H_5$; $R_{15}$=Cl; $R_{16}$=—$CH_2C_6H_5$; $Ar_1$=—$C_6H_3$-(2,6)-$Cl_2$; 1 mmol]in methanol (2 mL) and THF (1 mL). The mixture is stirred at room temperature. The reaction is monitored by tlc and after reaction occurs, the mixture is filtered through Celite and rinsed with ethyl acetate. Ethyl acetate is added to the filtrate and the solution is washed successively with aq. NaHCO$_3$ and with half-saturated brine, then dried (Na$_2$SO$_4$), filtered and concentrated under reduced pressure to give the crude product. Formula I compound 150 [R=—(CH$_2$)$_4$—; R$_1$=H; R$_{14}$=—CH$_2$C$_6$H$_4$-(p)-C$_6$H$_5$; R$_{15}$=Cl; R$_{16}$=—CH$_2$C$_6$H$_5$; Ar$_1$=—C$_6$H$_3$-(2,6)-Cl$_2$] is obtained by purification of the crude product with HPLC.

Figure 23:
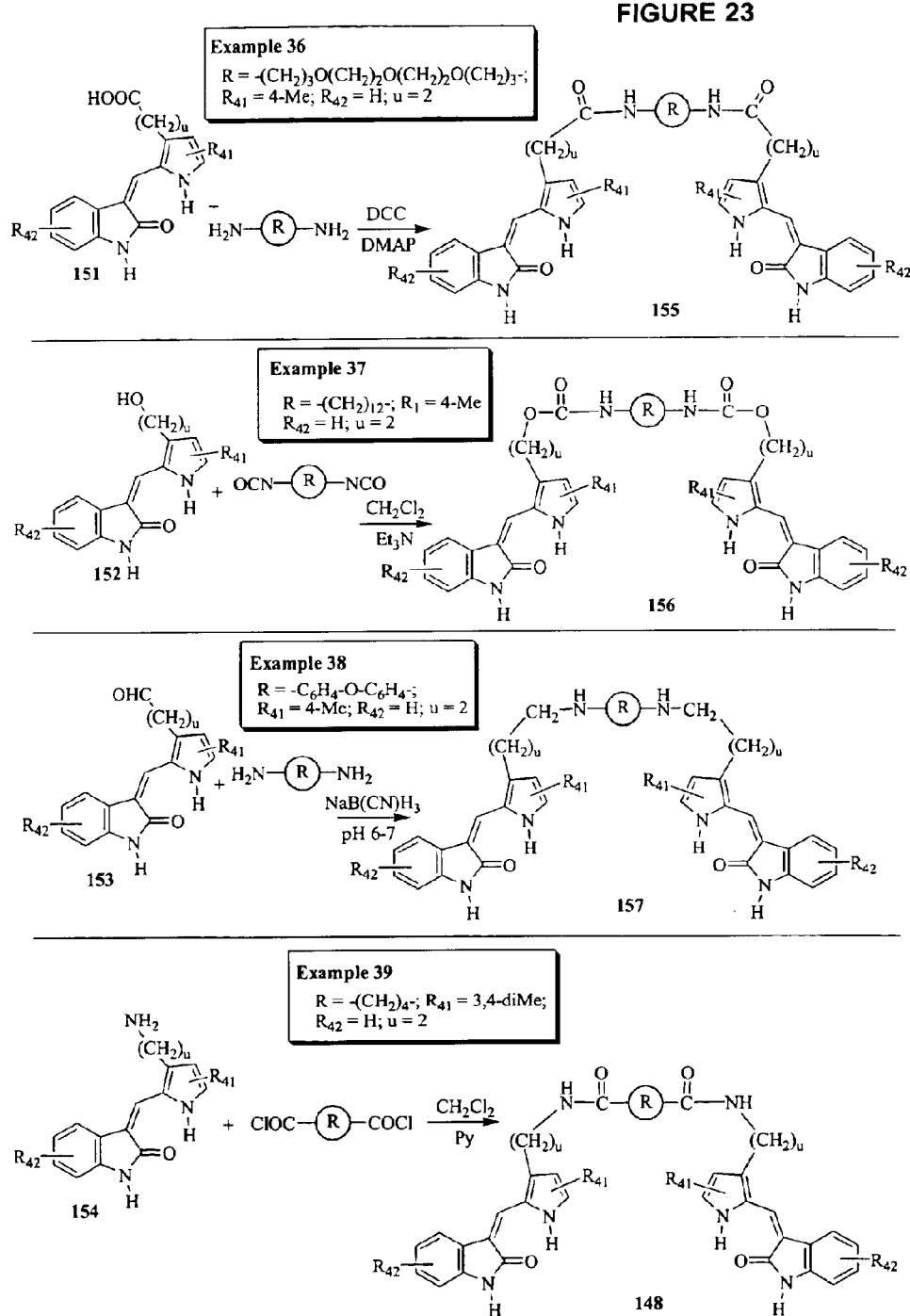
FIG. 23 is a schematic representation of the methods of Examples 36–39.

Example 36 (See FIG. 23)

Preparation of a Formula I Compound wherein p is 2, q is 1, and the Ligand, L, is (Z)-3-{[3-(2-carboxyethyl)-4-methylpyrrol-2-yl]methylidenyl}indolin-2-one (1, R$_{41}$=4-CH$_3$; R$_{42}$=H and u=2) Linked through an Amide Bond to the Linker X.

A solution of (Z)-3-{[3-(2-carboxyethyl)-4-methylpyrrol-2-yl]methylidenyl}indolin-2-one (151, R$_{41}$=4-CH$_3$; R$_{42}$=H and u=2; 2 mmols) (L. Sun, et. al., J. Med. Chem. 1998, 41, 2588–2603), 4,7,10-trioxa-1,13-tridecanediamine (1 mmol), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired Formula I compound (155, wherein R=—CH$_2$CH$_2$CH$_2$OCH$_2$CH$_2$—OCH$_2$CH$_2$OCH$_2$CH$_2$CH$_2$—; R$_{41}$=CH$_3$; R$_{42}$=H and u=2) is obtained by purification of the crude product with the use of HPLC.

Preparation 10

Preparation of (Z)-3-{[3-(2-Hydroxyethyl)-4-methylpyrrol-2-yl]methylidenyl}indolin-2-one (152).

A solution of (Z)-3-{[(3-(2-methoxycarbonyl)ethyl)-4-methylpyrrol-2-yl]methylidenyl}indolin-2-one (5 mmols) (L. Sun, et. al., J. Med. Chem. 1998, 41, 2588–2603) in ether (8 mL) is added dropwise to a stirred mixture of lithium aluminum hydride (50 mmols) and ether (5 mL) under an inert atmosphere. The progress of the reaction is followed by tlc and when complete, first EtOAc (1 mL) is carefully added to the mixture and then H$_2$O is added dropwise to destroy the excess hydride reagent. The mixture is filtered through Celite and the filtrate is washed with aq 5% Na$_2$CO$_3$, with water, and with half-saturated brine. The organic layer is dried (Na$_2$SO$_4$), filtered, and concentrated under reduced pressure. The residue is chromatographed, giving pure 152.

Preparation 11

Preparation of (Z)-3-{[3-(2-hydroxyethyl)-4-methylpyrrol-2-yl]methylidenyl}indolin-2-one (153).

A solution of (Z)-3-{[3-(2-hydroxyethyl)-4-methylpyrrol-2-yl]methylidenyl}indolin-2-one (152; 2 mmol) in methylene chloride (5 mL) is added to a solution of chromium(VI) oxide.(pyridine)$_2$ (12 mmol) in methylene chloride (5 mL) stirred under an inert atmosphere. The resulting solution is stirred at room temperature for 30 minutes after which excess reagent is destroyed by the addition of cold aq 10% Na$_2$CO$_3$. Celite is added to the mixture and stirred thoroughly. The solids are removed by filtration and the organic phase of the filtrate is separated, washed with water and with half-saturated brine, dried (Na$_2$SO$_4$), filtered, and concentrated under reduced pressure. The residue is chromatographed, giving pure 153.

Preparation 12

Preparation of (Z)-3-{[3-(2-Aminoethyl)-4-methylpyrrol-2-yl]methylidenyl}indolin-2-one (154).

A mixture of ammonium bromide (25 mmols) with methanol (8 mL) is acidified with acetic acid to pH 5.5 (pH meter) under a nitrogen atmosphere. (Z)-3-{[3-(2-Oxoethyl)-4-methylpyrrol-2-yl]methylidenyl}indolin-2-one (153, R$_1$=Me; R$_2$=H; n=2; 2 mmols) is added neat followed by sodium cyanoborohydride (3.1 mmols). The course of the reaction is followed by thin layer chromatography. After reaction occurs, the reaction solution is quenched in water and the pH of the aqueous mixture is adjusted to greater than 10 with aqueous NaOH. The mixture is extracted with ether, the organic extracts are washed with half-saturated saline, dried (Na$_2$SO$_4$), filtered and concentrated under reduced pressure to give the crude product. The desired 154 is obtained by purification of the crude product with the use of HPLC.

Example 37 (See FIG. 23)

Preparation of a Formula I Compound wherein p is 2, q is 1, and the Ligand, L, is (Z)-3-{[3-(2-hydroxyethyl)-4-methylpyrrol-2-yl]methylidenyl}indolin-2-one (152, R$_{41}$=4-CH$_3$; R$_{42}$=H and u=2) Linked through a Urethane Bond to the Linker X.

A solution of 1,12-diisocyanatododecane (1 mmol) in CH$_2$Cl$_2$(5 mL) containing Et$_3$N (0.2 mL) is stirred and cooled in an ice-water bath under an inert atmosphere. To this is added dropwise a solution of (Z)-3-{[3-(2-hydroxyethyl)-4-methylpyrrol-2-yl]methylidenyl}indolin-2-one (152, R$_{41}$=Me; R$_{42}$=H; u=2; 2 mmols) in CH$_2$Cl$_2$ (5 mL) After addition is complete, the cooling bath is removed and the reaction solution is allowed to warm to room temperature. The progress of the reaction is followed by tlc and when reaction has occurred, the reaction solution is quenched in cold 5% aqueous Na$_2$CO$_3$. The layers are separated and the organic layer is washed with aqueous Na$_2$CO$_3$, with water and is dried (Na$_2$SO$_4$), filtered and concentrated under reduced pressure to give the crude product. The desired Formula I compound 156, wherein R=—(CH$_2$)$_{12}$—; R$_{41}$=Me; R$_{42}$=H; u=2 is obtained by purification of the crude product with the use of HPLC.

Example 38 (See FIG. 23)

Preparation of a Formula I Compound wherein p is 2, q is 1, and the Ligand, L, is (Z)-3-{1[3-(2-oxoethyl)-4-methylpyrrol-2-yl]methylidenyl}indolin-2-one (153, R$_{41}$=4-CH$_3$; R$_{42}$=H and u=2) Linked through an Amine Bond to the Linker X.

A solution of 4,4'-oxydianiline in methanol (8 mL) is acidified with acetic acid to pH 6–6.5 (pH meter) under a nitrogen atmosphere. (Z)-3-{[3-(2-Oxoethyl)-4-methylpyrrol-2-yl]methylidenyl}indolin-2-one (153, R$_{41}$=Me; R$_{42}$=H; u=2; 2 mmols) is added neat followed by sodium cyanoborohydride (3.1 mmols). The course of the reaction is followed by thin layer chromatography. After reaction occurs, the reaction solution is quenched in water and the pH of the aqueous mixture is adjusted to greater than 10 with aqueous NaOH. The mixture is extracted with ether, the organic extracts are washed with half-saturated saline, dried (Na$_2$SO$_4$), filtered and concentrated under reduced pressure to give the crude product. The desired Formula I compound (157, wherein R=—C$_6$H$_4$OC$_6$H$_4$—; R$_{41}$=4-CH$_3$; R$_{42}$=H and u=2) is obtained by purification of the crude product with the use of HPLC.

Example 39 (See FIG. 23)

Preparation of a Formula I Compound wherein p is 2, q is 1, and the Ligand, L, is (Z)-3-{[3-(2-aminoethyl)-4-methylpyrrol-2-yl]methylidenyl}indolin-2-one (154, $R_{41}$=4, 5-di$CH_3$; $R_{42}$=H and u=2) Linked through an Amide Bond to the Linker X.

A solution of (Z)-3-{[3-(2-aminoethyl)$_4$-methylpyrrol-2-yl]methylidenyl}indolin-2-one (154, $R_{41}$=4-$CH_3$; $R_{42}$=H and u=2; 2 mmols) and adipoyl chloride (1 mmol) in $CH_2Cl_2$ (5 mL) containing pyridine is stirred at room temperature. The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound 158, wherein R=—($CH_2$)$_4$—; $R_{41}$=4-$CH_3$; $R_{42}$=H and u=2 is obtained by purification of the crude product with the use of HPLC.

Figure 24:
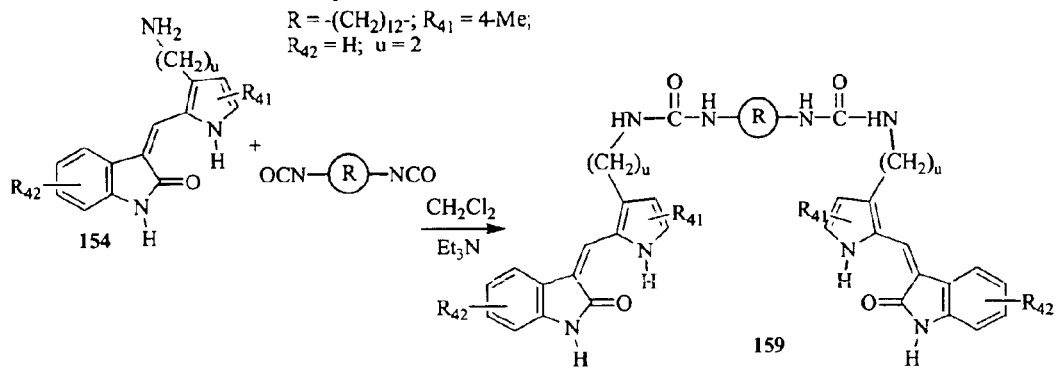
FIG. 24 is a schematic representation of the methods of Examples 40–42.
Figure 24:
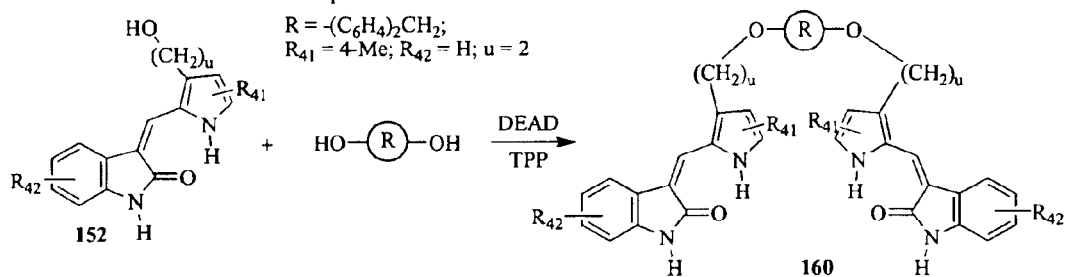
Figure 24:
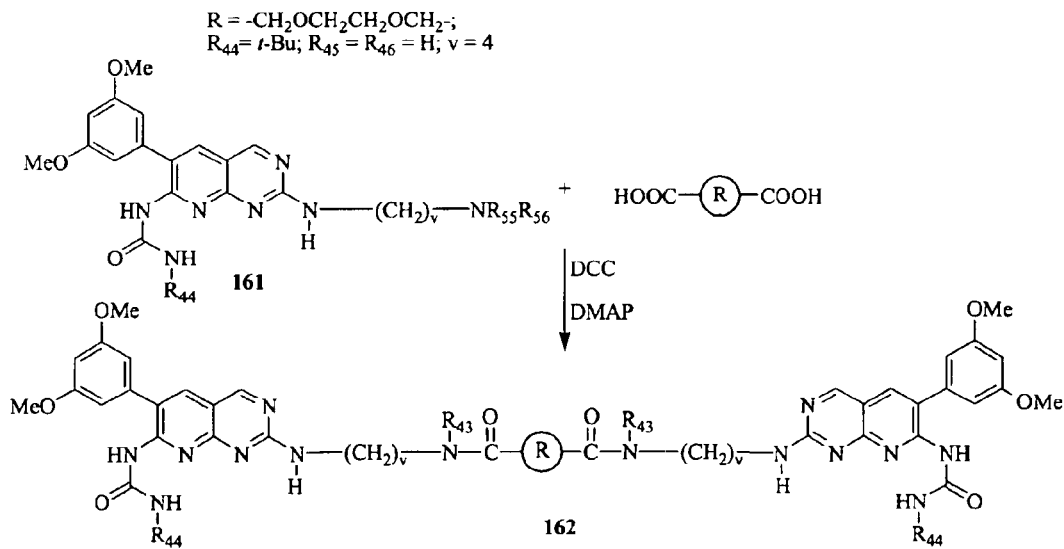

Example 40 (See FIG. 24)

Preparation of a Formula I Compound wherein p is 2, q is 1, and the Ligand, L, is (Z)-3-{[3-(2-aminoethyl)-4-methylpyrrol-2-yl]methylidenyl}indolin-2-one (154, $R_{41}$=4-$CH_3$; $R_{42}$=H and u=2) Linked through a Urea Bond to the Linker X.

A solution of 1,12-diisocyanatododecane (1 mmol) in $CH_2Cl_2$ (5 mL) containing $Et_3N$ (0.2 mL) is stirred and cooled in an ice-water bath under an inert atmosphere. To this is added dropwise a solution of (Z)-3-{[3-(2-aminoethyl)-4-methylpyrrol-2-yl]methylidenyl}indolin-2-one (154, $R_{41}$=4-$CH_3$; $R_{42}$=H and u=2; 2 mmols) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired Formula I compound 159, wherein R=—($CH_2$)$_{12}$—; $R_{41}$=4-$CH_3$; $R_{42}$=H and u=2 is obtained by purification of the crude product with the use of HPLC.

Example 41 (See FIG. 24)

Preparation of a Formula I Compound wherein p is 2, q is 1, and the Ligand, L, is (Z)-3-{[3-(2-hydroxyethyl)-$_4$-methylpyrrol-2-yl]methylidenyl}indolin-2-one (152, $R_{41}$=4-$CH_3$; $R_{42}$=H and u=2) Linked through an Ether Bond to the Linker X.

Diethyl azodicarboxylate (2 mmol) is added dropwise via a syringe to a stirred solution of triphenylphosphine (2 mmol) in THF (5 mL) under an inert atmosphere and at room temperature. To this is added a solution of (Z)-3-{[3-(2-hydroxyethyl)-4-methylpyrrol-2-yl]methylidenyl}indolin-2-one (152, $R_{41}$=4-Me; $R_{42}$=H; u=2; 2 mmols) and bis(4-hydroxyphenyl)methane (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired Formula I compound 160, wherein R=1,4-$C_6H_4CH_2C_6H_4$—; $R_{41}$=4-Me; $R_{42}$=H; and u=2.

Example 42 (See FIG. 24)

Preparation of a Formula I Compound wherein p is 2, q is 1, and the Ligand, L, is 1-tert-butyl-3-{6-(3,5-dimethoxyphenyl)-2-[[4-(amino)butyl]amino]pyrido[2,3-d] pyrimidin-7-yl}urea (161, $R_{44}$=t-Bu; $R_{45}$=$R_{46}$=H; v=4) Linked through an Amide Bond to the Linker X.

A solution of 1-tert-butyl-3-{6-(3,5-dimethoxyphenyl)-2-[[4-(amino)butyl]amino]pyrido[2,3-d]pyrimidin-7-yl}urea (161, $R_{44}$=t-Bu; $R_{45}$=$R_{46}$=H; v=4) (J. M. Hamby, et. al.; J. Med. Chem. 1997, 40, 2296–2303) (2 mmol), 3,6-dioxaoctanedioic acid (1 mmol), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 2.2 mmol) and the resulting solution is stirred at room temperature. The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound (162, wherein R=—$CH_2OCH_2CH_2OCH_2$—; $R_{44}$=t-Bu; $R_{45}$=H; v=4) is obtained by purification of the crude product with the use of HPLC.

Figure 25:
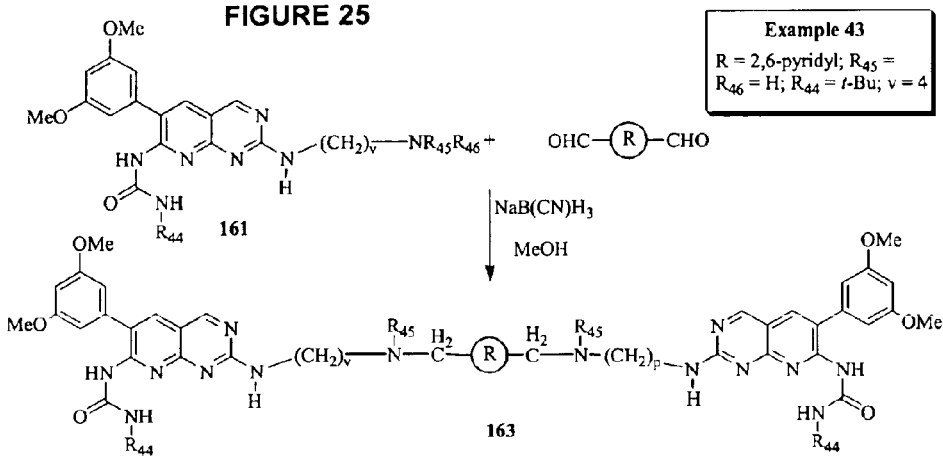
FIG. 25 is a schematic representation of the methods of Examples 43–45.
Figure 25:
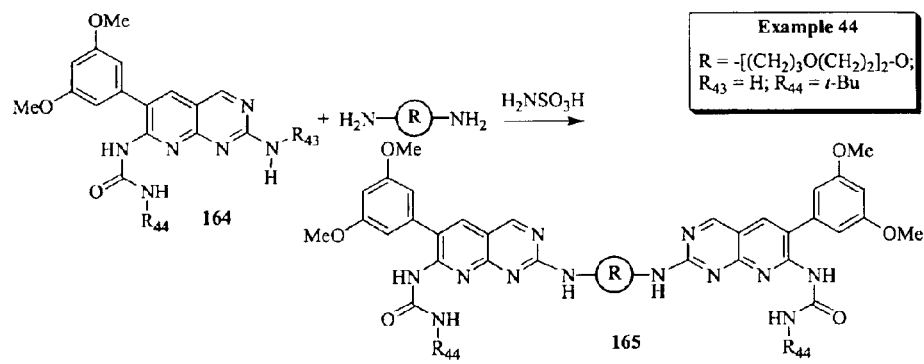
Figure 25:
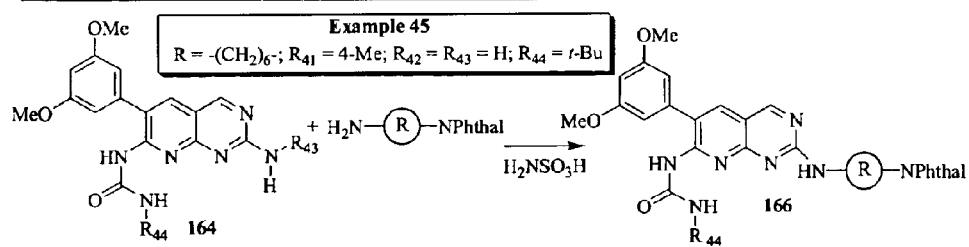
Figure 25:
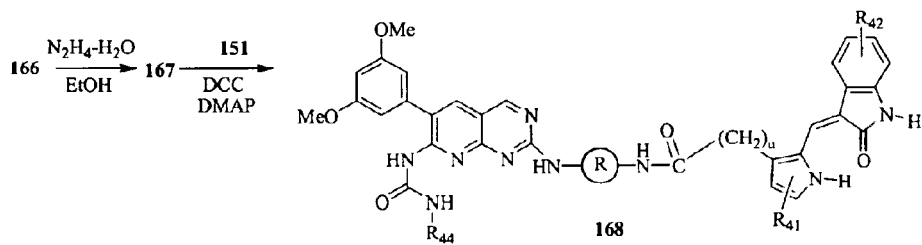

Example 43 (See FIG. 25)

Preparation of a Formula I Compound wherein p is 2, q is 1, and the Ligand, L, is 1-tert-butyl-3-{6-(3,5-dimethoxyphenyl)-2-[[4-(amino)butyl]amino]pyrido[2,3-d] pyrimidin-7-yl}urea (163, $R_{44}$=t-Bu; $R_{45}$=$R_{46}$=H; v=4) Linked through an Amine Bond to the Linker X.

A solution of 1-tert-butyl-3-{6-(3,5-dimethoxyphenyl)-2-[[4-(amino)butyl]amino]pyrido[2,3-d]pyrimidin-7-yl}urea (161, $R_{44}$=t-Bu; $R_{45}$=$R_{46}$=H; v=4; 2 mmols) in methanol (8 mL) is acidified with acetic acid to pH 6.5 (pH meter) under a nitrogen atmosphere. 2,6-Pyridinedicarboxaldehyde (1 mmol) is added neat followed by sodium cyanoborohydride (3.1 mmols). The course of the reaction is followed by thin layer chromatography. After reaction occurs, the reaction solution is quenched in water and the pH of the aqueous mixture is adjusted to greater than 10 with aqueous NaOH. The mixture is extracted with ether, the organic extracts are washed with half-saturated saline, dried ($Na_2SO_4$), filtered and concentrated under reduced pressure to give the crude product. The desired Formula I compound (163, wherein R=2,6-$C_5H_3N$—; $R_{44}$=t-Bu; $R_{45}$=H; v=4) is obtained by purification of the crude product with the use of HPLC.

Example 44 (See FIG. 25)

Preparation of a Formula I Compound wherein p is 2, q is 1, and the Ligand, L, is 1-[2-amino-6-(3,5-dimethoxyphenyl)pyrido[2,3-d]pyrimidin-7-yl]-3-tert-butyl urea (164, $R_{43}$=H; $R_{44}$=t-Bu) Linked through the 2-amino Group to the Linker X.

A mixture of 1-[2-amino-6-(3,5-dimethoxyphenyl)pyrido [2,3-d]pyrimidin-7-yl]-3-tert-butyl urea (164, $R_{43}$=H; $R_{44}$=t-Bu; 2 mmols), sulfamic acid (4 mmols), and 4,7,10-trioxa-1,13-tridecanediamine (1 mmol) and DMF (1 mL) is stirred and heated to 150° C. under an inert atmosphere. The reaction is monitored by tlc and, when complete, is cooled to room temperature and aqueous $Na_2CO_3$ (10 mL) is added. The mixture is extracted with $CH_2Cl_2$, the organic extract is washed with half-saturated saline, dried ($Na_2SO_4$), filtered and concentrated under reduced pressure to give the crude product. The desired Formula I compound (165, wherein R=—$CH_2CH_2CH_2OCH_2CH_2OCH_2CH_2OCH_2CH_2CH_2$—;

$R_{44}$=t-Bu) is obtained by purification of the crude product with the use of HPLC.

Example 45 (See FIG. 25)

Preparation of a Formula I Compound wherein p is 2, q is 1, Ligand, $L_1$, is 1-[2-amino-6-(3,5-dimethoxyphenyl) pyrido[2,3-d]pyrimidin-7-yl]-3-tert-butyl urea (164, $R_{43}$=H; $R_{44}$=t-Bu) Linked through the 2-amino Group to the Linker X and a Second Ligand, $L_2$, is (Z)-3-{[3-(2-carboxyethyl)-4-methylpyrrol-2-yl]methylidenyl}indolin-2-one (151, $R_{41}$=Me; $R_{42}$=H; u=2) Linked through an Amide Bond to the Linker X.

Step 1. A mixture of 1-[2-amino-6-(3,5-dimethoxyphenyl) pyrido[2,3-d]pyrimidin-7-yl]-3-tert-butyl urea (164, $R_{43}$=H; $R_{44}$=t-Bu; 2 mmols), sulfamic acid (4 mmols), and 1,6-hexanediamine monophthalimide (30 mmols) is stirred and heated to 150° C. under an inert atmosphere. The reaction is monitored by tlc and when complete, is cooled to room temperature and aqueous $Na_2CO_3$ (10 mL) is added. The mixture is extracted with $CH_2Cl_2$, the organic extract is washed with half-saturated saline, dried ($Na_2SO_4$), filtered and concentrated under reduced pressure to give the crude product. The desired compound [166, wherein R=—($CH_2$)$_6$—; $R_{44}$=t-Bu] is obtained by chromatographic purification of the crude product.

Step 2. A mixture of 166 ($R_{43}$=H; $R_{44}$=t-Bu; 2 mmols) and hydrazine hydrate (4 mmols) in absolute ethanol is warmed to 75° C. and stirred under an inert atmosphere. The progress of the reaction is monitored by TLC and when the reaction is complete, the mixture is cooled in an ice bath and the solids are removed by filtration. The solids are washed with ethanol and $CH_2Cl_2$. The combined filtrates are mixed with cold half-saturated brine and extracted with $CH_2Cl_2$. The combined organic layers are washed with water, dried ($Na_2SO_4$), filtered and concentrated under reduced pressure giving the crude product. The desired compound [167, wherein R=—($CH_2$)$_6$—; $R_{44}$=t-Bu] is obtained by purification of the crude product with the use of HPLC.

Step 3. A solution of (Z)-3-{[3-(2-carboxyethyl)-4-methylpyrrol-2-yl]methylidenyl}indolin-2-one (151, $R_{41}$=Me; $R_{42}$=H; u=2; 2 mmols), 167 (R=—($CH_2$)$_6$—; $R_{44}$=t-Bu; 2 mmols), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound [168, wherein R=—($CH_2$)$_6$—; $R_{41}$=Me; $R_{42}$=H; u=2; $R_{44}$=t-Bu] is obtained by purification of the crude product with the use of HPLC.

Figure 26:
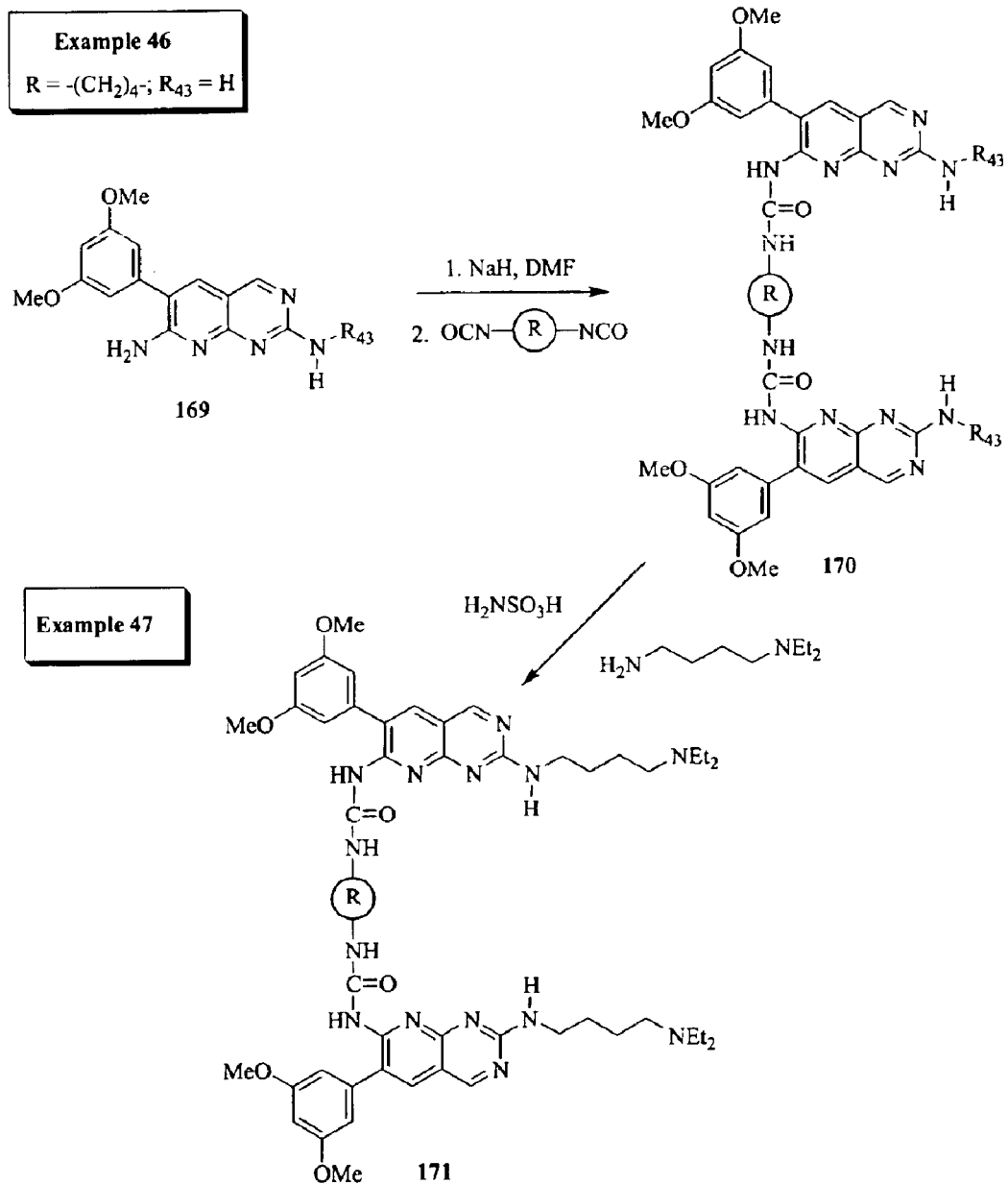
FIG. 26 is a schematic representation of the methods of Examples 46–47.

Example 46 (See FIG. 26)

Preparation of a Formula I Compound wherein p is 2, q is 1, and the Ligand, L, is 2,7-diamino-6-(3,5-dimethoxyphenyl)pyrido[2,3-d]pyrimidine (169, $R_{43}$=H) Linked to X via the 7-amine through a Urea Group.

Sodium hydride (3.3 mmols) is added in portions to a stirred mixture of 2,7-diamino-6-(3,5-dimethoxyphenyl) pyrido[2,3-d]pyrimidine (169, $R_{43}$=H; 3 mmols) (J. M. Hamby, et. al.) and DMF (5 mL) under an inert atmosphere. After stirring for one hour at room temperature, 1,4-diisocyanatobutane (1.5 mmols) is added and the mixture is stirred an additional 18 hours. The reaction mixture is filtered and the solids are washed with DMF. The combined filtrate is concentrated by evaporation under reduced pressure. Water is added to the residue and the solids are collected by filtration, washed with water and a small portion of ether, and air dried. The solids are purified by chromatography, giving the desired Formula I compound 170 wherein R=—($CH_2$)$_4$— and $R_{43}$=H.

Example 47 (See FIG. 26)

Preparation of a Formula I Compound wherein p is 2, q is 1, and the Ligand, L, is 6-(3,5-dimethoxyphenyl)-$N^2$-[4-(diethylamino)butyl]pyrido[2,3-d]pyrimidine-2,7-diamine Linked to X via the 7-amine through a Urea Group.

A mixture of 170, prepared as in Example 46, (2 mmols), sulfamic acid (4 mmols), and 4-(diethylamino)butylamine (30 mmols) is stirred and heated to 150° C. under an inert atmosphere. The reaction is monitored by tlc and when complete, is cooled to room temperature and aqueous $Na_2CO_3$ (10 mL) is added. The mixture is extracted with $CH_2Cl_2$, the organic extract is washed with half-saturated saline, dried ($Na_2SO_4$), filtered and concentrated under reduced pressure to give the crude product. The desired Formula I compound [171, wherein R=—($CH_2$)$_4$-] is obtained by chromatographic purification of the crude product.

Figure 27:
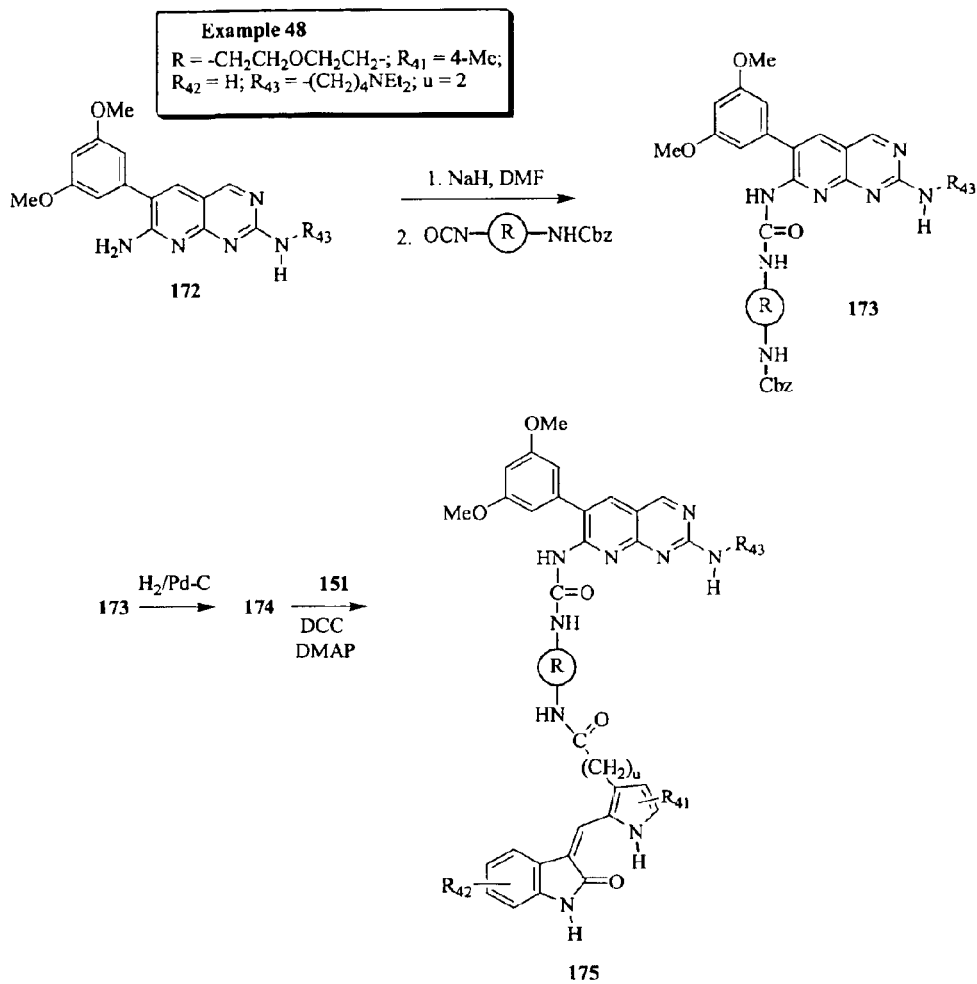
FIG. 27 is a schematic representation of the methods of Examples 48–49.
Figure 27:
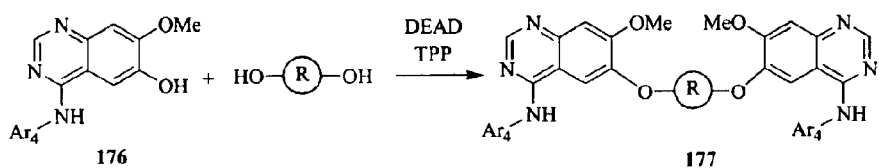

Example 48 (See FIG. 27)

Preparation of a Formula I Compound wherein p is 2, q is 1, one Ligand, $L_1$, is 6-(3,5-dimethoxyphenyl)-$N^2$-[4-(diethylamino)butyl]pyrido[2,3-d]pyrimidine-2,7-diamine (172, $R_{43}$=—($CH_2$)$_4$$NEt_2$) linked to X via the 7-amine through a Urea Group and a Second Ligand, $L_2$, is (Z)-3-{[3-(2-carboxyethyl)-4-methylpyrrol-2-yl]methylidenyl})indolin-2-one (151, $R_{41}$=Me; $R_{42}$=H; u=2) linked through an amide Bond to the Linker X.

Step 1. Sodium hydride (2.2 mmols) is added in portions to a stirred mixture of 6-(3,5-dimethoxyphenyl)-$N^2$-[4-(diethylamino)butyl]pyrido[2,3-d]pyrimidine-2,7-diamine (172, $R_{43}$=—($CH_2$)$_4$$NEt_2$; 2 mmols) (J. M. Hamby, et. al.; J. Med. Chem. 1997, 40, 2296–2303) and DMF (5 mL) under an inert atmosphere. After stirring for one hour at room temperature, 1-isocyanatobutan-4-(N-benzyloxycarbonyl) amine (1 mmol) is added and the mixture is stirred an additional 18 hours. The reaction mixture is filtered and the solids are washed with DMF. The combined filtrate is concentrated by evaporation under reduced pressure. Water is added to the residue and the solids are collected by filtration, washed with water and a small portion of ether, and air dried. The solids are purified by chromatography, giving the desired compound 173 wherein R=—$CH_2CH_2OCH_2CH_2$— and $R_{43}$=—($CH_2$)$_4$$NEt_2$.

Step 2. Ammonium formate (159 mg, 2.5 mmol) and 10% Pd/C (50 mg) are added to a solution of 173, R=—$CH_2CH_2OCH_2CH_2$— and $R_{43}$=—($CH_2$)$_4$$NEt_2$; 2 mmol) in methanol (4 mL) and THF (2 mL). The mixture is stirred at room temperature. The reaction is monitored by tlc and after reaction occurs, the mixture is filtered through Celite and rinsed with ethyl acetate. Additional ethyl acetate is added to the filtrate which then is washed successively with aq. $NaHCO_3$ and with half-saturated brine, then dried ($Na_2SO_4$), filtered and concentrated under reduced pressure to give the crude product. The desired compound [174, wherein R=—$CH_2CH_2OCH_2CH_2$— and $R_{43}$=—($CH_2$)$_4$$NEt_2$] is obtained following chromatography of the crude material.

Step 3. A solution of (Z)-3-{[3-(2-carboxyethyl)-4-methylpyrrol-2-yl]methylidenyl}indolin-2-one (151, $R_{41}$=4-Me; $R_{42}$=H; n=2; 2 mmols), 174 (R=—

$CH_2CH_2OCH_2CH_2$— and $R_{43}$=—$(CH_2)_4NEt_2$; 2 mmols), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound [175, wherein R=—$CH_2CH_2OCH_2CH_2$—; $R_{41}$=4-$CH_3$; $R_{42}$=H; $R_{43}$=—$(CH_2)_4NEt_2$ and u=2] is obtained by purification of the crude product with the use of HPLC.

Example 49 (See FIG. 27)

Preparation of a Formula I Compound wherein p is 2, q is 1, and the Ligand, L, is 4-[(3-chloro-4-fluorophenyl)amino]-6-hydroxy-7-methoxyquinazoline (176, where $Ar_4$=3-Cl4—F—$C_6H_3$) Linked through a 6-oxy Ether Bond to the Linker X.

Diethyl azodicarboxylate (2 mmol) is added dropwise via a syringe to a stirred solution of triphenylphosphine (2 mmol) in THF (5 mL) under an inert atmosphere and at room temperature. To this is added a solution of 4-[(3-chloro-4-fluorophenyl)amino]-6-hydroxy-7-methoxyquinazoline (176, Ar=3-Cl4-F—$C_6H_3$; 2 mmols) (K. H. Gibson, PCT Int. Appl. WO 96 33,980; Chem. Abstr. Vol. 126: P 47235r) and hexa(ethylene glycol) (1 mmol) in THF (1 mL). The resulting solution is stirred at RT and the progress of the reaction is followed by tlc. After reaction occurs, solvent is removed by evaporation under reduced pressure and the residue is purified by HPLC, giving the desired Formula I compound 177, wherein R=—$(CH_2CH_2O)_5CH_2CH_2$— and $Ar_4$=3-Cl4—F—$C_6H_3$.

Figure 28:
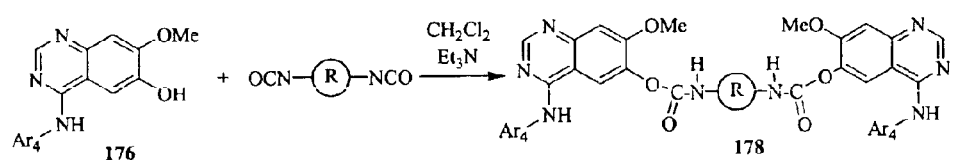
FIG. 28 is a schematic representation of the methods of Example 50.

Example 50 (See FIG. 28)

Preparation of a Formula I Compound wherein p is 2, q is 1, and the Ligand, L, is 4-[(3-chloro-4-fluorophenyl)amino]-6-hydroxy-7-methoxyquinazoline (176, where $Ar_4$=3-Cl-4-F—$C_6H_3$) Linked through a 6-urethane Bond to the Linker X.

A solution of 1,4-phenylene diisocyanate (1 mmol) in $CH_2Cl_2$ (5 mL) containing $Et_3N$ (0.2 mL) is stirred and cooled in an ice-water bath under an inert atmosphere. To this is added dropwise a solution of 4-[(3-chloro-4-fluorophenyl)amino]-6-hydroxy-7-methoxyquinazoline (176, $Ar_4$=3-Cl-4-F—$C_6H_3$; 2 mmols) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$ and with water and is dried ($Na_2SO_4$), filtered and concentrated under reduced pressure to give the crude product. The desired Formula I compound (178 wherein R=—$C_6H_4$— and $Ar_4$=3-Cl-4-F—$C_6H_3$) is obtained by purification of the crude product with the use of HPLC.

Figure 29:
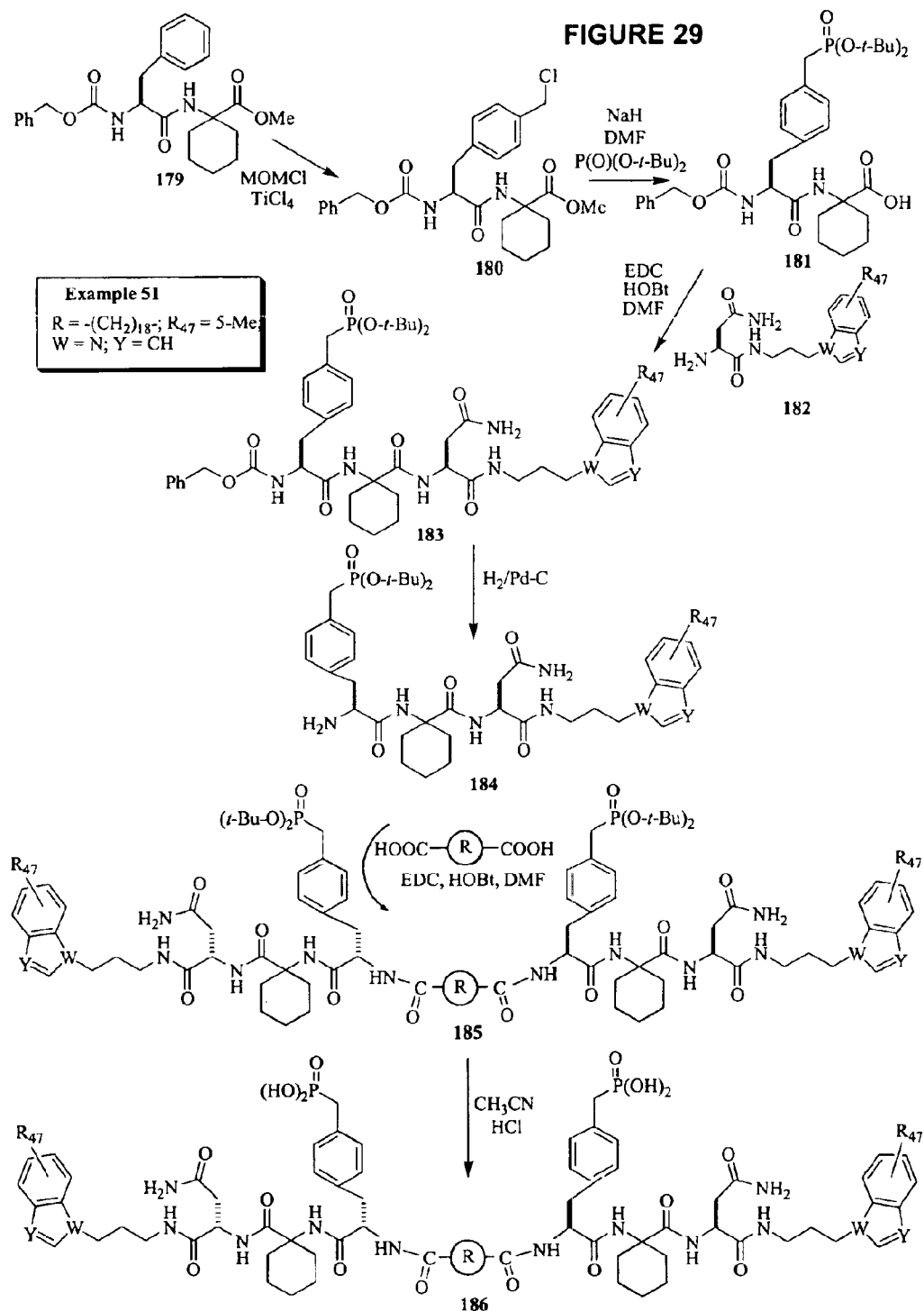
FIG. 29 is a schematic representation of the methods of Example 51.

Example 51 (See FIG. 29)

Preparation of a Formula I Compound wherein p is 2, q is 1, and the Ligand, L, is the Molecule E, where $R_{48}$=—$C_6H_4$-p-$CH_2P(O)(OH)_2$; $R_{47}$=5-$CH_3$; W=N; and Y=CH, Linked through an Amide Bond to the Linker X.

Step 1. A mixture of N-Cbz-phenylalanine-(1-methoxycarbonylcyclohexyl)amide (179; 5 mmols) (J. Schoepfer, et. al.; Bioorg. Med. Chem. Letters 1999, 9, 221–226), chloromethyl methyl ether (25 mmols), and titanium(IV) chloride (10 mmols) is stirred at 50° C. under an inert atmosphere. The progress of the reaction is followed by tlc. When the reaction is complete, it is quenched by the addition of ice and aqueous $Na_2CO_3$. The resulting mixture is extracted with $CH_2Cl_2$, the organic extract is washed with half-saturated saline, dried ($Na_2SO_4$), filtered and concentrated under reduced pressure to give the crude product. The desired compound (180) is obtained by chromatographic purification of the crude product.

Step 2. A solution of di-t-butyl phosphite (4.2 mmols) in dry DMF (1 mL) is added to a stirred mixture of 180 (4 mmols) and NaH (5 mmols) in dry DMF (5 mL). The resulting mixture is stirred at RT under an inert atmosphere and is monitored by tlc. When reaction is complete, the mixture is added slowly to ice and aqueous 1N NaOH. The aqueous mixture is extracted with ether, the layers separated and the aqueous layer is carefully acidified with cold aqueous 10% $NaHSO_4$. The acidic aqueous mixture is extracted with $CH_2Cl_2$, the organic extract is washed with half-saturated saline, dried ($Na_2SO_4$), filtered and concentrated under reduced pressure to give the crude product. The desired compound (181) is used without further purification in the next reaction.

Step 3. The product (181; 2 mmols) from the preceding experiment is dried and placed in a solution in dry DMF (5 mL) with the amine 182 ($R_{47}$=5-$CH_3$; W=N; and Y=CH; 2 mmols) (Schoepfer, et. al.) and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried ($Na_2SO_4$), and concentrated under reduced pressure. The product, 183, $R_{47}$=5-$CH_3$; W=N; and Y=CH, is obtained by purification of the crude product by use of HPLC.

Step 4. Ammonium formate (160 mg, 2.5 mmol) and 10% Pd/C (50 mg) are added to a solution of the compound (183, $R_{47}$=5-$CH_3$; W=N; and Y=CH) from the preceding reaction in methanol (2 mL) and THF (1 mL). The mixture is stirred at room temperature. The reaction is monitored by tlc and after reaction occurs, the mixture is filtered through Celite and rinsed with ethyl acetate. Ethyl acetate is added to the filtrate and the solution is washed successively with aq. $NaHCO_3$ and with half-saturated brine, then dried ($Na_2SO_4$), filtered and concentrated under reduced pressure to give the crude product. The desired compound (184, $R_{47}$=5-$CH_3$; W=N; and Y=CH) is obtained by purification of the crude product with HPLC.

Step 5. The product (184, $R_{47}$=5-$CH_3$; W=N; and Y=CH; 2 mmols) obtained from the preceding reaction is carefully dried and placed in a solution in dry DMF (5 mL) with the eicosa-1,20-dioic acid (1 mmol) and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried (Na$_2$SO$_4$), filtered and concentrated under reduced pressure. The product, 185, R=—(CH$_2$)$_{18}$—; R$_{47}$=5-CH$_3$; W=N; and Y=CH, is obtained by purification of the crude product by use of HPLC.

Step 6. A solution of the product (185, R=—(CH$_2$)$_{18}$—; R$_{47}$=5-CH$_3$; W=N; and Y=CH; 2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 186, wherein R=—(CH$_2$)$_{18}$—; R$_{47}$=5-CH$_3$; W=N; and Y=CH, as the ammonium salt.

Figure 30:
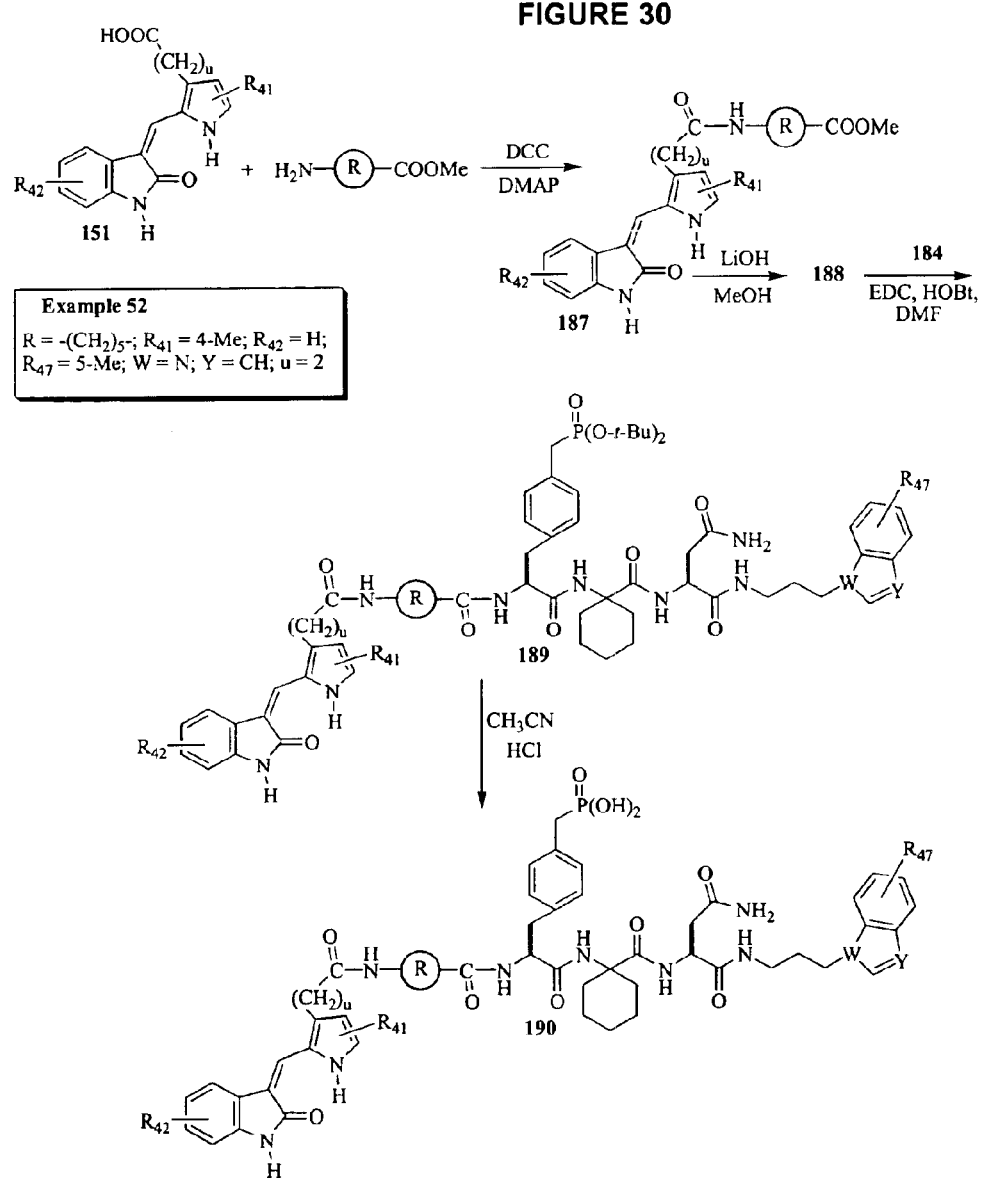
FIG. 30 is a schematic representation of the methods of Example 52.

Example 52 (See FIG. 30)

Preparation of a Formula I Compound wherein p is 2, q is 1, one Ligand, L$_1$, is the Molecule E, where R$_{48}$=—C$_6$H$_4$-p-CH$_2$P(O)(OH)$_2$; R$_{47}$=5CH$_3$; W=N; and Y=CH, Linked through an Amide Bond to the Linker X and a Second Ligand, L, is (Z)-3-{[3-(2-carboxyethyl)-4-methylpyrrol-2-yl]methylidenyl}indolin-2-one (151, R$_{41}$=4-Me; R$_{42}$=H; u=2) Linked through an Amide Bond to the Linker X.

Step 1. A solution of (Z)-3-{[3-(2-carboxyethyl)-4-methylpyrrol-2-yl]methylidenyl}indolin-2-one (151, R$_{41}$=4-Me; R$_{42}$=H; u=2; 2 mmols), 6-aminohexanoic acid methyl ester (2 mmols), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound (187, wherein R=—CH$_2$)$_5$—; R$_{41}$=4-CH$_3$; R$_{42}$=H; u=2) is obtained by purification of the crude product with the use of HPLC.

Step 2. A solution of the product (187, R=—(CH$_2$)$_5$—; R$_{41}$=4-CH$_3$; R$_{42}$=H; u=2; 2 mmols) of the preceding reaction and lithium hydroxide (100 mmols) in methanol (6 mL) and water (2 mL) is stirred at room temperature. After reaction is followed by thin layer chromatography. After reaction occurs, the pH of the solution is adjusted to 7 by the addition of dilute aq. hydrochloric acid. The solvent is removed by lyophilization and the dry, crude product (188, R=—(CH$_2$)$_5$—; R$_{41}$=4-CH$_3$; R$_{42}$=H; u=2) is used directly in the next reaction.

Step 3. A solution of 188 (R=—(CH$_2$)$_5$—; R$_{41}$=4-CH$_3$; R$_{42}$=H; u=2; 2 mmol), 184 (R$_{47}$=5-Me; W=N; Y=CH; 2 mmol), and 1-hydroxybenzotriazole (2.5 mmols) in dry DMF (5 mL) is prepared under an inert atmosphere. The solution is stirred, cooled in an ice-water bath and protected from the atmosphere with a drying tube. To the stirred solution is added 1-ethoxy-3-[3-(dimethylamino)propyl] carbodiimide hydrochloride (2.1 mmol). The course of the reaction is followed by tlc. The cooling bath is removed and after reaction occurs, the reaction mixture is partitioned between methylene chloride and saturated aqueous NaHCO$_3$. The organic layer is washed with water and brine, dried (Na$_2$SO$_4$), filtered and concentrated under reduced pressure. The product, 189, R=—(CH$_2$)$_5$—; R$_{41}$=4-CH$_3$; R$_{42}$=H; u=2 is obtained by purification of the crude product by use of HPLC.

Step 4. A solution of the product (189, R=—(CH$_2$)$_5$—; R$_{41}$=4-CH$_3$; R$_{42}$=H; R$_{47}$=5-Me; W=N; Y=CH; u=2; 2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 190, wherein R=—(CH$_2$)$_5$—; R$_{41}$=4-CH$_3$; R$_{42}$=H; R$_{47}$=5-CH$_3$; W=N; Y=CH and u=2, as the ammonium salt.

Figure 31:
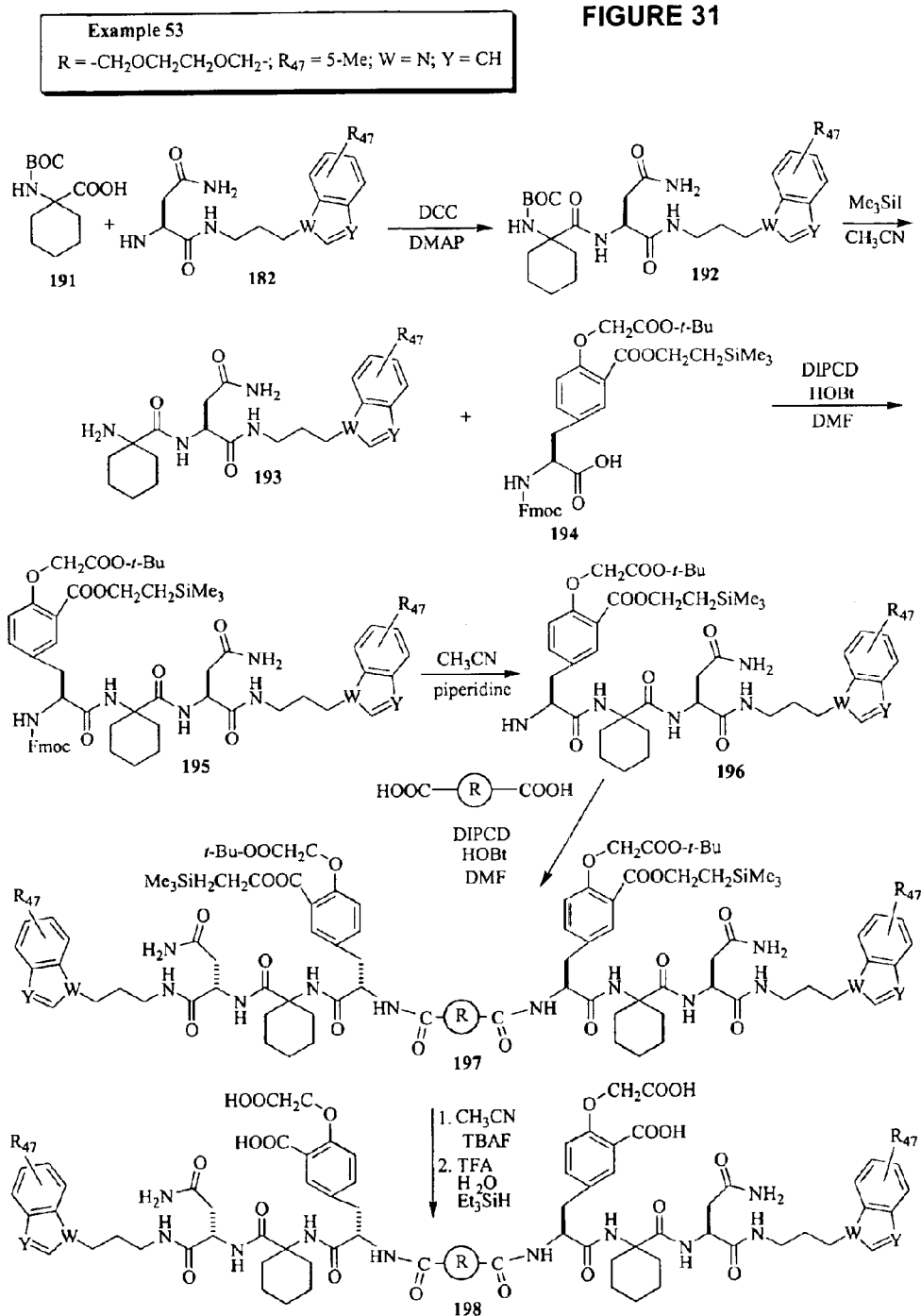
FIG. 31 is a schematic representation of the methods of Example 53.

Example 53 (See FIG. 31)

Preparation of a Formula I Compound wherein p is 2, q is 1, and the Ligand, L, is the Molecule E, where R$_{48}$=—C$_6$H$_4$-4—OCH$_2$COOH-3-COOH; R$_{47}$=5-CH$_3$; W=N; and Y=CH Linked through an Amide Bond to the Linker X.

Step 1. A solution of N-BOC-1-aminocyclohexane carboxylic acid (191; 3 mmols), the asparagine amide 182, (R$_{47}$=5-CH$_3$; W=N; Y=CH; 3 mmols) (Schoepfer, et. al.), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 3.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound (192, wherein R$_{47}$=5-CH$_3$; W=N; and Y=CH) is obtained by purification of the crude product with the use of HPLC.

Step 2. A solution of the product (192, R$_{47}$=5-CH$_3$; W=N; and Y=CH; 3 mmols) from the preceding reaction and Me$_3$Si1 in MeCN (5 mL) is stirred at room temperature. After reaction occurs as detected by tlc, the solution is diluted with EtOAc and then washed with 10% Na$_2$CO$_3$ and with water-brine. The organic layer is dried (Na$_2$SO$_4$), filtered and concentrated under reduced pressure to give the crude product. The desired compound (193, wherein R$_{47}$=5-CH$_3$; W=N; and Y=CH) is obtained by purification of the crude product with the use of HPLC.

Step 3. The product (193, R$_{47}$=5-CH$_3$; W=N; and Y=CH; 2 mmols) from the preceding experiment is carefully dried and placed in a solution in dry DMF (5 mL) with the carboxylic acid 194 (2 mmols) (Z.-J. Yao, et. al.; J. Med. Chem. 1999, 42, 25–35), and 1-hydroxybenzotriazole (2.5 mmols) under an inert atmosphere. The solution is stirred, cooled in an ice-water bath and protected from the atmosphere with a drying tube. To the stirred solution is added diisopropylcarbodiimide (2.1 mmol). The course of the reaction is followed by tlc. The cooling bath is removed and after reaction occurs, the reaction mixture is partitioned between methylene chloride and saturated aqueous NaHCO$_3$. The organic layer is washed with water and brine, dried and concentrated under reduced pressure. The desired product, 195 wherein R$_{47}$=5-CH$_3$; W=N; and Y=CH is obtained by purification of the crude product by use of HPLC.

Step 4. A solution of 195 (R$_{47}$=5-CH$_3$; W=N; and Y=CH; 2 mmols) in dry acetonitrile (5 mL) and piperidine (0.25 mL) is stirred at RT under an inert atmosphere for 3 hours. The solvent is removed under reduced pressure and the crude residual product (196, R$_{47}$=5-CH$_3$; W=N; Y=CH) is used directly in the following reaction.

Step 5. The dry product (196, R$_{47}$=5-CH$_3$; W=N; and Y=CH; 2 mmols) from the preceding experiment is placed in a solution in dry DMF (5 mL) with 3,6-dioxaoctanedioic acid (1 mmol), and 1-hydroxybenzotriazole (2.5 mmols)

under an inert atmosphere. The solution is stirred, cooled in an ice-water bath and protected from the atmosphere with a drying tube. To the stirred solution is added diisopropylcarbodiimide (2.1 mmol). The course of the reaction is followed by tlc. The cooling bath is removed and after reaction occurs, the reaction mixture is partitioned between methylene chloride and saturated aqueous NaHCO$_3$. The organic layer is washed with water and brine, dried and concentrated under reduced pressure. The desired product, 197 wherein R=—CH$_2$OCH$_2$CH$_2$OCH$_2$—; R$_{47}$=5-CH$_3$; W=N; and Y=CH is obtained by purification of the crude product by use of HPLC.

Step 6. The compound 197 (R=—CH$_2$OCH$_2$CH$_2$OCH$_2$—; R$_{47}$=5-CH$_3$; W=N; and Y=CH (2 mmols) obtained by the preceding reaction is stirred in acetonitrile (4 mL) containing tetrabutylammonium fluoride for 48 hours. Solvent is removed, and the residue is dissolved in a mixture of trifluoroacetic acid-water-triethylsilane (95:5:3) and is stirred at room temperature for 2 hours. Solvent is removed under reduced pressure and the residue is purified by chromatography, giving the Formula I compound 198, R=—CH$_2$OCH$_2$CH$_2$OCH$_2$—; R$_{47}$=5-CH$_3$; W=N; and Y=CH.

Figure 32:
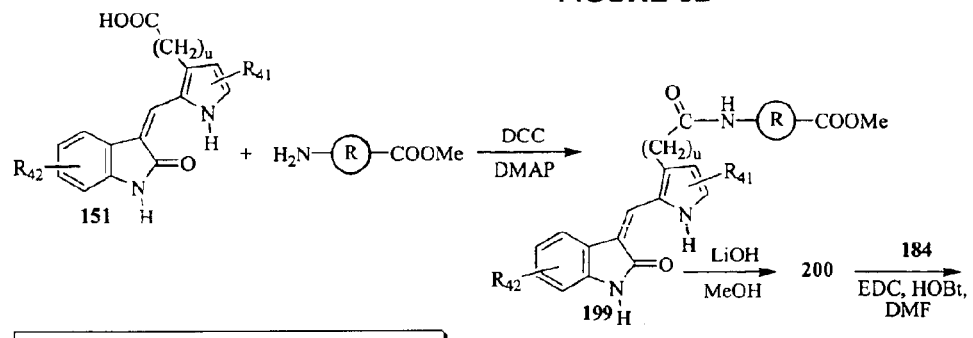
FIG. 32 is a schematic representation of the methods of Example 54.
Figure 32:
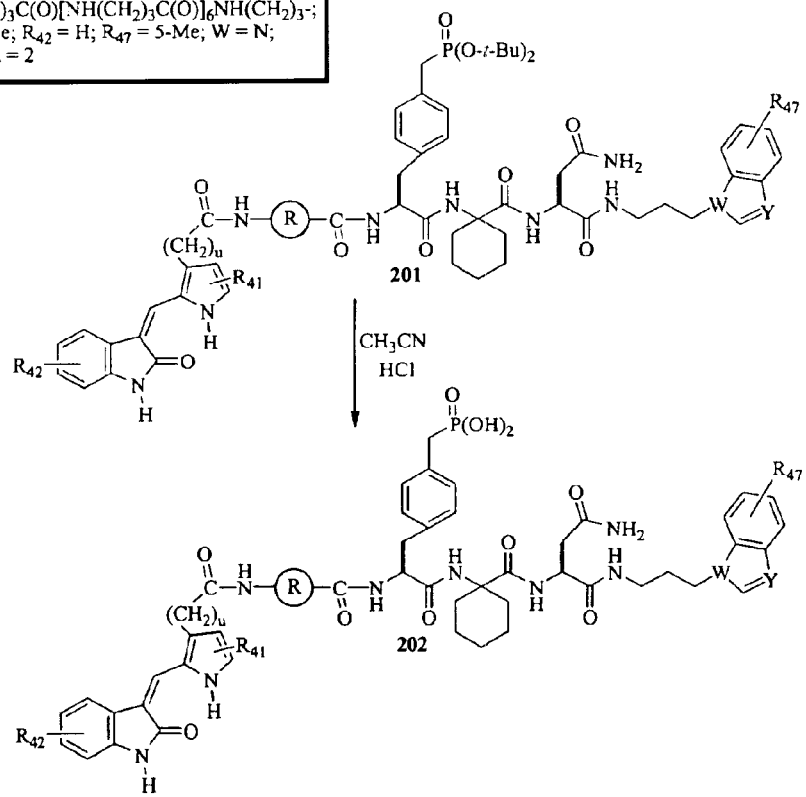

Example 54 (See FIG. 32)

Preparation of a Formula I Compound wherein p is 2, q is 1, one Ligand, L$_1$, is the Molecule E, where R$_{48}$=—C$_6$H$_4$-p-CH$_2$P(O)(OH)$_2$; R$_{47}$=5-CH$_3$; W=N; and Y=CH, Linked through an Amide Bond to the Linker X and a Second Ligand, L$_2$, is (Z)-3-{[3-(2-carboxyethyl)-4-methylpyrrol-2-yl]methylidenyl}indolin-2-one (151, R$_{41}$=4-Me; R$_{42}$=H; u=2) Linked through an Amide Bond to the Linker X.

Step 1. A solution of (Z)-3-{[3-(2-carboxyethyl)-4-methylpyrrol-2-yl]methylidenyl}indolin-2-one (151, R$_{41}$=4-Me; R$_{42}$=H; u=2; 2 mmols), (abu)$_8$ (where abu is γ-aminobutyric acid; 2 mmols) (A. A. Profit, et. al.; J. Am. Chem. Soc. 1999, 121, 280–283), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound 199, [R=—(CH$_2$)$_3$C(O)[HN(CH$_2$)$_3$C(O)]$_6$NH(CH$_2$)$_3$—; R$_{41}$=4-CH$_3$; R$_{42}$=H; u=2] is obtained by purification of the crude product with the use of HPLC.

Step 2. A solution of the product (199, R=—(CH$_2$)$_3$C(O)[HN(CH$_2$)$_3$C(O)]$_6$NH(CH$_2$)$_3$—; R$_{41}$=4-CH$_3$; R$_{42}$=H; u=2; 2 mmols) of the preceding reaction and lithium hydroxide (100 mmols) in methanol (6 mL) and water (2 mL) is stirred at room temperature. The reaction is followed by thin layer chromatography. After reaction is complete, the pH of the solution is adjusted to 7 by the addition of dilute aq. hydrochloric acid. The solvent is removed by lyophilization and the dry, crude product 200, R=—(CH$_2$)$_3$C(O)[HN(CH$_2$)$_3$C(O)]$_6$NH(CH$_2$)$_3$—; R$_{41}$=4-CH$_3$; R$_{42}$=H; u=2, is used directly in the next reaction.

Step 3. The product 200 [R=—(CH$_2$)$_3$C(O)[HN(CH$_2$)$_3$C(O)]$_6$NH(CH$_2$)$_3$—; R$_{41}$=4-CH$_3$; R$_{42}$=H; 2 mmols] from the preceding experiment is carefully dried and placed in a solution in dry DMF (5 mL) with the amine 184, (R$_{47}$=5-CH$_3$; W=N; and Y=CH; 2 mmols) prepared in Example 51 and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous NaHCO$_3$. The organic layer is washed with water and brine, dried and concentrated under reduced pressure. The product, 201 [R=—(CH$_2$)$_3$C(O)[HN(CH$_2$)$_3$C(O)]$_6$NH(CH$_2$)$_3$—; R$_{41}$=4-CH$_3$; R$_{42}$=H; u=2] is obtained by purification of the crude product by use of HPLC.

Step 4. A solution of the product (201, R=—(CH$_2$)$_3$C(O)[HN(CH$_2$)$_3$C(O)]$_6$NH(CH$_2$)$_3$—; R$_{41}$=4-CH$_3$; R$_{42}$=H; u=2; 2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 202, wherein R=—(CH$_2$)$_3$C(O)[HN(CH$_2$)$_3$C(O)]$_6$NH(CH$_2$)$_3$—; R$_{41}$=4-CH$_3$; R$_{42}$=H; R$_{47}$=5-CH$_3$; W=N; Y=CH and u=2, as the ammonium salt.

Figure 33:
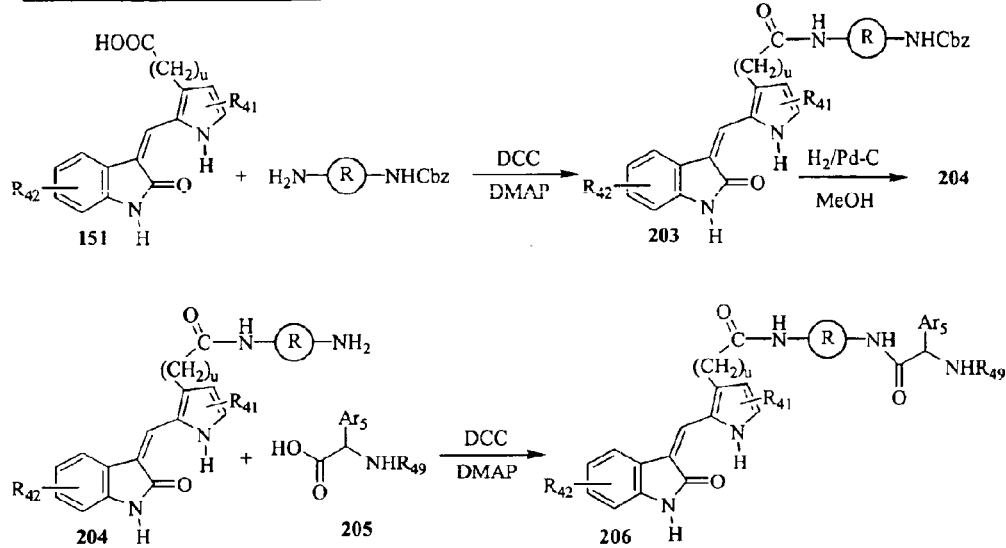
FIG. 33 is a schematic representation of the methods of Examples 55–56.
Figure 33:
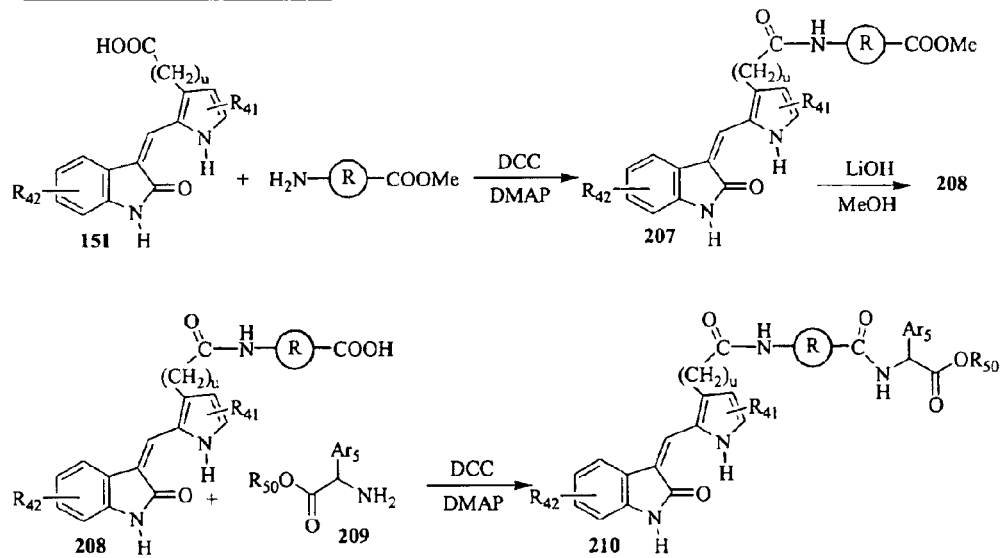

Example 55 (See FIG. 33)

Preparation of a Formula I Compound wherein p is 2, q is 1, one ligand, L$_1$, is 2-(pentafluorophenyl)glycine (205, Ar$_5$=C$_6$F$_5$; R$_{49}$=Ac) Linked via the Carboxylic Acid Group through an Amide Bond to the Linker X and a Second Ligand, L$_2$, is (Z)-3-{[3-(2-carboxyethyl)-4-methylpyrrol-2-yl]methylidenyl}indolin-2-one (151, R$_{41}$=4-Me; R$_{42}$=H; u=2) linked through an amide bond to the linker X.

Step 1. A solution of(Z)-3-{[3-(2-carboxyethyl)-4-methylpyrrol-2-yl]methylidenyl}indolin-2-one (151, R$_{41}$=4-Me; R$_{42}$=H; u=2; 2 mmols), 3-(N-benzyloxycarbonyl) aminopropyl amine (2 mmols), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound (203, wherein R=—(CH$_2$)$_3$—; R$_{41}$=4-CH$_3$; R$_{42}$=H; u=2) is obtained by purification of the crude product with the use of HPLC.

Step 2. Ammonium formate (160 mg, 2.5 mmol) and 10% Pd/C (50 mg) are added to a solution of the compound (203, R=—(CH$_2$)$_3$—; R$_{41}$=4-CH$_3$; R$_{42}$=H; u=2; 2 mmol) from the preceding reaction in methanol (2 mL) and THF (1 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. NaHCO$_3$ and with half-saturated brine, then dried (Na$_2$SO$_4$), filtered and concentrated under reduced pressure to give the crude product 204, R=—(CH$_2$)$_3$—; R$_{41}$=4-CH$_3$; R$_{42}$=H; u=2), which is used without further purification in the next step.

Step 3. A solution of 204 (R=—(CH$_2$)$_3$—; R$_{41}$=4-Me; R$_{42}$=H; u=2; 2 mmols), N-acetyl-2-(pentafluorophenyl) glycine (205, Ar$_5$=C$_6$F$_5$; R$_{49}$=Ac; 2 mmols), and 4-dimethylaminopyridine (DMAP; 10 mg) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound (206, R=—($CH_2$)$_3$—; $R_{41}$=4-$CH_3$; $R_{42}$=H; $R_{49}$=Ac; $Ar_5$=$C_6F_5$; u=2) is obtained by purification of the crude product with the use of HPLC.

Example 56 (See FIG. 33)

Preparation of a Formula I Compound wherein p is 2, q is 1, one Ligand, $L_1$, is 2-(pentafluorophenyl)glycine (205, $Ar_5$=$C_6F_5$; $R_{50}$=Me) linked via the amino group through an Amide Bond to the Linker X and a Second Ligand, $L_2$, is (Z)-3-{[3-(2-carboxyethyl)-4-methylpyrrol-2-yl]methylidenyl}indolin-2-one (151, $R_{41}$=4-Me; $R_{42}$=H; u=2) Linked through an Amide Bond to the Linker X.

Step 1. A solution of (Z)-3-{[3-(2-carboxyethyl)-4-methylpyrrol-2-yl]methylidenyl}indolin-2-one (151, $R_{41}$=4-Me; $R_{42}$=H; u=2; 2 mmols), methyl 3-aminobutyrate (2 mmols), and 4-dimethylaminopyridine (DMAP; 10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound (207, wherein R=—($CH_2$)$_3$—; $R_{41}$=4-$CH_3$; $R_{42}$=H; u=2) is obtained by purification of the crude product with the use of HPLC.

Step 2. A solution of the product (207, R=—($CH_2$)$_3$—; $R_{41}$=4-$CH_3$; $R_{42}$=H; u=2; 2 mmols) of the preceding reaction and lithium hydroxide (100 mmols) in methanol (6 mL) and water (2 mL) is stirred at room temperature. Progress of the reaction is followed by thin layer chromatography. After reaction occurs, the pH of the solution is adjusted to 7 by the addition of dilute aq. hydrochloric acid. The solvent is removed by lyophilization and the dry, crude product (208, R=—($CH_2$)$_3$—; $R_{41}$=4-$CH_3$; $R_{42}$=H; u=2) is used directly in the next reaction.

Step 3. A solution of 208 (R=—($CH_2$)$_3$—; $R_{41}$=4-Me; $R_{42}$=H; u=2; 2 mmols), 2-(pentafluorophenyl)glycine methyl ester (209, $Ar_5$=$C_6F_5$; $R_{50}$=Me; 2 mmols), and 4-dimethylaminopyridine (DMAP; 10 mg) in DMF (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound (210, wherein R=—($CH_2$)$_3$—; $R_{41}$=4-$CH_3$; $R_{42}$=H; $R_{50}$=Me; $Ar_5$=$C_6F_5$; u=2) is obtained by purification of the crude product with the use of HPLC.

Preparation 13

Preparation of Asparagin-N-{3-{5-methyl-3-[2-(N-benzyloxycarbonyl)aminoethyl]-1H-indol-1-yl}propyl}amide (212).

Compound 212 is prepared with the procedure used by J. Schoepfer, et. al., Bioorg. Med. Chem. Letters, 1999, 9, 221–226 for the synthesis of 182 except that 5-methyl-3-[2-(N-benzyloxycarbonyl)aminoethyl]-1H-indole is used in place of 5-methyl-1H-indole.

Figure 34:
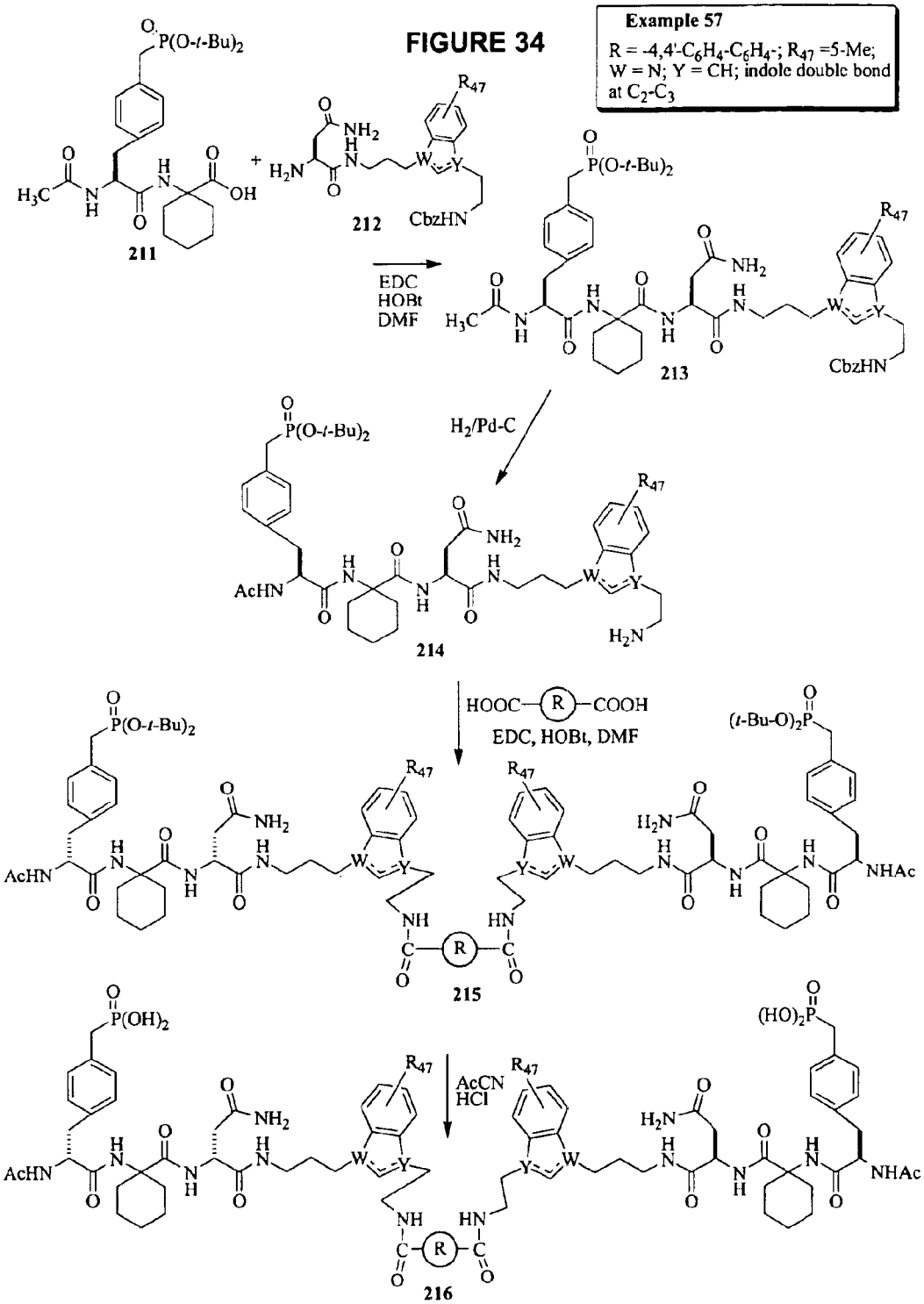
FIG. 34 is a schematic representation of the methods of Example 57.

Example 57 (See FIG. 34)

Preparation of a Formula I Compound wherein p is 2, q is 1, and the Ligand, L, is the Molecule F, where $R_{48}$=—$C_6H_4$-p-$CH_2P(O)(OH)_2$; $R_{47}$=5-$CH_3$; W=N; and Y=CH, Linked through an Amide Bond to the Linker X.

Step 1. A solution of N-acetyl-[4-(di-t-butylphosphonyl)methyl]phenylalanine-(1-methoxycarbonylcyclohexyl)amide (211; 2 mmols) (J. Schoepfer, et. al.; Bioorg. Med. Chem. Letters 1999, 9, 221–226), 212 ($R_{47}$=5-$CH_3$; W=N; and Y=CH; indole double bond at $C_2$–$C_3$; 2 mmols), and 1-hydroxybenzotriazole (2.5 mmols) in dry DMF (5 mL) is prepared under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried and concentrated under reduced pressure. The product 213 ($R_{47}$=5-$CH_3$; W=N; and Y=CH) is obtained by purification of the crude product by use of HPLC.

Step 2. Ammonium formate (160 mg, 2.5 mmol) and 10% Pd/C (50 mg) are added to a solution of the compound (213, $R_{47}$=5-$CH_3$; W=N; and Y=CH; 2 mmol) from the preceding reaction in methanol (4 mL) and THF (2 mL). The mixture is stirred at room temperature. The reaction is monitored by tlc and after reaction occurs, the mixture is filtered through Celite and rinsed with ethyl acetate. The filtrate is diluted with ethyl acetate and is washed successively with aq. $NaHCO_3$ and with half-saturated brine, then dried ($Na_2SO_4$), filtered and concentrated under reduced pressure to give the crude product. The desired compound (214, $R_{47}$=5-$CH_3$; W=N; and Y=CH) is obtained by purification of the crude product with HPLC.

Step 3. The product (214, $R_{47}$=5-$CH_3$; W=N; and Y=CH; 2 mmols) obtained from the preceding reaction is dried and placed in a solution in dry DMF (5 mL) with the 4,4'-biphenyldicarboxylic acid (1 mmol) and 1-hydroxybenzotriazole (2.5 mmols) under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried ($Na_2SO_4$), filtered and concentrated under reduced pressure. The product, 215, R=—$C_6H_4$—$C_6H_4$—; $R_{47}$=5-$CH_3$; W=N; and Y=CH, is obtained by purification of the crude product by use of HPLC.

Step 4. A solution of the product (215, R=—$C_6H_4$—$C_6H_4$—; $R_{47}$=5-$CH_3$; W=N; and Y=CH; 2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the Formula I compound 216 (R=—$C_6H_4$—$C_6H_4$—; $R_{47}$=5-$CH_3$; W=N; and Y=CH; indole double bond at C-2, C-3) as the ammonium salt.

Prreparation 14

Preparation of 3-Amino-ZpTyr-$Ac_6c$-(1S,2R)-Achec-$NH_2$, di-t-butyl ester (217)

Compound 217 is prepared with the method used by P. Furet, et. al., J. Med Chem. 1999, 42, 2358–2363 for the synthesis of 3-Amino-Z-pTyr-$Ac_6c$-(1S,2R)-Achec-$NH_2$ except that $N^3$-Fmoc-Tyr[$PO_3$(t-Bu)$_2$]-OH is used in place of $N^3$-Fmoc-Tyr($PO_3H_2$)—OH.

Figure 35:
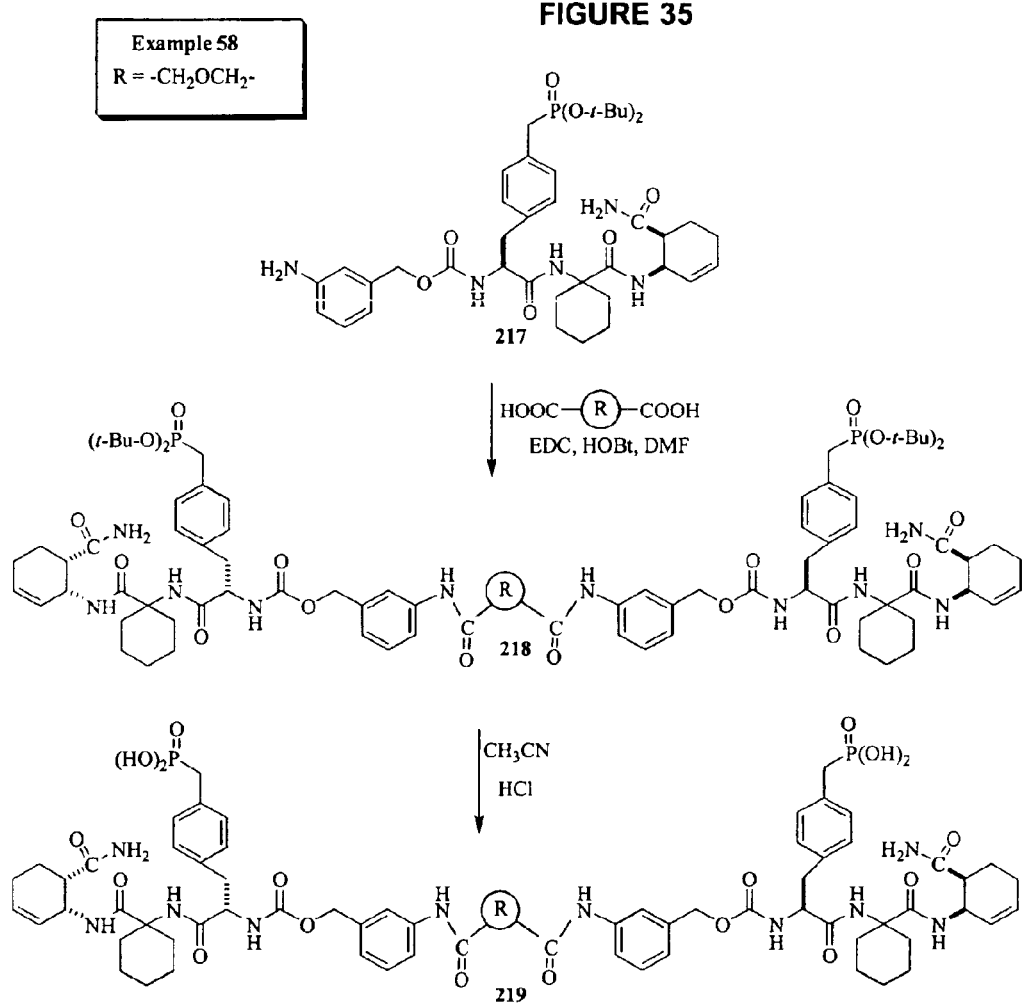
FIG. 35 is a schematic representation of the methods of Example 58.

Example 58 (See FIG. 35)

Preparation of a Formula I Compound wherein p is 2, q is 1, and the Ligand, L, is the Molecule I, where $R_{48}$=—$C_6H_4$-p-$CH_2P(O)(OH)_2$, Linked through an Amide Bond to the Linker X.

Step 1. A solution of 217 (2 mmol), adipic acid (1 mmol), and 1-hydroxybenzotriazole (2.5 mmols) in dry DMF (5 mL is prepared under an inert atmosphere. The solution is stirred, cooled in an ice-water bath and protected from the atmosphere with a drying tube. To the stirred solution is added 1-ethoxy-3-[3-(dimethylamino)propyl]carbodiimide hydrochloride (2.1 mmol). The course of the reaction is followed by tlc. The cooling bath is removed and after reaction occurs, the reaction mixture is partitioned between methylene chloride and saturated aqueous $NaHCO_3$. The organic layer is washed with water and brine, dried ($Na_2SO_4$), filtered and concentrated under reduced pressure. The product, 218, is obtained by purification of the crude product by use of HPLC.

Step 2. A solution of the product 218 (2 mmols) obtained in the preceding reaction in acetonitrile (5 mL) containing aqueous 4 N HCl is stirred and the reaction monitored carefully by tlc. The reaction solution is neutralized with the addition of aqueous ammonium hydroxide and the resulting solution is lyophilized, giving a solid residue. Chromatography of this residue over a reversed phase column gives the desired Formula I compound 219 as the ammonium salt.

Example 59

In Vitro and In Vivo Assays

The binding and activity of the compounds of the invention is studied in vitro using a modification of the method of Favata (Favata, M F. et al. J. Biol. Chem. 273(29):18623 and Kolb, A J., et al. 1998. DDT 3(7): 333). Effect of inhibitors on phosphorylation is assessed following the procedure of Yang (Yang, C., et al., 1994. Eur. J. Biochem. 221(3): 973).

The ability of the compounds to inhibit activation-dependent TCR tyrosine phosphorylation, intracellular calcium mobilization, and proliferation are evaluated in Jurkat T cells (Trevillyan, J M. 1999. Arch Biochem. Biophys. 364(1);19).

The therapeutic efficacy of the compounds is evaluated in vivo. For example the prophylactic effect of the compounds on recurrent ocular herpetic keratitis is demonstrated in squirrel monkeys (Kaufman, H E., et al. 1996. Antiviral Res. 33(1):65).

The effect of the compounds on ocular diseases such as diabetic retinopathy is shown in human patients according to the method of Celebi (Celebi, S., et al 1998. Turk. J. Med. Sci. 28(6): 637) in which the blood flow velocity and vascular resistance parameters of the central retinal artery are assessed by color Doppler ultrasonography. A newborn rat model of the retinopathy of prematurity is used to test effects of compounds following the method of Niesman (Niesman, M. et al Niesman, and M. 1997 Neurochem. Res. 22(5): 597). The ability of compounds to suppress VEGF induced angiogenesis, a model of macular degeneration, is studied in mice (Masayuki, I., 1997. Brit. J. Pharmacol. 122(6): 1061).

The compounds of the invention are also tested in animal models of several vascular diseases. For example the effect of the compounds is demonstrated ex vivo using Langenedorff-perfused rat heart, a model of ischemia (Yao, K., 1994. Biol. Pharm. Bull. 17(4):517). The anti-atherosclerosis effect of the compounds is assessed in spontaneously hypertensive rats (Kubo, M., 1992 J. Pharmacobio-Dyn. 15(11):657).

The efficacy of the compounds of the invention to alleviate the symptoms of chronic inflammatory disease is determined. For example, the effects of compounds on psoriasis are determined in a rat model of the disease (Smith, S., et al. 1993. Immunopharmacol. Immunotoxicol. 15(1): 13). The anti-arthritic effect is evaluated using a mouse model of mBAS-induced delayed type hypersensitivity granuloma to measure immune-mediated chronic inflammatory tissue formation (Dunn, C J. 1991. Int. J. Immunopharmacol. 12(8):94530).

The anti-neoplastic effects are shown in mice with implants of colon carcinomas following the method of Sebolt-Leopold (Sebolt-Leopold, J S., et al. 1999. Nature Medicine, 5(7):810).

Each of the journal articles cited in Example 59 is hereby incorporated by reference in its entirety.

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A compound of formula II:

L-X-L  II or a pharmaceutically acceptable salt thereof wherein:
one L is selected from the group consisting of:
(a) a moiety of formula XI:

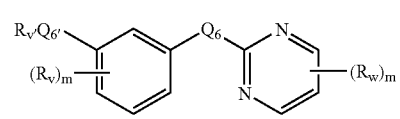

wherein
each $R_v$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;
$R_{v'}$ is a covalent bond linking the moiety to the linker;
each $R_w$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$Q_6$ is $NR_{w'}$, O, S or alkylene, where $R_{w'}$ is hydrogen, alkyl, substituted alkyl, alkenyl, substituted alkenyl, alkynyl, substituted alkynyl or acyl;

$Q_{6'}$ is $NR_{v''}$, O, S or alkylene, where $R_{v''}$ is hydrogen, alkyl, substituted alkyl, alkenyl, substituted alkenyl, alkynyl, substituted alkynyl or acyl;

each m is independently an integer from 1 to 3;

(b) a moiety of formula XII:

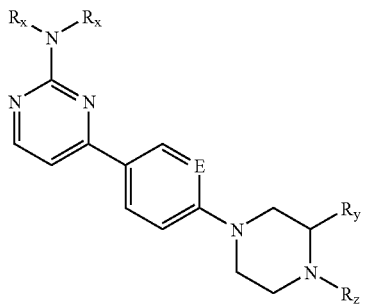

XII wherein each $R_x$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;

$R_y$ is independently selected from the group consisting of hydrogen, alkyl, substituted alkyl, alkenyl, substituted alkenyl, alkynyl and substituted alkynyl;

$R_z$ is a covalent bond linking the moiety to the linker;

E is CH or N; and (c) a moiety of formula XIII:

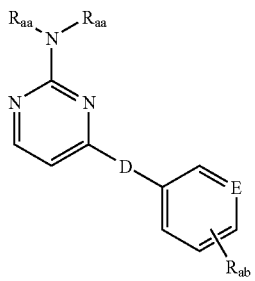

XIII wherein each $R_{aa}$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;

$R_{ab}$ is alkyl, substituted alkyl, alkoxy, substituted alkoxy, amino, substituted amino, thioalkoxy, substituted thioalkoxy, wherein the alkyl, substituted alkyl, alkoxy, substituted alkoxy, amino, substituted amino, thioalkoxy or substituted thioalkoxy group is substituted with a covalent bond linking the moiety to the linker;

D is a covalent bond, $NR_{ab'}$, O or S, where $R_{ab'}$ is hydrogen, alkyl, substituted alkyl, alkenyl, substituted alkenyl, alkynyl, substituted alkynyl or acyl;

E is CH or N;

and the other L is selected from the group consisting of:

(d) a moiety of formula XI;

(e) a moiety of formula XII;

(f) a moiety of formula XIII:

(g) a moiety of formula VI:

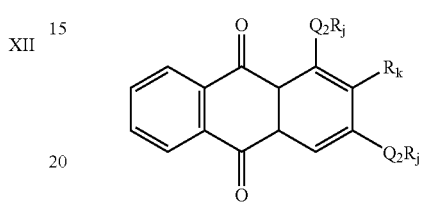

VI wherein each $R_j$ is independently selected from the group consisting of hydrogen, alkyl, substituted alkyl, alkenyl, substituted alkenyl, alkynyl, substituted alkynyl, acyl and a covalent bond linking the moiety to the linker;

$R_k$ is selected from the group consisting of hydrogen, alkyl, substituted alkyl, alkenyl, substituted alkenyl, alkynyl, substituted alkynyl, alkoxy, hydroxy, halogen and —CHO;

each $Q_2$ is independently $NR_{j'}$, O and S, where $R_{j'}$ is hydrogen, alkyl, substituted alkyl, alkenyl, substituted alkenyl, alkynyl, substituted alkynyl or acyl;

provided one and only one of $R_j$ comprises a covalent bond linking the moiety to the linker;

(h) a moiety of formula VIII:

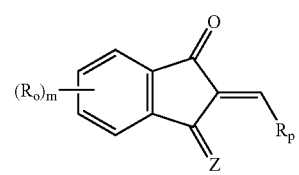

VIII wherein each $R_o$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$R_p$ is aryl or heteroaryl, wherein the aryl or heteroaryl group is substituted with a covalent bond linking the moiety to the linker or with —OZ' where Z' is a covalent bond linking the moiety to the linker;

Z is 2H or O;

m is an integer from 1 to 3;

(i) a moiety of formula IX:

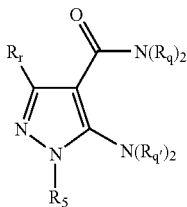

IX wherein each $R_q$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl, heterocyclic and a covalent bond linking the moiety to the linker;

each $R_{q'}$ is independently selected from the group consisting of hydrogen, alkyl, substituted alkyl, alkenyl, substituted alkenyl, alkynyl, substituted alkynyl and acyl;

$R_s$ is selected from the group consisting of hydrogen, alkyl substituted alkyl alkenyl, substituted alkenyl, alkynyl, substituted alkynyl and acyl;

$R_r$ is aryl or heteroaryl, wherein the aryl or heteroaryl group is substituted with a covalent bond linking the moiety to the linker;

provided one and only one of $R_q$ or $R_r$ comprises a covalent bond linking the moiety to the linker;

(j) a moiety of formula X:

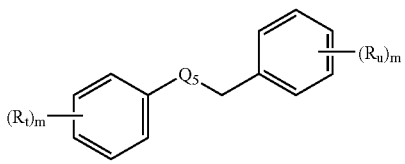

X wherein each $R_t$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

each $R_u$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy and a covalent bond linking the moiety to the linker;

$Q_5$ is $NR_{t'}$, O, S or alkylene, where $R_{t'}$ is hydrogen, alkyl, substituted alkyl, alkenyl, substituted alkenyl, alkynyl, substituted alkynyl or acyl;

each m is independently an integer from 1 to 3;

provided one and only one of $R_u$ comprises a covalent bond linking the moiety to the linker;

(k) a moiety of formula XIV:

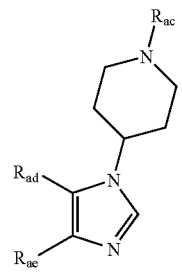

XIV wherein $R_{ac}$ is a covalent bond linking the moiety to the linker;

$R_{ad}$ is selected from the group consisting of hydrogen, alkyl, substituted alkyl, alkenyl, substituted alkenyl, alkynyl, substituted alkynyl, cycloalkyl, substituted cycloalkyl, aryl, heteroaryl and heterocyclic;

$R_{ae}$ is aryl or heteroaryl;

(l) a moiety of formula XV:

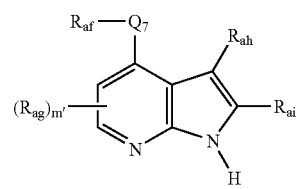

XV wherein $R_{af}$ is selected from the group consisting of hydrogen, alkyl, substituted alkyl, alkenyl, substituted alkenyl, alkynyl, substituted alkynyl and acyl;

each $R_{ag}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$R_{ah}$ is aryl or heteroaryl;

$R_{ai}$ is aryl or heteroaryl, wherein the aryl or heteroaryl group is substituted with a covalent bond linking the moiety to the linker;

$Q_7$ is $NR_{af'}$, O, S or alkylene, where $R_{af'}$ is hydrogen, alkyl, substituted alkyl, alkenyl, substituted alkenyl, alkynyl, substituted alkynyl or acyl;

m' is 1 or 2;

(m) a moiety of formula XVI:

$$\text{XVI}$$

wherein each $R_{aj}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

$R_{al}$ is aryl or heteroaryl;

each $R_{ak}$ is independently selected from the group consisting of hydrogen, alkyl, substituted alkyl, alkenyl, substituted alkenyl, alkynyl, substituted alkynyl, cycloalkyl, substituted cycloalkyl, aryl, heteroaryl, heterocyclic, and a covalent bond linking the moiety to the linker;

$Q_8$ is $NR_{al'}$, O, S or alkylene, where $R_{al'}$ is hydrogen, alkyl, substituted alkyl, alkenyl, substituted alkenyl, alkynyl, substituted alkynyl or acyl;

m is an integer from 1 to 3;

provided one and only one of $R_{ak}$ comprises a covalent bond linking the moiety to the linker;

(n) a moiety of formula XIX:

$$\text{XIX}$$

wherein $R_{as}$ is selected from the group consisting of hydrogen, alkyl, substituted alkyl, alkenyl, substituted alkenyl, alkynyl, substituted alkynyl, acyl and a covalent bond linking the moiety to the linker;

$R_{at}$ is selected from the group consisting of 4-phosphonomethylphenyl, 4-phosphonodifluoromethylphenyl, 3-carboxy-4-carboxymethoxyphenyl and 3,4-dihydroxyphenyl;

$R_{au}$ is aryl or heteroaryl, wherein the aryl or heteroaryl group is substituted with a covalent bond linking the moiety to the linker or with —OZ', where Z' is a covalent bond linking the moiety to the linker;

$R_{av}$ is selected from the group consisting of hydrogen, alkyl, substituted alkyl, alkenyl, substituted alkenyl, alkynyl, substituted alkynyl, acyl and alkaryl;

provided one and only one of $R_{as}$ and $R_{au}$ comprises a covalent bond linking the moiety to the linker;

(o) a moiety of formula XX:

$$\text{XX}$$

wherein each $R_{aw}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy and substituted thioalkoxy;

each $R_{ax}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy, a covalent bond linking the moiety to the linker and —OZ', where Z' is a covalent bond linking the moiety to the linker;

each m is independently an integer from 1 to 3;

provided one and only one of $R_{ax}$ comprises a covalent bond linking the moiety to the linker;

(p) a moiety of formula XXIV:

$$\text{XXIV}$$

wherein $R_{be}$ is a covalent bond linking the moiety to the linker;

(q) a moiety of formula XXVI:

$$\text{XXVI}$$

wherein $R_{bi}$ is a covalent bond linking the moiety to the linker;

(s) a moiety of formula XXVII:

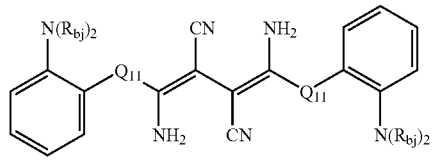

XXVII wherein each $R_{bj}$ is independently selected from the group consisting of hydrogen, alkyl, substituted alkyl, alkenyl, substituted alkenyl, alkynyl, substituted alkynyl, acyl and a covalent bond linking the moiety to the linker;

$Q_{11}$ is $NR_{bj'}$, O, S or alkylene, where $R_{bj'}$ is hydrogen, alkyl, substituted alkyl, alkenyl, substituted alkenyl, alkynyl, substituted alkynyl or acyl;

provided one and only one of $R_{bj}$ comprises a covalent bond linking the moiety to the linker;

(t) a moiety of formula XXVIII:

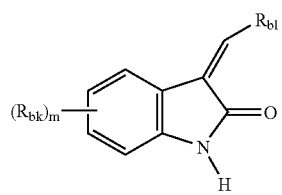

XXVIII wherein each $R_{bk}$ is independently selected from the group consisting of hydrogen, alkyl, substituted alkyl, alkenyl, substituted alkenyl, alkynyl, substituted alkynyl, acyl, acylamino, acyloxy, alkoxy, substituted alkoxy, amino, substituted amino, aminoacyl, aminoacyloxy, aryl, carboxyl, carboxyalkyl, cyano, cycloalkyl, substituted cycloalkyl, halogen, heteroaryl, heterocyclic, hydroxy, oxyacylamino, nitro, thioalkoxy, substituted thioalkoxy, —SO—$R_{bk'}$ and —SO$_2$—$R_{bk'}$, where $R_{bk'}$ is alkyl, substituted alkyl, alkenyl, substituted alkenyl, alkynyl, substituted alkynyl, cycloalkyl, substituted cycloalkyl, aryl, heteroaryl or heterocyclic;

$R_{bl}$ is aryl or heteroaryl, wherein the aryl or heteroaryl group is substituted with a covalent bond linking the moiety to the linker or with —(CH$_2$)$_u$-Z', where Z' is a covalent bond linking the moiety to the linker and u is an integer from 1 to 3;

m is an integer from 1 to 3; and (u) a moiety of formula XXIX:

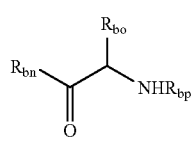

XXIX wherein $R_{bn}$ is selected from the group consisting of alkoxy, substituted alkoxy, hydroxy and —OZ', where Z' is a covalent bond linking the moiety to the linker;

$R_{bo}$ is aryl or heteroaryl;

$R_{bp}$ is acyl, alkoxycarbonyl and a covalent bond linking the moiety to the linker;

provided one and only one of $R_{bn}$ and $R_{bp}$ comprises a covalent bond linking the moiety to the linker;

and each X is a linker independently selected from a group of the formula:

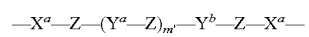

wherein m' is an integer of from 0 to 20;

$X^a$ at each separate occurrence is selected from the group consisting of —O—, —S—, —NR—, —C(O)—, —C(O)O—, —C(O)NR—, —C(S)—, —C(S)O—, —C(S)NR— or a covalent bond;

Z is at each separate occurrence is selected from the group consisting of alkylene, substituted alkylene, cycloalkylene, substituted cycloalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of: —C(O)NR'—, —NR'C(O)—, —NR'C(O)NR'—, —C(=NR')—NR'—, —NR'—C(=NR')—, —NR'—C(O)—O—, —N=C(R)—NR'—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

2. The compound of claim 1, wherein one or both ligands are a moiety of formula XI.

3. The compound of claim 1, wherein one or both ligands are a moiety of formula XII.

4. The compound of claim 1, wherein one or both ligands are a moiety of formula XIII.

5. The compound of claim 1, wherein one L is selected from the group consisting of:

(a) a moiety of formula O:

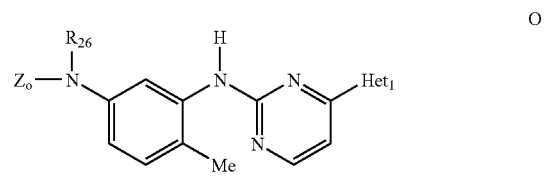

O wherein $R_{26}$ is selected from the group consisting of hydrogen and acyl;

$Het_1$ is heterocyclic or heteroaryl;

(b) a moiety of formula P:

[Structure P]

wherein $R_{27}$ is selected from the group consisting of hydrogen, alkyl of 1 to 6 carbon atoms and substituted alkyl;

$Ar_3$ is aryl; and (c) a moiety of formula S:

[Structure S]

wherein

D is selected from the group consisting of a covalent bond, —NH—, —S— and —O—;

E is selected from the group consisting of CH and N;

$Ar_3$ is aryl;

and the other L is selected from the group consisting of:

(d) a moiety of formula O;

(e) a moiety of formula P;

(f) a moiety of formula S;

(g) a moiety of formula D:

[Structure D]

wherein $R_6$ is selected from the group consisting of substituted alkyl and —CHO;

$R_7$ is selected from the group consisting of hydrogen, alkyl and acyl;

(h) a moiety of formula F:

[Structure F]

wherein $R_{10}$ is selected from the group consisting of hydrogen, alkoxy, amino and substituted amino;

$R_{11}$ is selected from the group consisting of hydrogen, alkoxy, halogens, amino, substituted amino and nitro;

$R_{12}$ is selected from the group consisting of hydrogen, hydroxy, alkoxy and halogen;

$R_{13}$ is selected from the group consisting of hydrogen, hydroxy, alkoxy and halogen;

Z is selected from the group consisting of 2H and O;

(i) a moiety of formula H:

[Structure H]

wherein $R_{17}$ and $R_{18}$ are independently selected from the group consisting of hydrogen and alkyl of 1 to 6 carbon atoms;

$R_{19}$ is selected from the group consisting of alkyl of 1 to 6 carbon atoms, $CH_2C(O)OEt$, —$(CH_2)_3OH$, alkaryl, aryl and heteroaryl;

(j) a moiety of formula N:

[Structure N]

(k) a moiety of formula U:

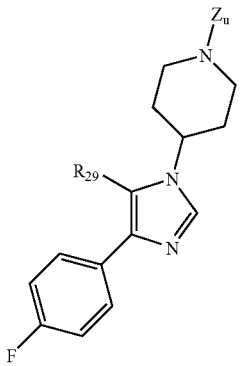

U wherein
R$_{29}$ is selected from the group consisting of 4-pyrimidinyl, 2-methylaminopyrimidin-4-yl, 2-phenoxypyrimidin-4-yl, 2-(4-methoxyphenoxy)pyrimidin-4-yl, 2-(4-fluorophenoxy)pyrimidin-4-yl, 2-(4-aminocarbonylphenoxy)pyrimidin-4-yl, 2-(4-ethylphenoxy)pyrimidin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, 2-(4-methoxyphenoxy)pyrimidin-4-yl, 4-pyridinyl, 2-phenoxypyridin-4-yl, 2-(4-methoxyphenoxy)pyridin-4-yl, 2-(4-fluorophenoxy)pyridin-4-yl, 2-(4-benzyloxyphenoxy)pyrimidin-4-yl, 2-(4-cyanophenoxy)pyrimidin-4-yl, 2-(4-hydroxyphenoxy)pyrimidin-4-yl, 2-(3-methoxyphenoxy)pyrimidin-4-yl, 2-(4-phenylphenoxy)pyrimidin-4-yl, 2-(4-phenoxyphenoxy)pyrimidin-4-yl, 2-(3-hydroxyphenoxy)pyrimidin-4-yl, 2-(2-hydroxyphenoxy)pyrimidin-4-yl, 2-(3,4-methylenedioxyphenoxy)pyrimidin-4-yl, 2-(3-fluorophenoxy)pyrimidin-4-yl, 2-(2-fluorophenoxy)pyrimidin-4-yl, 2-(2-methoxyphenoxy)pyrimidin-4-yl, 2-(3-trifluoromethylphenoxy)pyrimidin-4-yl, 2-(3,4-difluorophenoxy)pyrimidin-4-yl, 2-(4-methylsulfonylphenoxy)pyrimidin-4-yl, and 2-(4-methoxyphenoxy)pyrimidin-4-yl;

(l) a moiety of formula V:

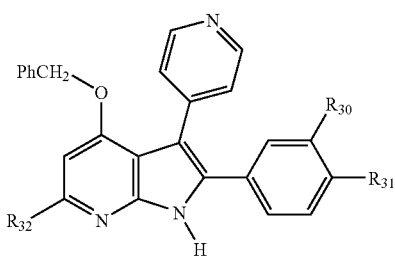

V wherein

R$_{30}$ is selected from the group consisting of hydrogen, alkyl of 1 to 6 carbon atoms, halogen and alkoxy;

R$_{31}$ is selected from the group consisting of hydrogen, alkyl of 1 to 6 carbon atoms, halogen, alkoxy and Z$_v$;

R$_{32}$ is selected from the group consisting of hydrogen, amino, substituted amino, alkoxy, —NHCOCH$_3$, and Z$_v$, provided one and only one of R$_{31}$ and R$_{32}$ is Z$_v$;

(m) a moiety of formula Z:

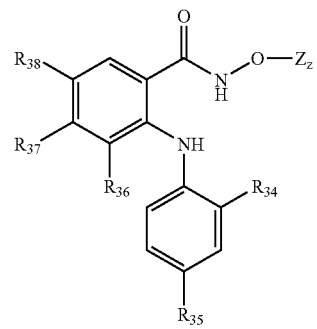

Z wherein

R$_{34}$ is selected from the group consisting of hydrogen, hydroxy, alkyl, alkoxy, halogen and substituted alkyl;

R$_{35}$ is selected from the group consisting of hydrogen and halogen;

R$_{36}$, R$_{37}$, and R$_{38}$ are selected from the group consisting of hydrogen, —NO$_2$, alkyl, substituted alkyl, amino, substituted amino, alkoxy, hydroxy and halogen;

(n) a moiety of formula L:

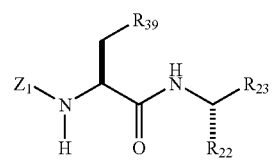

L (o) a moiety of formula M:

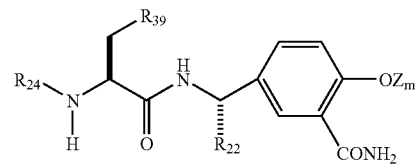

M wherein, in formula L and M,

R$_{22}$ is selected from the group consisting of hydrogen, alkyl of 1 to 6 carbon atoms and substituted alkyl;

$R_{23}$ is

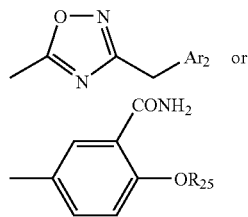 or

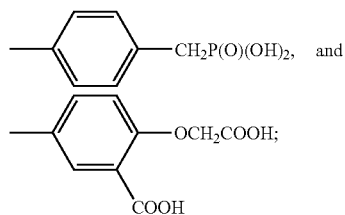

$R_{24}$ is selected from the group consisting of hydrogen and acyl;

$R_{25}$ is selected from the group consisting of alkyl and cycloalkyl;

$R_{39}$ is selected from the group consisting of

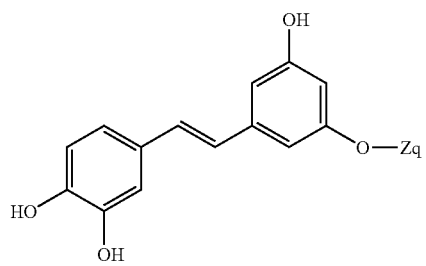

$Ar_2$ is selected from the group consisting of alkyl of 1 to 6 carbon atoms, substituted alkyl and aryl;

(p) a moiety of formula Q:

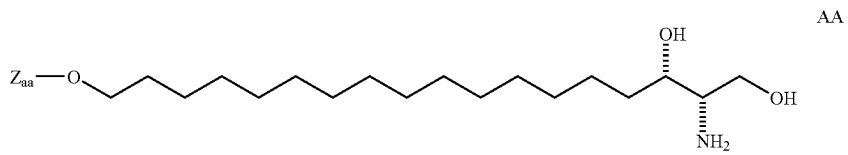

(q) a moiety of formula AA:

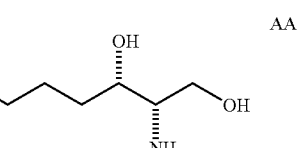

(r) a moiety of formula X:

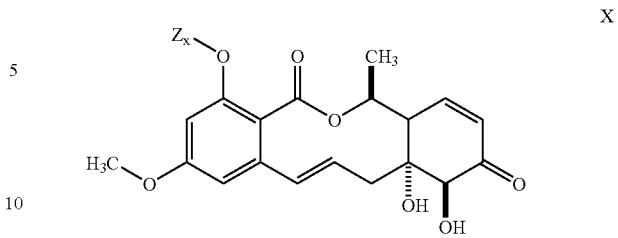

(s) a moiety of formula Y:

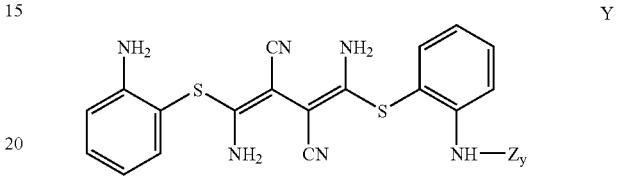

(t) a moiety of formula AB:

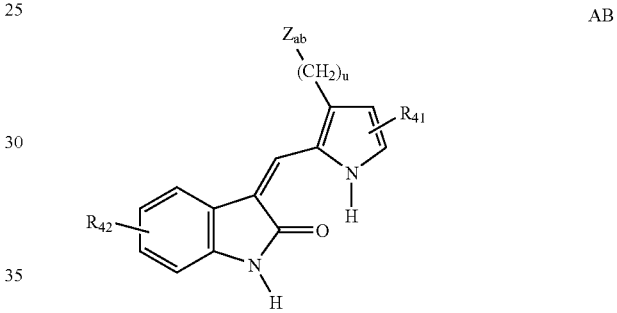

(u) a moiety of formula AH:

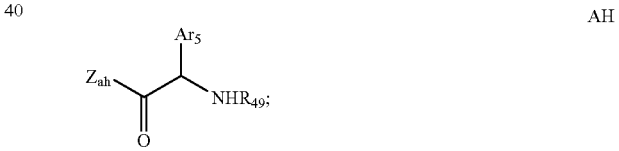

(v) a moiety of formula AI:

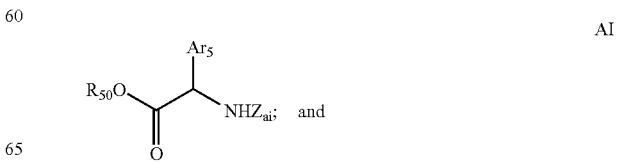

and (w) a moiety of formula AB':

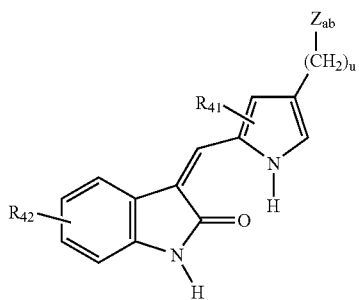

wherein
- $R_{41}$ is independently selected from the group consisting of hydrogen, 4-$CH_3$, 5-$CH_3$ and 4,5-di-$CH_3$;
- $R_{42}$ is independently selected from the group consisting of hydrogen, $CH_3$, —F, —Cl and —$NO_2$;
- $R_{49}$ is independently selected from the group consisting of acetyl, t-BOC, -Cbz, and —C(O)Ph;
- $R_{50}$ is independently selected from the group consisting of $C_{1-5}$ alkyl;
- $Ar_5$ is independently selected from the group consisting of $C_6H_5$, p-$C_6H_4OH$, and other substituted phenyl groups;
- u is an integer from 1 to 3,
- and further wherein $Z_d$, $Z_f$, $Z_h$, $Z_l$, $Z_m$, $Z_n$, $Z_o$, $Z_p$, $Z_q$, $Z_s$, $Z_u$, $Z_v$, $Z_x$, $Z_y$, $Z_z$, $Z_{aa}$, $Z_{ab}$, $Z_{ah}$, and $Z_{ai}$ are covalent bonds linking the moiety to the linker;
- and stereoisomers and analogs thereof.

6. The compound of claim 5, wherein one L is a moiety of formulae O, P, or S, and the other L is a moiety of formulae D, F, H, N, O, P, S, U, V, or Z.

7. The compound of claim 5, wherein one L is a moiety of formulae O, P, or S, and the other L is a moiety of formulae L or M.

8. The compound of claim 5, wherein one L is a moiety of formulae O, P, or S, and the other L is a moiety of formula Q.

9. The compound of claim 5, wherein one L is a moiety of formulae O, P, or S, and the other L is a moiety of formula AA.

10. The compound of claim 5, wherein one L is a moiety of formulae O, P, or S, and the other L is a moiety of formulae X or Y.

11. The compound of claim 5, wherein one L is a moiety of formulae O, P, or S, and the other L is a moiety of formulae AB, AH, or AI.

12. The compound of claim 5, wherein one or both L is a moiety of formulae O.

13. The compound of claim 5, wherein one or both L is a moiety of formulae P.

14. The compound of claim 5, wherein one or both L is a moiety of formulae S.

15. A pharmaceutical composition comprising a pharmaceutically acceptable carrier and a therapeutically effective amount of a compound of claim 1.

16. A pharmaceutical composition comprising a pharmaceutically acceptable carrier and a therapeutically effective amount of a compound of claim 5.

17. A method of treating a disease or medical disorder mediated by a protein kinase wherein the disease or medical disorder is selected from the group consisting of recurrent ocular herpetic keratitis, diabetic retinopathy, VEGF-induced angiogenesis, macular degeneration, ischemia, atherosclerosis, and psoriasis, the method comprising administering to a mammal in need of such treatment a pharmaceutical composition comprising a pharmaceutically acceptable carrier and a therapeutically effective amount of a compound of claim 1.

* * * * *

UNITED STATES PATENT AND TRADEMARK OFFICE
CERTIFICATE OF CORRECTION

PATENT NO. : 7,037,912 B2
APPLICATION NO. : 10/824005
DATED : May 2, 2006
INVENTOR(S) : Griffin et al.

Page 1 of 1

It is certified that error appears in the above-identified patent and that said Letters Patent is hereby corrected as shown below:

In Column 165, at line 13, "$R_5$" should read --$R_s$--.

In Column 177, at line 30, delete "and analogs" after stereoisomers.

Signed and Sealed this

Fifteenth Day of August, 2006

JON W. DUDAS
*Director of the United States Patent and Trademark Office*